US006160106A

United States Patent [19]
Kimchi

[11] Patent Number: 6,160,106
[45] Date of Patent: *Dec. 12, 2000

[54] TUMOR SUPPRESSOR GENES, PROTEINS ENCODED THEREBY AND USE OF SAID GENES AND PROTEINS

[75] Inventor: Adi Kimchi, Raanana, Israel

[73] Assignee: Yeda Research & Development Co., Ltd., Rehovot, Israel

[*] Notice: This patent is subject to a terminal disclaimer.

[21] Appl. No.: 08/810,712

[22] Filed: Mar. 3, 1997

Related U.S. Application Data

[63] Continuation-in-part of application No. 08/631,097, Apr. 12, 1996, Pat. No. 5,968,816.

[30] Foreign Application Priority Data

Oct. 12, 1993 [IL] Israel ..................................... 107256

[51] Int. Cl.$^7$ .......................... C07H 21/04; C12N 15/12; C12N 15/63

[52] U.S. Cl. ....................... 536/23.2; 536/23.5; 536/24.5; 435/320.1

[58] Field of Search ...................... 435/6, 320.1; 514/44; 536/23.1, 23.2, 23.5, 24.3, 24.31, 24.5

[56] References Cited

U.S. PATENT DOCUMENTS

| | | | |
|---|---|---|---|
| 4,542,096 | 9/1985 | Leder | 435/6 |
| 4,798,787 | 1/1989 | McCormick et al. | 435/7.21 |
| 5,015,570 | 5/1991 | Scangos et al. | 435/6 |
| 5,527,676 | 6/1996 | Vogelstein et al. | 435/6 |
| 5,646,008 | 7/1997 | Thompson et al. | 435/69.1 |

FOREIGN PATENT DOCUMENTS

| | | |
|---|---|---|
| 0 475 623 A1 | 3/1992 | European Pat. Off. . |
| WO 93/07872 | 4/1993 | WIPO . |
| WO 95/10630 | 4/1995 | WIPO . |

OTHER PUBLICATIONS

L.P. Deiss et al., Identification of a novel serine/threonine kinase and a novel 15-kDa protein as potential mediators of the gamma-interferon-induced cell death EMBL Database Entry HSDAP1, Accession No. X76105, 1993, XP002102391.

Deiss et al., Genes Development, vol. 9, No. 1, 1995, pp. 15–30, XP002102392.

Baker et al., Suppression of Human Colorectal Carinoma Cell Growth by Wild–Type P53, Science, vol. 249, No. 4971, 1990, pp. 912–915, XP000293056.

Coetzer et al., Anti–Peptide antibodies to cathepsins B, L and D and type IV collegenase, Journal of Immunological Methods, vol. 136, 1991, pp. 199–200, XP002102393.

Kissel et al., Isolation of DAP3, mediator of IFN–gamma induced cell death, Journal of Biological Chenmistry, vol. 46, No. 270, 1995, pp. 27932, XP0020805782.

Feinstein et al., Assignment of DAP1 and DAPK–genes that positively mediate programmed cell death triggered by IFN–gamma–to chromosome regions 5p12.2 and 9q34.1, respectively. Genomics, vol. 29, 1995, pp. 305–307, XP002080573.

Tsujimoto, Y. et al.; Clustering of Breakpoints on Chromosome 11 in Human B–cell Neoplasms with the t(11;14) Chromosome Translocation; Nature, vol. 315; 340–343; 1985.

Lowe, S.W. et al.; P53 is Required for Radiation Induced Apoptosis in Mouse Thymocytes; Nature, vol. 362; 874–849; 1993.

Morin, P.J. et al.; Apoptosis and APC in Colorectal Tumorigenesis; Proc. Natl. Acad. Sci., vol. 93; 7950–7954, 1996.

Holmgren, L. et al.; Dormancy of Micrometasteses: Balanced Proliferation and Apostosi in the Presence of Angiogenesis Suppression; Nature Medicine, vol. 1, No. 2; 149–153, 1995.

Feinstein, E. et al.; The Death Domain: A Module Shared by Proteins with Diverse Cellular Functions; TIBS 20; 342–344, 1995.

Deiss, L.P. et al.; Identification of a Novel Serine/Threonine Kinase and a Novel 15–KD Protein as Potential Mediators of the γ Interferon–Induced Cell Death; Genes & Development, 9:15–30, 1995.

Deiss, Louis P. et al. "A Genetic Tool Used to Identify . . . Signal" Sci., vol. 252, pp. 117–120 (1991).

Faust, Phyllis L. et al. "Cloning and Sequence . . . Cathepsin D" Proc. Natl. Acad. Sci. USA, vol. 82, pp. 4910–4914 (1985).

Owens, Gregory P. et al. "Identification of mRNAs . . . Thymocytes", Mol. & Cell. Bio., vol. 11, No. 8, pp. 4177–4188 (1991).

Wong, Paul et al. "Genomic Organization . . . Apoptosis" J. Bio. Chem., vol. 268, No. 7, pp. 5021–5031 (1993).

Nakano, Teruaki et al. "Transfection of Interferon–γ . . . Death" Experimental Hematology, vol. 21, No. 11, pp. 1498–1503 (1993).

D'Mello, Santosh R. et al. "SGP2, Ubiquitin, 14K . . . Apoptosis" Molecular Neuroscience, vol. 4, No. 4, pp. 355–358 (1993).

Yonish–Rouach, Ellsheva et al. "Wild–type p53 Induces . . . Interleukin–6" Nature, vol. 352, pp. 345–347 (1991).

Itoh, Naoto et al. "A Novel Protein . . . Apoptosis" J. Bio. Chem., vol. 268, No. 15, pp. 10932–10937 (1993).

Moore, Jason et al. "Mutant H–RAS . . . Cells" Leukemia Report, vol. 1, No. 8, pp. 703–709 (1993).

(List continued on next page.)

*Primary Examiner*—Robert A. Schwartzman
*Attorney, Agent, or Firm*—Blank, Rome, Comisky & McCauley LLP

[57] ABSTRACT

DNA molecules comprising a nucleic acid sequence expressed in cells, the expression product of which is involved in programmed cell death. Also disclosed are methods of therapeutic treatment using the DNA molecules and their expression products, and pharmaceutical compositions containing them.

10 Claims, 58 Drawing Sheets

OTHER PUBLICATIONS

Miura, Masayuki et al. "Induction of Apoptosis . . . Gene ced–3" Cell, vol. 75, pp. 653–660 (1993).

Abbadie, Corinne et al. "High Levels of c–rel . . . In Vitro" Cell, vol. 75, pp. 899–912 (1993).

Katre, Nandini V. et al. "Chemical Modification . . . Model" Proc. Natl. Acad. Sci. USA, vol. 84, pp. 1487–1491 (1987).

Cavailles et al. (1993) Cathepsin D gene is controlled by a mixed promoter, and estrogens stimulate only TATA–dependent transcription in breast cancer cells. Proc. Natl. Acad. Sci. USA 90:203–207, Jan. 1993.

Friedmann (1997) Overcoming the obstacles to gene therapy. Scientific American, Jun., pp. 96–101.

SIGMA Chemical Company Catalog (1990) p. 119.

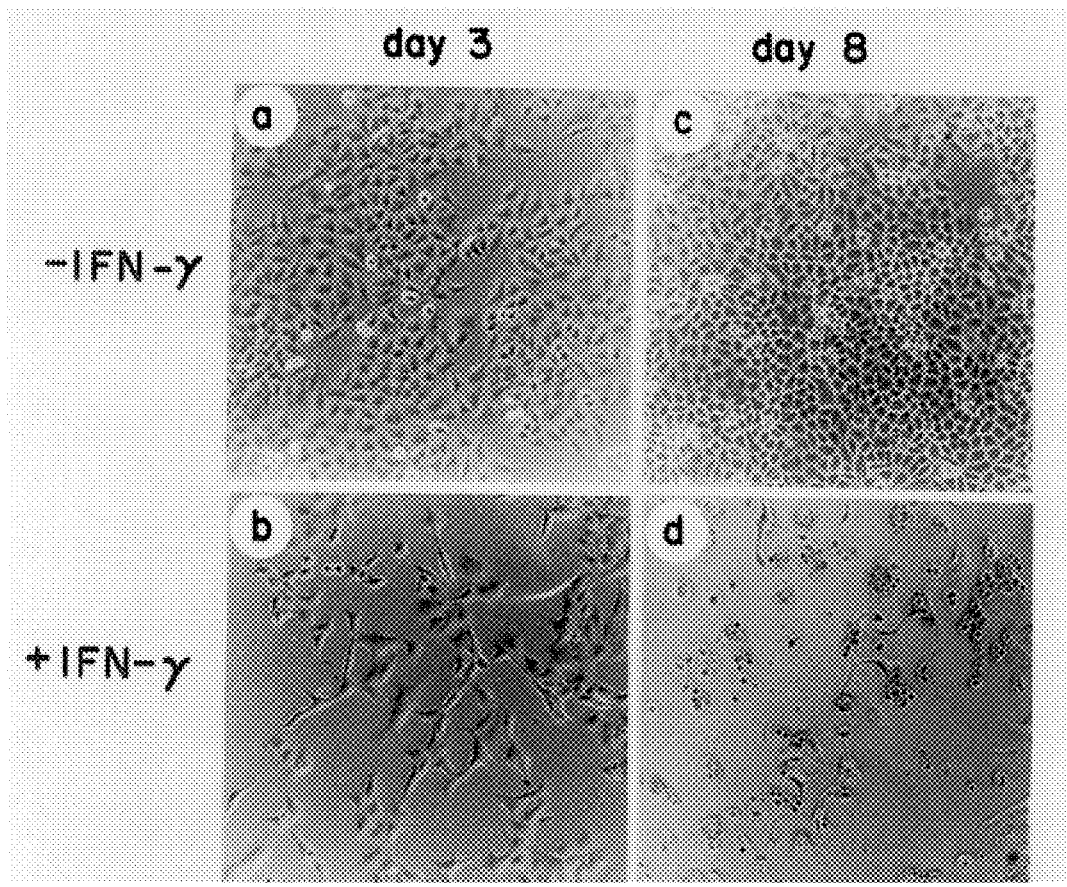

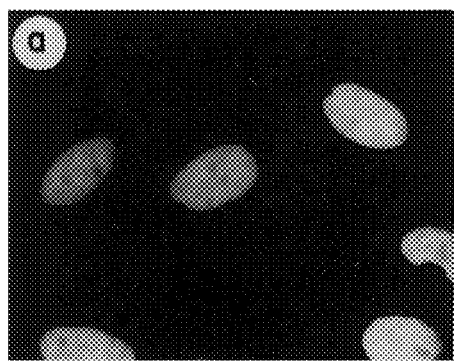
FIG. 3B(a)
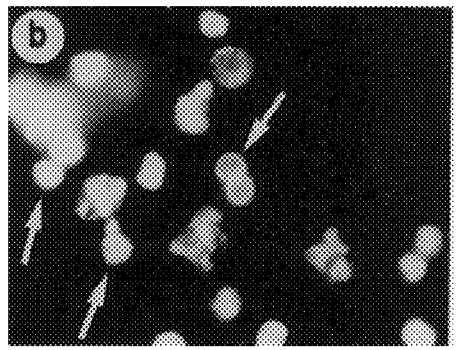
FIG. 3B(b)
FIG. 3C(a)    FIG. 3C(c)    FIG. 3C(e)
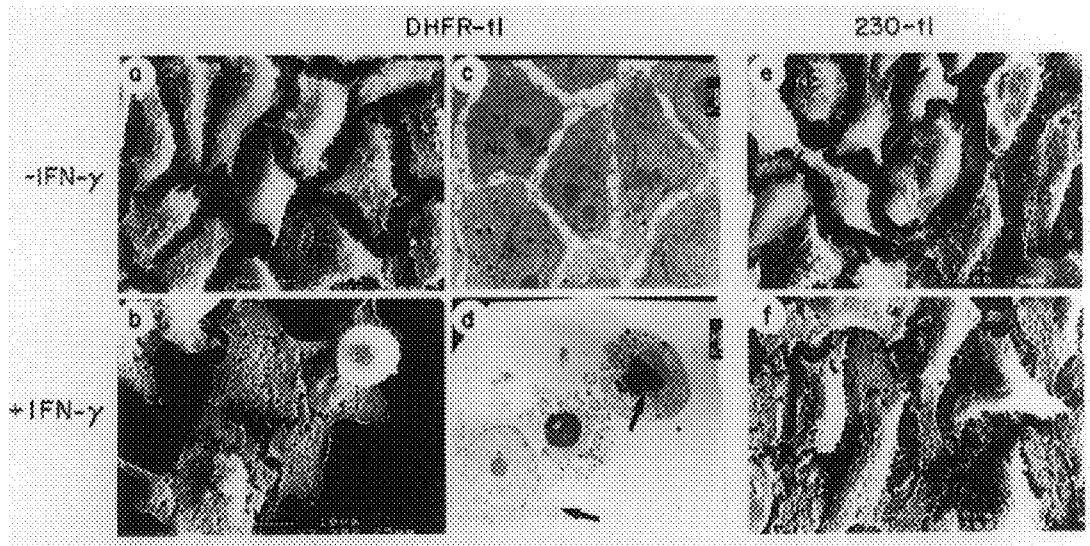
FIG. 3C(b)    FIG. 3C(d)    FIG. 3C(f)

FIG. 6A

```
CCTGGTGTGTGCACAGTCTGCCTGGGTCCATTGTCACTTGGGTGGTGCATCAGGTTGTCTCCTGTCTCAGATGAGTTTCCTGTCTAGAGATGTC  1530
CTAGTCTGCTCACTGGCTGGTGGTGGCAGTAGGGTACCCTGGTCTCCTGGAAAAGCCAGAGGGTTCACCTAGTCAGACGAAACTCAGAACAGT   1620
GCTTGTGGAGGGCCTGACTGTCCTGTCCACCACAGCCTGATCTGCTGCAGGTCAGCAACTGTGTCGTGAGCAGTCAGCCTCCAACCACCAGCCT  1710
TTCTGGTGCTGTTCTCAGTTCACGTCTGCCAGCTGGTGAGGGCAGAGGCAGAGACCTGGTCAGACCTTAAGGAAGCCAGCCCCTCCTCCTGAGGGAGC  1800
ATGGCACAGCCTCACACTTGAAAGACAGGTGTTTGGTTTCCCATCTAATCAACTTAAGGGATATAAAACTGGTATAAAACACCCAGACTTGGTGCCATGTACCCTGGAACACCCTGTCA  1890
CCACTATTTTCCTGATCAGTTGCCTTTTCGGAGCAGCAGCATCCTTAATGCACCCAGGAGGGATGCCGCGTCAGGTCAGGCCTGTGCAGACCCTGCC  1980
AAGCACCTCCCAGCCTGCCTTTTCGGAAGCATCCTTAATGCACCCAGGAGGGATGCCGCGTCAGGTCAGGCCTGTGCAGACCCTGCC  2070
CTGCCGCTGCAGAAATCCAGAAGCATGCATGCATGTGTGAGCTTTAGATGTGAGGGAGGGGAGGGTGTATTTCCAGAGGTGCGTTTTATG  2160
TACTTTTAGCTAGATGTGCATGCATGTGTGAGCTTTAGATCATTAAATCCAAAATGTTTGCCTAAATGAGG  2232
```

FIG. 6B

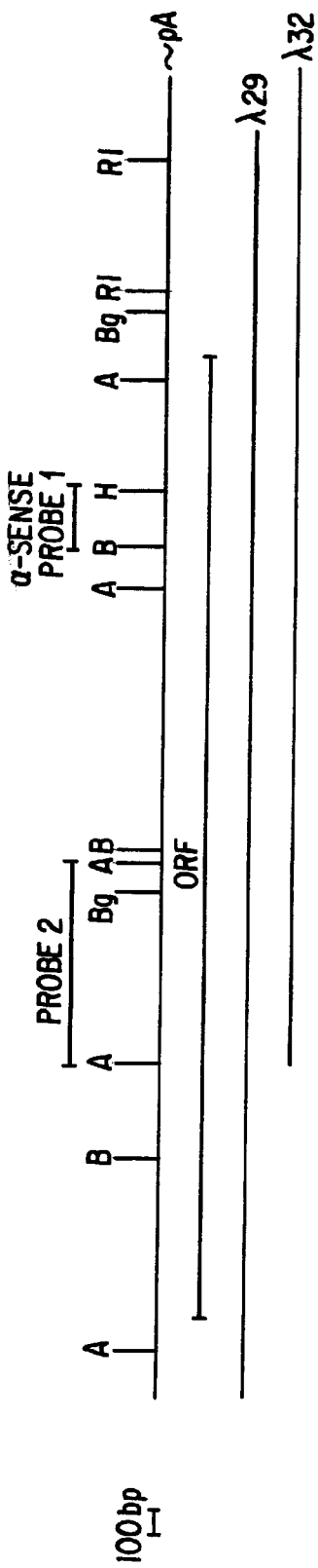

```
          E  D  K  S  P  I  A  P  E  E  L  A  L  V  H  N  L  R  K  M
 961  GATGAAAAATGATTGGCATGGAGGCGCCATTGTGTCTGGCTTTGAGCAGACTGGGTCTCT   1020
          M  K  N  D  W  H  G  A  I  V  S  A  L  S  Q  T  G  S  L
1021  CTTTAAGCCCCGGAAAGCCTATCTGCCCCAGGAGTTGCTGGGAAAGGAAGGATTTGATGC   1080
          F  K  P  R  K  A  Y  L  P  E  L  L  G  K  E  G  F  D  A
1081  CCTGGATCCCTTATTCCCATCCGGTTTCCAACTATAACCCAAAGGAATTTGAAAGTTG     1140
          L  D  P  F  I  P  I  L  V  S  N  Y  N  P  K  E  F  E  S  C
1141  TATTCAGTATTATTGGAAAACAATTGGCTTCAACATGGAGAAAGCTCCTACAGAAGAAGG   1200
          I  Q  Y  L  E  N  N  W  L  Q  H  E  K  A  P  T  E  E  G
1201  GAAAAAGAGCTGTGTTCTGTTCCTAAGCAACGGAACCCCTCGCTGCTGGAGCGGCACTGTGC  1260
          K  K  E  L  F  L  S  N  A  N  P  S  L  L  E  R  H  C  A
1261  CTACCTCTAAGCCAAGATCACAGCATGTGAGGAAGACAGTGCTTGTTGCATCTGTTTATGCTGG  1320
          Y  L
1321  ACCCAGTAGATGAGGAAGTCGGGCAGTACACAGGAAGAGAGCCAGGCCCTTGTACCTA   1380
1381  TGGGATTGGACAGGACTGGCTCAGTTGGCTCTGGACCTTGGACTTGCTGAAATGGGTTTCACTGTGAA 1440
1441  TGGGTGACAATAAGATATTCCTTGTTCCTAAAACTTTATCAGTTTATTGGATGTGGG   1500
1501  TTTtTCACATTTAAGATAATTATGGCTCTTTTCCTAAAAAATAAATATCTTTCTAAAAA 1560
1561  AAAAAAAA  1568
```

```
CGGAGGACAGCCGGAGCCGAGCGCAACGCTGCAGCGGACTTTGTTCCCTCCACGGAGAGGACTCGGCAGCGGCAGGGTCTGGGGCCGG                                  90
CGCCTGGGAGGGATCTGCGCCCCCCAGGCCCACTCACTCCCTAGTGTGTTCCGCGGCTGGGCTGGCGCTGGCGCTGGTCG                                           180
GCCTCCGACAGGCCTCCGGAGGGACTCCCGGGGAGCTCCCAGGCGACCGATGATGCATACGGAGAGGCGAGGAG                                                 270
                                                                      M  T  V  F  R  Q  E  N                                 8
CGGTGGTGATGGTCTGGAAGCTGGAGCTGAAGTCCCCTGGGCTTTGGTGAGGCGTGACAGTTTATCATGACCGTGTTCAGGCAGGAAAAC                                 360
         ↓─PROTEIN KINASE DOMAIN
  V  D  D  Y  Y  D  T  G  E  E  L  G  S  G  Q  F  A  V  V  K  K  C  R  E  K  S  T  G  L  Q                                  38
GTGGATGATTACTACGACACCGGGGAGGAACTTGGCAGTGGACAGTTTGCCGTGGTGAAGAAATGCCGGGAGAAAAGTACCGGCCTCCAG                                 450

Y  P  A  K  F  I  K  K  R  R  T  K  S  R  R  G  V  S  R  E  D  I  E  R  E  V  S  I  L                                     68
TATCCCGCCAAATTCATCAAGAAAAGGAGGACTAAGTCCAGGCGGGGTGTGAGCCGGGAGGACATCGAGCGGGAGGTCAGCATCCTG                                    540

K  E  I  Q  H  P  N  V  I  T  L  H  E  V  Y  E  N  K  T  D  V  I  L  E  L  V  A  G                                        98
AAGGAGATCCAGCACCCCAATGTCATCACCCTGCACGAGGTCTATGAGAACAAGACGGACGTCATCCTGGAACTCGTTGCAGGT                                       630

G  E  L  F  D  F  L  A  E  K  E  S  L  T  E  E  A  T  E  F  L  K  Q  I  L  N  G  V  Y                                     128
GGCGAGCTGTTTGACTTCTTAGCTGAAAAGGAATCTTTAACTGAAGAGGAAGCAACTGAATTTCTCAAACAAATTCTTAATGGTGTTTAC                                720

Y  L  H  S  L  Q  I  A  H  F  D  L  K  P  E  N  I  M  L  L  D  R  N  V  P  K  P  R  I  K                                  158
TACCTGCACTCCCTTCAAATCGCCCACTTTGATCTTAAGCCTGAGAACATAATGCTTTTGGATAGAAATGTCCCAAACCTGGATCAAG                                  810

I  I  D  F  G  N  E  F  K  N  I  F  G  T  P  E  F  V  A  P  E  I  V  N  Y  E  P  L  G  L                                  188
ATCATTGACTTTGGAAATGAATTTAAAAACATATTTGGACTCCAGAGTTTGTCCTGAGATAGTCAACTATGAACCTCTTGGTCTT                                     900
```

FIG. 8A

```
E  A  D  M  W  S  I  G  V  I  T  Y  I  L  L  S  G  A  S  P  F  L  G  D  T  K  Q  E  T  L           218
GAGGCAGATATGTGGAGTATCGGGGTAATAACCTATATCCTCCTAAGTGGGGCCTCCCATTTCTTGGAGACACTAAGCAAGAAACGTTA          990

A  N  V  S  A  V  N  Y  E  F  E  D  E  Y  F  S  N  T  S  A  L  A  K  Q  F  I  R  R  L  L           248
GCAAATGTATCCGCTGTCAACTACGAGTTTGAGGATGAATACTTCAGTAATACCAGTGCCCTAGCCAAAGATTTCATAAGAAGACTTCTG        1080

V  K  D  P  K  K  R  M  T  I  Q  D  S  L  Q  H  P  W  I  K  P  K  D  T  Q  Q  A  L  S  R           278
GTCAAGGATCCAAAGAAGAGAATGACAATTCAAGATAGTTTGCAGCATCCCTGGATCAAGCCTAAAGATACACAAGCACTTAGTAGA          1170
                                   PROTEIN KINASE DOMAIN ───
K  A  S  A  V  N  M  E  K  F  K  F  A  R  K  K  W  K  Q  S  V  R  L  I  S  L  C  Q               308
AAAGCATCAGCAGTAAACATGGAGAAATTCAAGTTTGCAGCCCGGAAAAAATGGAAACAATCCGTTCGTTTGATATCACTGTGCCAA          1260
   CALMODULIN REGULATORY REGION

R  L  S  R  S  F  L  S  R  S  N  M  S  V  A  R  S  Q  D  T  L  D  E  E  D  S  F  V  J M K          338
AGATTATCCAGGTCATTCCTGTCCAGAAGTAACATGAGTGTTGCCAGAAGCGATGATACTCTGGATGAGGAAGACTCCTTTGTGATGAAA       1350
   gr1

A  I  H  A  I  N  Q  D  N  V  P  G  L  Q  H  L  L  G  S  L  S  N  Y  D  V  N  Q P  N              368
GCCATTCATGCCATCAACGATGACAATGTCCCAGGCCTGCAGCAGTTCTTGGGCTCACTCAGTAACTATGATGTTAACCAACCAAC           1440

K  H  G  T  P  P  L  L  I  A  G  C  G  N  I  Q  L  Q  L  L  I  K  R  G  S  R T  D                 398
AAGCACGGGACACTCCAATTACTCATTGCTGGCTGTGGGAATATTCAAATACTACAGTGCTCATTAAAAGAGGCTCGAGAATCGAT          1530
                                                         gr2

V  Q  D  K  G  G  S  N  A  V  Y  W  A  A  R  H  G  H  V  D  T  L  K  F  L  S  E  N  K  C          428
GTCCAGGATAAGGGCGGTCCAATGCCGTCTACTGGGCCATGCCACGTGCTGATACCTTGAAATTTCTCAGTGAGAACAAATGC            1620
                                      gr3

P  L  D  V  K  D  K  S  G  E  M  A  L  H  V  A  A  R  Y  G  H  A  D  V  A  Q V T C A              458
CCTTTGGATGTGAAAGACAAGAGTGGGGAGATGGCCCTCCACGTGGCAGCTCGTTATGGCCATGCTGACGTGGCTCAAGTACTTGTGCA        1710
```

```
L  A  S  K  P  T  V  S  V  S  I  N  N  L  Y  P  G  C  E  N  V  S  V  R  S  R  S  M  M  F          758
CTGGCTTCTAAGCCAACAGTCTCAGTGAGCATCAACAACCTGTACCCAGGCTGCGAGAATGTGAGTGTGAGGAGCCGGAGCATGATGTTC        2610

E  P  G  L  T  K  G  M  L  E  V  F  V  A  P  T  H  P  H  C  S  A  D  D  Q  S  T  K  A             788
GAGCCGGGGTCTTACCAAAGGGATGCTGGAGGTGTTTGTGGCCCCGACCCACCCGCACTGCTCGGCCGATGACCAGTCCACCAAGGCC         2700

I  Q  I  Q  N  A  Y  L  N  G  V  G  D  F  S  V  W  E  F  S  G  N  P  V  Y  F  C  C  Y  D          818
ATCGACATCCAGAACGCTTATTTGAATGGCGTGGGAGTTTCAGTGTGGGAGTTCTCTGGAAATCCTGTGTATTTCTGTGTTATGAC           2790

Y  F  A  N  D  P  T  S  I  H  V  V  F  S  L  E  E  P  Y  E  I  Q  L  N  P  V  I  F             848
TATTTTGCTAACGATCCACTGTCCATCATGTTGTTCTTTAGTCTAGAAGAGCCCTATGAGATCCAGCTGAACCCAGTGATTTTC            2880

W  L  S  F  L  K  S  L  V  P  V  E  E  P  I  A  F  G  G  K  L  K  N  P  L  Q  V  V  L  V          878
TGGCTCAGTTTCCTGAAGTCCCTGGTCCCAGTTGAAGAACCCATAGCCTTCGGTGGCAAGCTCAAGAACCCACTCCAAGTTGTCCTGGTG      2970

A  T  H  A  D  I  M  N  V  P  R  P  A  G  G  E  F  G  Y  D  K  Q  T  S  L  L  K  E  I  R          908
GCCACCCACGCTGACATCATGAATGTTCCTCGACCGGCTGGAGGCGAGTTTGGATATGACAAAGACACATCGTTGCTGAAAGAGATTAGG      3060

N  R  F  G  N  D  L  H  I  S  N  K  L  F  V  L  D  A  G  A  S  G  S  K  D  M  K  V  L  R          938
AACAGGTTTGGAAATGACCTTCACATTTCAAATAAGCTGTTTGTTCTTGATGCTGGGGCTTCTGGGTCAAAGGACATGAAGGTACTTCGA      3150

N  H  L  Q  E  I  R  S  Q  I  V  S  V  C  P  P  M  T  H  L  C  E  K  I  I  S  T  L  P  S          968
AATCATCTGCAAGAAATACGAAGCCAGATTGTTTCGGTCTGTCCTCCCATGACTCACCTGTGTGAGAAAATCATCTCCACGCTGCCTTCC      3240

W  R  K  L  N  G  P  N  Q  L  M  S  L  Q  Q  F  V  Y  D  V  Q  Q  Q  L  N  P  L  A  S  E         998
TGGAGGAAGCTCAATGGACCCAACCAGCTGATGTCGCTGCAGCAGTTTGTGTACGACGTGCAGGACCAGCTGAACCCCCTGGCCAGCGAG     3330
```

FIG. 8D

```
E  D  L  R  R  I  A  Q  Q  L  H  S  T  G  E  I  N  I  M  Q  S  E  T  V  Q  D  V  L  L         1025
GAGGACCTCAGGCGGATTGCTCAGGCAGCTCCACAGGGGAGATCAACATGCAAAGTGAAACAGTTCAGGACGTGCTGCTCCTG                  3420

D  P  R  W  L  C  T  N  V  L  G  K  L  L  S  V  E  T  P  R  A  L  H  H  Y  R  G  R  Y  T         1058
GACCCCCGCTGGCTCTGCACAAACGTGCTGGGGAAGTTGCTGTCCGTGGAGACCCCACGGGCTGTGCACCACTACCGGGGCCGCTACACC          3510

V  E  D  I  Q  R  L  V  P  D  S  Q  V  E  E  L  L  Q  I  L  D  A  M  D  I  C  A  R  Q  L         1088
GTGGAGGACATCCAGCGCCTGGTGCCCGACAGCCAGGTGGAGGAGCTGCTGCAGATCCTGGATGCCATGGACATCTGCGCCCGGCAGCTG          3600

S  S  G  T  M  V  D  V  P  A  L  I  K  T  D  N  L  H  R  S  W  A  D  E  E  D  E  V  M  V         1118
AGCAGCGGGACCATGGTGGACGTCCCAGCTCTGATCAAGACAGACAACCTGCATCGCTCCTGGGCTGATGAGGAGGACGAGGTGATGGTG          3690

Y  G  G  V  R  I  V  P  V  E  H  L  T  P  F  P  C  G  I  F  H  K  V  Q  V  N  L  C  R  W         1148
TATGGTGGTGTGCGCATCGTGCCCGTGGAACACCTCACCCCTTTCCCATGTGGCATCTTTCACAAGGTCCAGGTGAACCTGTGCCGGTGG          3780

I  H  Q  S  T  E  G  D  A  D  I  R  L  W  V  N  G  C  K  L  A  N  R  G  A  E  L  L  V         1178
ATCCACCAGAGCACAGAGGGCGACGCGGACATCCGCCTGTGGGTGAATGGCTGCAAGCTGGCCAACCGTGGGGCCGAGCTGCTGGTG            3870

L  L  V  N  H  G  Q  G  I  E  V  Q  V  R  G  L  E  T  E  K  I  K  C  L  L  L  D  S  V         1208
CTGCTGGTCAACCACGGCCAGGGCATTGAGGTCCAGGTTCGTGGCCTGGAGACAGAGAAGATCAAGTGTCTGCTGCTGGACTCGGTG            3960

C  S  T  I  E  N  V  M  A  T  T  L  P  G  L  L  T  V  K  H  Y  L  S  P  Q  Q  L  R  E  H         1238
TGCAGCACCATTGAGAACGTCATGGCCACAACCCTGCCTGGTCTCCTGACCGTGAAGCATTACCTGAGCCCCCAGCAGCTGCGGGAGCAC         4050

H  E  P  V  M  I  Y  Q  P  R  D  F  F  R  A  Q  T  L  K  E  T  S  L  T  N  T  M  G  G  Y         1268
CATGAGCCCGTCATGATCTACCAGCCCCGGGACTTCTTCCGGGCACAGACTCTGAAGGAAACCTCACTGACCAACACCATGGGGGGGTAC         4140
```

```
  1 GAATTCCGCCGGCCCCAGGCAGGTGTGTCGCCTAGGCTGGAGAACTAGTCCTCGA      60
 61 CTCACGTGCAAGGATGATGCTGAAAGGAATAACAAGGCTTATCTCTAGGATCCATAAGTT 120
    			    M  M  L  K  G  I  T  R  L  I  S  R  I  H  K  L
121 GGACCCTGGGCGTTTTTACACATGGGAACCCAGGCTGCGCAAAGCTGCTCACCT        180
     D  P  G  R  F  L  H  M  G  T  Q  A  R  Q  S  I  A  H  L
181 AGATAACCAGGTTCCAGTTGAGAGTCCGAGAGCTATTTCCCGCCACCAATGAATGACCC  240
     D  N  Q  V  P  V  E  S  P  R  A  I  S  R  T  N  E  D  P
241 GGCCAAGCATGGGGATCAGTCAGGGTCAGCACTACAACATCTCCCCCAGGATTTGGA    300
     A  K  H  G  D  H  E  G  Q  H  Y  N  I  S  P  Q  D  L  E
301 GACTGTATTTCCCATGGCCTTCTGGTGATGCAGGTGAAGACATTCAGTGA            360
     T  V  F  P  H  G  L  P  P  R  F  V  M  Q  V  K  T  F  S  E
361 AGCTTGCTGATGGTAAGGAAACCAGCTAGAACTTCTGAAAAACACCAG             420
     A  L  M  V  R  K  P  A  L  E  L  L  H  Y  L  K  N  T  S
421 TTTTGCTTATCCAGCTATACGATATCTTCATTGTATGGAGAAGGAACAGGAAAAACCCT  480
     F  A  Y  P  A  I  R  Y  L  L  Y  G  E  K  G  T  G  K  T  L
481 AAGTCTTTGCCATGTCATTTGGGTGAAAATGTCGGGATCTTCTGCAGTGACATATATTCC 540
     S  L  C  H  V  I  H  F  C  A  K  Q  D  W  L  I  L  H  I  P
541 AGATGCTCATCTTTGGGTGAAAATGTCGGGATCTTCTGCAGTGACATACAAACA        600
     D  A  H  L  W  V  K  N  C  R  D  L  L  Q  S  S  Y  N  K  Q
601 GCGCTTTGATCAACCTTGAGAGGCTTCAACCTGGCTGAAGAGTATGTCTGAATAAGAGAAAGCAC 660
     R  F  D  Q  P  L  E  A  S  T  W  L  K  N  F  K  T  T  N  E
661 GCCGTTCCTGAACCAGATAAAGTTCAAGAAGTTGGTTGAACAGGGCATAACGCAAGTTCTTTGGGTATGTT 720
     R  F  L  N  Q  I  K  V  Q  E  K  Y  V  W  N  K  R  E  S  T
721 TGAGAAAGGGAGTCCTCTGGGAATTGTGCTGAAAGAGCTAAGATGCTTTGGGGAAGAACCACTCTGAAAAG 780
     E  K  G  S  P  L  G  E  V  V  E  Q  G  I  T  R  V  R  N  A
781 CACAGATGCAGTGGCCGTGGATGGAATCAATGCTCTTTGGGGGAAGAACCACTCTGAAAG 840
     T  D  A  V  G  I  V  L  K  E  L  K  R  Q  S  S  L  G  M  F
841 TCACCTCCTAGTGGCCGTTGCCGATTGCCCGAGGAATTAGCACTTGTTCACAACTTGAGGAAAAT 900
     H  L  V  A  V  D  G  I  N  A  L  W  G  R  T  T  L  K  R
901 AGAAGATAAAAAGCCCGATTGCCCGAGGAATTAGCACTTGTTCACAACTTGAGGAAAAT  960
```

FIG. 13

| | |
|---|---|
| CTAGATGAGGCAGATATAAGAGTCA | 25 |
| TCCAAAAAAGGACAGAGAAAAAAA | 50 |
| CAGACAAATCAGTTGTCAGTATCCA | 75 |
| TGGCCTCTGATTCTGTCTCAACCAT | 100 |
| GAAACAGAAGTGACACATATAC | 122 |
| CTGCTAAAAG | |

```
  1 GGCTATAAGGCAGGCTTCGGCGACCCTTCGGACCCGGCGCGCCGGCCATGCAGCCC          60
                                                M  Q  P
 61 TCCAGCCTTCTGCCGCTGCCCCTCTGCTGCTCCTGGCTGCACCGGCTTCGGCTGTCAGG     120
     S  S  L  L  P  L  A  L  L  L  L  L  A  P  A  S  A  L  V  R
121 ATCCCGCTGCACAAGTTCAGTCACACATCCATCCGCAGGACCATGTCGGAGGTTGGGGGCTCTGTG  180
     I  P  L  H  K  F  S  I  R  R  T  M  S  E  V  G  G  S  V
181 GAGGACCTGATTGCCAAAGGCCCCGTCTTCAAAGTACTCAAGAACTACATGGACGCCCAGTACTACGGGGAGATT 240
     E  D  L  I  A  K  G  P  V  S  K  Y  N  M  D  A  Q  Y  Y  G  E  I
241 GAGGGGCCCATTCCCGAGGTGCTCAAGAACTACATGGACGCCCAGTACTACGGGGAGATT    300
     E  G  P  I  P  E  V  L  K  N  Y  M  D  A  Q  Y  Y  G  E  I
301 GGCATCGGGACGCCCCCCCAGTGCTTCACAGTGTTGTTTGACACGGGTTCCTCCAACCTG   360
     G  I  G  T  P  P  Q  C  F  T  V  V  F  D  T  G  S  S  N  L
361 TGGGTCCCTCCCATCCATTGCAAACTGCTGGATATCGCCTGCTGGATCCACAAGTAC    420
     W  V  P  S  I  H  C  K  L  L  D  I  A  C  W  I  H  K  Y
421 AACAGCGACAAGTCCAGCACCTACGTGAAGAATGGTACCTCGTTTGACATCCACTATGGC  480
     N  S  D  K  S  S  T  Y  V  K  N  G  T  S  F  D  I  H  Y  G
481 TCGGGCAGCCTCTCCGGGTACCTGAGCCAGGACACTGTGTCCGTGCCTTGCCAGTCAGCG  540
     S  G  S  L  S  G  Y  L  S  Q  D  T  V  S  V  P  C  Q  S  A
541 TCGTCAGCCTCTGCCCTGGGCGGGGTGAAAGTGGAGAGGCAGGTCTTTGGGGAGGCCACC  600
     S  S  A  S  A  L  G  G  V  K  V  E  R  Q  V  F  G  E  A  T
601 AAGCAGCCAGGCATCACTTTCATCGCAGCCAAGTTCGATGGCATCCTGGGCATGGCCTAC  660
     K  Q  P  G  I  T  F  I  A  A  K  F  D  G  I  L  G  M  A  Y
661 CCCCGCATCTCGGTCAACAACGTGCTGCCCGTCTTCGACAACCTGATGCAGCAGAAGCTG  720
     P  R  I  S  V  N  N  V  L  P  V  F  D  N  L  M  Q  Q  K  L
721 GTGGACCAGAACATCTTCTCCTTCTACTTGAGCAGGGACCCAGATGCCCAGCCTGGGGGT  780
     V  D  Q  N  I  F  S  F  Y  L  S  R  D  P  D  A  Q  P  G  G
781 GAGCTGATGCTGGGTGGCACAGACTCCAAGTATTACAAGGGTTCTCTGTCCTACCTGAAT  840
     E  L  M  L  G  G  T  D  S  K  Y  Y  K  G  S  L  S  Y  L  N
```

FIG.14A

```
     V  T  R  K  A  Y  W  Q  V  H  L  D  G  V  E  V  A  S  G  L
841  GTCACCCGCAAGGCCTACTGGCAGGTCCACCTGGACCAGGTGGAGGTGGCCAGCGGGCTG  900
     T  L  C  K  E  G  C  E  A  I  V  D  T  G  T  S  L  M  V  G
901  ACCCTGTGCAAGGAGGGCTGTGAGGCCATTGTGGACACAGGCACTTCCCTCATGGTGGGC  960
     P  V  D  E  V  R  E  L  Q  K  A  I  G  A  V  P  L  I  Q  G
961  CCGGTGGATGAGGTGCGCGAGCTGCAGAAGGCCATCGGGGCCGTGCCGCTGATTCAGGGC  1020
     E  Y  M  I  P  C  E  K  V  S  T  L  P  A  I  T  L  K  L  G
1021 GAGTACATGATCCCCTGTCAGAAGGTGTCCACCCTGCCCGCGATCACACTGAAGCTGGGA  1080
     G  K  G  Y  K  L  S  P  E  D  Y  T  L  K  V  S  Q  A  G  K
1081 GGCAAAGGCTACAAGCTGTCCCCAGAGGACTACACGCTCAAGGTGTCGCAGGCCGGGAAG  1140
     T  L  C  L  S  G  F  M  G  M  D  I  P  P  P  S  G  P  L  W
1141 ACCCTCTGCCTGAGCGGCTTCATGGGCATGGACATCCCGCCACCCAGCGGGCCACTCTGG  1200
     I  L  G  D  V  F  I  G  R  Y  Y  T  V  F  D  R  D  N  N  R
1201 ATCCTGGGCGACGTCTTCATCGGCCGCTACTACACTGTGTTTGACCGTGACAACAACAGG  1260
     V  G  F  A  E  A  A  R  L  *
1261 GTGGGCTTCGCCGAGGCTGCCCGCCTCTAGTTCCCAAGGCGTCCGCGCGCCAGCACAGAA  1320
1321 ACAGAGGAGAGTCCCAGAGCAGGAGGCCCCTGGCCCAGCGGCCCCTCCCACACACACCCA  1380
1381 CACACTCGCCCGCCCACTGTCCTGGGCGCCCTGGAAGCCGGCGGCCCAAGCCCGACTTGC  1440
1441 TGTTTTGTTCTGTGGTTTTCCCCTCCCTGGGTTCAGAAATGCTGCCTGCCTGTCTGTCTC  1500
1501 TCCATCTGTTTGGTGGGGGTAGAGCTGATCCAGAGCACAGATCTGTTTCGTGCATTGGAA  1560
1561 GACCCCACCCAAGCTTGGCAGCCGAGCTCGTGTATCCTGGGGCTCCCTTCATCTCCAGGG  1620
1621 AGTCCCCTCCCCGGCCCTACCAGCGCCCGCTGGGCTGAGCCCCTACCCCACACCAGGCCG  1680
1681 TCCTCCCGGGCCCTCCCTTGGAAACCTGCCCTGCCTGAGGGCCCCTCTGCCCAGCTTGGG  1740
1741 CCCAGCTGGGCTCTGCCACCCTACCTGTTCAGTGTCCCGGGCCCGTTGAGGATGAGGCCG  1800
1801 CTAGAGGCCTGAGGATGAGCTGGAAGGAGTGAGAGGGGACAAAACCCACCTTGTTGGAGC  1860
1861 CTGCAGGGTGGTGCTGGGACTGAGCCAGTCCCAGGGGCATGTATTGGCCTGGAGGTGGGG  1920
1921 TTGGGATTGGGGGCTGGTGCCAGCCTTCCTCTGCAGCTGACCTCTGTTGTCCTCCCCTTG  1980
1981 GGCGGCTGAGAGCCCCAGCTGACATGGAAATACAGTTGTTGGCCTCCGGCCTCCCCTC    2038
```

FIG.14B

```
                                            10                    30                        50
                                   GAATTCCGGCTCTCTATGGAGGTGGCAGCGGGTACCGAGTGGCGCTGCAGCAGGACTCCTC 70                    90                       110
                                   TGAGCTGAGTTTGAGGCCCGTCCCCGACTCCTTCCTCCCCCTTCCCTCCCCTTTTTTTG 130                   150                       170
                                   TTTCCGTTCCCCTTTCCCCTCCCCCTTCCCCTATCCCCGACGACCGGATCCTGAGGAGGGCA 190                   210                       230
                                   GCTGCGGGTGGCAGCTGCTGAGTTCTCGGTTCTGAAGGTATTTCATTTCTCCTGTCCCCTCCCC
                                                    V  L  G  E  G  I  S  F  L  S  P  P  L
                                           250                   270                       290
                                   TCCCCACCCCATCTATTAATATTATTCTTTGAAGATTCTTCGTTGTCAAGCCGGGAAAG
                                    P  T  P  S  I  N  I  I  L  L  K  I  L  R  C  Q  A  A  K  V
                                           310                   330                       350
                                   TGGAGAGTGCGATTGCAGAAGGGGGTGCTTCTCGTTTCAGTGCTTCTTCGGGCGGAGGAG
                                    E  S  A  I  A  E  G  G  A  S  R  F  S  A  S  S  G  G  G  G
                                           370                   390                       410
                                   GAAGTAGGGGGTGCACCTCAGCACTATCCCAAGACTGCTGGCAACAGCGAGTTCCTGGGGA
                                    S  R  G  A  P  Q  H  Y  P  K  T  A  G  N  S  E  F  L  G  K
                                           430                   450                       470
                                   AAACCCCAGGGCAAAACGCTCAGAAAATGGATTCCTGCACGAAGCACTAGACGAGATGACA
                                    T  P  G  Q  N  A  Q  K  W  I  P  A  R  S  T  R  R  D  D  N
```

FIG. 15A

```
490
ACTCCGCAGCAAACAACTCCGCAAAGAACGAAAAGAACGACATGATGCAATCTTCAGGAAAG
 S  A  N  N  S  A  N  E  K  E  R  H  D  A  I  F  R  K  V 550                              570                    590
TAAGAGGCATACTAAATAAGCTTACTCCTGAAAAGTTTGACAAGCTATGCCTTGAGCTCC
 R  G  I  L  N  K  L  T  P  E  K  F  D  K  L  C  L  E  L  L 610                              630                    650
TCAATGTGGGGTGTAGAGTCTAAACTCATCCTTAAAGGGGTCATACTGCTGATTGTGGACA
 N  V  G  V  E  S  K  L  I  L  K  G  V  I  L  L  I  V  D  K 670                              690                    710
AAGCCCTAGAAGAGCCAAAGTATAGCTCACTGTATGCTCAGCTATGTCTGCGATTGGCAG
 A  L  E  E  P  K  Y  S  S  L  Y  A  Q  L  C  L  R  L  A  E 730                              750                    770
AAGATGCACCAAACTTTGATGGCCCAGCAGCAGAGGGTCAACCAGGACAGAAGCAAAGCA
 D  A  P  N  F  D  G  P  A  A  E  G  Q  P  G  Q  K  Q  S  T 790                              810                    830
CCACATTCAGACGCGCCTCCTAATTTCCAAATTACAAGATGAATTTGAAAACCGAACTAGAA
 T  F  R  R  L  L  I  S  K  L  Q  D  E  F  E  N  R  T  R  N 850                              870                    890
ATGTTGATGTCTATGATAAGCGTGAAAATCCCCTCCTCCCGAGGAGGAACAGAGAG
 V  D  V  Y  D  K  R  E  N  P  L  L  P  E  E  E  Q  R  A
```

FIG. 15B

```
                910
CCATTGCTAAGATCAAGATGTTGGGAAACATCAAATTCATTGGAGAGCTTGGCAAGCTTG
 I  A  K  I  K  M  L  G  N  I  K  F  I  G  E  L  G  K  L  D
                            950

970
ATCTTATTCACGAATCTATCCTTCATAAGTGCATCAAAACACTTTTGGAAAAGAAGAAGA
 L  I  H  E  S  I  L  H  K  C  I  K  T  L  L  E  K  K  K  R
                            1010

1030
GAGTCCAACTCAAAGATATGGGAGAGGATTTGGAGTGCCTCTGTCAGATAATGAGGACAG
 V  Q  L  K  D  M  G  E  D  L  E  C  L  C  Q  I  M  R  T  V
                            1070

1090
TGGGACCTAGATTAGACCATGAACGAGCCAAGTCCTTAATGGATCAGTACTTTGCCCGAA
 G  P  R  L  D  H  E  R  A  K  S  L  M  D  Q  Y  F  A  R  M
                            1130

1150
TGTGCTCCTTGATGTTAAGTAAGGAATTGCCAGCAAGGATTCGTTTCCTGCTGCAGGATA
 C  S  L  M  L  S  K  E  L  P  A  R  I  R  F  L  L  Q  D  T
                            1190

1210
CCGTAGAGTTGCGAGAACACCATTGGGTTCCTCGCAAGGCTTTTCTTGACAATGGACCAA
 V  E  L  R  E  H  H  W  V  P  R  K  A  F  L  D  N  G  P  K
                            1250

1270
AGACGATCAATCAAATTCGTCAAGATGCAGTAAAAGATCTAGGGGTGTTTATTCCTGCTC
 T  I  N  Q  I  R  Q  D  A  V  K  D  L  G  V  F  I  P  A  P
                            1310
```

FIG. 15C

```
                          1350
     1330
CTATGGCTCAAGGGATGAGAAGTGACTTCTTTCTGGAGGGACCGTTCATGCCACCCAGGA
 M  A  Q  G  M  R  S  D  F  F  L  E  G  P  P  F  M  P  P  R  M 1410
     1390
TGAAAATGGATAGGGACCCCACTTGGAGGACTTGCTGATATGTTTGGACAAATGCCAGGTA
 K  M  D  R  D  P  L  G  G  L  A  D  M  F  G  Q  M  P  G  S 1470
     1450
GCGGAATTGGTACTGGTCCAGGAGTTATCCAGGATAGATTTTCACCCACCATGGGACGTC
 G  I  G  T  G  P  G  V  I  Q  D  R  F  S  P  T  M  G  R  H 1530
     1510
ATCGTTCAAATCAACTCTTCAATGGCCATCCCACACAATCATGCCTCCACACAATCGC
 R  S  N  Q  L  F  N  G  H  G  G  H  I  M  P  P  T  Q  S  Q 1590
     1570
AGTTTGGAGAGATGGGAGGCAAGTTTATGAAAAGCCAGGGCTAAGGCTCTACCATA
 F  G  E  M  G  G  K  F  M  K  S  Q  G  L  S  Q  L  Y  H  N 1650
     1630
ACCAGAGTCAGGGACTCTTATCCCAGCTGCAAGGACAGTCGAAGGATATGCCACCTCGGT
 Q  S  Q  G  L  L  S  Q  L  Q  G  Q  S  K  D  M  P  P  R  F 1710
     1690
TTTCTAAGAAAGGACAGCTTAATGCAGATGAGATTAGCCTGAGGCCTGCTCAGTCGTTCC
 S  K  K  G  Q  L  N  A  D  E  I  S  L  R  P  A  Q  S  F  L
```

FIG. 15D

```
                              1790
                 1770    CAGCCCCAGATAACTATGATTCCTCCTAGTG
          1750   TAATGAAAAATCAAGTGCCAAAGCTTCAGCCCCAGATAACTATGATTCCTCCTAGTG
TAATGAATAAAAATCAAGTGCCAAAGCTTCAGCCCCAGATAACTATGATTCCTCCTAGTG
 M  N  K  N  Q  V  P  K  L  Q  P  Q  I  T  M  I  P  P  S  A 1850
                 1830   CACCCTCAGCTTGGTCTCAAAA
          1810  CACAACCACCACGCACTCAAACACACCTCTGGGACAGACACCTCAGCTTGGTCTCAAAA
 Q  P  P  R  T  Q  T  P  P  L  G  Q  T  P  Q  L  G  L  K  T 1910
                 1890   AAAAGCCACCACCGTCAA
          1870  CTAATCCACCACTTATCCAGGAAAAGCCTGCCAAGACCAGCAAAAAGCCACCACCGTCAA
 N  P  P  L  I  Q  E  K  P  A  K  T  S  K  K  P  P  P  S  K 1970
                 1950   AAAYAHYHHAAAATH
          1930  AGGAAGAACYCCYYAAACYAACYHAAACYHYYYHYYHACYHAAYAYCYAAAYAHYHHAAAATH
 E  E  L  L  K  L  T  E  T  V  V  T  E  Y  L  N  S  G  N  A 2030
                 2010   CCTAAACACTTTCTTCCTGAGA
          1990  CAAATGAGGCTGTCAATGGTGTAAGAGAAATGAGGGCTCCTAAACACTTTCTTCCTGAGA
 N  E  A  V  N  G  V  R  E  M  R  A  P  K  H  F  L  P  E  M 2090
                 2070   AAAGAAAAAGCAA
          2050  TGTTAAGCAAAGTAATCATCCTGTCACTAGATAGAAGCGATGAAGATAAAGAAAAAGCAA
 L  S  K  V  I  I  L  S  L  D  R  S  D  E  D  K  E  K  A  S 2150
                 2130   GACAACTTCATGCAGG
          2110  GTTCTTTGATCAGTTTACTCAAACAGGAAGGGATAGCCACAAGTGACAACTTCATGCAGG
 S  L  I  S  L  L  K  Q  E  G  I  A  T  S  D  N  F  M  Q  A
```

```
      2170                    2190                         2210
CTTTCCTGAATGTATTGGACCAGTGTCCCAAACTGGAGGTTGACATCCCTTTGGTGAAAT
 F   L   N   V   L   D   Q   C   P   K   L   E   V   D   I   P   L   V   K   S 2230                    2250                         2270
CCTATTTAGCACAGTTTGCAGCTCGTGCCATCATTTCAGAGGTGGTGAGCATTTCAGAAC
 Y   L   A   Q   F   A   A   R   A   I   I   S   E   L   V   S   I   S   E   L 2290                    2310                         2330
TAGCTCAACCACTAGAAAAGTGGCACCCATTTTCCTCTCTCCTACTTTGTCTTCAGCAGT
 A   Q   P   L   E   S   G   T   H   F   P   L   F   L   L   C   L   Q   Q   L 2350                    2370                         2390
TAGCTAAAATTACAAGATCGAGAATGGTTAACAGAACTTTTTCAACAAAGCAAGGTCAATA
 A   K   L   Q   D   R   E   W   L   T   E   L   F   Q   Q   S   K   V   N   M 2410                    2430                         2450
TGCAGAAAAATGCTCCCAGAAAATTGATCAGAATAAGGACCGCATGTTGGAGATTTTGGAAG
 Q   K   M   L   P   E   I   D   Q   N   K   D   R   M   L   E   I   L   E   G 2470                    2490                         2510
GAAAGGGACTGAGTTTCTTATTCCCACTCCTCAAATTGGAGAAGGAACTGTTGAAGCAAAA
 K   G   L   S   F   L   F   P   L   L   K   L   E   K   E   L   L   K   Q   I 2530                    2550                         2570
TAAAGTTGGATCCATCCCCTCAAACCATATATAAATGGATTAAAGATAACATCTCTCCCA
 K   L   D   P   S   P   Q   T   I   Y   K   W   I   K   D   N   I   S   P   K
```

```
                                              2630
        2590                AACTTCATGATAAAGGATTTGTGAACATCTTAATGACTAGCTTCTTACAGTACATT
        AACTTCATGATAAAGGATTTGTGAACATCTTAATGACTAGCTTCTTACAGTACATT
        L  H  V  D  K  G  F  V  N  I  L  M  T  S  F  L  Q  Y  I  S 2670                              2690
        CTAGTGAAGTAAACCCCCCAGCGATGAAACAGATTCATCCTCTGCTCCTTCCAAAGAAC
        S  E  V  N  P  P  S  D  E  T  D  S  S  A  P  S  K  W  Q 2730                              2750
        AGTTAGAGCAGGAGAAAAAGAAGTACTACTATCTTTCAAGCCAGTAATGCAGAAATTTCTTC
        L  E  Q  E  K  Q  L  L  L  S  F  K  P  V  M  Q  K  F  L  H 2790                              2810
        ATGATCACGTTGATCTCTACAAGTCAGTGCCCTGTATGCTCTCCAGGRGCACTGCRARAACA
        D  H  V  D  L  Q  V  S  A  L  Y  A  L  Q  V  H  C  Y  N  S 2850                              2870
        GCAACTTCCCAAAAGGCATGTTACTTCGCTTTTTGTGCACTTCTATGACATGGAAATTA
        N  F  P  K  G  M  L  R  F  F  V  H  F  Y  D  M  E  I 2910                              2930
        TTGAAGAAGAAGCTTTCTTGGCTTGGAAAGAAGATATAACCCAAGAGTTTCCGGGAAAG
        E  E  E  A  F  L  A  W  K  E  D  I  T  Q  E  F  P  G  K  G 2970                              2990
        GCAAGGCTTTGTTCCAGGTGAATCAGTGGCTAACCTGGTTAGAAAGTGCTGAAGAAGAAG
        K  A  L  F  Q  V  N  Q  W  L  T  W  L  E  T  A  E  E  E  E
```

FIG. 15G

```
                    3030
        AATCAGAGGAAGAAGCTGACTAAAGAAGGCGCCAAAGCCTTAAATTGTGCAAAAGATACT
3010     S  E  E  E  A  D                                              3050

GTTGCTATGATGTAACTGCATTGACCTAACCACTGCGAAAATTCATTCCGCTGTAATGT
3070                   3090                  3110

TTTCACAATATTTAAAGCAGAAGCACGTCAGTTAGGATTTCCTTCTGCATAAGGTTTTT
3130                  3150                   3170

TGTAGTGTAATGTCTTAATCATAGTCTACCATCAAATATTTAGGAGTATCTTTAATGTT
3190                  3210                   3230

TAGATAGTATATTAGCAGCATGCAATAATTACATCATAAGTTCTCAAGCAGAGGCAGTCT
3250                  3270                   3290

ATTGCAAGGACCTTCTTGCTGCCAGTTATCATAGGCTGTGTTTAAGCTAGAAAACTGAAT
3310                  3330                   3350

AGCAACACACTGAATACTGTAGAAATGCACTTTGCTCAGTAATACTTGAGTTGTTGCAATAT
3370                  3390                   3410

TTGATTATCCATTGGTTGTTACAGAAAAATTCTTAACTGTAATTGATGGTTGTTGCCGT
3430                  3450                   3470

AATAGTATATTGCCTGTATTTCTACCTGTAGTAATGGGCTTTATGTGCTAGATTTTAATA
3490                  3510                   3530
```

FIG. 15H

```
       3570                                    3590
TCCTTGAGCCTGGGCAAGTGCAGAGAAGTCTTTTAAAAGAAACATGGTTTACTTGCACAAA
3550
    3610                             3630
ACTGATCAGTTTTGAGAGATCGTTAATGCCCTTGAAGTGGTTTTTGTGGGTGTGAAACAA
                                3650
   3670                       3690                       3710
ATGGTGAGAATTTGAATTGGTCCCTCCTATTATAGTATTGAAATTAAGTCTACTTAATTT
    3730                                    3750                3770
ATCAAGTCATGTTCATGCCCTGATTTTATATACTTGTATCTATCAATAAACATTGTGATA
   3790                  3810
CTTGAAAAAAAAAAAAAAAAAAAAAAAAAAAAGGGAATTC
```

Time (hours)

A.

B.

A.
pCDNA3
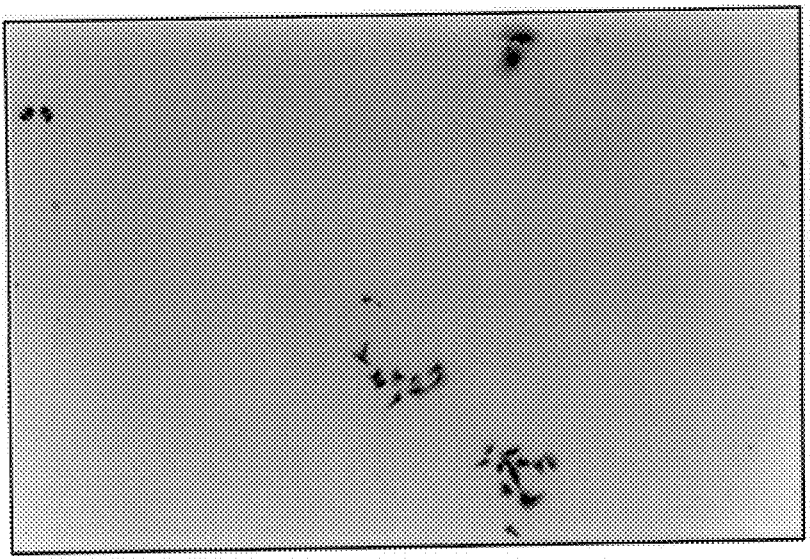
DAP-kinase K42A
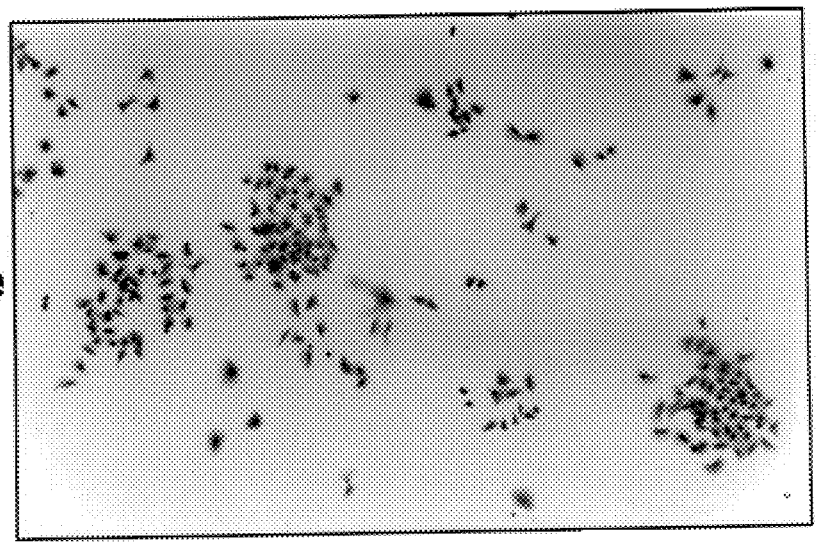
Fig. 35A

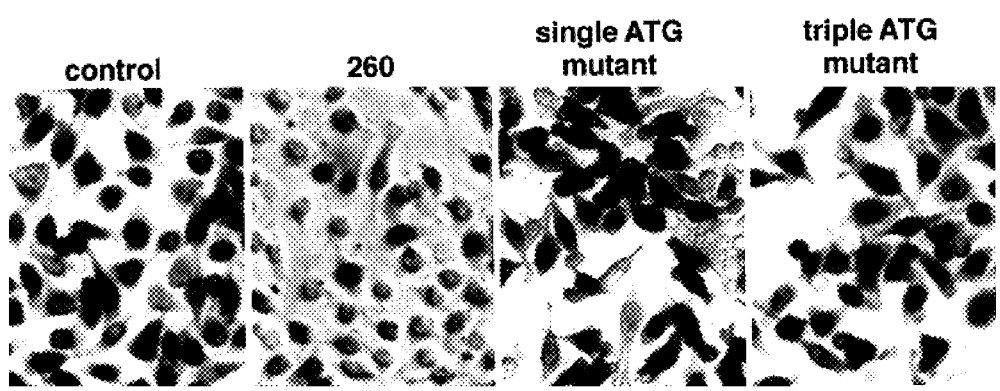
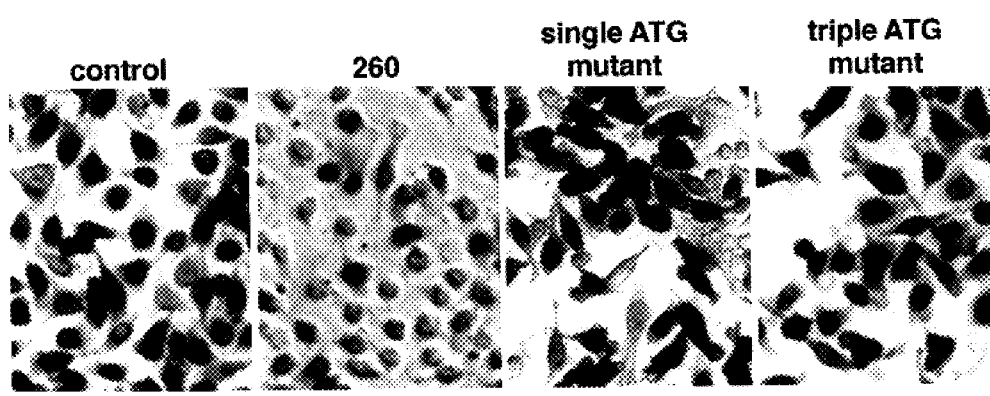
Fig. 39

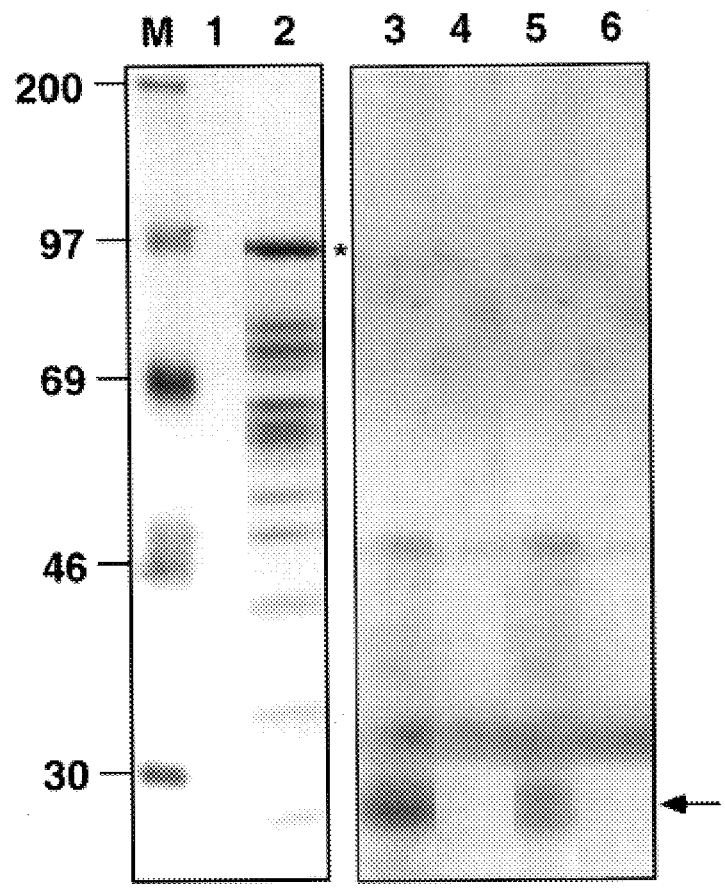
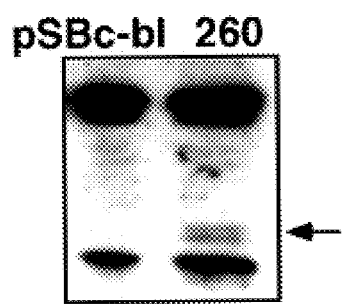
Fig. 40

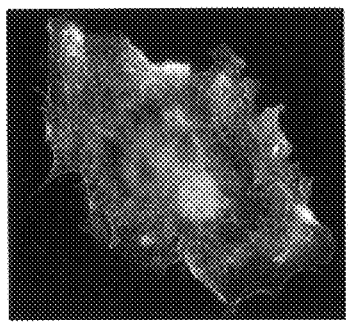
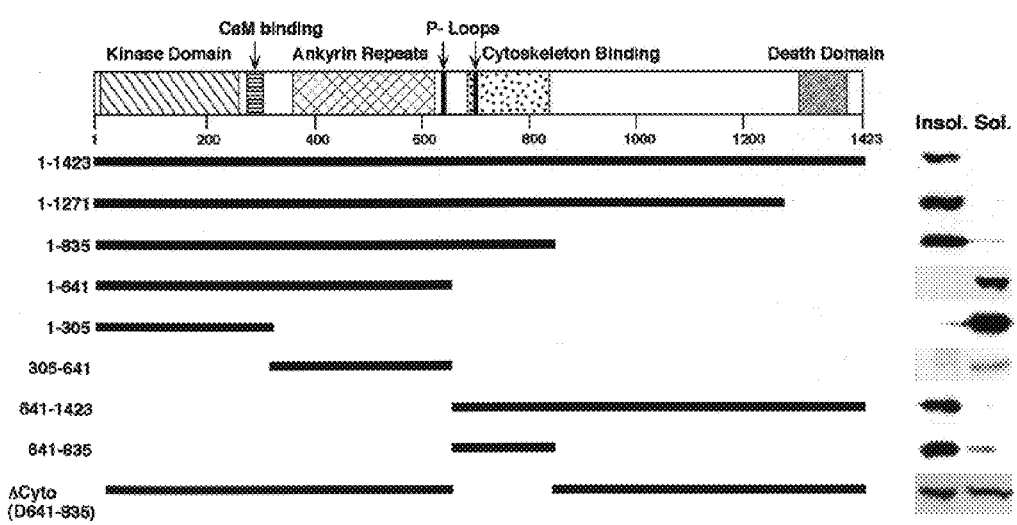
Fig. 46

SEQUENCE LISTING

```
<160> NUMBER OF SEQ ID NOS: 31

<210> SEQ ID NO 1
<211> LENGTH: 309
<212> TYPE: DNA
<213> ORGANISM: Homo sapiens

<400> SEQUENCE: 1
atgtcttcgc ctcccgaagg gaaactagag actaaagctg gacaccgcc cgccgtgaaa      60 gctggtggaa tgcgaattgt ggagaaacac ccacatacag gagacaccaa agaagagaaa     120
gacaaggatg accaggaatg ggaaagcccc agtccaccta aacccactgt gttcatctct     180
ggggtcatcg cccggggtga caaagatttc ccccggcgg ctgcgcaggt ggctcaccag      240
aagccgcatg cctccatgga caagcatcct tccccaagaa cccagcacat ccagcagcca     300
cgcaagtga                                                            309

<210> SEQ ID NO 2
<211> LENGTH: 531
<212> TYPE: DNA
<213> ORGANISM: Homo sapiens

<400> SEQUENCE: 2
atgaccagga atgggaaagc cccagtccac ctaaacccac tgtgttcatc tctggggtca      60
tcgcccgggg tgacaaagat ttcccccccgg cggctgcgca ggtggctcac cagaagccgc    120
atgcctccat ggacaagcat ccttccccaa gaacccagca catccagcag ccacgcaagt    180
```

-continued
gagcctggag tccaccagcc tgccccatgg ccccggctct gctgcacttg gtatttccct 240
gacagagaga accagcagtt tcgcccaaat cctactctgc tgggaaatct aaggcaaaac 300
caagtgctct gtcctttgcc ttacatttcc atatttaaaa ctagaaacag cttcagccca 360
aaccttgttt atggggagtc tggttgcatg tcatttgagg atcattgtgc ccctagaggt 420
gccattagca gaatttgcca agatccgaga aaaattttag ctttagttct atttcagcag 480
tcacctgacg tccttgtcta tggtcttaaa aacaagaagg cacacatttg a 531

<210> SEQ ID NO 3
<211> LENGTH: 1568
<212> TYPE: DNA
<213> ORGANISM: Homo sapiens
<220> FEATURE:
<221> NAME/KEY: CDS
<222> LOCATION: (74)..(1270)

<400> SEQUENCE: 3
gaattccgcc ggccccaggc agcgtgtgtc ggtcgcctag gctggagaac tagtcctcga 60
ctcacgtgca agg atg atg ctg aaa gga ata aca agg ctt atc tct agg 109
Met Met Leu Lys Gly Ile Thr Arg Leu Ile Ser Arg
1 5 10
atc cat aag ttg gac cct ggg cgt ttt tta cac atg ggg acc cag gct 157
Ile His Lys Leu Asp Pro Gly Arg Phe Leu His Met Gly Thr Gln Ala
15 20 25
cgc caa agc att gct gct cac cta gat aac cag gtt cca gtt gag agt 205
Arg Gln Ser Ile Ala Ala His Leu Asp Asn Gln Val Pro Val Glu Ser
30 35 40
ccg aga gct att tcc cgc acc aat gag aat gac ccg gcc aag cat ggg 253
Pro Arg Ala Ile Ser Arg Thr Asn Glu Asn Asp Pro Ala Lys His Gly
45 50 55 60
gat cag cac gag ggt cag cac tac aac atc tcc ccc cag gat ttg gag 301
Asp Gln His Glu Gly Gln His Tyr Asn Ile Ser Pro Gln Asp Leu Glu
65 70 75
act gta ttt ccc cat ggc ctt cct cct cgc ttt gtg atg cag gtg aag 349
Thr Val Phe Pro His Gly Leu Pro Pro Arg Phe Val Met Gln Val Lys
80 85 90
aca ttc agt gaa gct tgc ctg atg gta agg aaa cca gcc cta gaa ctt 397
Thr Phe Ser Glu Ala Cys Leu Met Val Arg Lys Pro Ala Leu Glu Leu
95 100 105
ctg cat tac ctg aaa aac acc agt ttt gct tat cca gct ata cga tat 445
Leu His Tyr Leu Lys Asn Thr Ser Phe Ala Tyr Pro Ala Ile Arg Tyr
110 115 120
ctt ctg tat gga gag aag gga aca gga aaa acc cta agt ctt tgc cat 493
Leu Leu Tyr Gly Glu Lys Gly Thr Gly Lys Thr Leu Ser Leu Cys His
125 130 135 140
gtt att cat ttc tgt gca aaa cag gac tgg ctg ata cta cat att cca 541
Val Ile His Phe Cys Ala Lys Gln Asp Trp Leu Ile Leu His Ile Pro
145 150 155
gat gct cat ctt tgg gtg aaa aat tgt cgg gat ctt ctg cag tcc agc 589
Asp Ala His Leu Trp Val Lys Asn Cys Arg Asp Leu Leu Gln Ser Ser
160 165 170
tac aac aaa cag cgc ttt gat caa cct tta gag gct tca acc tgg ctg 637
Tyr Asn Lys Gln Arg Phe Asp Gln Pro Leu Glu Ala Ser Thr Trp Leu
175 180 185
aag aat ttc aaa act aca aat gag cgc ttc ctg aac cag ata aaa gtt 685
Lys Asn Phe Lys Thr Thr Asn Glu Arg Phe Leu Asn Gln Ile Lys Val
190 195 200
caa gag aag tat gtc tgg aat aag aga gaa agc act gag aaa ggg agt 733

```
                 Gln Glu Lys Tyr Val Trp Asn Lys Arg Glu Ser Thr Glu Lys Gly Ser
                 205                 210                 215                 220 cct ctg gga gaa gtg gtt gaa cag ggc ata aca cgg gtg agg aac gcc       781
Pro Leu Gly Glu Val Val Glu Gln Gly Ile Thr Arg Val Arg Asn Ala
                225                 230                 235 aca gat gca gtt gga att gtg ctg aaa gag cta aag agg caa agt tct       829
Thr Asp Ala Val Gly Ile Val Leu Lys Glu Leu Lys Arg Gln Ser Ser
            240                 245                 250 ttg ggt atg ttt cac ctc cta gtg gcc gtg gat gga atc aat gct ctt       877
Leu Gly Met Phe His Leu Leu Val Ala Val Asp Gly Ile Asn Ala Leu
        255                 260                 265 tgg gga aga acc act ctg aaa aga gaa gat aaa agc ccg att gcc ccc       925
Trp Gly Arg Thr Thr Leu Lys Arg Glu Asp Lys Ser Pro Ile Ala Pro
    270                 275                 280 gag gaa tta gca ctt gtt cac aac ttg agg aaa atg atg aaa aat gat       973
Glu Glu Leu Ala Leu Val His Asn Leu Arg Lys Met Met Lys Asn Asp
285                 290                 295                 300 tgg cat gga ggc gcc att gtg tcg gct ttg agc cag act ggg tct ctc      1021
Trp His Gly Gly Ala Ile Val Ser Ala Leu Ser Gln Thr Gly Ser Leu
                305                 310                 315 ttt aag ccc cgg aaa gcc tat ctg ccc cag gag ttg ctg gga aag gaa      1069
Phe Lys Pro Arg Lys Ala Tyr Leu Pro Gln Glu Leu Leu Gly Lys Glu
                320                 325                 330 gga ttt gat gcc ctg gat ccc ttt att ccc atc ctg gtt tcc aac tat      1117
Gly Phe Asp Ala Leu Asp Pro Phe Ile Pro Ile Leu Val Ser Asn Tyr
            335                 340                 345 aac cca aag gaa ttt gaa agt tgt att cag tat tat ttg gaa aac aat      1165
Asn Pro Lys Glu Phe Glu Ser Cys Ile Gln Tyr Tyr Leu Glu Asn Asn
        350                 355                 360 tgg ctt caa cat gag aaa gct cct aca gaa gaa ggg aaa aaa gag ctg      1213
Trp Leu Gln His Glu Lys Ala Pro Thr Glu Glu Gly Lys Lys Glu Leu
    365                 370                 375                 380 ctg ttc cta agt aac gcg aac ccc tcg ctg ctg gag cgg cac tgt gcc      1261
Leu Phe Leu Ser Asn Ala Asn Pro Ser Leu Leu Glu Arg His Cys Ala
                385                 390                 395 tac ctc taa gccaagatca cagcatgtga ggaagacagt ggacatctgc              1310
Tyr Leu tttatgctgg acccagtaag atgaggaagt cgggcagtac acaggaagag gagccaggcc    1370
cttgtaccta tgggattgga caggactgca gttggctctg gacctgcatt aaaatgggtt    1430
tcactgtgaa tgcgtgacaa taagatattc ccttgttcct aaaactttat atcagtttat    1490
tggatgtggg tttttcacat ttaagataat tatggctctt ttcctaaaaa ataaaatatc    1550
tttctaaaaa aaaaaaaa                                                  1568

<210> SEQ ID NO 4
<211> LENGTH: 398
<212> TYPE: PRT
<213> ORGANISM: Homo sapiens

<400> SEQUENCE: 4

Met Met Leu Lys Gly Ile Thr Arg Leu Ile Ser Arg Ile His Lys Leu
1               5                   10                  15

Asp Pro Gly Arg Phe Leu His Met Gly Thr Gln Ala Arg Gln Ser Ile
            20                  25                  30

Ala Ala His Leu Asp Asn Gln Val Pro Val Glu Ser Pro Arg Ala Ile
        35                  40                  45

Ser Arg Thr Asn Glu Asn Asp Pro Ala Lys His Gly Asp Gln His Glu
    50                  55                  60
```

```
Gly Gln His Tyr Asn Ile Ser Pro Gln Asp Leu Glu Thr Val Phe Pro
 65                  70                  75                  80

His Gly Leu Pro Pro Arg Phe Val Met Gln Val Lys Thr Phe Ser Glu
                 85                  90                  95

Ala Cys Leu Met Val Arg Lys Pro Ala Leu Glu Leu Leu His Tyr Leu
            100                 105                 110

Lys Asn Thr Ser Phe Ala Tyr Pro Ala Ile Arg Tyr Leu Leu Tyr Gly
        115                 120                 125

Glu Lys Gly Thr Gly Lys Thr Leu Ser Leu Cys His Val Ile His Phe
130                 135                 140

Cys Ala Lys Gln Asp Trp Leu Ile Leu His Ile Pro Asp Ala His Leu
145                 150                 155                 160

Trp Val Lys Asn Cys Arg Asp Leu Leu Gln Ser Ser Tyr Asn Lys Gln
                165                 170                 175

Arg Phe Asp Gln Pro Leu Glu Ala Ser Thr Trp Leu Lys Asn Phe Lys
            180                 185                 190

Thr Thr Asn Glu Arg Phe Leu Asn Gln Ile Lys Val Gln Glu Lys Tyr
        195                 200                 205

Val Trp Asn Lys Arg Glu Ser Thr Glu Lys Gly Ser Pro Leu Gly Glu
    210                 215                 220

Val Val Glu Gln Gly Ile Thr Arg Val Arg Asn Ala Thr Asp Ala Val
225                 230                 235                 240

Gly Ile Val Leu Lys Glu Leu Lys Arg Gln Ser Ser Leu Gly Met Phe
                245                 250                 255

His Leu Leu Val Ala Val Asp Gly Ile Asn Ala Leu Trp Gly Arg Thr
            260                 265                 270

Thr Leu Lys Arg Glu Asp Lys Ser Pro Ile Ala Pro Glu Glu Leu Ala
        275                 280                 285

Leu Val His Asn Leu Arg Lys Met Met Lys Asn Asp Trp His Gly Gly
    290                 295                 300

Ala Ile Val Ser Ala Leu Ser Gln Thr Gly Ser Leu Phe Lys Pro Arg
305                 310                 315                 320

Lys Ala Tyr Leu Pro Gln Glu Leu Leu Gly Lys Glu Gly Phe Asp Ala
                325                 330                 335

Leu Asp Pro Phe Ile Pro Ile Leu Val Ser Asn Tyr Asn Pro Lys Glu
            340                 345                 350

Phe Glu Ser Cys Ile Gln Tyr Tyr Leu Glu Asn Asn Trp Leu Gln His
        355                 360                 365

Glu Lys Ala Pro Thr Glu Glu Gly Lys Lys Glu Leu Leu Phe Leu Ser
    370                 375                 380

Asn Ala Asn Pro Ser Leu Leu Glu Arg His Cys Ala Tyr Leu
385                 390                 395
```

<210> SEQ ID NO 5
<211> LENGTH: 132
<212> TYPE: DNA
<213> ORGANISM: Homo sapiens

<400> SEQUENCE: 5

```
ctagatgagg cagatataag agtcatggaa aaaaggacag agaaaaaaaa cagacaaatc    60
agttgtcagt atccatggcc tctgattctg tctcaaccat gaaacagaag tgacacatat   120
acctgctaaa ag                                                       132
```

```
<210> SEQ ID NO 6
<211> LENGTH: 3829
<212> TYPE: DNA
<213> ORGANISM: Homo sapiens
<220> FEATURE:
<221> NAME/KEY: CDS
<222> LOCATION: (201)..(3020)

<400> SEQUENCE: 6
gaattccgct ctatggaggt ggcagcgggt accgagtggc ggctgcagca gcgactcctc      60
tgagctgagt ttgaggccgt ccccgactcc ttcctccccc ttccctcccc ctttttttg     120 ttttccgttc ccctttcccc tcccttccct atccccgacg accggatcct gaggagggca    180
gctgcggtgg cagctgctga gtt ctc ggt gaa ggt att tca ttt ctc ctg tcc    233
                       Val Leu Gly Glu Gly Ile Ser Phe Leu Leu Ser
                         1               5                      10 cct ccc ctc ccc acc cca tct att aat att att ctt ttg aag att ctt      281
Pro Pro Leu Pro Thr Pro Ser Ile Asn Ile Ile Leu Leu Lys Ile Leu
                15                  20                  25 cgt tgt caa gcc gcc aaa gtg gag agt gcg att gca gaa ggg ggt gct      329
Arg Cys Gln Ala Ala Lys Val Glu Ser Ala Ile Ala Glu Gly Gly Ala
         30                  35                  40 tct cgt ttc agt gct tct tcg ggc gga gga gga agt agg ggt gca cct      377
Ser Arg Phe Ser Ala Ser Ser Gly Gly Gly Gly Ser Arg Gly Ala Pro
     45                  50                  55 cag cac tat ccc aag act gct ggc aac agc gag ttc ctg ggg aaa acc      425
Gln His Tyr Pro Lys Thr Ala Gly Asn Ser Glu Phe Leu Gly Lys Thr
 60                  65                  70                  75 cca ggg caa aac gct cag aaa tgg att cct gca cga agc act aga cga      473
Pro Gly Gln Asn Ala Gln Lys Trp Ile Pro Ala Arg Ser Thr Arg Arg
                 80                  85                  90 gat gac aac tcc gca gca aac aac tcc gca aac gaa aaa gaa cga cat      521
Asp Asp Asn Ser Ala Ala Asn Asn Ser Ala Asn Glu Lys Glu Arg His
             95                 100                 105 gat gca atc ttc agg aaa gta aga ggc ata cta aat aag ctt act cct      569
Asp Ala Ile Phe Arg Lys Val Arg Gly Ile Leu Asn Lys Leu Thr Pro
        110                 115                 120 gaa aag ttt gac aag cta tgc ctt gag ctc ctc aat gtg ggt gta gag      617
Glu Lys Phe Asp Lys Leu Cys Leu Glu Leu Leu Asn Val Gly Val Glu
    125                 130                 135 tct aaa ctc atc ctt aaa ggg gtc ata ctg ctg att gtg gac aaa gcc      665
Ser Lys Leu Ile Leu Lys Gly Val Ile Leu Leu Ile Val Asp Lys Ala
140                 145                 150                 155 cta gaa gag cca aag tat agc tca ctg tat gct cag cta tgt ctg cga      713
Leu Glu Glu Pro Lys Tyr Ser Ser Leu Tyr Ala Gln Leu Cys Leu Arg
                160                 165                 170 ttg gca gaa gat gca cca aac ttt gat ggc cca gca gca gag ggt caa      761
Leu Ala Glu Asp Ala Pro Asn Phe Asp Gly Pro Ala Ala Glu Gly Gln
            175                 180                 185 cca gga cag aag caa agc acc aca ttc aga cgc ctc cta att tcc aaa      809
Pro Gly Gln Lys Gln Ser Thr Thr Phe Arg Arg Leu Leu Ile Ser Lys
        190                 195                 200 tta caa gat gaa ttt gaa aac cga act aga aat gtt gat gtc tat gat      857
Leu Gln Asp Glu Phe Glu Asn Arg Thr Arg Asn Val Asp Val Tyr Asp
    205                 210                 215 aag cgt gaa aat ccc ctc ctc ccc gag gag gag gaa cag aga gcc att      905
Lys Arg Glu Asn Pro Leu Leu Pro Glu Glu Glu Glu Gln Arg Ala Ile
220                 225                 230                 235 gct aag atc aag atg ttg gga aac atc aaa ttc att gga gag ctt ggc      953
Ala Lys Ile Lys Met Leu Gly Asn Ile Lys Phe Ile Gly Glu Leu Gly
                240                 245                 250
```

```
aag ctt gat ctt att cac gaa tct atc ctt cat aag tgc atc aaa aca     1001
Lys Leu Asp Leu Ile His Glu Ser Ile Leu His Lys Cys Ile Lys Thr
            255                 260                 265 ctt ttg gaa aag aag aag aga gtc caa ctc aaa gat atg gga gag gat     1049
Leu Leu Glu Lys Lys Lys Arg Val Gln Leu Lys Asp Met Gly Glu Asp
        270                 275                 280 ttg gag tgc ctc tgt cag ata atg agg aca gtg gga cct aga tta gac     1097
Leu Glu Cys Leu Cys Gln Ile Met Arg Thr Val Gly Pro Arg Leu Asp
285                 290                 295 cat gaa cga gcc aag tcc tta atg gat cag tac ttt gcc cga atg tgc     1145
His Glu Arg Ala Lys Ser Leu Met Asp Gln Tyr Phe Ala Arg Met Cys
300                 305                 310                 315 tcc ttg atg tta agt aag gaa ttg cca gca agg att cgt ttc ctg ctg     1193
Ser Leu Met Leu Ser Lys Glu Leu Pro Ala Arg Ile Arg Phe Leu Leu
            320                 325                 330 cag gat acc gta gag ttg cga gaa cac cat tgg gtt cct cgc aag gct     1241
Gln Asp Thr Val Glu Leu Arg Glu His His Trp Val Pro Arg Lys Ala
        335                 340                 345 ttt ctt gac aat gga cca aag acg atc aat caa att cgt caa gat gca     1289
Phe Leu Asp Asn Gly Pro Lys Thr Ile Asn Gln Ile Arg Gln Asp Ala
    350                 355                 360 gta aaa gat cta ggg gtg ttt att cct gct cct atg gct caa ggg atg     1337
Val Lys Asp Leu Gly Val Phe Ile Pro Ala Pro Met Ala Gln Gly Met
365                 370                 375 aga agt gac ttc ttt ctg gag gga ccg ttc atg cca ccc agg atg aaa     1385
Arg Ser Asp Phe Phe Leu Glu Gly Pro Phe Met Pro Pro Arg Met Lys
380                 385                 390                 395 atg gat agg gac cca ctt gga gga ctt gct gat atg ttt gga caa atg     1433
Met Asp Arg Asp Pro Leu Gly Gly Leu Ala Asp Met Phe Gly Gln Met
            400                 405                 410 cca ggt agc gga att ggt act ggt cca gga gtt atc cag gat aga ttt     1481
Pro Gly Ser Gly Ile Gly Thr Gly Pro Gly Val Ile Gln Asp Arg Phe
        415                 420                 425 tca ccc acc atg gga cgt cat cgt tca aat caa ctc ttc aat ggc cat     1529
Ser Pro Thr Met Gly Arg His Arg Ser Asn Gln Leu Phe Asn Gly His
    430                 435                 440 ggg gga cac atc atg cct ccc aca caa tcg cag ttt gga gag atg gga     1577
Gly Gly His Ile Met Pro Pro Thr Gln Ser Gln Phe Gly Glu Met Gly
445                 450                 455 ggc aag ttt atg aaa agc cag ggg cta agc cag ctc tac cat aac cag     1625
Gly Lys Phe Met Lys Ser Gln Gly Leu Ser Gln Leu Tyr His Asn Gln
460                 465                 470                 475 agt cag gga ctc tta tcc cag ctg caa gga cag tcg aag gat atg cca     1673
Ser Gln Gly Leu Leu Ser Gln Leu Gln Gly Gln Ser Lys Asp Met Pro
            480                 485                 490 cct cgg ttt tct aag aaa gga cag ctt aat gca gat gag att agc ctg     1721
Pro Arg Phe Ser Lys Lys Gly Gln Leu Asn Ala Asp Glu Ile Ser Leu
        495                 500                 505 agg cct gct cag tcg ttc cta atg aat aaa aat caa gtg cca aag ctt     1769
Arg Pro Ala Gln Ser Phe Leu Met Asn Lys Asn Gln Val Pro Lys Leu
    510                 515                 520 cag ccc cag ata act atg att cct cct agt gca caa cca cca cgc act     1817
Gln Pro Gln Ile Thr Met Ile Pro Pro Ser Ala Gln Pro Pro Arg Thr
525                 530                 535 caa aca cca cct ctg gga cag aca cct cag ctt ggt ctc aaa act aat     1865
Gln Thr Pro Pro Leu Gly Gln Thr Pro Gln Leu Gly Leu Lys Thr Asn
540                 545                 550                 555 cca cca ctt atc cag gaa aag cct gcc aag acc agc aaa aag cca cca     1913
Pro Pro Leu Ile Gln Glu Lys Pro Ala Lys Thr Ser Lys Lys Pro Pro
```

```
                           560                 565                 570
ccg tca aag gaa gaa ctc ctt aaa cta act gaa act gtt gtg act gaa          1961
Pro Ser Lys Glu Glu Leu Leu Lys Leu Thr Glu Thr Val Val Thr Glu
            575                 580                 585 tat cta aat agt gga aat gca aat gag gct gtc aat ggt gta aga gaa          2009
Tyr Leu Asn Ser Gly Asn Ala Asn Glu Ala Val Asn Gly Val Arg Glu
            590                 595                 600 atg agg gct cct aaa cac ttt ctt cct gag atg tta agc aaa gta atc          2057
Met Arg Ala Pro Lys His Phe Leu Pro Glu Met Leu Ser Lys Val Ile
            605                 610                 615 atc ctg tca cta gat aga agc gat gaa gat aaa gaa aaa gca agt tct          2105
Ile Leu Ser Leu Asp Arg Ser Asp Glu Asp Lys Glu Lys Ala Ser Ser
620                 625                 630                 635 ttg atc agt tta ctc aaa cag gaa ggg ata gcc aca agt gac aac ttc          2153
Leu Ile Ser Leu Leu Lys Gln Glu Gly Ile Ala Thr Ser Asp Asn Phe
            640                 645                 650 atg cag gct ttc ctg aat gta ttg gac cag tgt ccc aaa ctg gag gtt          2201
Met Gln Ala Phe Leu Asn Val Leu Asp Gln Cys Pro Lys Leu Glu Val
            655                 660                 665 gac atc cct ttg gtg aaa tcc tat tta gca cag ttt gca gct cgt gcc          2249
Asp Ile Pro Leu Val Lys Ser Tyr Leu Ala Gln Phe Ala Ala Arg Ala
            670                 675                 680 atc att tca gag ctg gtg agc att tca gaa cta gct caa cca cta gaa          2297
Ile Ile Ser Glu Leu Val Ser Ile Ser Glu Leu Ala Gln Pro Leu Glu
            685                 690                 695 agt ggc acc cat ttt cct ctc ttc cta ctt tgt ctt cag cag tta gct          2345
Ser Gly Thr His Phe Pro Leu Phe Leu Leu Cys Leu Gln Gln Leu Ala
700                 705                 710                 715 aaa tta caa gat cga gaa tgg tta aca gaa ctt ttt caa caa agc aag          2393
Lys Leu Gln Asp Arg Glu Trp Leu Thr Glu Leu Phe Gln Gln Ser Lys
            720                 725                 730 gtc aat atg cag aaa atg ctc cca gaa att gat cag aat aag gac cgc          2441
Val Asn Met Gln Lys Met Leu Pro Glu Ile Asp Gln Asn Lys Asp Arg
            735                 740                 745 atg ttg gag att ttg gaa gga aag gga ctg agt ttc tta ttc cca ctc          2489
Met Leu Glu Ile Leu Glu Gly Lys Gly Leu Ser Phe Leu Phe Pro Leu
            750                 755                 760 ctc aaa ttg gag aag gaa ctg ttg aag caa ata aag ttg gat cca tcc          2537
Leu Lys Leu Glu Lys Glu Leu Leu Lys Gln Ile Lys Leu Asp Pro Ser
            765                 770                 775 cct caa acc ata tat aaa tgg att aaa gat aac atc tct ccc aaa ctt          2585
Pro Gln Thr Ile Tyr Lys Trp Ile Lys Asp Asn Ile Ser Pro Lys Leu
780                 785                 790                 795 cat gta gat aaa gga ttt gtg aac atc tta atg act agc ttc tta cag          2633
His Val Asp Lys Gly Phe Val Asn Ile Leu Met Thr Ser Phe Leu Gln
            800                 805                 810 tac att tct agt gaa gta aac ccc ccc agc gat gaa aca gat tca tcc          2681
Tyr Ile Ser Ser Glu Val Asn Pro Pro Ser Asp Glu Thr Asp Ser Ser
            815                 820                 825 tct gct cct tcc aaa gaa cag tta gag cag gaa aaa caa cta cta cta          2729
Ser Ala Pro Ser Lys Glu Gln Leu Glu Gln Glu Lys Gln Leu Leu Leu
            830                 835                 840 tct ttc aag cca gta atg cag aaa ttt ctt cat gat cac gtt gat cta          2777
Ser Phe Lys Pro Val Met Gln Lys Phe Leu His Asp His Val Asp Leu
            845                 850                 855 caa gtc agt gcc ctg tat gct ctc cag gtg cac tgc tat aac agc aac          2825
Gln Val Ser Ala Leu Tyr Ala Leu Gln Val His Cys Tyr Asn Ser Asn
860                 865                 870                 875 ttc cca aaa ggc atg tta ctt cgc ttt ttt gtg cac ttc tat gac atg          2873
```

-continued

```
                Phe Pro Lys Gly Met Leu Leu Arg Phe Val His Phe Tyr Asp Met
                            880                 885                 890 gaa att att gaa gaa gaa gct ttc ttg gct tgg aaa gaa gat ata acc      2921
Glu Ile Ile Glu Glu Glu Ala Phe Leu Ala Trp Lys Glu Asp Ile Thr
            895                 900                 905 caa gag ttt ccg gga aaa ggc aag gct ttg ttc cag gtg aat cag tgg      2969
Gln Glu Phe Pro Gly Lys Gly Lys Ala Leu Phe Gln Val Asn Gln Trp
        910                 915                 920 cta acc tgg tta gaa act gct gaa gaa gaa tca gag gaa gaa gct          3017
Leu Thr Trp Leu Glu Thr Ala Glu Glu Glu Ser Glu Glu Glu Ala
    925                 930                 935 gac taaagaacca gccaaagcct taaattgtgc aaaacatact gttgctatga           3070
Asp
940 tgtaactgca tttgacctaa ccactgcgaa aattcattcc gctgtaatgt tttcacaata    3130
tttaaagcag aagcacgtca gttaggattt ccttctgcat aaggtttttt tgtagtgtaa    3190
tgtcttaatc atagtctacc atcaaatatt ttaggagtat ctttaatgtt tagatagtat    3250
attagcagca tgcaataatt acatcataag ttctcaagca gaggcagtct attgcaagga    3310
ccttctttgc tgccagttat cataggctgt tttaagctag aaaactgaat agcaacactg    3370
aatactgtag aaatgcactt tgctcagtaa tacttgagtt gttgcaatat ttgattatcc    3430
atttggttgt tacagaaaaa ttcttaactg taattgatgg ttgttgccgt aatagtatat    3490
tgcctgtatt tctacctcta gtaatgggct ttatgtgcta gattttaata tccttgagcc    3550
tgggcaagtg cacaagtctt tttaaaagaa acatggttta cttgcacaaa actgatcagt    3610
tttgagagat cgttaatgcc cttgaagtgg tttttgtggg tgtgaaacaa atggtgagaa    3670
tttgaattgg tccctcctat tatagtattg aaattaagtc tacttaattt atcaagtcat    3730
gttcatgccc tgattttata tacttgtatc tatcaataaa cattgtgata cttgaaaaaa    3790
aaaaaaaaaa aaaaaaaaa aaaaaaaaaa agggaattc                            3829
```

```
<210> SEQ ID NO 7
<211> LENGTH: 940
<212> TYPE: PRT
<213> ORGANISM: Homo sapiens

<400> SEQUENCE: 7

Val Leu Gly Glu Gly Ile Ser Phe Leu Leu Ser Pro Leu Pro Thr
 1               5                  10                  15

Pro Ser Ile Asn Ile Ile Leu Leu Lys Ile Leu Arg Cys Gln Ala Ala
                20                  25                  30

Lys Val Glu Ser Ala Ile Ala Glu Gly Gly Ala Ser Arg Phe Ser Ala
            35                  40                  45

Ser Ser Gly Gly Gly Ser Arg Gly Ala Pro Gln His Tyr Pro Lys
        50                  55                  60

Thr Ala Gly Asn Ser Glu Phe Leu Gly Lys Thr Pro Gly Gln Asn Ala
    65                  70                  75                  80

Gln Lys Trp Ile Pro Ala Arg Ser Thr Arg Arg Asp Asp Asn Ser Ala
                85                  90                  95

Ala Asn Asn Ser Ala Asn Glu Lys Glu Arg His Asp Ala Ile Phe Arg
            100                 105                 110

Lys Val Arg Gly Ile Leu Asn Lys Leu Thr Pro Glu Lys Phe Asp Lys
        115                 120                 125

Leu Cys Leu Glu Leu Leu Asn Val Gly Val Glu Ser Lys Leu Ile Leu
    130                 135                 140
```

```
Lys Gly Val Ile Leu Ile Val Asp Lys Ala Leu Glu Glu Pro Lys
145                 150                 155                 160

Tyr Ser Ser Leu Tyr Ala Gln Leu Cys Leu Arg Leu Ala Glu Asp Ala
                165                 170                 175

Pro Asn Phe Asp Gly Pro Ala Ala Glu Gly Gln Pro Gly Gln Lys Gln
            180                 185                 190

Ser Thr Thr Phe Arg Arg Leu Leu Ile Ser Lys Leu Gln Asp Glu Phe
        195                 200                 205

Glu Asn Arg Thr Arg Asn Val Asp Val Tyr Asp Lys Arg Glu Asn Pro
    210                 215                 220

Leu Leu Pro Glu Glu Glu Gln Arg Ala Ile Ala Lys Ile Lys Met
225                 230                 235                 240

Leu Gly Asn Ile Lys Phe Ile Gly Glu Leu Gly Lys Leu Asp Leu Ile
                245                 250                 255

His Glu Ser Ile Leu His Lys Cys Ile Lys Thr Leu Leu Glu Lys Lys
                260                 265                 270

Lys Arg Val Gln Leu Lys Asp Met Gly Glu Asp Leu Glu Cys Leu Cys
            275                 280                 285

Gln Ile Met Arg Thr Val Gly Pro Arg Leu Asp His Glu Arg Ala Lys
290                 295                 300

Ser Leu Met Asp Gln Tyr Phe Ala Arg Met Cys Ser Leu Met Leu Ser
305                 310                 315                 320

Lys Glu Leu Pro Ala Arg Ile Arg Phe Leu Leu Gln Asp Thr Val Glu
                325                 330                 335

Leu Arg Glu His His Trp Val Pro Arg Lys Ala Phe Leu Asp Asn Gly
            340                 345                 350

Pro Lys Thr Ile Asn Gln Ile Arg Gln Asp Ala Val Lys Asp Leu Gly
            355                 360                 365

Val Phe Ile Pro Ala Pro Met Ala Gln Gly Met Arg Ser Asp Phe Phe
            370                 375                 380

Leu Glu Gly Pro Phe Met Pro Pro Arg Met Lys Met Asp Arg Asp Pro
385                 390                 395                 400

Leu Gly Gly Leu Ala Asp Met Phe Gly Gln Met Pro Gly Ser Gly Ile
                405                 410                 415

Gly Thr Gly Pro Gly Val Ile Gln Asp Arg Phe Ser Pro Thr Met Gly
                420                 425                 430

Arg His Arg Ser Asn Gln Leu Phe Asn Gly His Gly His Ile Met
            435                 440                 445

Pro Pro Thr Gln Ser Gln Phe Gly Glu Met Gly Gly Lys Phe Met Lys
            450                 455                 460

Ser Gln Gly Leu Ser Gln Leu Tyr His Asn Gln Ser Gln Gly Leu Leu
465                 470                 475                 480

Ser Gln Leu Gln Gly Gln Ser Lys Asp Met Pro Pro Arg Phe Ser Lys
            485                 490                 495

Lys Gly Gln Leu Asn Ala Asp Glu Ile Ser Leu Arg Pro Ala Gln Ser
            500                 505                 510

Phe Leu Met Asn Lys Asn Gln Val Pro Lys Leu Gln Pro Gln Ile Thr
            515                 520                 525

Met Ile Pro Pro Ser Ala Gln Pro Pro Arg Thr Gln Thr Pro Pro Leu
            530                 535                 540

Gly Gln Thr Pro Gln Leu Gly Leu Lys Thr Asn Pro Pro Leu Ile Gln
545                 550                 555                 560
```

```
Glu Lys Pro Ala Lys Thr Ser Lys Lys Pro Pro Ser Lys Glu Glu
            565                 570                 575

Leu Leu Lys Leu Thr Glu Thr Val Val Thr Glu Tyr Leu Asn Ser Gly
        580                 585                 590

Asn Ala Asn Glu Ala Val Asn Gly Val Arg Glu Met Arg Ala Pro Lys
        595                 600                 605

His Phe Leu Pro Glu Met Leu Ser Lys Val Ile Ile Leu Ser Leu Asp
    610                 615                 620

Arg Ser Asp Glu Asp Lys Glu Lys Ala Ser Ser Leu Ile Ser Leu Leu
625                 630                 635                 640

Lys Gln Glu Gly Ile Ala Thr Ser Asp Asn Phe Met Gln Ala Phe Leu
            645                 650                 655

Asn Val Leu Asp Gln Cys Pro Lys Leu Glu Val Asp Ile Pro Leu Val
            660                 665                 670

Lys Ser Tyr Leu Ala Gln Phe Ala Ala Arg Ala Ile Ile Ser Glu Leu
            675                 680                 685

Val Ser Ile Ser Glu Leu Ala Gln Pro Leu Glu Ser Gly Thr His Phe
    690                 695                 700

Pro Leu Phe Leu Leu Cys Leu Gln Gln Leu Ala Lys Leu Gln Asp Arg
705                 710                 715                 720

Glu Trp Leu Thr Glu Leu Phe Gln Gln Ser Lys Val Asn Met Gln Lys
            725                 730                 735

Met Leu Pro Glu Ile Asp Gln Asn Lys Asp Arg Met Leu Glu Ile Leu
            740                 745                 750

Glu Gly Lys Gly Leu Ser Phe Leu Phe Pro Leu Leu Lys Leu Glu Lys
        755                 760                 765

Glu Leu Leu Lys Gln Ile Lys Leu Asp Pro Ser Pro Gln Thr Ile Tyr
    770                 775                 780

Lys Trp Ile Lys Asp Asn Ile Ser Pro Lys Leu His Val Asp Lys Gly
785                 790                 795                 800

Phe Val Asn Ile Leu Met Thr Ser Phe Leu Gln Tyr Ile Ser Ser Glu
            805                 810                 815

Val Asn Pro Pro Ser Asp Glu Thr Asp Ser Ser Ser Ala Pro Ser Lys
            820                 825                 830

Glu Gln Leu Glu Gln Glu Lys Gln Leu Leu Leu Ser Phe Lys Pro Val
        835                 840                 845

Met Gln Lys Phe Leu His Asp His Val Asp Leu Gln Val Ser Ala Leu
    850                 855                 860

Tyr Ala Leu Gln Val His Cys Tyr Asn Ser Asn Phe Pro Lys Gly Met
865                 870                 875                 880

Leu Leu Arg Phe Phe Val His Phe Tyr Asp Met Glu Ile Ile Glu Glu
            885                 890                 895

Glu Ala Phe Leu Ala Trp Lys Asp Ile Thr Gln Glu Phe Pro Gly
        900                 905                 910

Lys Gly Lys Ala Leu Phe Gln Val Asn Gln Trp Leu Thr Trp Leu Glu
        915                 920                 925

Thr Ala Glu Glu Glu Glu Ser Glu Glu Ala Asp
    930                 935                 940

<210> SEQ ID NO 8
<211> LENGTH: 2232
<212> TYPE: DNA
<213> ORGANISM: Homo sapiens

<400> SEQUENCE: 8
```

```
cgtggcactc acccggctcg cgcggccccg gccgcccacg ccgcgcgtcg ttctcccgcc      60
cgctcgctcc ccggcgctca cacctgagct cactcgcgca cgcccgcccg gcccgagaac     120
cgcgccgccg cctcggcccc gcggaagccc cgccgcgcca tgtcttcgcc tcccgaaggg     180
aaactagaga ctaaagctgg acacccgccc gccgtgaaag ctggtggaat gcgaattgtg     240
cagaaacacc cacatacagg agacaccaaa gaagagaaag acaaggatga ccaggaatgg     300
gaaagcccca gtccacctaa acccactgtg ttcatctctg gggtcatcgc ccggggtgac     360
aaagatttcc ccccggcggc tgcgcaggtg gctcaccaga agccgcatgc ctccatggac     420
aagcatcctt ccccaagaac ccagcacatc cagcagccac gcaagtgagc ctggagtcca     480
ccagcctgcc ccatggcccc ggctctgctg cacttggtat ttccctgaca gagagaacca     540
gcagtttcgc ccaaatccta ctctgctggg aaatctaagg caaaaccaag tgctctgtcc     600
tttgccttac atttccatat ttaaaactag aaacagcttc agcccaaacc ttgtttatgg     660
ggagtctggt tggatgtcat ttgaggatca ttgtgcccct agaggtgcca ttagcagaat     720
ttgccaagat ccgagaaaaa ttttagcttt agttctattt cagcagtcac ctgacgtcct     780
tgtctatggt cttaaaaaca agaaggcaca catttgagaa gatgagatta aggttaggag     840
aaaacctcag tcattgcatg cttttttagta tgggccaata aaatctcaac acctgtggga     900
gagtaagaac taagggaatg agtttgggcg cccccctcata aaggaccttaa gaggcaggga    960
acagcaatgc caaatttccc tctctcgtga gatgggggat cctgtgcagg ctgatgaggc    1020
acccatgaga aaagccgaaa aagcatgcat cttagaaata gcccctcaat tccaggagtc    1080
aacatgccaa agaatgaggc tggagacagg tagctccgag ggaggacttc tggcatgaga    1140
tctcggcacg gcaagcccag catcgcctca gcccagacag gctccaccag gagatcaagc    1200
aagggctgcc tttcaggagt cacctcctga gccacttcag agttctggaa gtgaccacgg    1260
accagggtgg aggaatagac ttctagttca ttctgggaca cttgagccag agagttgaaa    1320
gcttggaaag accagataag aaacctgccc tttgtctccc tagggacatg agacaccaca    1380
ttccatttgt gctagaaaaa cctatccact gatgagtcta actgttccaa acgcctccca    1440
cctggtgtgc acagctgcct gggtccattg tcacttgggt gcatcaggtt gtcctccgat    1500
ttttagatga gtttcctgtc tagagatgtc ctagtctgct cactggctgg tggcagtagg    1560
gtaccctgcg tcctcgaaaa gccagagggt tcacctagtc agacgaaact ccagaacagt    1620
gcttgtggag ggcctgactg tcctgctcac ccacagccga tctgctgcag gtcagcaact    1680
gtgtcgtgag cagctgccaa ccaccagcct ttctggtgct gttctccagt tcacgtctgc    1740
cagctggtga gggcagaggc agacctggtc agacccagcg cccctcctcc ctgagggagc    1800
atggcacagc ctcacacttg aaagacggtg tttggtttcc catctaatca acttaaggga    1860
agccggcatg taccccttcaa ggccctgtca ccacctattt tcctgatcag ttggtataaa    1920
ctgagggtgg cttttagaga cccagacttg gttggcagcg ctgccatgga cacccagc     1980
aagcacctcc cagcctgcct ttcggagcag cacccaggag gggatgccgc gctccagcaa    2040
caccaggtca ggcctgtgca gacccctgcc ctgccgctgc agaaatccag aagcatcctt    2100
aatgcttctc agtcttcagc cagagggagg gctgttattt ccagaggtgc gcttttatg     2160
tactttagc tagatgtggc atgcatctgt gagctttaga tcattaaatc caaatgtttt    2220
gcctaaatga gg                                                        2232
```

<210> SEQ ID NO 9

```
<211> LENGTH: 5886
<212> TYPE: DNA
<213> ORGANISM: Homo sapiens
<220> FEATURE:
<221> NAME/KEY: CDS
<222> LOCATION: (337)..(4605)

<400> SEQUENCE: 9
cggaggacag ccggaccgag ccaacgccgg ggactttgtt ccctccacgg aggggactcg      60
gcaactcgca gcggcagggt ctggggccgg cgcctgggag ggatctgcgc cccccactca     120
ctccctagct gtgttcccgc cgccgccccg gctagtctcc ggcgctggcg cctatggtcg     180
gcctccgaca gcgctccgga gggaccgggg gagctcccag gcgcccggga ctggagactg     240
atgcatgagg ggcctacgga ggcgcaggag cggtggtgat ggtctgggaa gcggagctga     300
agtcccctgg gctttggtga ggcgtgacag tttatc atg acc gtg ttc agg cag      354
                                    Met Thr Val Phe Arg Gln
                                      1               5 gaa aac gtg gat gat tac tac gac acc ggc gag gaa ctt ggc agt gga      402
Glu Asn Val Asp Asp Tyr Tyr Asp Thr Gly Glu Glu Leu Gly Ser Gly
             10                  15                  20 cag ttt gcg gtt gtg aag aaa tgc cgt gag aaa agt acc ggc ctc cag      450
Gln Phe Ala Val Val Lys Lys Cys Arg Glu Lys Ser Thr Gly Leu Gln
         25                  30                  35 tat ccc gcc aaa ttc atc aag aaa agg agg act aag tcc agc cgg cgg      498
Tyr Pro Ala Lys Phe Ile Lys Lys Arg Arg Thr Lys Ser Ser Arg Arg
     40                  45                  50 ggt gtg agc cgc gag gac atc gag cgg gag gtc agc atc ctg aag gag      546
Gly Val Ser Arg Glu Asp Ile Glu Arg Glu Val Ser Ile Leu Lys Glu
 55                  60                  65                  70 atc cag cac ccc aat gtc atc acc ctg cac gag gtc tat gag aac aag      594
Ile Gln His Pro Asn Val Ile Thr Leu His Glu Val Tyr Glu Asn Lys
                 75                  80                  85 acg gac gtc atc ctg atc ttg gaa ctc gtt gca ggt ggc gag ctg ttt      642
Thr Asp Val Ile Leu Ile Leu Glu Leu Val Ala Gly Gly Glu Leu Phe
             90                  95                 100 gac ttc tta gct gaa aag gaa tct tta act gaa gag gaa gca act gaa      690
Asp Phe Leu Ala Glu Lys Glu Ser Leu Thr Glu Glu Glu Ala Thr Glu
        105                 110                 115 ttt ctc aaa caa att ctt aat ggt gtt tac tac ctg cac tcc ctt caa      738
Phe Leu Lys Gln Ile Leu Asn Gly Val Tyr Tyr Leu His Ser Leu Gln
120                 125                 130 atc gcc cac ttt gat ctt aag cct gag aac ata atg ctt ttg gat aga      786
Ile Ala His Phe Asp Leu Lys Pro Glu Asn Ile Met Leu Leu Asp Arg
135                 140                 145                 150 aat gtc ccc aaa cct cgg atc aag atc att gac ttt gga aat gaa ttt      834
Asn Val Pro Lys Pro Arg Ile Lys Ile Ile Asp Phe Gly Asn Glu Phe
                155                 160                 165 aaa aac ata ttt ggg act cca gag ttt gtc gct cct gag ata gtc aac      882
Lys Asn Ile Phe Gly Thr Pro Glu Phe Val Ala Pro Glu Ile Val Asn
            170                 175                 180 tat gaa cct ctt ggt ctt gag gca gat atg tgg agt atc ggg gta ata      930
Tyr Glu Pro Leu Gly Leu Glu Ala Asp Met Trp Ser Ile Gly Val Ile
        185                 190                 195 acc tat atc ctc cta agt ggg gcc tcc cca ttt ctt gga gac act aag      978
Thr Tyr Ile Leu Leu Ser Gly Ala Ser Pro Phe Leu Gly Asp Thr Lys
    200                 205                 210 caa gaa acg tta gca aat gta tcc gct gtc aac tac gaa ttt gag gat     1026
Gln Glu Thr Leu Ala Asn Val Ser Ala Val Asn Tyr Glu Phe Glu Asp
215                 220                 225                 230
```

-continued

| | | |
|---|---|---|
| gaa tac ttc agt aat acc agt gcc cta gcc aaa gat ttc ata aga aga<br>Glu Tyr Phe Ser Asn Thr Ser Ala Leu Ala Lys Asp Phe Ile Arg Arg<br>               235                  240                245 | 1074 |
| ctt ctg gtc aag gat cca aag aag aga atg aca att caa gat agt ttg<br>Leu Leu Val Lys Asp Pro Lys Lys Arg Met Thr Ile Gln Asp Ser Leu<br>         250                  255                  260 | 1122 |
| cag cat ccc tgg atc aag cct aaa gat aca caa cag gca ctt agt aga<br>Gln His Pro Trp Ile Lys Pro Lys Asp Thr Gln Gln Ala Leu Ser Arg<br>       265                  270                  275 | 1170 |
| aaa gca tca gca gta aac atg gag aaa ttc aag aag ttt gca gcc cgg<br>Lys Ala Ser Ala Val Asn Met Glu Lys Phe Lys Lys Phe Ala Ala Arg<br>280                  285                  290 | 1218 |
| aaa aaa tgg aaa caa tcc gtt cgc ttg ata tca ctg tgc caa aga tta<br>Lys Lys Trp Lys Gln Ser Val Arg Leu Ile Ser Leu Cys Gln Arg Leu<br>295                 300                305               310 | 1266 |
| tcc agg tca ttc ctg tcc aga agt aac atg agt gtt gcc aga agc gat<br>Ser Arg Ser Phe Leu Ser Arg Ser Asn Met Ser Val Ala Arg Ser Asp<br>               315                  320                325 | 1314 |
| gat act ctg gat gag gaa gac tcc ttt gtg atg aaa gcc atc atc cat<br>Asp Thr Leu Asp Glu Glu Asp Ser Phe Val Met Lys Ala Ile Ile His<br>       330                  335                  340 | 1362 |
| gcc atc aac gat gac aat gtc cca ggc ctg cag cac ctt ctg ggc tca<br>Ala Ile Asn Asp Asp Asn Val Pro Gly Leu Gln His Leu Leu Gly Ser<br>345                  350                  355 | 1410 |
| tta tcc aac tat gat gtt aac caa ccc aac aag cac ggg aca cct cca<br>Leu Ser Asn Tyr Asp Val Asn Gln Pro Asn Lys His Gly Thr Pro Pro<br>         360                  365                  370 | 1458 |
| tta ctc att gct gct ggc tgt ggg aat att caa ata cta cag ttg ctc<br>Leu Leu Ile Ala Ala Gly Cys Gly Asn Ile Gln Ile Leu Gln Leu Leu<br>375                  380                  385               390 | 1506 |
| att aaa aga ggc tcg aga atc gat gtc cag gat aag ggc ggg tcc aat<br>Ile Lys Arg Gly Ser Arg Ile Asp Val Gln Asp Lys Gly Gly Ser Asn<br>               395                  400                405 | 1554 |
| gcc gtc tac tgg gct gct cgg cat ggc cac gtc gat acc ttg aaa ttt<br>Ala Val Tyr Trp Ala Ala Arg His Gly His Val Asp Thr Leu Lys Phe<br>               410                  415                420 | 1602 |
| ctc agt gag aac aaa tgc cct ttg gat gtg aaa gac aag tct gga gag<br>Leu Ser Glu Asn Lys Cys Pro Leu Asp Val Lys Asp Lys Ser Gly Glu<br>       425                  430                  435 | 1650 |
| atg gcc ctc cac gtg gca gct cgc tat ggc cat gct gac gtg gct caa<br>Met Ala Leu His Val Ala Ala Arg Tyr Gly His Ala Asp Val Ala Gln<br>440                  445                  450 | 1698 |
| gtt act tgt gca gct tcg gct caa atc cca ata tcc agg aca aag gaa<br>Val Thr Cys Ala Ala Ser Ala Gln Ile Pro Ile Ser Arg Thr Lys Glu<br>455                  460                  465               470 | 1746 |
| gaa gaa acc ccc ctg cac tgt gct gct tgg cac ggc tat tac tct gtg<br>Glu Glu Thr Pro Leu His Cys Ala Ala Trp His Gly Tyr Tyr Ser Val<br>               475                  480                485 | 1794 |
| gcc aaa gcc ctt tgt gaa gcc ggc tgt aac gtg aac atc aag aac cga<br>Ala Lys Ala Leu Cys Glu Ala Gly Cys Asn Val Asn Ile Lys Asn Arg<br>         490                  495                  500 | 1842 |
| gaa gga gag acg ccc ctc ctg aca gcc tct gcc agg ggc tac cac gac<br>Glu Gly Glu Thr Pro Leu Leu Thr Ala Ser Ala Arg Gly Tyr His Asp<br>             505                  510                515 | 1890 |
| atc gtg gag tgt ctg gcc gaa cat gga gcc gac ctt aat gct tgc gac<br>Ile Val Glu Cys Leu Ala Glu His Gly Ala Asp Leu Asn Ala Cys Asp<br>520                  525                  530 | 1938 |
| aag gac gga cac att gcc ctt cat ctg gct gta aga cgg tgt cag atg<br>Lys Asp Gly His Ile Ala Leu His Leu Ala Val Arg Arg Cys Gln Met<br>535                  540                  545               550 | 1986 |

```
gag gta atc aag act ctc ctc agc caa ggg tgt ttc gtc gat tat caa    2034
Glu Val Ile Lys Thr Leu Leu Ser Gln Gly Cys Phe Val Asp Tyr Gln
            555                 560                 565 gac agg cac ggc aat act ccc ctc cat gtg gca tgt aaa gat ggc aac    2082
Asp Arg His Gly Asn Thr Pro Leu His Val Ala Cys Lys Asp Gly Asn
        570                 575                 580 atg cct atc gtg gtg gcc ctc tgt gaa gca aac tgc aat ttg gac atc    2130
Met Pro Ile Val Val Ala Leu Cys Glu Ala Asn Cys Asn Leu Asp Ile
    585                 590                 595 tcc aac aag tat ggg cga acg cct ctg cac ctt gcg gcc aac aac gga    2178
Ser Asn Lys Tyr Gly Arg Thr Pro Leu His Leu Ala Ala Asn Asn Gly
600                 605                 610 atc cta gac gtg gtc cgg tat ctc tgt ctg atg gga gcc agc gtt gag    2226
Ile Leu Asp Val Val Arg Tyr Leu Cys Leu Met Gly Ala Ser Val Glu
615                 620                 625                 630 gcg ctg acc acg gac gga aag acg gca gaa gat ctt gct aga tcg gaa    2274
Ala Leu Thr Thr Asp Gly Lys Thr Ala Glu Asp Leu Ala Arg Ser Glu
            635                 640                 645 cag cac gag cac gta gca ggt ctc ctt gca aga ctt cga aag gat acg    2322
Gln His Glu His Val Ala Gly Leu Leu Ala Arg Leu Arg Lys Asp Thr
        650                 655                 660 cac cga gga ctc ttc atc cag cag ctc cga ccc aca cag aac ctg cag    2370
His Arg Gly Leu Phe Ile Gln Gln Leu Arg Pro Thr Gln Asn Leu Gln
    665                 670                 675 cca aga att aag ctc aag ctg ttt ggc cac tcg gga tcc ggg aaa acc    2418
Pro Arg Ile Lys Leu Lys Leu Phe Gly His Ser Gly Ser Gly Lys Thr
680                 685                 690 acc ctt gta gaa tct ctc aag tgt ggg ctg ctg agg agc ttt ttc aga    2466
Thr Leu Val Glu Ser Leu Lys Cys Gly Leu Leu Arg Ser Phe Phe Arg
695                 700                 705                 710 agg cgt cgg ccc aga ctg tct tcc acc aac tcc agc agg ttc cca cct    2514
Arg Arg Arg Pro Arg Leu Ser Ser Thr Asn Ser Ser Arg Phe Pro Pro
            715                 720                 725 tca ccc ctg gct tct aag ccc aca gtc tca gtg agc atc aac aac ctg    2562
Ser Pro Leu Ala Ser Lys Pro Thr Val Ser Val Ser Ile Asn Asn Leu
        730                 735                 740 tac cca ggc tgc gag aac gtg agt gtg agg agc cgc agc atg atg ttc    2610
Tyr Pro Gly Cys Glu Asn Val Ser Val Arg Ser Arg Ser Met Met Phe
    745                 750                 755 gag ccg ggt ctt acc aaa ggg atg ctg gag gtg ttt gtg gcc ccg acc    2658
Glu Pro Gly Leu Thr Lys Gly Met Leu Glu Val Phe Val Ala Pro Thr
760                 765                 770 cac cac ccg cac tgc tcg gcc gat gac cag tcc acc aag gcc atc gac    2706
His His Pro His Cys Ser Ala Asp Asp Gln Ser Thr Lys Ala Ile Asp
775                 780                 785                 790 atc cag aac gct tat ttg aat gga gtt ggc gat ttc agc gtg tgg gag    2754
Ile Gln Asn Ala Tyr Leu Asn Gly Val Gly Asp Phe Ser Val Trp Glu
            795                 800                 805 ttc tct gga aat cct gtg tat ttc tgc tgt tat gac tat ttt gct gca    2802
Phe Ser Gly Asn Pro Val Tyr Phe Cys Cys Tyr Asp Tyr Phe Ala Ala
        810                 815                 820 aat gat ccc acg tca atc cat gtt gtt gtc ttt agt cta gaa gag ccc    2850
Asn Asp Pro Thr Ser Ile His Val Val Val Phe Ser Leu Glu Glu Pro
    825                 830                 835 tat gag atc cag ctg aac cca gtg att ttc tgg ctc agt ttc ctg aag    2898
Tyr Glu Ile Gln Leu Asn Pro Val Ile Phe Trp Leu Ser Phe Leu Lys
840                 845                 850 tcc ctt gtc cca gtt gaa gaa ccc ata gcc ttc ggt ggc aag ctg aag    2946
Ser Leu Val Pro Val Glu Glu Pro Ile Ala Phe Gly Gly Lys Leu Lys
```

```
                855               860               865              870
aac cca ctc caa gtt gtc ctg gtg gcc acc cac gct gac atc atg aat      2994
Asn Pro Leu Gln Val Val Leu Val Ala Thr His Ala Asp Ile Met Asn
            875               880              885 gtt cct cga ccg gct gga ggc gag ttt gga tat gac aaa gac aca tcg      3042
Val Pro Arg Pro Ala Gly Gly Glu Phe Gly Tyr Asp Lys Asp Thr Ser
            890               895              900 ttg ctg aaa gag att agg aac agg ttt gga aat gat ctt cac att tca      3090
Leu Leu Lys Glu Ile Arg Asn Arg Phe Gly Asn Asp Leu His Ile Ser
            905               910              915 aat aag ctg ttt gtt ctg gat gct ggg gct tct ggg tca aag gac atg      3138
Asn Lys Leu Phe Val Leu Asp Ala Gly Ala Ser Gly Ser Lys Asp Met
            920               925              930 aag gta ctt cga aat cat ctg caa gaa ata cga agc cag att gtt tcg      3186
Lys Val Leu Arg Asn His Leu Gln Glu Ile Arg Ser Gln Ile Val Ser
935             940               945              950 gtc tgt cct ccc atg act cac ctg tgt gag aaa atc atc tcc acg ctg      3234
Val Cys Pro Pro Met Thr His Leu Cys Glu Lys Ile Ile Ser Thr Leu
            955               960              965 cct tcc tgg agg aag ctc aat gga ccc aac cag ctg atg tcg ctg cag      3282
Pro Ser Trp Arg Lys Leu Asn Gly Pro Asn Gln Leu Met Ser Leu Gln
            970               975              980 cag ttt gtg tac gac gtg cag gac cag ctg aac ccc ctg gcc agc gag      3330
Gln Phe Val Tyr Asp Val Gln Asp Gln Leu Asn Pro Leu Ala Ser Glu
            985               990              995 gag gac ctc agg cgc att gct cag cag ctc cac agc aca ggc gag atc      3378
Glu Asp Leu Arg Arg Ile Ala Gln Gln Leu His Ser Thr Gly Glu Ile
1000            1005              1010 aac atc atg caa agt gaa aca gtt cag gac gtg ctg ctc ctg gac ccc      3426
Asn Ile Met Gln Ser Glu Thr Val Gln Asp Val Leu Leu Leu Asp Pro
1015            1020              1025             1030 cgc tgg ctc tgc aca aac gtc ctg ggg aag ttg ctg tcc gtg gag acc      3474
Arg Trp Leu Cys Thr Asn Val Leu Gly Lys Leu Leu Ser Val Glu Thr
            1035              1040             1045 cca cgg gcg ctg cac cac tac cgg ggc cgc tac acc gtg gag gac atc      3522
Pro Arg Ala Leu His His Tyr Arg Gly Arg Tyr Thr Val Glu Asp Ile
            1050              1055             1060 cag cgc ctg gtg ccc gac agc gac gtg gag gag ctg ctg cag atc ctc      3570
Gln Arg Leu Val Pro Asp Ser Asp Val Glu Glu Leu Leu Gln Ile Leu
            1065              1070             1075 gat gcc atg gac atc tgc gcc cgg gac ctg agc agc ggg acc atg gtg      3618
Asp Ala Met Asp Ile Cys Ala Arg Asp Leu Ser Ser Gly Thr Met Val
1080            1085              1090 gac gtc cca gcc ctg atc aag aca gac aac ctg cac cgc tcc tgg gct      3666
Asp Val Pro Ala Leu Ile Lys Thr Asp Asn Leu His Arg Ser Trp Ala
1095            1100              1105             1110 gat gag gag gac gag gtg atg gtg tat ggt ggc gtg cgc atc gtg ccc      3714
Asp Glu Glu Asp Glu Val Met Val Tyr Gly Gly Val Arg Ile Val Pro
            1115              1120             1125 gtg gaa cac ctc acc ccc ttc cca tgt ggc atc ttt cac aag gtc cag      3762
Val Glu His Leu Thr Pro Phe Pro Cys Gly Ile Phe His Lys Val Gln
            1130              1135             1140 gtg aac ctg tgc cgg tgg atc cac cag caa agc aca gag ggc gac gcg      3810
Val Asn Leu Cys Arg Trp Ile His Gln Gln Ser Thr Glu Gly Asp Ala
            1145              1150             1155 gac atc cgc ctg tgg gtg aat ggc tgc aag ctg gcc aac cgt ggg gcc      3858
Asp Ile Arg Leu Trp Val Asn Gly Cys Lys Leu Ala Asn Arg Gly Ala
1160            1165              1170 gag ctg ctg gtg ctg ctg gtc aac cac ggc cag ggc att gag gtc cag      3906
```

```
Glu Leu Leu Val Leu Leu Val Asn His Gly Gln Gly Ile Glu Val Gln
1175                1180                1185                1190 gtc cgt ggc ctg gag acg gag aag atc aag tgc tgc ctg ctg ctg gac      3954
Val Arg Gly Leu Glu Thr Glu Lys Ile Lys Cys Cys Leu Leu Leu Asp
                1195                1200                1205 tcg gtg tgc agc acc att gag aac gtc atg gcc acc acg ctg cca ggg      4002
Ser Val Cys Ser Thr Ile Glu Asn Val Met Ala Thr Thr Leu Pro Gly
            1210                1215                1220 ctc ctg acc gtg aag cat tac ctg agc ccc cag cag ctg cgg gag cac      4050
Leu Leu Thr Val Lys His Tyr Leu Ser Pro Gln Gln Leu Arg Glu His
        1225                1230                1235 cat gag ccc gtc atg atc tac cag cca cgg gac ttc ttc cgg gca cag      4098
His Glu Pro Val Met Ile Tyr Gln Pro Arg Asp Phe Phe Arg Ala Gln
    1240                1245                1250 act ctg aag gaa acc tca ctg acc aac acc atg ggg ggg tac aag gaa      4146
Thr Leu Lys Glu Thr Ser Leu Thr Asn Thr Met Gly Gly Tyr Lys Glu
1255                1260                1265                1270 agc ttc agc agc atc atg tgc ttc ggg tgt cac gac gtc tac tca cag      4194
Ser Phe Ser Ser Ile Met Cys Phe Gly Cys His Asp Val Tyr Ser Gln
                1275                1280                1285 gcc agc ctc ggc atg gac atc cat gca tca gac ctg aac ctc ctc act      4242
Ala Ser Leu Gly Met Asp Ile His Ala Ser Asp Leu Asn Leu Leu Thr
            1290                1295                1300 cgg agg aaa ctg agt cgc ctg ctg gac ccg ccc gac ccc ctg ggg aag      4290
Arg Arg Lys Leu Ser Arg Leu Leu Asp Pro Pro Asp Pro Leu Gly Lys
        1305                1310                1315 gac tgg tgc ctt ctc gcc atg aac tta ggc ctc cct gac ctc gtg gca      4338
Asp Trp Cys Leu Leu Ala Met Asn Leu Gly Leu Pro Asp Leu Val Ala
    1320                1325                1330 aag tac aac acc aat aac ggg gct ccc aag gat ttc ctc ccc agc ccc      4386
Lys Tyr Asn Thr Asn Asn Gly Ala Pro Lys Asp Phe Leu Pro Ser Pro
1335                1340                1345                1350 ctc cac gcc ctg ctg cgg gaa tgg acc acc tac cct gag agc aca gtg      4434
Leu His Ala Leu Leu Arg Glu Trp Thr Thr Tyr Pro Glu Ser Thr Val
                1355                1360                1365 ggc acc ctc atg tcc aaa ctg agg gag ctg ggt cgc cgg gat gcc gca      4482
Gly Thr Leu Met Ser Lys Leu Arg Glu Leu Gly Arg Arg Asp Ala Ala
            1370                1375                1380 gac ctt ttg ctg aag gca tcc tct gtg ttc aaa atc aac ctg gat ggc      4530
Asp Leu Leu Leu Lys Ala Ser Ser Val Phe Lys Ile Asn Leu Asp Gly
        1385                1390                1395 aat ggc cag gag gcc tat gcc tcg agc tgc aac agc ggc acc tct tac      4578
Asn Gly Gln Glu Ala Tyr Ala Ser Ser Cys Asn Ser Gly Thr Ser Tyr
    1400                1405                1410 aat tcc att agc tct gtt gta tcc cgg tgagggcagc ctctggcttg            4625
Asn Ser Ile Ser Ser Val Val Ser Arg
1415                1420 gacagggtct gtttggactg cagaaccaag ggggtgatgt agcccatcct tcccttttgga   4685 gatgctgagg gtgtttcttc ctgcacccac agccaggggg atgccactcc tccctccggc    4745
ttgacctgtt tctctgccgc tacctccctc cccgtctcat tccgttgtct gtggatggtc    4805
attgcagttt aagagcagaa cagatctttt actttggccg cttgaaaagc tagtgtacct    4865
cctctcagtg ttttggactc catctctcat cctccagtac cttgcttctt actgataatt    4925
ttgctggaat tcctaacttt tcaatgacat tttttttaac tatcatattg attgtccttt    4985
aaaaaagaaa agtgcatatt tatccaaaat gtgtatttct tatacgcttt tctgtgttat    5045
accatttcct cagcttatct cttttatatt tgtaggagaa actcccatgt atggaatccc    5105
```

-continued

```
actgtatgat ttataaacag acaatatgtg agtgccttt  gcagaagagg gtgtgtttga      5165
aatcatcgga gtcagccagg agctgtcacc aaggaaacgc tacctctctg tcccttgctg      5225
tatgctgatc atcgccagag gtgcttcacc ctgagttttg ttttgtattg ttttctgaca      5285 gttttctgt  tttgtttggc aaggaaaggg gagaagggaa tcctcctcca gggtgatttt      5345
atgatcagtg ttgttgctct aggaagacat ttttccgttt gcttttgttc caatgtcaat      5405
gtgaacgtcc acatgaaacc tacacactgt catgcttcat cattccctct catctcaggt      5465
agaaggttga cacagttgta gggttacaga gacctatgta agaattcaga agaccctga       5525 ctcatcattt gtggcagtcc cttataattg gtgcatagca gatggtttcc acatttagat      5585
cctggtttca taacttctcg tacttgaagt ctaaaagcag aaaataaagg aagcaagttt      5645
tcttccatga ttttaaattg tgatcgagtt ttaaattgat aggagggaac atgtcctaat      5705
tcttctgtcc tgagaagcat gtaatgttaa tgttatatca tatgtatata tatatatgca      5765
ctatgtatat acatatatat taatactggt atttttactt aatctataaa atgtcgttaa      5825
aaagttgttt gttttttcct  ttttttataa ataaactgtt gctcgttaaa aaaaaaaaa      5885 a                                                                      5886
```

<210> SEQ ID NO 10
<211> LENGTH: 1423
<212> TYPE: PRT
<213> ORGANISM: Homo sapiens

<400> SEQUENCE: 10

```
Met Thr Val Phe Arg Gln Glu Asn Val Asp Asp Tyr Tyr Asp Thr Gly
  1               5                  10                  15

Glu Glu Leu Gly Ser Gly Gln Phe Ala Val Val Lys Lys Cys Arg Glu
                 20                  25                  30

Lys Ser Thr Gly Leu Gln Tyr Pro Ala Lys Phe Ile Lys Lys Arg Arg
             35                  40                  45

Thr Lys Ser Ser Arg Arg Gly Val Ser Arg Glu Asp Ile Glu Arg Glu
         50                  55                  60

Val Ser Ile Leu Lys Glu Ile Gln His Pro Asn Val Ile Thr Leu His
 65                  70                  75                  80

Glu Val Tyr Glu Asn Lys Thr Asp Val Ile Leu Ile Leu Glu Leu Val
                 85                  90                  95

Ala Gly Gly Glu Leu Phe Asp Phe Leu Ala Glu Lys Glu Ser Leu Thr
            100                 105                 110

Glu Glu Glu Ala Thr Glu Phe Leu Lys Gln Ile Leu Asn Gly Val Tyr
        115                 120                 125

Tyr Leu His Ser Leu Gln Ile Ala His Phe Asp Leu Lys Pro Glu Asn
    130                 135                 140

Ile Met Leu Leu Asp Arg Asn Val Pro Lys Pro Arg Ile Lys Ile Ile
145                 150                 155                 160

Asp Phe Gly Asn Glu Phe Lys Asn Ile Phe Gly Thr Pro Glu Phe Val
                165                 170                 175

Ala Pro Glu Ile Val Asn Tyr Glu Pro Leu Gly Leu Glu Ala Asp Met
            180                 185                 190

Trp Ser Ile Gly Val Ile Thr Tyr Ile Leu Leu Ser Gly Ala Ser Pro
        195                 200                 205

Phe Leu Gly Asp Thr Lys Gln Glu Thr Leu Ala Asn Val Ser Ala Val
    210                 215                 220

Asn Tyr Glu Phe Glu Asp Glu Tyr Phe Ser Asn Thr Ser Ala Leu Ala
```

-continued

```
            225                 230                 235                 240

Lys Asp Phe Ile Arg Arg Leu Leu Val Lys Asp Pro Lys Lys Arg Met
                245                 250                 255

Thr Ile Gln Asp Ser Leu Gln His Pro Trp Ile Lys Pro Lys Asp Thr
                260                 265                 270

Gln Gln Ala Leu Ser Arg Lys Ala Ser Ala Val Asn Met Glu Lys Phe
                275                 280                 285

Lys Lys Phe Ala Ala Arg Lys Lys Trp Lys Gln Ser Val Arg Leu Ile
                290                 295                 300

Ser Leu Cys Gln Arg Leu Ser Arg Ser Phe Leu Ser Arg Ser Asn Met
305                 310                 315                 320

Ser Val Ala Arg Ser Asp Asp Thr Leu Asp Glu Glu Asp Ser Phe Val
                325                 330                 335

Met Lys Ala Ile Ile His Ala Ile Asn Asp Asp Asn Val Pro Gly Leu
                340                 345                 350

Gln His Leu Leu Gly Ser Leu Ser Asn Tyr Asp Val Asn Gln Pro Asn
                355                 360                 365

Lys His Gly Thr Pro Pro Leu Leu Ile Ala Ala Gly Cys Gly Asn Ile
                370                 375                 380

Gln Ile Leu Gln Leu Leu Ile Lys Arg Gly Ser Arg Ile Asp Val Gln
385                 390                 395                 400

Asp Lys Gly Gly Ser Asn Ala Val Tyr Trp Ala Ala Arg His Gly His
                405                 410                 415

Val Asp Thr Leu Lys Phe Leu Ser Glu Asn Lys Cys Pro Leu Asp Val
                420                 425                 430

Lys Asp Lys Ser Gly Glu Met Ala Leu His Val Ala Ala Arg Tyr Gly
                435                 440                 445

His Ala Asp Val Ala Gln Val Thr Cys Ala Ala Ser Ala Gln Ile Pro
                450                 455                 460

Ile Ser Arg Thr Lys Glu Glu Thr Pro Leu His Cys Ala Ala Trp
465                 470                 475                 480

His Gly Tyr Tyr Ser Val Ala Lys Ala Leu Cys Glu Ala Gly Cys Asn
                485                 490                 495

Val Asn Ile Lys Asn Arg Glu Gly Glu Thr Pro Leu Leu Thr Ala Ser
                500                 505                 510

Ala Arg Gly Tyr His Asp Ile Val Glu Cys Leu Ala Glu His Gly Ala
                515                 520                 525

Asp Leu Asn Ala Cys Asp Lys Asp Gly His Ile Ala Leu His Leu Ala
                530                 535                 540

Val Arg Arg Cys Gln Met Glu Val Ile Lys Thr Leu Leu Ser Gln Gly
545                 550                 555                 560

Cys Phe Val Asp Tyr Gln Asp Arg His Gly Asn Thr Pro Leu His Val
                565                 570                 575

Ala Cys Lys Asp Gly Asn Met Pro Ile Val Val Ala Leu Cys Glu Ala
                580                 585                 590

Asn Cys Asn Leu Asp Ile Ser Asn Lys Tyr Gly Arg Thr Pro Leu His
                595                 600                 605

Leu Ala Ala Asn Asn Gly Ile Leu Asp Val Val Arg Tyr Leu Cys Leu
                610                 615                 620

Met Gly Ala Ser Val Glu Ala Leu Thr Thr Asp Gly Lys Thr Ala Glu
625                 630                 635                 640

Asp Leu Ala Arg Ser Glu Gln His Glu His Val Ala Gly Leu Leu Ala
                645                 650                 655
```

```
Arg Leu Arg Lys Asp Thr His Arg Gly Leu Phe Ile Gln Gln Leu Arg
            660                 665                 670

Pro Thr Gln Asn Leu Gln Pro Arg Ile Lys Leu Lys Leu Phe Gly His
            675                 680                 685

Ser Gly Ser Gly Lys Thr Thr Leu Val Glu Ser Leu Lys Cys Gly Leu
            690                 695                 700

Leu Arg Ser Phe Phe Arg Arg Arg Pro Arg Leu Ser Ser Thr Asn
705                 710                 715                 720

Ser Ser Arg Phe Pro Pro Ser Pro Leu Ala Ser Lys Pro Thr Val Ser
            725                 730                 735

Val Ser Ile Asn Asn Leu Tyr Pro Gly Cys Glu Asn Val Ser Val Arg
            740                 745                 750

Ser Arg Ser Met Met Phe Glu Pro Gly Leu Thr Lys Gly Met Leu Glu
            755                 760                 765

Val Phe Val Ala Pro Thr His Pro His Cys Ser Ala Asp Asp Gln
            770                 775                 780

Ser Thr Lys Ala Ile Asp Ile Gln Asn Ala Tyr Leu Asn Gly Val Gly
785                 790                 795                 800

Asp Phe Ser Val Trp Glu Phe Ser Gly Asn Pro Val Tyr Phe Cys Cys
            805                 810                 815

Tyr Asp Tyr Phe Ala Ala Asn Asp Pro Thr Ser Ile His Val Val Val
            820                 825                 830

Phe Ser Leu Glu Glu Pro Tyr Glu Ile Gln Leu Asn Pro Val Ile Phe
            835                 840                 845

Trp Leu Ser Phe Leu Lys Ser Leu Val Pro Val Glu Glu Pro Ile Ala
            850                 855                 860

Phe Gly Gly Lys Leu Lys Asn Pro Leu Gln Val Val Leu Val Ala Thr
865                 870                 875                 880

His Ala Asp Ile Met Asn Val Pro Arg Pro Ala Gly Glu Phe Gly
            885                 890                 895

Tyr Asp Lys Asp Thr Ser Leu Leu Lys Glu Ile Arg Asn Arg Phe Gly
            900                 905                 910

Asn Asp Leu His Ile Ser Asn Lys Leu Phe Val Leu Asp Ala Gly Ala
            915                 920                 925

Ser Gly Ser Lys Asp Met Lys Val Leu Arg Asn His Leu Gln Glu Ile
            930                 935                 940

Arg Ser Gln Ile Val Ser Val Cys Pro Pro Met Thr His Leu Cys Glu
945                 950                 955                 960

Lys Ile Ile Ser Thr Leu Pro Ser Trp Arg Lys Leu Asn Gly Pro Asn
            965                 970                 975

Gln Leu Met Ser Leu Gln Gln Phe Val Tyr Asp Val Gln Asp Gln Leu
            980                 985                 990

Asn Pro Leu Ala Ser Glu Glu Asp Leu Arg Arg Ile Ala Gln Gln Leu
            995                 1000                1005

His Ser Thr Gly Glu Ile Asn Ile Met Gln Ser Glu Thr Val Gln Asp
            1010                1015                1020

Val Leu Leu Leu Asp Pro Arg Trp Leu Cys Thr Asn Val Leu Gly Lys
1025                1030                1035                1040

Leu Leu Ser Val Glu Thr Pro Arg Ala Leu His His Tyr Arg Gly Arg
            1045                1050                1055

Tyr Thr Val Glu Asp Ile Gln Arg Leu Val Pro Asp Ser Asp Val Glu
            1060                1065                1070
```

```
Glu Leu Leu Gln Ile Leu Asp Ala Met Asp Ile Cys Ala Arg Asp Leu
         1075                1080                1085

Ser Ser Gly Thr Met Val Asp Val Pro Ala Leu Ile Lys Thr Asp Asn
1090                1095                1100

Leu His Arg Ser Trp Ala Asp Glu Glu Asp Glu Val Met Val Tyr Gly
1105                1110                1115                1120

Gly Val Arg Ile Val Pro Val Glu His Leu Thr Pro Phe Pro Cys Gly
             1125                1130                1135

Ile Phe His Lys Val Gln Val Asn Leu Cys Arg Trp Ile His Gln Gln
         1140                1145                1150

Ser Thr Glu Gly Asp Ala Asp Ile Arg Leu Trp Val Asn Gly Cys Lys
     1155                1160                1165

Leu Ala Asn Arg Gly Ala Glu Leu Leu Val Leu Leu Val Asn His Gly
1170                1175                1180

Gln Gly Ile Glu Val Gln Val Arg Gly Leu Glu Thr Glu Lys Ile Lys
1185                1190                1195                1200

Cys Cys Leu Leu Leu Asp Ser Val Cys Ser Thr Ile Glu Asn Val Met
             1205                1210                1215

Ala Thr Thr Leu Pro Gly Leu Leu Thr Val Lys His Tyr Leu Ser Pro
         1220                1225                1230

Gln Gln Leu Arg Glu His His Glu Pro Val Met Ile Tyr Gln Pro Arg
     1235                1240                1245

Asp Phe Phe Arg Ala Gln Thr Leu Lys Glu Thr Ser Leu Thr Asn Thr
1250                1255                1260

Met Gly Gly Tyr Lys Glu Ser Phe Ser Ser Ile Met Cys Phe Gly Cys
1265                1270                1275                1280

His Asp Val Tyr Ser Gln Ala Ser Leu Gly Met Asp Ile His Ala Ser
             1285                1290                1295

Asp Leu Asn Leu Leu Thr Arg Arg Lys Leu Ser Arg Leu Leu Asp Pro
         1300                1305                1310

Pro Asp Pro Leu Gly Lys Asp Trp Cys Leu Leu Ala Met Asn Leu Gly
     1315                1320                1325

Leu Pro Asp Leu Val Ala Lys Tyr Asn Thr Asn Asn Gly Ala Pro Lys
1330                1335                1340

Asp Phe Leu Pro Ser Pro Leu His Ala Leu Leu Arg Glu Trp Thr Thr
1345                1350                1355                1360

Tyr Pro Glu Ser Thr Val Gly Thr Leu Met Ser Lys Leu Arg Glu Leu
             1365                1370                1375

Gly Arg Arg Asp Ala Ala Asp Leu Leu Leu Lys Ala Ser Ser Val Phe
         1380                1385                1390

Lys Ile Asn Leu Asp Gly Asn Gly Gln Glu Ala Tyr Ala Ser Ser Cys
     1395                1400                1405

Asn Ser Gly Thr Ser Tyr Asn Ser Ile Ser Ser Val Val Ser Arg
  1410                1415                1420

<210> SEQ ID NO 11
<211> LENGTH: 2038
<212> TYPE: DNA
<213> ORGANISM: Homo sapiens

<400> SEQUENCE: 11
ggctataagc gcacggcctc ggcgacccte tccgacccgg ccgccgccgc catgcagccc    60
tccagccttc tgccgctcgc cctctgcctg ctggctgcac ccgcctccgc gctcgtcagg   120
atcccgctgc acaagttcac gtccatccgc cggaccatgt cggaggttgg gggctctgtg   180
```

-continued

```
gaggacctga ttgccaaagg ccccgtctca aagtactccc aggcggtgcc agccgtgacc      240
gaggggccca ttcccgaggt gctcaagaac tacatggacg cccagtacta cggggagatt      300
ggcatcggga cgccccccca gtgcttcaca gtcgtcttcg acacgggctc ctccaacctg      360
tgggtcccct ccatccactg caaactgctg gacatcgctt gctggatcca ccacaagtac      420
aacagcgaca agtccagcac ctacgtgaag aatggtacct cgtttgacat ccactatggc      480
tcgggcagcc tctccgggta cctgagccag gacactgtgt cggtgccctg ccagtcagcg      540
tcgtcagcct ctgccctggg cggtgtcaaa gtggagaggc aggtctttgg ggaggccacc      600
aagcagccag gcatcacctt catcgcagcc aagttcgatg gcatcctggg catggcctac      660
ccccgcatct ccgtcaacaa cgtgctgccc gtcttcgaca acctgatgca gcagaagctg      720
gtggaccaga acatcttctc cttctacctg agcagggacc cagatgcgca gcctggggt      780
gagctgatgc tgggtggcac agactccaag tattacaagg gttctctgtc ctacctgaat      840
gtcacccgca aggcctactg gcaggtccac ctggaccagg tggaggtggc cagcgggctg      900
accctgtgca aggagggctg tgaggccatt gtggacacag gcacttccct catggtgggc      960
ccggtggatg aggtgcgcga gctgcagaag gccatcgggg ccgtgccgct gattcagggc     1020
gagtacatga tcccctgtga aaggtgtcc accctgcccg cgatcacact gaagctggga     1080
ggcaaaggct acaagctgtc cccagaggac tacacgctca aggtgtcgca ggccgggaag     1140
accctctgcc tgagcggctt catgggcatg gacatcccgc cacccagcgg gccactctgg     1200
atcctgggcg acgtcttcat cggccgctac tacactgtgt ttgaccgtga caacaacagg     1260
gtgggcttcg ccgaggctgc ccgcctctag ttcccaaggc gtccgcgcgc cagcacagaa     1320
acagaggaga gtcccagagc aggaggcccc tggcccagcg gccctccca cacacaccca      1380
cacactcgcc cgcccactgt cctgggcgcc ctggaagccg gcggcccaag cccgacttgc     1440
tgttttgttc tgtggttttc ccctccctgg gttcagaaat gctgcctgcc tgtctgtctc     1500
tccatctgtt tggtgggggt agagctgatc cagagcacag atctgtttcg tgcattggaa     1560
gaccccaccc aagcttggca gccgagctcg tgtatcctgg ggctcccttc atctccaggg     1620
agtcccctcc ccggccctac cagcgcccgc tgggctgagc ccctaccca caccaggccg     1680
tcctcccggg ccctcccttg gaaacctgcc ctgcctgagg gcccctctgc ccagcttggg     1740
cccagctggg ctctgccacc ctacctgttc agtgtcccgg gccgttgag gatgaggccg     1800
ctagaggcct gaggatgagc tggaaggagt gagagggac aaaacccacc ttgttggagc     1860
ctgcagggtg gtgctgggac tgagccagtc ccaggggcat gtattggcct ggaggtgggg      1920
ttgggattgg gggctggtgc cagccttcct ctgcagctga cctctgttgt cctcccttg      1980
ggcggctgag agccccagct gacatggaaa tacagttgtt ggcctccggc ctcccctc       2038
```

<210> SEQ ID NO 12
<211> LENGTH: 5
<212> TYPE: PRT
<213> ORGANISM: Homo sapiens

<400> SEQUENCE: 12

Ser Pro Ser Pro Pro
 1               5

<210> SEQ ID NO 13
<211> LENGTH: 10
<212> TYPE: PRT
<213> ORGANISM: Homo sapiens

```
<400> SEQUENCE: 13

Lys Lys Arg Arg Thr Lys Ser Ser Arg Arg
 1               5                   10

<210> SEQ ID NO 14
<211> LENGTH: 7
<212> TYPE: PRT
<213> ORGANISM: Homo sapiens

<400> SEQUENCE: 14

Pro Ser Thr Ala Ile Arg Glu
 1               5

<210> SEQ ID NO 15
<211> LENGTH: 7
<212> TYPE: PRT
<213> ORGANISM: Homo sapiens

<400> SEQUENCE: 15

Pro Ser Ser Ala Leu Arg Glu
 1               5

<210> SEQ ID NO 16
<211> LENGTH: 7
<212> TYPE: PRT
<213> ORGANISM: Homo sapiens

<400> SEQUENCE: 16

Pro Cys Thr Ala Ile Arg Glu
 1               5

<210> SEQ ID NO 17
<211> LENGTH: 7
<212> TYPE: PRT
<213> ORGANISM: Homo sapiens

<400> SEQUENCE: 17

Lys Lys Ile Ala Leu Arg Glu
 1               5

<210> SEQ ID NO 18
<211> LENGTH: 8
<212> TYPE: PRT
<213> ORGANISM: Homo sapiens

<400> SEQUENCE: 18

Ala Leu Thr Thr Asp Gly Lys Thr
 1               5

<210> SEQ ID NO 19
<211> LENGTH: 8
<212> TYPE: PRT
<213> ORGANISM: Homo sapiens

<400> SEQUENCE: 19

Gly His Ser Gly Ser Gly Lys Thr
 1               5

<210> SEQ ID NO 20
<211> LENGTH: 8
<212> TYPE: PRT
<213> ORGANISM: Homo sapiens
<220> FEATURE:
<223> OTHER INFORMATION: consensus sequence wherein Xs may be any amino
``` acid

<400> SEQUENCE: 20

Gly Xaa Xaa Xaa Xaa Gly Lys Thr
 1               5

<210> SEQ ID NO 21
<211> LENGTH: 23
<212> TYPE: DNA
<213> ORGANISM: Homo sapiens

<400> SEQUENCE: 21
gtatcccgcc gcattcatca aga                                    23

<210> SEQ ID NO 22
<211> LENGTH: 36
<212> TYPE: DNA
<213> ORGANISM: Homo sapiens

<400> SEQUENCE: 22
cagcatccct ggatcaagtc cagaagtaac atgagt                      36

<210> SEQ ID NO 23
<211> LENGTH: 30
<212> TYPE: DNA
<213> ORGANISM: Homo sapiens

<400> SEQUENCE: 23
aagacggcag aagatctaga agagccctat                             30

<210> SEQ ID NO 24
<211> LENGTH: 331
<212> TYPE: PRT
<213> ORGANISM: Homo sapiens

<400> SEQUENCE: 24

Met Thr Val Phe Arg Gln Glu Asn Val Asp Asp Tyr Tyr Asp Thr Gly
 1               5                  10                  15

Glu Leu Gly Ser Gly Gln Phe Ala Val Val Lys Lys Cys Arg Glu
            20                  25                  30

Lys Ser Thr Gly Leu Gln Tyr Pro Ala Lys Phe Ile Lys Lys Arg Arg
        35                  40                  45

Thr Lys Ser Ser Arg Arg Gly Val Ser Arg Glu Asp Ile Glu Arg Glu
    50                  55                  60

Val Ser Ile Leu Lys Glu Ile Gln His Pro Asn Val Ile Thr Leu His
65                  70                  75                  80

Glu Val Tyr Glu Asn Lys Thr Asp Val Ile Leu Ile Leu Glu Leu Val
                85                  90                  95

Ala Gly Gly Glu Leu Phe Asp Phe Leu Ala Glu Lys Glu Ser Leu Thr
            100                 105                 110

Glu Glu Glu Ala Thr Glu Phe Leu Lys Gln Ile Leu Asn Gly Val Tyr
        115                 120                 125

Tyr Leu His Ser Leu Gln Ile Ala His Phe Asp Leu Lys Pro Glu Asn
    130                 135                 140

Ile Met Leu Leu Asp Arg Asn Val Pro Lys Pro Arg Ile Lys Ile Ile
145                 150                 155                 160

Asp Phe Gly Asn Glu Phe Lys Asn Ile Phe Gly Thr Pro Glu Phe Val
                165                 170                 175

Ala Pro Glu Ile Val Asn Tyr Glu Pro Leu Gly Leu Glu Ala Asp Met

-continued

```
                180                 185                 190
Trp Ser Ile Gly Val Ile Thr Tyr Ile Leu Leu Ser Gly Ala Ser Pro
            195                 200                 205
Phe Leu Gly Asp Thr Lys Gln Glu Thr Leu Ala Asn Val Ser Ala Val
210                 215                 220
Asn Tyr Glu Phe Glu Asp Glu Tyr Phe Ser Asn Thr Ser Ala Leu Ala
225                 230                 235                 240
Lys Asp Phe Ile Arg Arg Leu Leu Val Lys Asp Pro Lys Arg Met
                245                 250                 255
Thr Ile Gln Asp Ser Leu Gln His Pro Trp Ile Lys Pro Lys Asp Thr
                260                 265                 270
Gln Gln Ala Leu Ser Arg Lys Ala Ser Ala Val Asn Met Glu Lys Phe
            275                 280                 285
Lys Lys Phe Ala Ala Arg Lys Lys Trp Lys Gln Ser Val Arg Leu Ile
    290                 295                 300
Ser Leu Cys Gln Arg Leu Ser Arg Ser Phe Leu Ser Arg Ser Asn Met
305                 310                 315                 320
Ser Val Ala Arg Ser Asp Asp Thr Leu Asp Glu
                325                 330
```

<210> SEQ ID NO 25
<211> LENGTH: 33
<212> TYPE: PRT
<213> ORGANISM: Homo sapiens

<400> SEQUENCE: 25

```
Asp Val Gln Asp Lys Gly Gly Ser Asn Ala Val Tyr Trp Ala Ala Arg
1               5                   10                  15
His Gly His Val Asp Thr Leu Lys Phe Leu Ser Glu Asn Lys Cys Pro
                20                  25                  30
Leu
```

<210> SEQ ID NO 26
<211> LENGTH: 33
<212> TYPE: PRT
<213> ORGANISM: Homo sapiens

<400> SEQUENCE: 26

```
Asp Val Lys Asp Lys Ser Gly Glu Met Ala Leu His Val Ala Ala Arg
1               5                   10                  15
Tyr Gly His Ala Asp Val Ala Gln Val Thr Cys Ala Ala Ser Ala Gln
                20                  25                  30
Ile
```

<210> SEQ ID NO 27
<211> LENGTH: 33
<212> TYPE: PRT
<213> ORGANISM: Homo sapiens

<400> SEQUENCE: 27

```
Ile Ser Arg Thr Lys Glu Glu Thr Pro Leu His Cys Ala Ala Trp
1               5                   10                  15
His Gly Tyr Tyr Ser Val Ala Lys Ala Leu Cys Glu Ala Gly Cys Asn
                20                  25                  30
Val
```

<210> SEQ ID NO 28

```
<211> LENGTH: 33
<212> TYPE: PRT
<213> ORGANISM: Homo sapiens

<400> SEQUENCE: 28

Asn Ile Lys Asn Arg Glu Gly Glu Thr Pro Leu Leu Thr Ala Ser Ala
 1               5                  10                  15

Arg Gly Tyr Met Asp Ile Val Glu Cys Leu Ala Glu His Gly Ala Asp
            20                  25                  30

Leu

<210> SEQ ID NO 29
<211> LENGTH: 33
<212> TYPE: PRT
<213> ORGANISM: Homo sapiens

<400> SEQUENCE: 29

Asn Ala Cys Asp Lys Asp Gly His Ile Ala Leu His Leu Ala Val Arg
 1               5                  10                  15

Arg Cys Gln Met Glu Val Ile Lys Thr Leu Leu Ser Gln Gly Cys Phe
            20                  25                  30

Val

<210> SEQ ID NO 30
<211> LENGTH: 33
<212> TYPE: PRT
<213> ORGANISM: Homo sapiens

<400> SEQUENCE: 30

Asp Tyr Gln Asp Arg His Gly Asn Thr Pro Leu His Val Ala Cys Lys
 1               5                  10                  15

Asp Gly Asn Met Pro Ile Val Val Ala Leu Cys Glu Ala Asn Cys Asn
            20                  25                  30

Leu

<210> SEQ ID NO 31
<211> LENGTH: 33
<212> TYPE: PRT
<213> ORGANISM: Homo sapiens

<400> SEQUENCE: 31

Asp Ile Ser Asn Lys Tyr Gly Arg Thr Pro Leu His Leu Ala Ala Asn
 1               5                  10                  15

Asn Gly Ile Leu Asp Val Val Arg Tyr Leu Cys Leu Met Gly Ala Ser
            20                  25                  30

Val
```

TUMOR SUPPRESSOR GENES, PROTEINS ENCODED THEREBY AND USE OF SAID GENES AND PROTEINS

RELATED APPLICATIONS

The present application is a continuation-in-part application of U.S. patent application Ser. No. 08/631,097 filed Apr. 12, 1996, U.S. Pat. No. 5,968,816, which claims priority from International Application No. PCT/US94/11598 filed Oct. 12, 1994.

FIELD OF THE INVENTION

The present invention relates to the field of tumor-suppressor genes in general, and programmed cell death in particular.

BACKGROUND OF THE INVENTION

One of the factors which determines the proliferation state of cells is the balance between the growth-promoting effects of proto-oncogenes, and the growth-constraining effects of tumor-suppressor genes.

One mechanism by which these tumor-suppressor genes exert their growth-constraining effect is by inducing the cell to undergo a physiological type of death. Such a controlled cell death is evident in a multitude of physiological conditions including metamorphosis, synaptogenesis of neurons, death of lymphocytes during receptor repertoire selection, controlled homeostasis in the bone-marrow and other proliferative tissues, and others. Such cell death is regulated by the interaction of the cell with other cells or with cell products, for example through the activity of suitable cytokines.

Genetic mutations that inactivate the suppressor genes, liberate the cell from normal growth constraints imposed by other cells or by cytokines, resulting in an uncontrolled growth or viability of the cell without any relation to external signals. This uncontrolled growth is a step in tumorigenesis.

To date, only a few tumor-suppressor genes have been fully characterized including the retinoblastoma (Rb) gene, p53, DCC, NM23 WT-1, NF-1, APC, and ras suppressor genes. A mutation in either of the above genes, probably in both alleles, which leads to either blockage of expression, or production of a faulty protein, hampers the normal control of growth and viability of cells and may thus give rise to cancer.

A number of links have been discovered between programmed cell death and the multi-stage process of tumorigenesis. The first discovery was the finding that the Bcl2 gene, activated by the typical chromosomal translocation in human follicular lymphomas, is a suppressor of cell death (Tsujimoto Y., et al., 1985, Nature 315:340–343). The second link was the finding that p53, the most commonly mutated tumor suppressor gene in various human tumors, functions as a positive mediator of apoptosis. p53 induces cell death in response to different stresses such as gentoxic damage and hypoxia. Thus, the extension of cell viability followed by the accumulation of genetic damage and by the uncontrolled growth of the tumor, are among the mechanisms through which inactivating mutations of p53 promote tumorigenesis (Lowe, S. W., et al., 1993, Nature 362:847–849). More recently it has been reported that the adenomatous polyposis coli (APC) tumor suppressor gene, that is frequently lost or inactivated in early stages of colorectal cancers, induced the death of colorectal cells in culture (Morin et al., 1996, Proc. Natl. Acad. Sci. 93:7950–54), thus providing a third link to apoptotic control. In another study, apoptosis in micrometastases was found to be significantly reduced after induction of angiogenesis as a result of a decrease in levels of circulating angiogenic inhibitors (Holmgren, L., et al. 1995, Nature Medicine 1:149–153). However, very little has been revealed with respect to earlier stages of metastasis such as detachment from the primary tumor, dissemination and invasion processes.

Growth-inhibiting cytokines have a double effect on the target cell. They can either inhibit the proliferation of the cell, and/or give rise to cell death. To date, blockage or activation of expression of known tumor-suppressor genes was shown to counteract or enhance, respectively, cytokines' inhibition of cells' growth (reviewed by A. Kimchi, 1992, J. Cell Biochem., 50:1–9) but did not have any effect on the death promoting action of cytokines. For example, the growth inhibitory response to cytokines such as TGF-β, was markedly reduced by the inactivation of the Rb gene, or the response to IL-6 was enhanced by introducing activated p53 genes (Pietenpol et al., 1990, Cell, 61:777–785; Levy et al., 1993, Mol. Cell. Bio., 13:7942–7952).

Thioredoxin, a small hydrogen carrier protein, has previously been implicated in the IFN-γ-mediated growth arrest of HeLa cells (Deiss, L. P. and Kimchi, A. 1991, Science 234:117–120).

SUMMARY OF THE INVENTION

In the following specification, the term "programmed cell death" will be used to denote a physiological type of cell death which results from activation of some cellular mechanisms, i.e. death which is controlled by the cell's machinery. Programmed cell death may, for example, be the result of activation of the cell machinery by an external trigger, e.g. a cytokine, which leads to cell death. The term "apoptosis" is also used interchangeably with programmed cell death.

The term "tumor" in the following specification denotes an uncontrolled growing mass of abnormal cells. This term includes both primary tumors, which may be benign or malignant, as well as secondary tumors, or metastases which have spread to other sites in the body.

The present invention is based on the pioneering finding that inhibition of expression of certain genes counteracts the cytokine-induced cell death. Namely, as long as these genes function normally, cytokine induces cell death; once the expression of said genes is inhibited, the cytokine-induced cell death is inhibited. It follows therefrom that the normal expression product of these genes is involved in programmed cell death, and particularly, although not necessarily exclusively, in cytokine-induced cell death. In HeLa cells, IFN-γ induces a biphasic process, which comprises an initial cytostatic phase and a subsequent cytotoxic phase (programmed cell death). The novel genes discovered in accordance with the present invention were found to affect only the later, cytotoxic phase. These genes will be referred to herein as "DAP (death-associated protein) genes". DNA molecules comprising a coding sequence encoding the expression products of the DAP genes, or expression products having a similar biological activity, will be referred to herein at times collectively as "DAP DNA molecules". The expression products of the DAP DNA molecules will be referred to herein at times collectively as "DAP products".

The present invention is further based on the pioneering finding that metastasizing cells may have a defective internal apoptosis mechanism. Thus, although during metastasis the tumor cells encounter several novel types of apoptotic stimuli, the cells continue to metastasize.

It has further been discovered that by correcting the deficiency which led to the malfunction of the apoptotic mechanism in the cell, the metastatic character of the cell is suppressed.

According to one aspect of the present invention, to be referred to herein as "the death-promoting aspect", the above DAP DNA molecules, expression vectors comprising them, or DAP products are used for promoting death of normal or tumor cells and for suppressing the metastatic activity of tumor cells. A particular application of the death-promoting aspect is in therapy of diseases or disorders associated with uncontrolled, pathological cell growth, e.g. cancer (primary tumors and metastasis), psoriasis, autoimmune diseases and others. The use of DAP DNA molecules in gene therapy or DAP products if produced extracellularly, in accordance with the death-promoting aspect of the invention, may be in conjunction with cytokines, e.g. IFN-γ.

According to another aspect of the invention, to be referred to herein as "the death-preventing aspect" agents which prevent the expression of said DAP DNA molecules, or agents which antagonize, inhibit or neutralize the DAP products, are used for protecting cells from programmed cell death. Examples of possible applications of the death preventing aspect of the invention are in prevention of cell death in various degenerative neurological diseases, such as Alzheimer's disease or Parkinson's disease, which are associated with premature death of particular subsets of neurons; prevention of death of T-cells in AIDS patients, which death resembles programmed cell death; prevention of rejection-associated cell death in transplants which is believed to result, at least in part, from programmed cell death; protection of normal cells from the cytotoxic effects of certain anti-cancer therapies; etc.

According to a further aspect of the present invention, referred to herein at times as "the screening aspect", DAP DNA molecules are used in order to screen individuals for predisposition to cancer. In accordance with this aspect, the screening is carried out by comparing the sequence of each of the DAP DNA molecules to each of the respective DAP genes in the individual, or by following RNA and/or protein expression. The absence of a DAP gene, a partial deletion or any other difference in the sequence that indicates a mutation in an essential region, or the lack of a DAP RNA and/or protein which may result in a loss of function may lead to a predisposition for cancer. For screening, preferably a battery of different DAP genes may be used, as well as different antibodies.

In the screening aspect, DAP molecules may also be used for prognostic purposes. For example, if a tumor cell lacks DAP activity, this may reflect high chances of developing metastasis. In addition, DAP positive cells may be more susceptible to control by chemotherapeutic drugs that work by inducing apoptosis, so that the choice of treatment modalities may made based on the DAP state of the cells.

The DAP genes seem to play an important role in programmed cell death and the inhibition of their expression or neutralization of their expression products protects the cell from cytokine-promoted cell death. Examples of such genes are those whose sequences are depicted in FIGS. 6 (SEQ ID NO: 8), 8 (SEQ ID NO: 9), 12 (SEQ ID NO: 3), 14 (SEQ ID NO: 11) and 15 (SEQ ID NO: 6) or whose partial sequences are depicted in FIG. 13 (SEQ ID NO: 5). The gene for the known protease cathepsin D, whose sequence is depicted in FIG. 14 (SEQ ID NO: 11), is also revealed here for the first time as functioning as a DAP gene.

DAP DNA molecules useful in the death-promoting aspect of the invention may have the nucleic acid sequence of the DAP gene or other sequences which encode a product having a similar biological activity to that of the DAP product. Such DAP molecules include DNA molecules having a sequence other than that of the DAP gene but which, owing to the degenerative nature of the genetic code, encode the same protein or polypeptide as that encoded by the DAP gene.

It is well known that it is possible at times to modify a protein by replacing or deleting certain amino acids which are not essential for a certain biological function, or adding amino acids in a region which is not essential for the protein's biological function, without such modification essentially affecting the biological activity of the protein. Thus, a DAP DNA molecule useful in the death promoting aspect of the invention may also have a modified sequence encoding such a modified protein. The modified sequence has a sequence derived from that of the DAP gene or from that of the above degenerative sequence, in which one or more nucleic acid triplets (in the open reading frame of the sequence), has been added, deleted or replaced, with the protein product encoded thereby retaining the essential biological properties of the DAP product. Furthermore, it is known that at times, fragments of proteins retain the essential biological properties of the parent, unfragmented protein, and accordingly, a DAP DNA molecule useful in the death promoting aspect of the invention may also have a sequence encoding such fragments.

For example, the deduced amino acid structure of DAP-2 (DAP-kinase) suggests that this enzyme is a serine/threonine-type kinase. Its kinase domain was found to be composed of 11 subdomains typical of serine/threonine kinases, and is followed by a region that shares a significant homology with the calmodulin regulatory domains of other kinases. Adjacent to the latter, eight ankyrin repeats were found followed by two P-loop motifs. Moreover, a typical death domain module was identified at the 3' end of the protein, followed by a stretch of amino acids that is rich in serines and threonines (Feinstein, et al., 1995, Trends Biochem. Sci. 20:342–44). The skilled artisan will know how to prepare active modified protein molecules and fragments on the basis of such information, and as further described below.

A DNA molecule useful in the death-preventing aspect of the invention may have a sequence which is an antisense sequence to that of the DAP gene, or an antisense sequence to part of the DAP gene, blocking of which is sufficient to inhibit expression of the DAP gene. The part of the gene can be either the coding or the non-coding part of the DAP gene. The mRNA transcripts of the antisense sequences hybridize to the mRNA transcripts of the DAP gene and interfere with the final protein expression.

Non-limiting examples of cDNA clones containing specific antisense sequences are given in Table 1 below. Preferred antisense sequences are those sequences beginning at position 1000 and ending at position 1320 of the DAP-1 gene in FIG. 6 (SEQ ID NO: 8), 3781–4148 of the DAP-2 gene in FIG. 8 (SEQ ID NO: 9), 108–360 of the DAP-3 gene in FIG. 12 (SEQ ID NO: 3), and 1203–1573 of the cathepsin D gene in FIG. 14 (SEQ ID NO: 11).

Another DNA molecule useful in the death preventing aspect of the invention is a DNA molecule coding for a modified DAP product which is capable of inhibiting the activities of the unmodified DAP product in a dominant negative manner, such as a catalytically inactive kinase (DAP-kinase) or any other modified protein whose presence in the cell interferes with the normal activity of the native protein, for example by producing faulty hetero dimers comprised of modified and unmodified proteins which are inactive and the like. For example, a catalytically inactive DAP-kinase mutant which carries a lysine to alanine substitution within the kinase domain (K42A) was found not to be cytotoxic and protected cells from IFN-γ-induced cell death.

DNA molecules useful in the screening aspect of the invention comprise the sequence of a DAP gene or a sequence of a fragment thereof or specific antibodies.

The present invention thus provides a DNA molecule comprising a sequence selected from the group consisting of:

(a) a gene whose expression is necessary for the mediation of cytokine-induced programmed cell death;

(b) a DNA sequence encoding the same protein or polypeptide encoded by the gene defined in (a);

(c) a modified DNA sequence of (a) or (b) in which one or more nucleic acid triplets has been added, deleted, or replaced, the protein or polypeptide encoded by the modified DNA sequence mediating the cytokine-induced programmed cell death similarly to the protein or polypeptide encoded by the gene as defined under (a) or (b);

(d) fragments of any of the DNA sequences of (a), (b) or (c), encoding a protein or a polypeptide having said biological activity;

(e) a sequence which is an antisense to the entire or part of the DNA molecule under (a) and capable of inhibiting the expression of said gene; and (f) a modified DNA sequence of (a) or (b) in which one or more nucleic acid triplets has been added, deleted or replaced, the protein or polypeptide encoded by the modified sequence having dominant negative effect manifested by the ability of said protein or polypeptide to inhibit said cytokine-induced programmed cell death.

In accordance with a specific embodiment, the present invention provides a DNA molecule comprising a nucleic acid sequence selected from the group consisting of:

(a) A DNA molecule comprising a nucleic acid sequence expressed in cells, the expression product of which is involved in cytokine-induced programmed cell death, being one of the following:

(i) a DNA sequence comprising a coding sequence beginning at the nucleic acid triplet at position 160–162 and ending at the triplet 466–468 of the sequence depicted in FIG. 6 (SEQ. ID. NO. 1);

(ii) a DNA sequence comprising a coding sequence beginning at nucleic acid triplet at position 287–289 and ending at a triplet at positions 816–818 of the sequence depicted in FIG. 6 (SEQ. ID. NO. 2);

(iii) a DNA sequence comprising a coding sequence beginning at nucleic acid triplet at position 337–339 and ending at the triplet at position 4603–4605 of the sequence depicted in FIG. 8 (SEQ ID NO: 9);

(iv) a DNA sequence comprising a coding sequence beginning at position 74–76 and ending at position 1268–1270 of the sequence depicted in FIG. 12 (SEQ ID NO: 3 and SEQ ID NO: 4);

(v) a DNA sequence comprising a sequence depicted in FIG. 13 (SEQ. ID. NO. 5);

(vi) a DNA sequence comprising a coding sequence beginning at the nucleic acid triplet at position 201–203 and ending at the triplet 3018–3020 of the sequence depicted in FIG. 15 (SEQ ID NO: 6 and SEQ ID NO: 7).

(b) a DNA molecule encoding the same protein or polypeptide encoded by any one of the DNA sequences of (a);

(c) a DNA molecule as in (a) or (b) in which one or more nucleic acid triplets has been added, deleted or replaced, the protein or polypeptide encoded by the sequence having essentially the same biological atctivity as that encoded by any one of the DNA molecules of either of cltims (a) or (b), respectively;

(d) a fragment of any one of the DNA molecules of (a)–(c) encoding a protein or polypeptide retaining a biological activity present in the protein or polypeptide encoded by any one of the DNA molecules of either of claims (a) or (b) with the proviso that nucleotide sequence 2556–2814 of FIG. 8 (SEQ ID NO: 9) and sequence 2221–2290 of FIG. 15 (SEQ ID NO: 6) are excluded;

(e) a molecule which comprises an antisense sequence complementary in sequence to the mRNA transcribed from the entire or part of any one of the DNA molecules according to (a) or (b) or of the cathepsin D gene in FIG. 14 and capable of inhibiting the expression of said sequences; and (f) a modified DNA sequence of any one of the sequences in (a) in which one or more nucleic acid triplets has been added, deleted or replaced, the protein or polypeptide encoded by the modified sequence having dominant negative effect and being capable of inhibiting the function of the protein or polypeptide encoded by any one of the sequences in (a).

The present invention also provides a DNA molecule, the expression product of which is involved in non-cytokine induced programmed cell death.

The term "biological activity" as used in this specification with respect to modified DNA or polypeptide molecules relates to the activity of the unmodified molecules with respect to the death-promoting, death preventing and screening aspects of the invention, as defined above.

The present invention also provides a vector comprising any of the above DNA molecules, the vector comprising also sequences required for maintaining and replicating it in a host cell. Vectors in accordance with the present invention may be transfer vectors for propagating and replicating the DNA sequences in a host cell or may be expression vectors comprising also sequences required for translation of said DNA sequences into an mRNA. Examples of such expression vectors are plasmids, e.g. episomes or viruses. Examples of episomes are those constructed by using the vehicles pTKO1, pTKO2 and pTKO3 (Deiss and Kimchi, supra).

The present invention further provides a DAP product which is a protein or polypeptide encoded by a DNA molecule of the invention, with the exception of the DNA molecules having an antisense sequence, or such a protein or polypeptide which has been chemically modified, for example, by methylation, glycosylation, etc. An example of a DAP product is that having the amino acid sequence depicted in FIGS. 6 (SEQ ID NO: 8), 8 SEQ ID NO: 9 and SEQ ID NO: 10, 12 SEQ ID NO: 3 and SEQ ID NO: 4, and 14 (SEQ ID NO: 7). The DAP product is useful in the death-promoting aspect of the present invention. In accordance with this aspect, the protein may be administered to patients, in particular, to cancer patients, which administration may cause death of the transformed tumor cells.

The present invention further provides agents which inhibit, antagonize or neutralize the DAP product, which are useful in the death-preventing aspect of the invention. Such agents are for example, antibodies directed against the DAP product; inhibitors or antagonists of the DAP product which are able to counteract their effect and prevent the death-promoting activity of the DAP product. A non-limiting specific example of such an agent is the K42A mutant of DAP-kinase (described below), which counteracts the effect of wild-type DAP-kinase.

The present invention further provides a pharmaceutical composition comprising a pharmaceutically acceptable carrier and a therapeutically effective amount of an active agent being selected from the group consisting of: (i) an expression vector comprising a DNA molecule of the invention or a DNA molecule coding for cathepsin D; (ii) a DAP product of the invention or cathepsin D; and (iii) an antibody, inhibitor or antagonist to the DAP product. The pharmaceutical composition of the present invention may also comprise means for targeting said active agent to the desired cell or tissue. Depending on the nature of the active agent, the composition is useful either in accordance with the death-promoting or the death-preventing aspect of the invention. In accordance with the death-promoting aspect of the invention, the pharmaceutical composition may also comprise a cytokine, e.g. IFN-γ, in combination with a suitable DAP product, or with an expression vector comprising a suitable DAP molecule.

The term "therapeutically effective amount" with respect to the active agent refers to an amount of the agent capable of inducing a therapeutic alteration in the physiological state of the patient receiving the pharmaceutical composition. Such an amount can be empirically determined by an average skilled medical care personal.

Further provided by the present invention is a method of treatment comprising administering said active agent to an individual. Similarly as in the pharmaceutical composition, depending on the nature of said active agent, the method is practicable in either the death-promoting aspect of the invention or the death-preventing aspect of the invention. In the death-promoting aspect of the invention, said active agent may be administered in conjunction with a cytokine, e.g. IFN-γ. In a specific aspect, the present invention provides a method of treatment of a disease or a disorder associated with malignant cell metastasis comprising inserting into the cells of a diseased individual a therapeutically effective amount of said active agent thereby inducing programmed cell death in said cells.

Also provided by the present invention is a method for choosing a chemotherapeutic treatment for a cancer patient comprising: determining whether the tumor cells of the patient comprise an active DAP gene; and choosing a chemotherapeutic drug whose mode of action induces apoptosis. DAP gene expression in tumor cells can increase the sensitivity of the cells to various chemotherapeutic drugs such as topoisomerase inhibitors (e.g. Adriamycin), mitotic inhibitors (e.g. Vincristine), glucocorticoids (e.g. Dexamethsone), folic acid antagonists (e.g. Methotrexate) and broad range protein kinase (PKC, PKA, etc.) inhibitors (e.g. Staurosporine).

In accordance with the screening aspect of the invention, there is provided a method for detecting the absence of a DAP gene, a partial deletion or a mutation (i.e. point mutation, deletion or any other mutation) in the DAP genes of an individual, or the absence of a DAP-related RNA or protein, comprising probing genomic DNA, cDNA or RNA from the individual with a DNA probe or a multitude of DNA probes having a complete or partial sequence of the DAP genes, or probing protein extracts with specific antibodies. A particular application of the screening aspect of the invention is in the screening for individuals having a predisposition to cancer, an absence of the gene or a detected mutation or deletion indicating that the individual has such predisposition.

One example of a method in accordance with the screening aspect typically comprises the following steps:

(a) obtaining a sample of either genomic DNA from cells of the individual or cDNA produced from mRNA of said cells;

(b) adding one or more DNA probes each of said probes comprising a complete or partial sequence of a DAP gene;

(c) providing conditions for hybridization between the DNA probe or probes and the DNA of said sample;

(d) on the basis of the hybridization determining whether the DAP gene is absent or there is a match between the sequence of the DNA probe or probes and a sequence in the DNA of said sample or a mismatch, a mismatch indicating a deletion or a mutation in the genomic DNA and a predisposition to cancer in the tested individual.

Other examples of the screening aspect of the invention are well known to the skilled artisan and include, but are not limited to, Northern blots, RNase protection assays and various PCR procedures.

A specific embodiment of the screening aspect of the invention involves use of a complete or partial sequence of that shown in FIGS. 6 (SEQ ID NO: 8), 8 (SEQ ID NO: 9), 12 (SEQ ID NO: 3), 13 (SEQ ID NO: 5), 14 (SEQ ID NO: 11).

The mutation in the DAP gene indicating a possible predisposition to cancer can also be detected by the aid of appropriate antibodies which are able to distinguish between a mutated and non-functional and a normal functional DAP gene product. In addition, mutations that abolish protein translation or loss of RNA due to promoter inactivation can be detected with the aid of antibodies that are reacted with protein cell extracts. One example is described below with respect to the loss of DAP-kinase RNA and protein in B cell lymphoma and bladder carcinoma cell lines. Screening is also possible with respect to metastases, as will be described below.

DESCRIPTION OF THE DRAWINGS

The present invention will be better understood from the following detailed description of preferred embodiments, taken in conjunction with the following drawings in which:

FIGS. 1A–D show RNA and protein expression of the DAP-1 gene, wherein:

FIG. 1(A) shows a Northern blot analysis of sense and antisense mRNA obtained from HeLa cells transfected with the constructs 230, 255, 260, 259 and control cells (parental cells) and probed by labeled cDNA fragments from construct 230. Total RNA was prepared from HeLa cells either before (parental) or after transfection with pTKO1 constructs #230 or #255 (group 1), #260 (group 5) and #259 (group 3) designated 230-t1, 255-t1, 260-t1 and 259-t1, respectively. Twenty μg RNA were processed on Northern blots and DNA fragment #230 was used as a probe. The arrows point to the position of sense and antisense RNAs.

FIG. 1(B) shows a Northern blot analysis of sense and antisense mRNA obtained from HeLa cells transfected with control construct (DHFR-t2), 230 construct or control cells (parental) cells treated with (+) or without (−) 750 U/ml of IFN-γ for 24 h. The RNA was extracted from the indicated HeLa cells which were grown for 4 days in the absence (−) or presence (+) of IFN-γ (750 U/ml). The Northern blot containing 20 μg RNA samples was hybridized with the cDNA insert of λ1 phage. The Ethidium Bromide staining of the mRNA samples is shown.

FIG. 1(C) shows an SDS polyacrylamide electrophoresis gel of the expressed protein product of DAP-1 cDNA translated in vitro in a reticulocyte lysate preparation. In vitro translation of RNA (0.5 μg) transcribed from the λ1 cDNA (lane 2) and from the subclones p6, p4, p5 and p8 are shown in lanes 3–6, respectively. Lane 1 corresponds to the background obtained in the absence of RNA administration to the reticulocyte lysates. The labeled proteins were fractionated on 12% SDS polyacrylamide gels. The position of the radioactive molecular weight markers (Amersham) is marked. The two translated proteins, the major 15 kDa and minor 22 kDa proteins, are indicated by arrows.

FIG. 1(D) shows an immunoblot analysis of recombinant and cellular 15 kDa DAP-1 protein. Bacterially produced DAP-1 protein (300 ng) and the indicated HeLa cell extracts (350 μg) were fractionated on SDS polyacrylamide gels (12%), blotted to nitrocellulose and reacted with affinity purified antibodies generated against the 15 kDa DAP-1. The cells were treated with IFN-γ (750 U/ml) for 4 days before their extraction. The two arrows point to the position of the cellular DAP-1 protein. The antibodies also recognize two non-relevant bands of 60 and 45 kDa that are not modulated by the antisense RNA expression. Quantitation of the reduction in DAP-1 protein was done by densitometric analysis. The calibration of the protein content in each slot was done by referring to the signals of the non-relevant bands. The prestained protein markers (Sigma) are marked.

FIGS. 2A–D show RNA and protein expression of the DAP-2 gene, wherein:

FIG. 2(A) shows a Northern blot analysis of sense and antisense mRNA obtained from two clones of HeLa cells transfected with the control constructs (DHFR-t1 and DHFR-t2) and two clones of cells transfected with the 256 construct (t1 and t2). Total RNA was prepared from the 256-t1 and 256-t2 HeLa cell transfectants either before (0 hours) or at 3 and 24 hours after treatment with IFN-γ (750 U/ml) and 20 μg samples were processed on Northern blots. Fragment #256 was used as a probe. The position of the sense and antisense mRNAs is indicated. The GAPDH mRNA levels were used for the calibration of the RNA amounts in each blot.

In FIG. 2(B) the blot consists of total RNA (20 μg) from K562 cells, parental HeLa cells, the two DHFR-transfected HeLa cell populations and the two HeLa cell populations that were transfected with the pTKO1-256. The blot was hybridized with the cDNA insert of λ29. The Ethidium Bromide staining of the RNA samples is shown.

FIG. 2(C) shows an in vitro phosphorylation assay. Cell lysates were prepared from COS-7 cells either before (lane 1) or after transfection with the PECE-FLAG expression vector that carries the coding region of the λ29 cDNA (lane 2). Samples of 400 μg were immunoprecipitated with anti-FLAG™ (M2) monoclonal antibodies (IBI) and subjected to phosphorylation assays.

FIG. 2(D) shows immunoblot analysis of recombinant and cellular DAP-2 protein. The COS-7 cells were transiently transfected with the PECE-FLAG-DAP-2 expression vector. Samples of cell lysates, 100 μg from COS-7 cells and 400 μg from HeLa cells, were fractionated on SDS polyacrylamide gels (7.5%), immunoblotted and reacted with affinity purified polyclonal antibodies raised against the N-terminal DAP-2 peptide. In the lower panel the blot was reacted with monoclonal antibodies against vinculin (Sigma Immunochemicals). Lanes: 1, non-transfected COS-1 cells; 2, transfected COS-1 cells; 3, DHFR-t1 cells; 4, 256-t1 cells; 5, 256-t2 cells. In lane 2 the same 160 kDa protein was also detected with anti-FLAG™ (M2) monoclonal antibodies (IBI) (not shown).

FIGS. 3A–C show morphological features of the cytostatic and cytotoxic responses to IFN-γ in HeLa cells. All cultures were seeded at an initial density of 10,000 cells per cm$^2$.

FIG. 3(A) shows light microscopy of HeLa cells transfected with pTKO1-DHFR construct (DHFR-t1 cells), on days 3 and 8 of culturing in the absence (a,c) or the presence (b,d) of IFN-γ (750 U/ml). (Magnification×400). Note the absence of refractile mitotic cells during the cytostatic phase of responses to IFN-γ (in b) and the appearance of round cells that were detached from the substratum during the killing phase (in d).

FIG. 3(B) shows staining of DNA with DAPI; a. DHFR-t1 non-treated cells removed by trypsinization and mounted on glass slides. b. Detached DHFR-t1 cells collected 7 days after IFN-γ treatment. Nuclei with condensed or fragmented chromatin are indicated by arrows. (Magnification×1000).

FIG. 3(C) shows scanning and transmission electron micrographs of cells transfected with the control construct DHFR-t1 and the 230-t1 construct. DHFR-t1 HeLa cell populations (a–d) and the 230-t1 antisense transfected cells (e and f), were cultured either in the absence (a, c, e) or in the presence (b, d, f) of IFN-γ (750 U/ml). (a,b,e,f), scanning electron micrographs were taken after 7 days using GSM 6400 SEM (Jeol). Bars=10 mm (×2200 magnitude in all the four samples). (c and d), transmission electron micrographs taken after 7 days using TEM (Philips 410) at a magnitude of ×2800. The condensed nuclei and the surface blebs are indicated by arrows.

FIGS. 4(A–B) show the number of viable cells as determined by light absorption at 540 nm, as a function of time; the cells being transfected either with the control construct DHFR-t1 (●—1(A) and 1(B)); the 255 or 230 construct (▲—1(A)) or with two clones t1 and t2 of the 256 construct (▲—1(B)). The results are shown both for cell growth with (+) and without (−) administration of 750 U/ml of IFN-γ. Each point is the average of a quadruplicate determination with a SD that ranged between 2–5%.

FIG. 4(C) shows a Northern blot analysis of 2–5A synthetase gene induction. The indicated HeLa cell transfectants were incubated for 24 hours in the presence (+) or absence (−) of IFN-γ (750 U/ml). Twenty mg of total RNA were analyzed. The cDNA of the 2–5A synthetase was used as probe.

FIG. 6 shows the DNA sequence and predicted amino acid sequence of DAP-1 (DNA SEQ ID NO: 8 and amino acid SEQ ID NOs 1 and 2).

FIG. 7 shows the restriction map of the λ29 cDNA clone, that carries the DAP-2 cDNA.

FIG. 8 shows the DNA sequence and predicted amino acid sequence of DAP-2 (DNA SEQ ID NO: 9 and amino acid SEQ ID NO: 10).

FIGS. 9A–D show DAP-2 sequence homologies to other serine/threonine kinases and alignment of the ankyrin repeats of DAP-2, wherein:

In FIG. 9(A) the protein kinase domain sequences of the DAP-2 are aligned with the corresponding domains of other calmodulin-dependent kinases (SEQ ID NO: 24). The kinase subdomain structure (numbered I–XI) and the region implicated in calmodulin recognition and binding (designated as calmodulin regulatory region) are indicated. The obligatory conserved amino acids within the kinase domain are labeled with asterisks. Numbers at the right mark positions relative to the N-terminus of primary translational products of each kinase. Solid background indicates identical amino acids within the compared kinases. Stippled background indicates positions where the amino acids are not identical but similar. nm-mlck—non-muscle myosin light chain kinase (chicken); sm-mlck—smooth muscle myosin light chain kinase (chicken); skm-mlck—skeletal muscle myosin light chain kinase (rat); camdk-alph, -beta, -gamm-calcium/calmodulin dependent protein kinase II-α-, β- and γ-subunits, respectively; mlck-dicdi—dictyostelium discoidium (slime mold) myosin light chain kinase.

FIG. 9(B) shows alignment of kinase subdomains II and III of DAP-2 and the corresponding domains of different cell cycle dependent kinases. dm2—Drosophila CDC2 homologue; pssalre—Human serine/threonine kinase PSSALRE (SEQ ID NO: 15); kpt2—Human serine/threonine protein kinase PCTAIRE-2 (SEQ ID NO: 16); kin28—yeast (S. cerevisiae) putative protein kinase; mo15—Xenopus protein kinase related to cdc2 that is a negative regulator of meiotic maturation; kkialre—human serine/threonine protein kinase KKIALRE (SEQ ID NO: 17).

FIG. 9(C–D) shows alignment of DAP-2 ankyrin repeats (SEQ ID NOS: 25–31). Solid background indicates identical amino acids. A consensus sequence of the DAP-2 ankyrin repeats is shown at the bottom. The position of each individual repeat along the cDNA is illustrated in FIG. 9(B). ar 1–8, ankyrin repeats.

FIG. 12 shows the DNA sequence and predicted amino acid sequence of DAP-3 (SEQ ID NO: 3) and (SEQ ID NO: 4).

FIG. 13 shows a partial DNA sequence of DAP-4 (SEQ ID NO: 5).

FIG. 14 shows the DNA sequence and amino acid sequence of cathepsin D (SEQ ID NO: 11).

FIG. 15 shows the DNA sequence and amino acid sequence of DAP-5 (SEQ ID NOS: 6 and 7).

(○) D122; (◇) 1-cont.; (□) 4-cont.; (X) 6-DAPk; (♦) 28-DAPk; (▼) 42-DAPk; (●) 48-DAPk.

Figure 18:
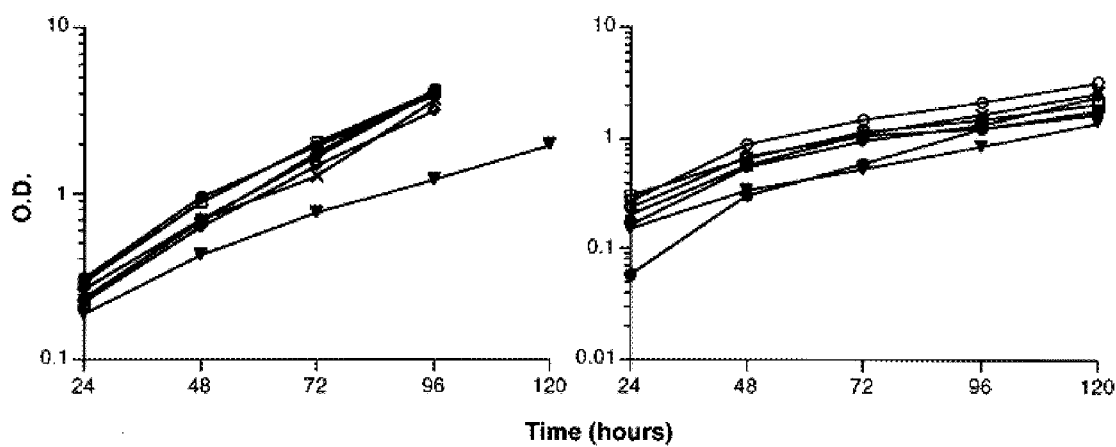
FIGS. 18A & B are in vitro growth curves of the transfected D122 clones. The cells were cultured in 24-well plates at an initial cell density of $1 \times 10^4$ cells per well; the medium was supplemented with either 10% (FIG. 18A) or 1% (FIG. 18B) fetal calf serum (FCS) (Gibco BRL). At 24 hours time intervals cell numbers were quantified by the crystal violet method (Kueng, W., et al., 1989, Anal Biochem. 182:16) and the O.D. of lysed cells was measured at λ=540 nm. Data are mean of duplicate determinations of two experiments. Symbols.
Figure 19:
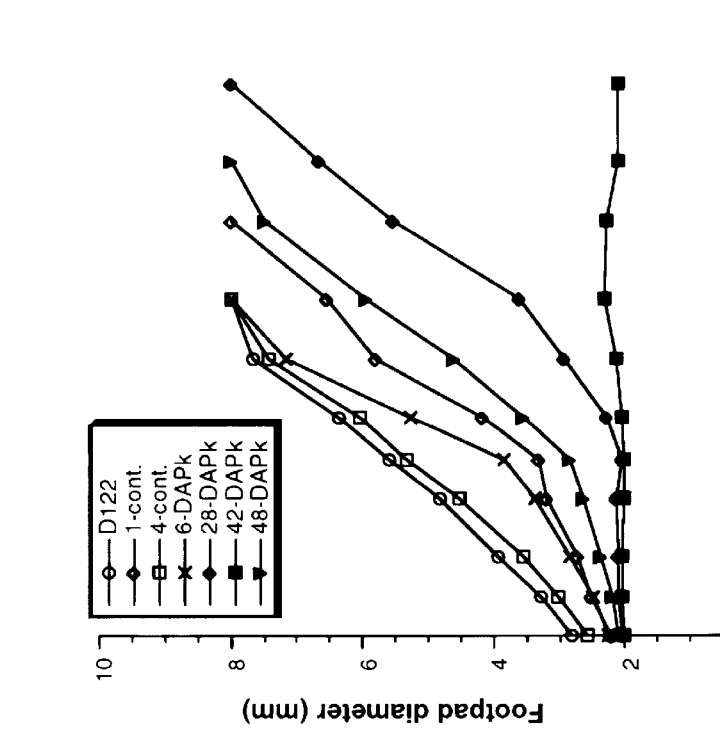

FIG. 19 shows local tumor growth in footpads as a function of number of days post injection. The different D122-transfected clones were injected into the footpads of C57BL/6 mice (10–12 week old females). Diameters of tumor bearing feet were measured every 1–3 days. Values represent the mean pad diameter of the individuals in each group (8 per group). The symbols are as in FIG. 18.

The SD ranged between 0% to 32% of the measurements. An unpaired one-tailed student's t-test performed at numerous time points indicated that differences between sizes of the growing tumor formed by the slowest growing control clone (1-cont.) and these formed by the 28-DAPk or 42-DAPk clones were significant at P<0.001. It can be seen that transfection with DAP-kinase delays the growth of local tumors.

Figure 20:
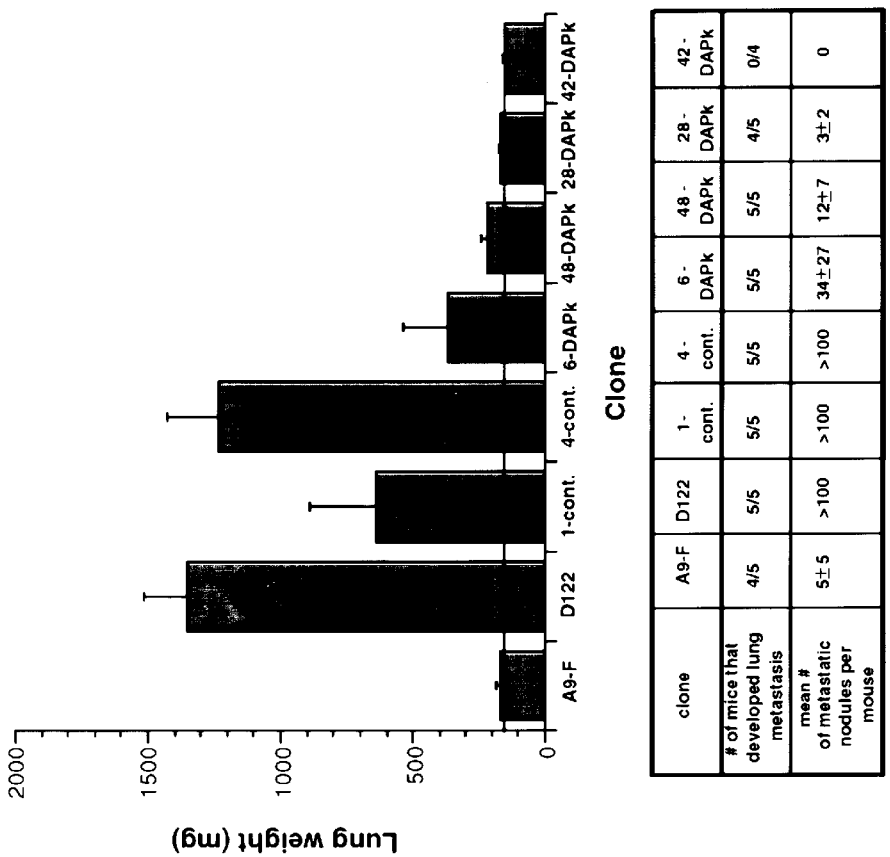

FIG. 20 shows average lung weight and mean number of metastatic lesions of intraveneous injected mice. Mice, as above, were injected in the tail vein and sacrificed 30–32 days later. Lungs were removed weighed and fixed in Bouin's solution. The number of metastatic nodules were determined by counting surface nodules under a binocular. Values are mean±SD of 5 individuals in a group, presenting either lung weight (in bars) or number of metastatic nodules per mouse (in Table). The solid line in the bars graph indicates the average lung weight of non-injected mice.

Differences between the less aggressive 1-cont. clone and each one of the DAP-kinase transfectants were significant at P<0.001 for 48-, 28- and 42-DAPk clones and 0.025<P<0.05 for the low expressing clone 6-DAPk (the latter clone differed from 4-cont. clone and parental D122 cells at P<0.001). Thus, transfection with DAP-kinase strongly suppressed experimental metastasis.

Figure 21:
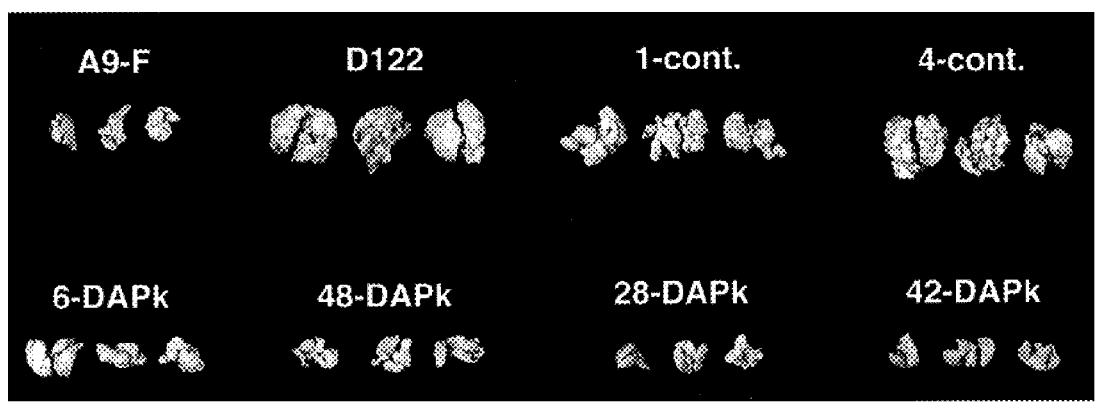

FIG. 21 are photographs of three representative lungs from each group of mice as in FIG. 20. Note the differences in lung size and surface nodules compared to lungs obtained after I.V. injections with the A9-F low metastatic clone (used as a reference). Scale bar, 1 cm.

Figure 16:
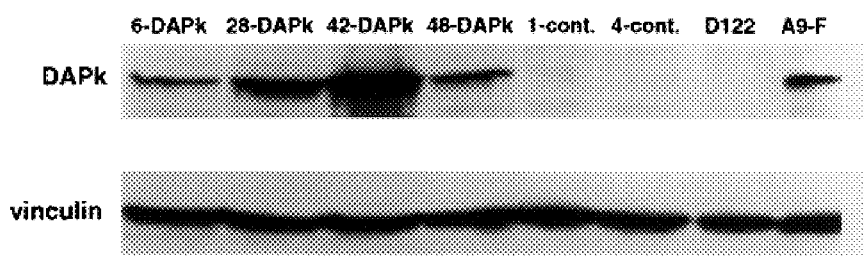
FIG. 16 shows an immunoblot analysis of DAP-kinase expression. Subconfluent cultures of parental D122 cells, and of the different G-418-resistant derivative clones transfected with the pcDNA control vector (-cont.) or with pcDNA-DAP-kinase (-DAPk) were lysed and processed (300 µg protein per sample) as detailed before (Deiss, L. P., et. al., 1995, Genes Dev. 9:15). Immunoblots were reacted with anti-DAP-kinase monoclonal antibodies (Sigma) and with anti-vinculin antibodies (Sigma). The endogenous levels of DAP-kinase in A9-F cells were used as a positive reference.
Figure 22:
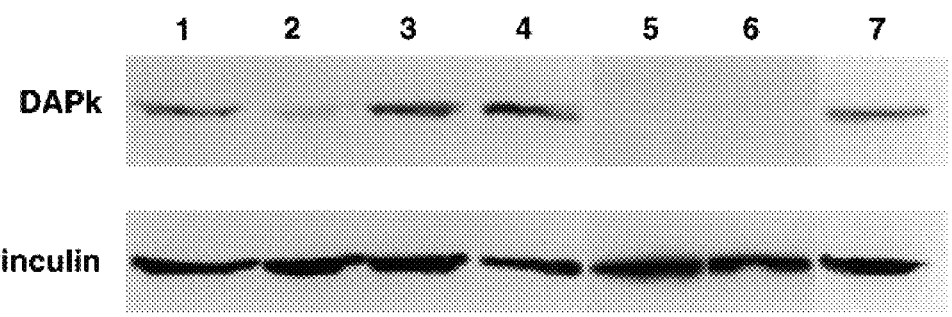

FIG. 22 shows immunoblot analysis for DAP-kinase protein levels of clone 28-DAPk, as in FIG. 16. The expression was tested both in the original clone used for the I.F.P. and I.V. injections (lanes 1 and 3, respectively) and in tumor cells that were re-cultured from the lungs of injected mice. The latter cell cultures were recovered either from the multiple spontaneous lung nodules that appeared 35 days post surgery (lane 2) or from the very few nodules that appeared in the experimental metastasis assays (lane 4).

The DAP-kinase levels were below detection limits in the 4-cont.-transfected clone both before injections as well as after recovery of tumor cells from the spontaneous lung lesions (lanes 5 and 6, respectively), confirming that the tumor cells were not contaminated with surrounding DAP-kinase positive primary lung cells. Lane 7 displays the expression levels of endogenous DAP-kinase in the low metastatic clone A9-F.

Figure 23:
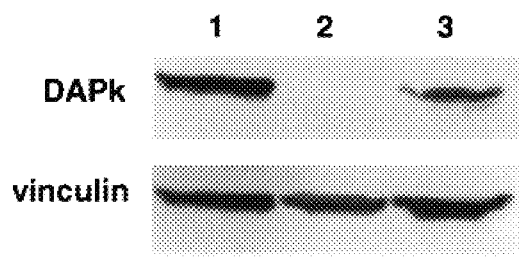

FIG. 23 shows immunoblot analysis of clone 42-DAPk tested before and after its recovery in culture from the spontaneous lung metastases formed 34 days post foot amputations (lanes 1 and 2, respectively). Lane 3 shows the expression levels of endogenous DAP-kinase in the low metastatic clone A9-F.

Figure 24:
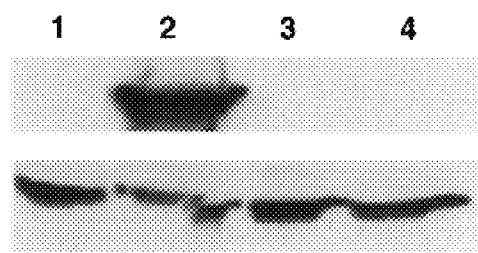

FIG. 24 shows an immunoblot analysis of cell cultures released from spontaneous lung metastatic lesions, formed after the I.F.P. injections of clone 28-DAPk. The cultures were treated in vitro with 10 µM 5-aza-2'-deoxycytidine for 24 hours. The non-treated and drug-treated cultures were tested for DAP-kinase protein expression either on day 3 (lanes 1 and 2, respectively) or on day 14 post treatment (lanes 3 and 4, respectively).

Figure 25:
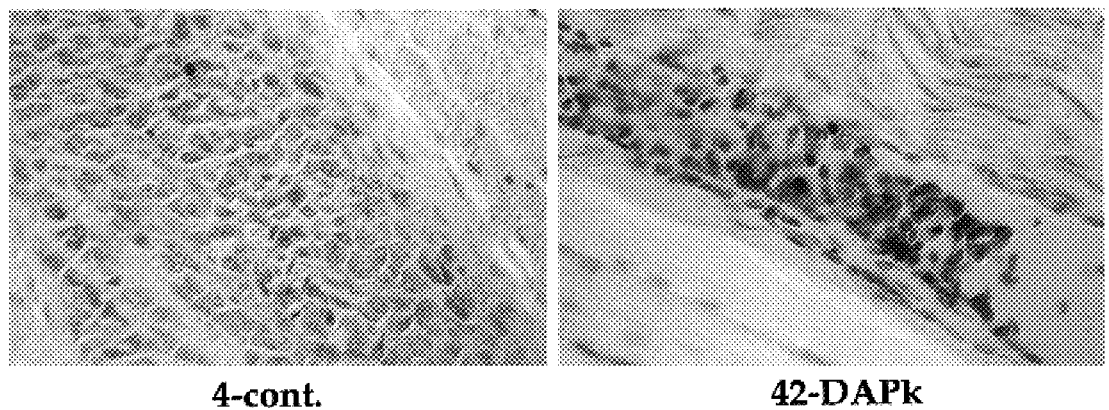

FIG. 25 shows in situ TUNEL staining of footpad sections prepared on day 5 after local injection of $2 \times 10^5$ 4-cont. cells (left-hand photograph) or 42-DAPk cells (right-hand photograph). Peroxidase staining of fragmented DNA and counterstaining of the sections of methyl green dye were performed according to the manufacturer's instructions (ApopTag® Plus Peroxidase Kit; Oncor, Gaithersburg). Scale bar, 100 µm.

Figure 26:
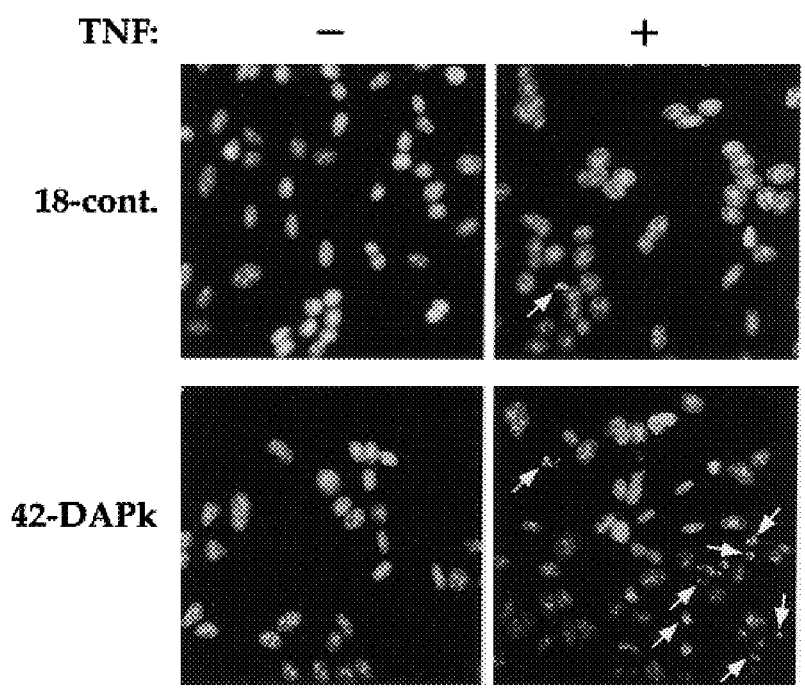

FIG. 26 shows DAPI staining of the nuclei before and after treatment with TNF-α. Exponentially growing cells corresponding to 18-cont. and 42-DAPk transfectants were treated with a combination of murine TNF-α (100 ng/ml; R&D systems, Minneapolis) and cycloheximide (5 µg/ml; Sigma) (right panels marked by +), or with cycloheximide alone (left panels marked by −). DAPI staining was performed after 6 hours. The arrows point to apoptotic nuclei.

Figures 27, 28:
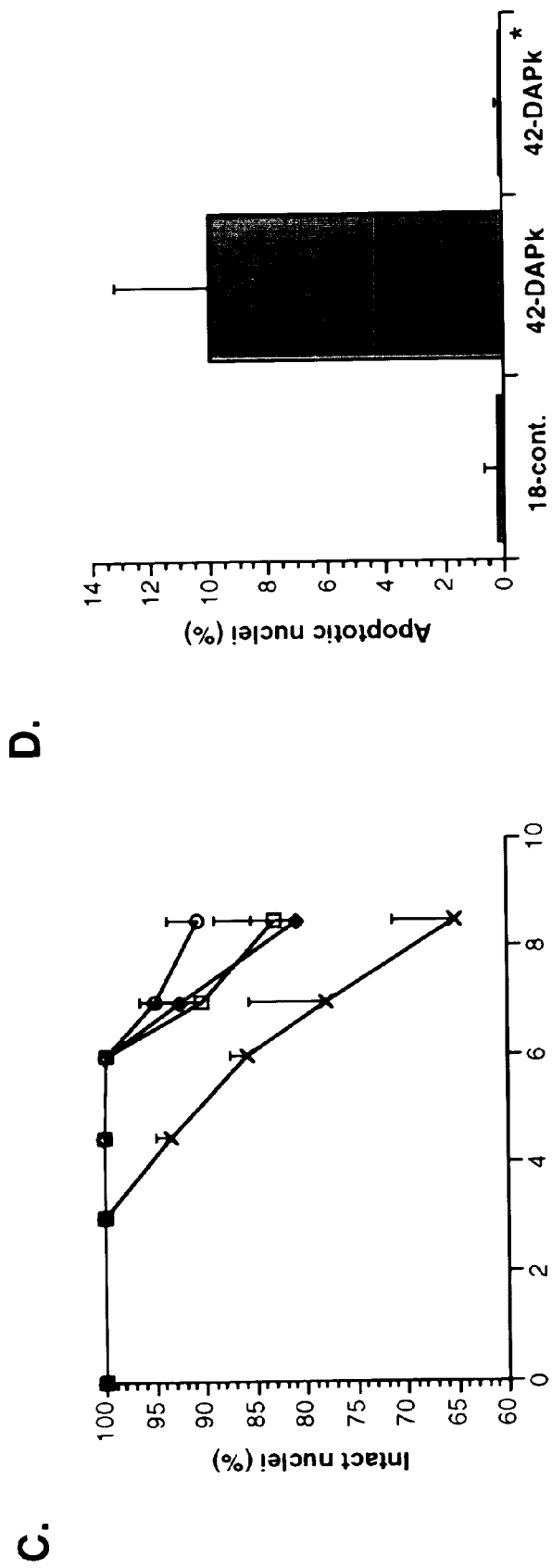

FIG. 27 illustrates time kinetics of killing by TNF-α. The conditions of treatment with TNF-α and cycloheximide and assessment of apoptotic nuclei by DAPI staining were as in FIG. 26. The 42-DAPk transfectants (X) were compared in this assay to the parental D122 cells (○), to 4-cont. (□) and to 18-cont. (◊). The values are the mean of percent of intact nuclei±SD counted by scoring 5 different fields, 100 total nuclei in each field, at the indicated time points.

The differences between 42-DAPk and 4-cont. clones were significant at $P<<0.001$ both at the 4.5 and 6 hours time points, and at $0.005<P<0.001$ with respect to the 7 hours time point.

FIG. 28 shows the results of assays of response to TNF-α and cycloheximide as described in FIGS. 26 and 27. The original 42-DAPk clone was compared to the cultures recovered from the spontaneous lung metastases described in FIG. 23 (named here 42-DAPk*). Values are mean of percent apoptotic nuclei±SD counted by scoring 5 different fields, 100 total nuclei in each field at 6 hours after exposure to the double treatment.

The results show that in vivo selection for attenuated DAP-kinase expression ablates the increased sensitivity of clone 42-DAPk to TNF-α.

Figure 29:
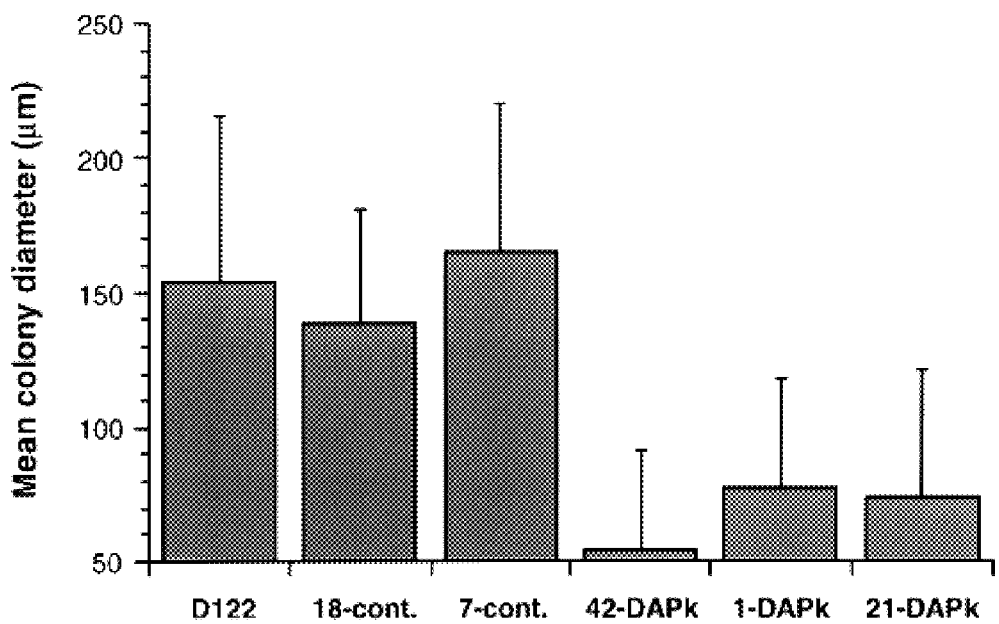

FIG. 29 shows the growth of the D122-transfectants in a semi-solid medium under anchorage-independent conditions. The different clones were cultured in 0.33% soft agar (Bacto-agar; Difco) at an initial cell number of $5 \times 10^3$ cells per 6 cm plate, on top of a layer containing 0.5% agar. The diameters of the clones that appeared on day 7 were measured under a light microscope. Values are the mean colony diameter of 100 clones from each group±SD.

Clones 1-DAPk and 21-DAPk expressed exogenous DAP-kinase protein at levels which were comparable to clone 28-DAPk (FIG. 16). The difference between the controls (e.g., 18-cont.) and the DAP-kinase-transfectants (e.g., 1-DAPk) was significant at $P<<0.001$.

Figure 30:
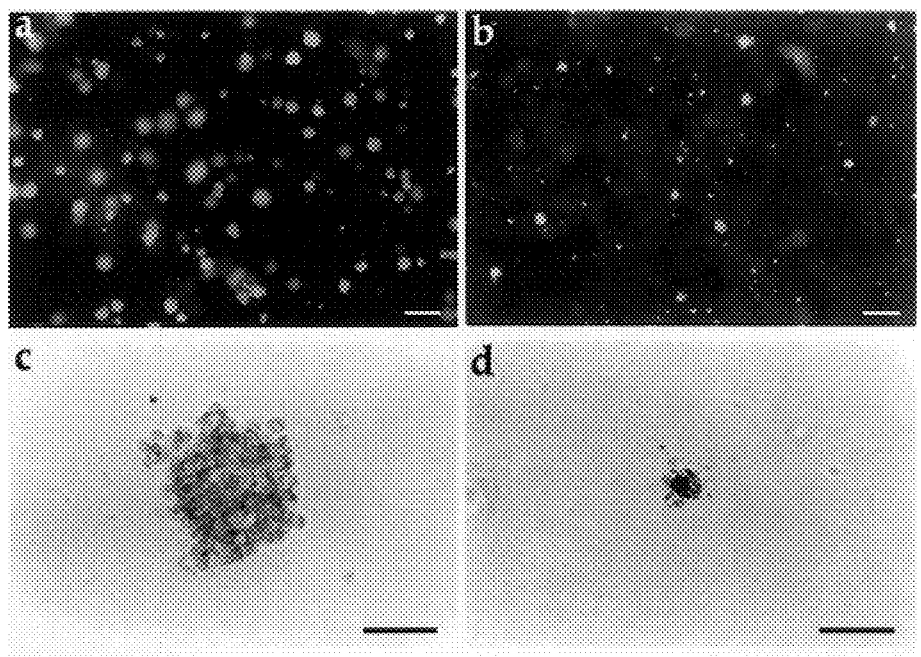

FIG. 30 shows microscopy of the clones cultured in soft agar for seven days as in FIG. 29, comparing the parental D122 cells (left: a,c) to DAPk-42 cells (right: b,d). The bars correspond to 350 µm in the upper panels (a,b) and to 80 µm in the lower panels (c,d).

Figure 31:
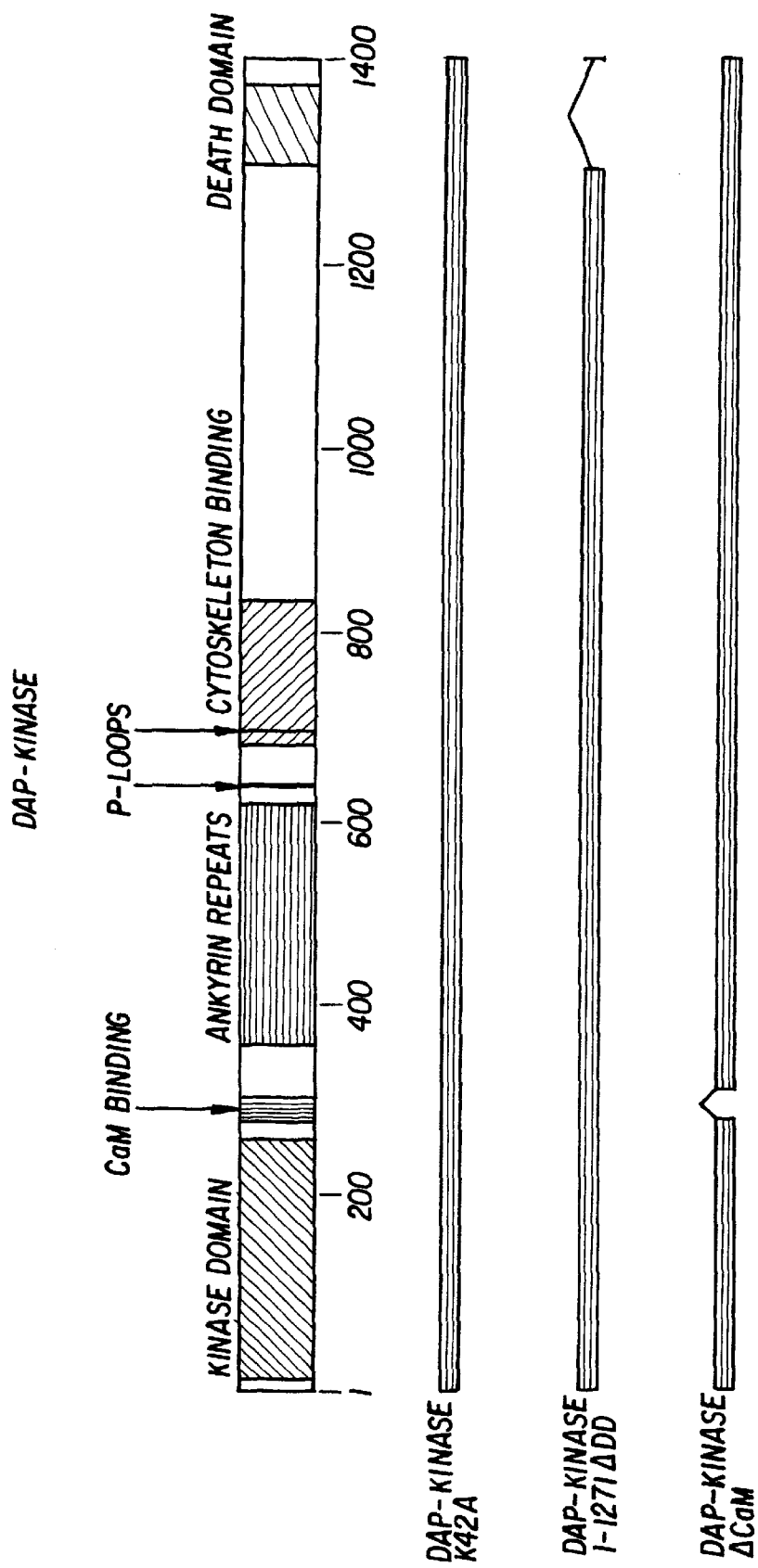

FIG. 31 is a schematic representation of DAP-kinase and its mutants used in these studies. The various motifs and domains as predicted by the deduced amino acid sequence and/or experimental work are shown. The numbers below indicate the amino acid positions. The K42A, ΔCaM and (1-1271)ΔDD mutants are presented schematically below.

Figure 32:
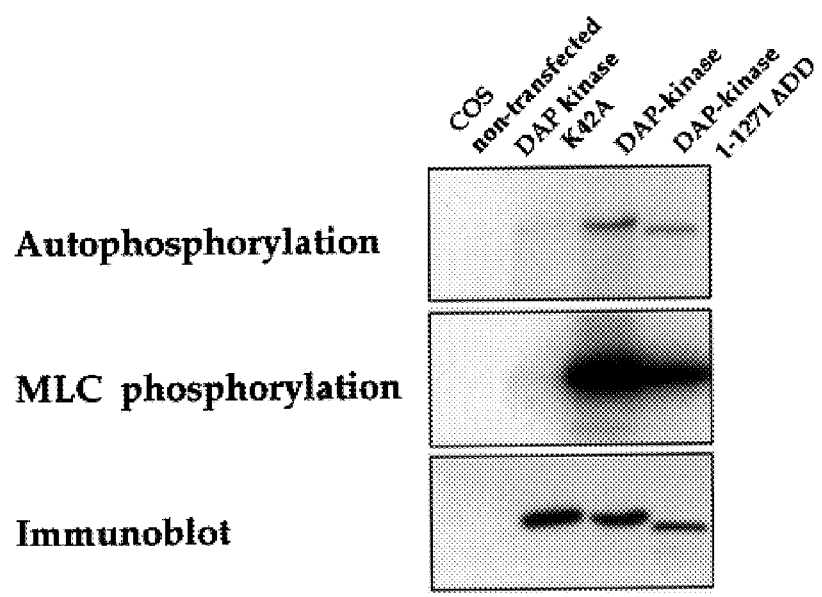

FIG. 32 shows in-vitro kinase activity of the DAP-kinase. DAP-kinase or DAP-kinase mutant proteins were assayed in-vitro for kinase activity in the presence of $Ca^{2+}$/CaM and MLC as described below. The proteins were run on 11% SDS-PAGE and blotted to nitrocellulose membrane. The upper and the middle panels show the autophosphorylation of DAP-kinase and MLC phosphorylation, respectively, as seen after exposure to X-ray film. The lower panel shows the DAP-kinase proteins by incubation of the same blot with anti-FLAG antibodies and ECL detection.

Figure 33:
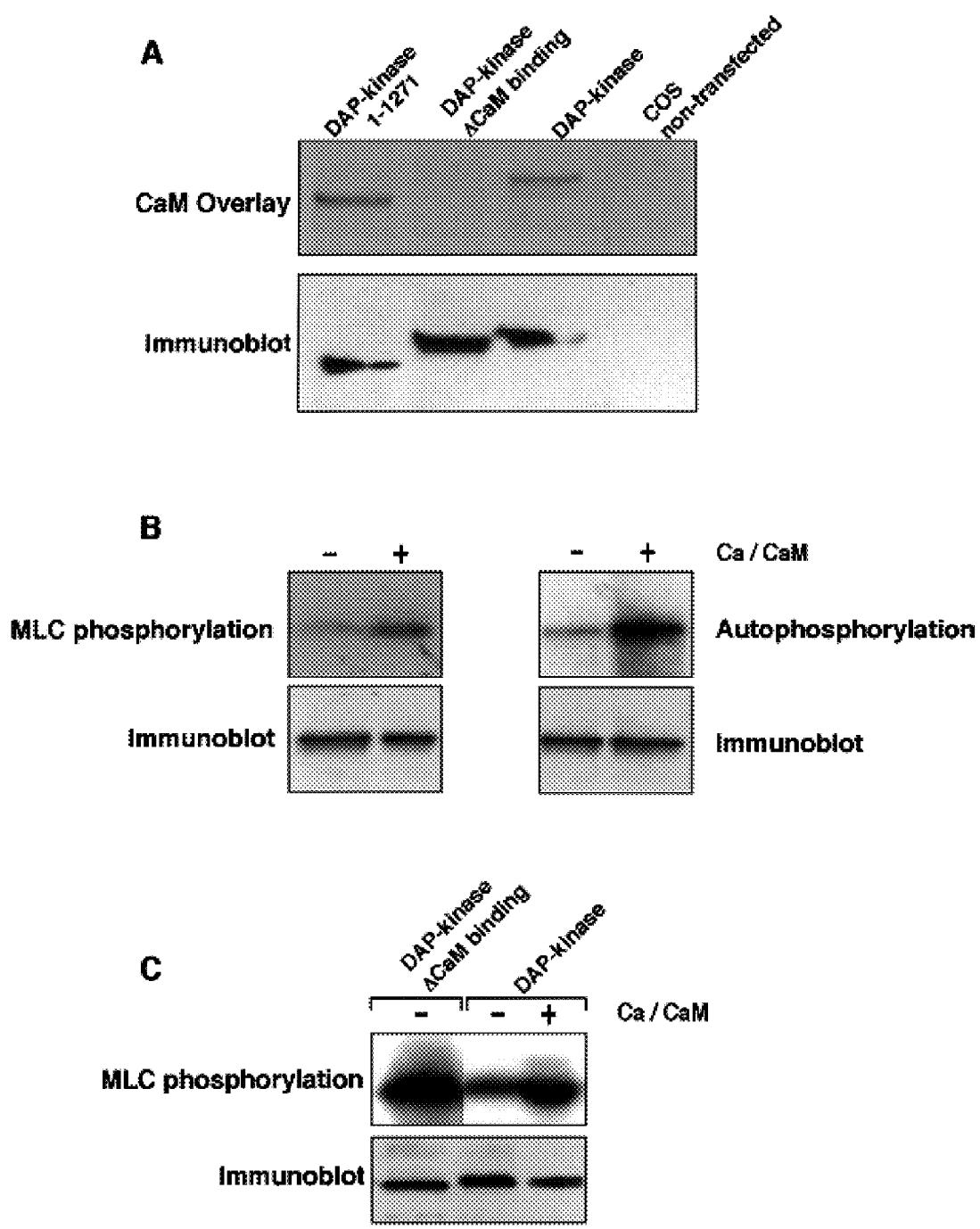

FIGS. 33A–33C show that DAP-kinase binds calmodulin and its activity is regulated by calcium/calmodulin.

FIG. 33A shows a calmodulin overlay on DAP-kinase. The upper panel displays the results of hybridization with $^{35}$S-met labeled recombinant CaM. The lower panel shows the results of hybridization of the same blot with anti-FLAG antibodies to detect the DAP-kinase protein.

FIG. 33B shows $Ca^{2+}$/CaM regulation of DAP-kinase activity. DAP-kinase was subjected to in-vitro kinase assay as described below, in the presence or absence of $Ca^{2+}$ and CaM (reaction was stopped after 15 min. for detecting the autophosphorylation, or after 2 min. to measure MLC phosphorylation). The lower panels shows the results of incubation with anti-FLAG antibodies (in the same blot).

FIG. 33C shows DAP-kinase DCaM activity is maximal in the absence of $Ca^{2+}$ΔCaM. Details are as in (33B).

Figure 34:
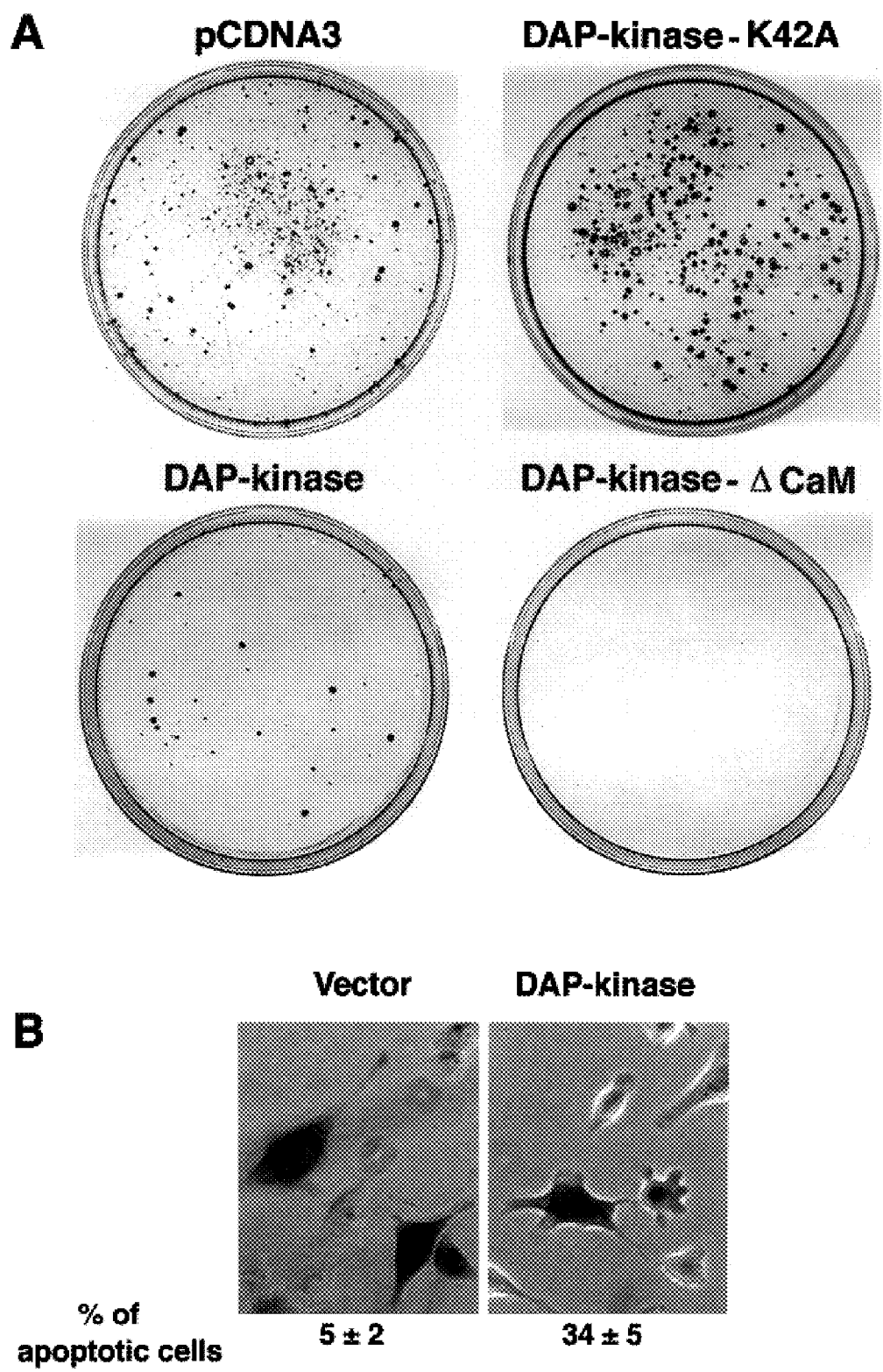

FIGS. 34A & 34B illustrate how ectopic expression of DAP-kinase induces cell death.

FIGS. 34A shows HeLa cells ($5 \times 10^5$ cells/plate) were transfected with 20 µg DNA of pcDNA3 vector or with DAP-kinase constructs cloned into the same vector. After 48 hours, the cell cultures were split 1:5 and subjected to selection with G-418. After 2–3 weeks the plates were stained with crystal-violet.

FIG. 34B shows HeLa cells ($5 \times 10^5$ cells/plate) were transfected with 20 µg DNA of the empty pSBC-bl plasmid, or with the vector which carries the wild-type DAP-kinase. The cells were grown for 48 hours in the absence of tetracycline and stained with X-Gal solution. The frequency of blue cells with an apoptotic rounded morphology was assessed by counting 600 total blue cells from 6 different fields coming from duplicate transfections. The arrow points to a transfected dying cell.

Figure 35B:
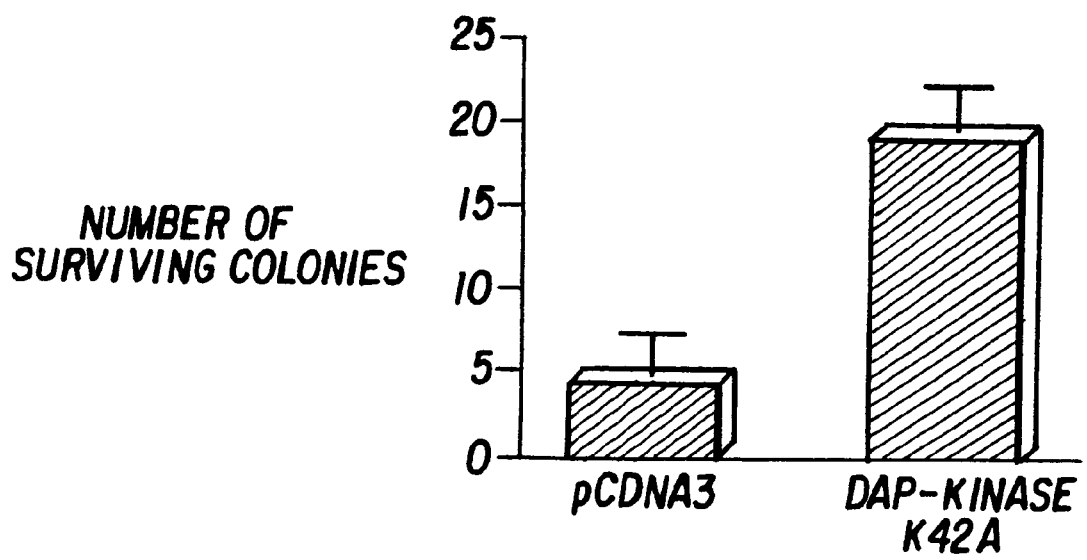

FIGS. 35A & 35B illustrate how a DAP-kinase K42A mutant protects HeLa cells from the IFN-γ-induced cell death.

FIG. 35A shows HeLa cells (5×10$^5$ cells/plate) were transfected with 20 μg DNA of empty pcDNA3 vector or DAP-kinase-K42A cloned into the same vector. After 48 hours, the cells were split 1:5 and subjected to selection with G-418 and 200 U/ml of IFN-γ. After 2–3 weeks of selection the plates were stained with crystal-violet. Pictures were taken under light microscopy using Kodak TMXIOO film (magnification ×40).

FIG. 35B shows number of surviving colonies per 1 cm$^2$ was counted and normalized according to the number of colonies appearing in G-418 selections which were performed in the absence of IFN-γ. Values represent the average of ten representative fields.

FIGS. 36A–36D illustrate analysis of DAP-kinase expression in various hematopoietic cell lines.

FIG. 36A shows a Northern blot analysis of poly A+RNA from various cell lines using probes for DAP-kinase.

FIG. 36B shows a Northern blot analysis of poly A+RNH from various cell line using probes for c-Abl.

FIG. 36C shows a: Western blot analysis of DAP-kinase protein.

FIG. 36D shows a Western blot analysis of vinculin as an unrelated protein reference.

Figure 37:
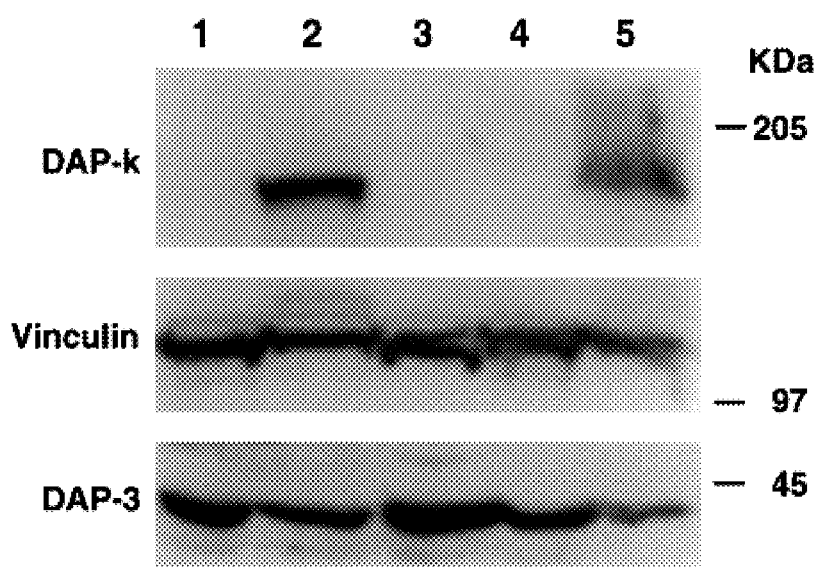

FIG. 37 shows Western blot analysis of DAP-kinase in the bladder carcinoma cell lines T24 and HT1376 treated with 5-azadeoxycytidine. Protein extracts were loaded as follows: Lane 1 and 4- T24 and HT1376 bladder carcinoma cells non-treated, respectively; lanes 2 and 5- T24 and HT1376 bladder carcinoma cells, treated with 5-azadeoxycytidine and collected after 2 passages without treatment, respectively. Lane 3- T24 bladder carcinoma cells collected after 6 passages without treatment. The same blots were reacted with anti-vinculin and anti-DAP3 antibodies.

Figure 38:
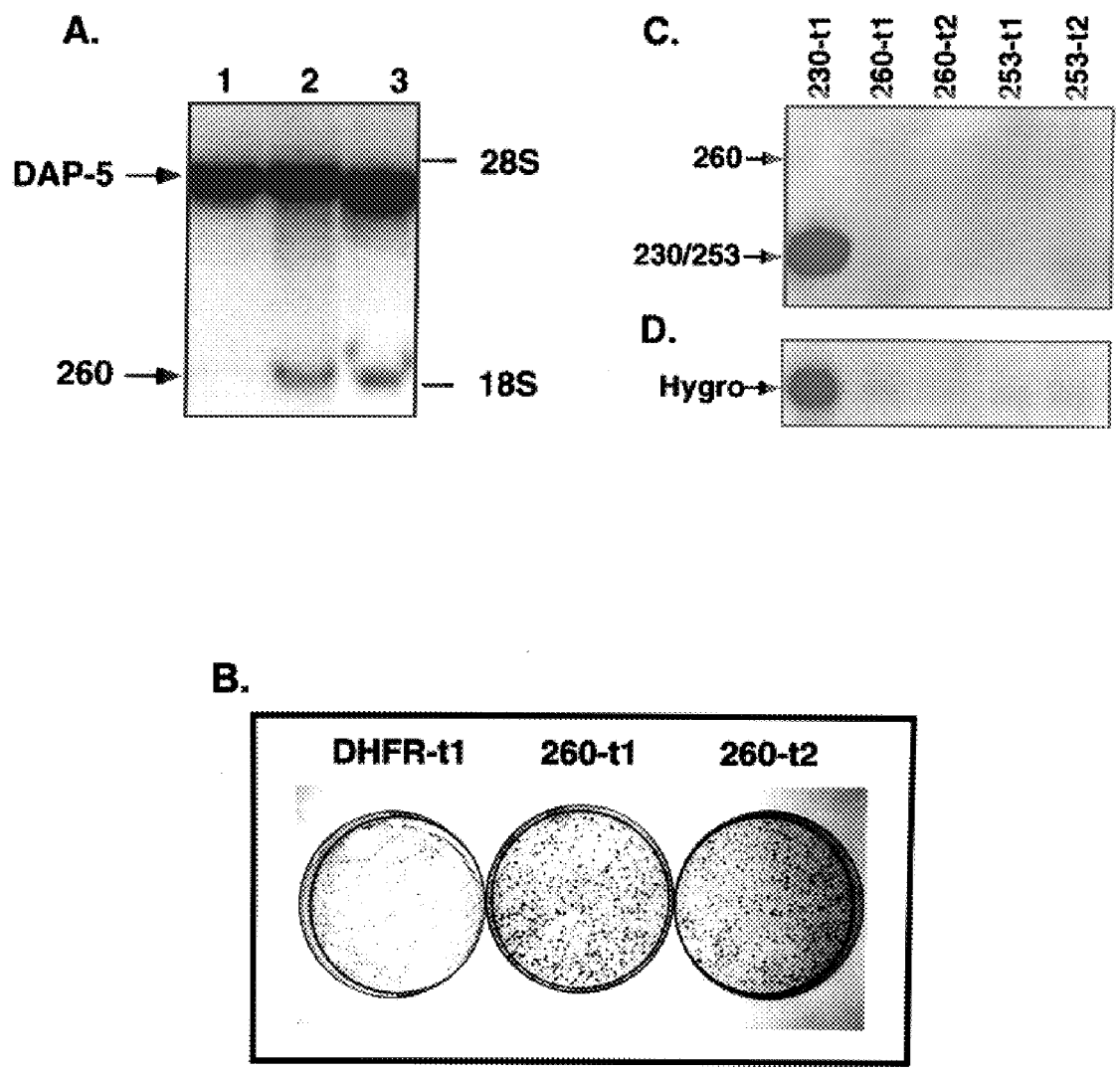

FIGS. 38A–38C show that the DAP-5 763 bp fragment is expressed in HeLa cells at very low levels, as compared to subgroup I cDNA fragment.

FIG. 38(A) shows a Northern blot analysis of RNA from pTKO1-260 or pTKO1-DHFR transfected cells. RNA was extracted from the indicated HeLa cells. The Northern blot containing 20 μg of total RNA samples was hybridized with the DAP-5 763 bp fragment (#260). 1. DHFR-t1; 2. 260-t1; 3. 260-t2.

FIG. 38B shows a IFN-γ resistant phenotype of HeLa cells transfected with pTKO1-260. HeLa cells were transfected with either control vector pTKO1-DHFR or with the isolated pTKO1-260. Pools of more than 10$^4$ independent clones were first selected with hygromycin B to generate polyclonal populations of stably transfected cells. These pools were plated in 9 cm plates (100,000 cells per plate) and double selected with IFN-γ (1000 units/ml) and hygromycin B (200 μg/ml). After 4 weeks of selection, the cells were stained with crystal-violet. In the absence of IFN-γ these plates reach confluency after 4 days.

FIG. 38C shows a comparison of the expression levels of RNAs from subgroup I and II. 260-t1 and 260-t2 represent the same extracts used in 38A. The Northern blot containing 20 μg of RNA samples was hybridized with the BglII-BamHI fragment containing the SV-40 splice and polyadenylation signal (Deiss & Kimchi, 1991) which is part of the SV-40 promoter driven, #260 containing, mRNA expressed from the episome. D. Same as in 5C but hybridized with a probe recognizing the hygromycin B resistance gene driven by the TK promoter.

FIGS. 39A & 39B show β-galactosidase activity assays of HeLa-tTA cells transfected with the DAP-5 763 bp fragment or its mutated versions.

Stable polyclonal populations transfected with the pSBc-bl vector (control), with the pSBc-bl-260 (260), or with the pSBc-bl vector harboring either the single or the triple ATG #260 mutant were established by selection with 10 μg/ml bleomycin. After two weeks the drug was removed and cultures were further expanded. Growing cells were fixed with 3% paraformaldehyde for 5 minutes, rinsed twice with PBS and checked for β-galactosidase activity using the X-gal as a substrate. Photography was done under phase microscopy using Kodak Ectachrome 160T.

FIGS. 40A & 40B show in vitro translation of the DAP-5 763 bp fragment and immunoblot analysis of the mini-protein in cells expressing the #260 fragment.

FIG. 40A shows an in vitro translation of RNA transcribed from Bluescript vector harboring various DAP-5 versions was done in rabbit reticulocyte lysates. The resulting $^{35}$S labeled proteins were fractionated on 12.5% SDS-PAGE. The position of radioactive molecular mass markers (Amersham) are marked. 1. non-programmed rabbit reticulocyte lysates; 2. Full length DAP-5 3.8 kb clone; 3. DAP-5 763 bp fragment (#260); 4. mutated #260 fragment: ATG at position 1785 converted to AAG (single ATG mutant); 5. mutated #260 fragment: ATG at position 2010 was converted to TTC and ATG at position 2040 to ATC; 6. triple ATG mutant harboring all the above mentioned mutations. The position of the translated mini-protein is marked by an arrow; the additional higher bands are non-specific background that often appears also in non-programmed reticulocyte lysates.

FIG. 40B shows HeLa-tTA cells transfected with either the pSBc-bl vector or the pSBc-1 vector harboring the #260 fragment were lysed and fractionated on 10% SDS-PAGE, blotted onto nitrocellulose and reacted with affinity purified polyclonal antibodies (1:20 dilution) raised against a GST-fused recombinant product. The arrow points the position of the DAP-5 mini—protein specific doublet that had an approximate size of 28 kDa.

FIGS. 41A, 41B, 41C & 41D show Involvement of cathepsin D protease in IFN-γ mediated cell death.

(41A). Protection from IFN-γ induced cell death by anti-sense RNA expression. (a) One of the DHFR-transfected polyclonal cell populations (squares) and of the anti-cath-D-transfected polyclonal cell populations (circles) were treated with IFN-γ (1000 U/ml; filled symbols) or left untreated (open symbols). Viable cells were stained with neutral-red and the dye uptake was measured at $\lambda_{540\ nm}$. Each point represents an average of a quadruplicate determination. (b) Two independent DHFR-transfected polyclonal cell populations (open and filled squares) and a pair of anti-cath-D-transfected polyclonal cell populations (open and filled circles) were treated with IFN-γ (1000 U/ml) or left untreated. Fraction of viable cells was determined by comparing neutral red dye uptake of IFN-γ treated cells to non-treated cultures at the indicated time points. Each point represents an average of a quadruplicate determination±S.E.

(41B) Regrowth of viable cells after withdrawal of IFN-γ (1000 U/ml) from DHFR and anti-cath-D transfectants. Cells were seeded at an initial density of 10,000 cells/cm$^2$, treated with a combination of hygromycin B and IFN-γ (1000 U/ml) for two weeks, washed and stained with crystal violet 7 days later.

(41C) Protection from IFN-γ-induced cell death by pepstatin A. The HeLa cells (DHFR and anti-cath-D transfectants), were incubated for 8 days with IFN-γ (1000 U/ml) either in the presence of pepstatin A (10$^{-4}$M in 0.2% DMSO) or in its absence (0.2% DMSO alone). The DHFR-transfected cells were also tested for responsiveness to pepstatin A in the absence of IFN-γ. Data are given as mean neutral-red dye uptake from quadruplicate samples±S.E.

(41D) Light microscopy of HeLa cells on day 8 of IFN-γ-treatment : (a) DHFR transfectants with no inhibitor; (b) anti-cath-D transfectants cultured in the presence of pepstatin A (Magnification, 200×).

FIGS. 42A, 42B, 42C & 42D show regulation of expression and processing of cathepsin D protease by IFN-γ and TNF-α.

(42A & B) Immunoblot analysis of cathepsin D forms before and after treatment with IFN-γ (1000 U/ml). Cell lysates were prepared at the indicated time points from parental HeLa cells (A) and from DHFR and anti-cath-D transfectants (B). Samples of 300 μg were fractionated on SDS-polyacrylamide gels (12%) blotted to nitrocellulose, and detected using the ECL system (Amersham). The sizes of cathepsin D forms are shown. The same blots were reacted with polyclonal antibodies generated against the copper zinc superoxide dismutase (SOD) to correct for possible differences in protein amounts in each slot.

(42C) A scheme that depicts the different steps of cathepsin D processing as previously reported for rat cathepsin D (Fujita et al., 1991, BBRC 179:190–196).

(42D) Immunoblot analysis of cathepsin D forms before (lane 1) and after treatment of U937 with TNF-α (lanes 2 and 3; 24 and 48 hours, respectively ).

Figure 43A:
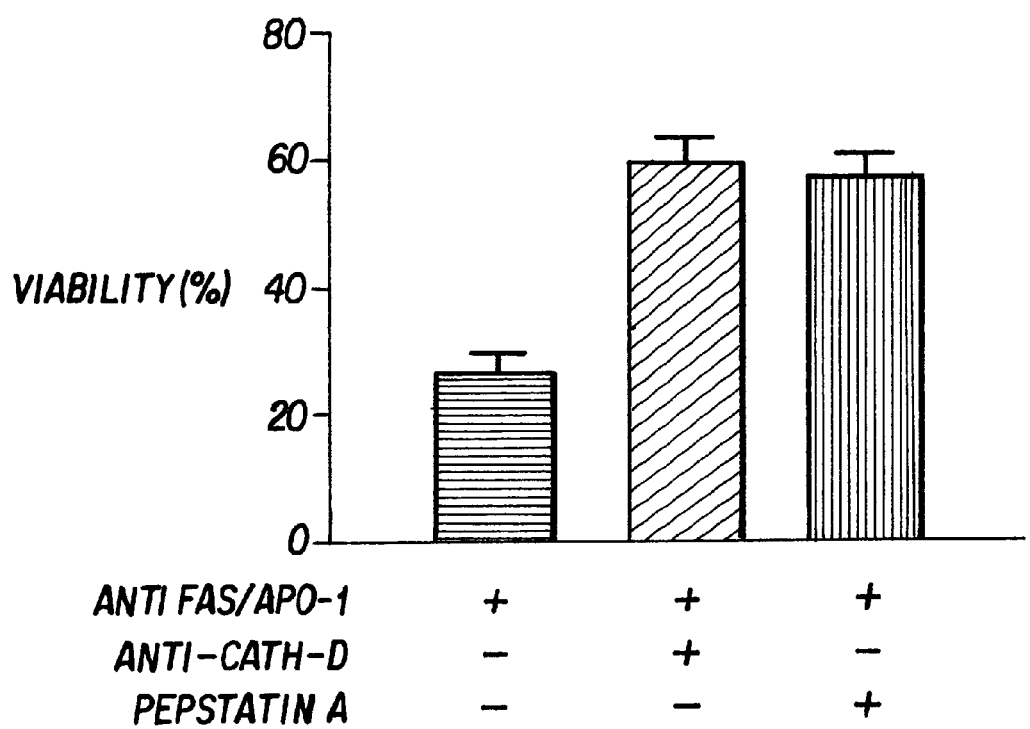
Figure 43B:
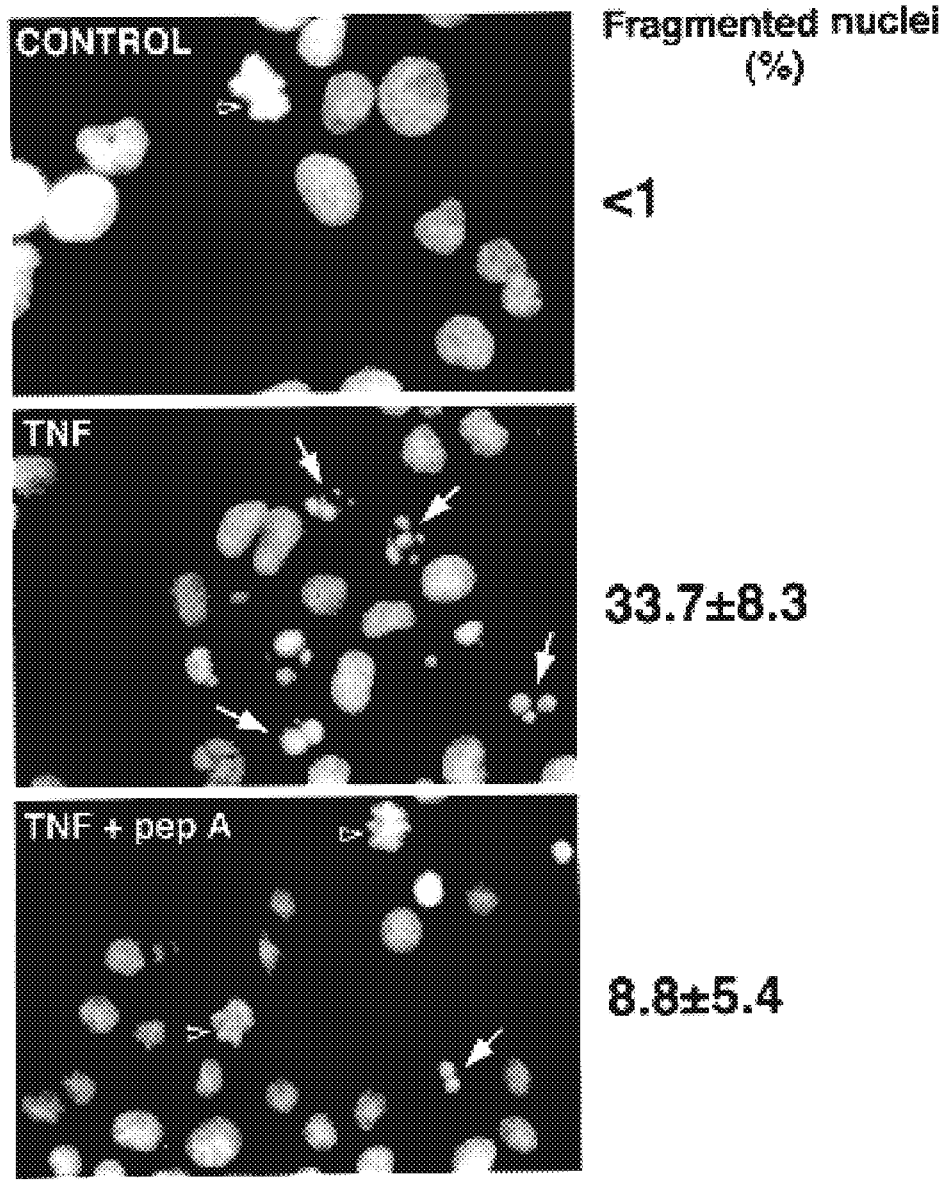

FIGS. 43A and 43B show involvement of cathepsin D protease in Fas/APO-1, and TNF-α mediated cell death.

(43A) Suppression of Fas/APO-1-mediated cell death by anti-cathepsin D RNA or by pepstatin A. The HeLa cells (DHFR and anti-cath-D transfectants; 20,000 cells per microtiter well), were exposed to anti-APO-1 antibodies for 40 hours as described below. Pepstatin A ($10^{-4}$M in 0.2% DMSO) was added where indicated to the DHFR transfectants 20 hours before their exposure to the anti-APO-1 antibodies. Viability was assessed by the neutral red assays in quadruplicate samples; results are expressed as percent of dye uptake at the end of each treatment out of the total uptake in the corresponding control wells, which were not exposed to the antibodies (100% viability).

(43B) Pepstatin A interferes with the TNF-α-induced apoptotic cell death in U937 cells. The cells were seeded at a density of $2 \times 10^5$ cells/ml, 24 hours after their preincubation with pepstatin A ($10^{-4}$M in 1% DMSO) or with DMSO alone. Where indicated, TNF-α (100 U/ml; 10 ng/ml) was added and 6 hours later samples were cytospinned on glass slides and stained with DAPI (0.5 μg/ml, Sigma). Microscopy was performed under fluorescent light conditions (Magnification, 1000×). Nuclei with fragmented chromatin are indicated by arrows; empty arrowhead point to mitotic nuclei. Data are presented as the percentage of cells with a fragmented nuclear morphology±S.E. For each condition a minimum of 400 cells in 14 separate fields were scored.

FIGS. 44A, 44B, 44C & 44D show that ectopic expression of cathepsin D reduces cell viability.

(44A & B) X-Gal staining of HeLa cells co-transfected with lacZ (driven by CMV promoter) and either with the cathepsin D cDNA (driven by a tetracycline-repressible promoter) or with the control vector. In both cases cells were cultured in the absence of tetracycline and stained after 48 hours with X-Gal solution for 3 hours. Light microscopy micrographs are shown (magnification, 200×). Examples of normal blue-stained cells (in A) and of apoptotic blue-stained cells (in B) are indicated by arrows.

(44C) The frequency of blue cells with an apoptotic rounded morphology was assessed by counting 800 total blue cells from 8 different fields coming from duplicate transfections (described in A and B).

(44D) Assessment of secreted alkaline phosphatase (SEAP) in the growth medium of HeLa cells, co-transfected with SEAP and with either the control vector or the above-mentioned cathepsin D vector; each transfection was divided into two plates, one of which was immediately supplemented with tetracycline (1.5 μg/ml). SEAP activity secreted into the growth medium during the last 5 h of incubation was determined 48 hours after transfections. Data of SEAP activity were obtained in duplicates from four experiments. The values give the percentage of SEAP activity measured in the absence of tetracycline out of total activity produced in the presence of tetracyline.

Figure 45:
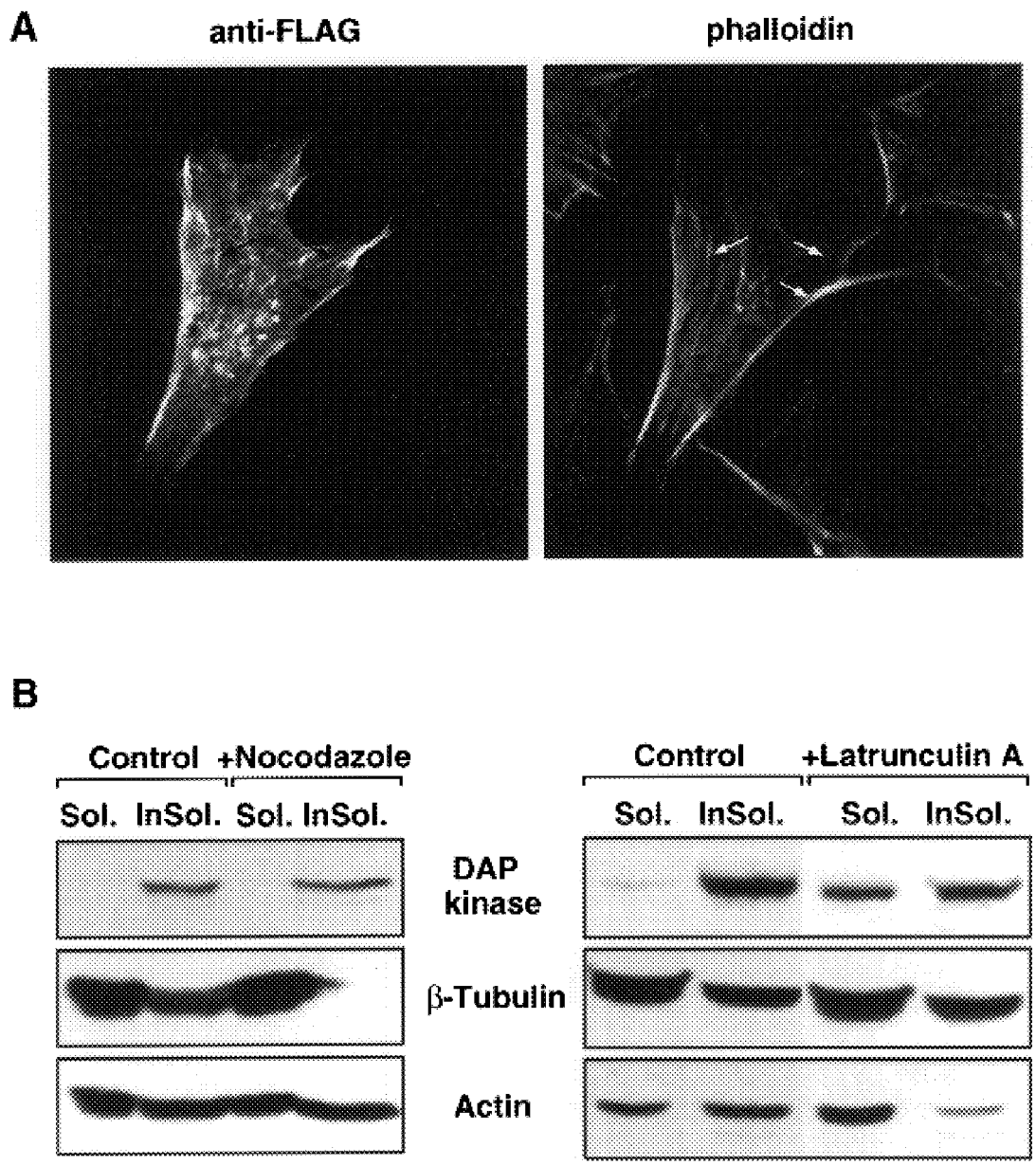

FIGS. 45A & 45B show how DAP-kinase is localized to the cytoskeleton.

FIG. 45A shows SV-80 cells transiently transfected with DAP-kinase-K42A were stained at 48 hours with anti-FLAG antibodies and fluoresceine-conjugated phalloidin as described below. Both pictures represent the same field (magnification×400).

FIG. 45B shows detergent extraction of HeLa cells. HeLa cells were extracted with 0.5% triton X-100 to soluble fraction (Sol) and insoluble fraction (InSol) as described below. The protein extracts were separated on 10% SDS-PAGE and blotted onto nitrocellulose membrane. The membrane was reacted with anti-DAP-kinase monoclonal antibodies, anti-tubulin antibodies and anti-actin antibodies as indicated.

FIGS. 46A & 46B illustrate mapping of the region responsible for cytoskeletal binding.

FIG. 46A shows immunostaining of recombinant DAP-kinase. COS cells, transfected with pECE-FLAG—DAP-kinase, were immunostained with anti-FLAG monoclonal antibodies as described below (Magnification×400).

FIG. 46B shows COS cells were transfected with pECE or pCDNA3 vectors carrying either DAP-kinase or DAP-kinase deletion mutants as indicated. The cells were extracted with 0.5% Triton X-100 as described in FIG. 45. Detection was carried out with anti-FLAG antibodies. Sol—soluble fraction, InSol—detergent insoluble fraction. Schematic representation of DAP-kinase deletion mutants is shown at the left.

Figure 47:
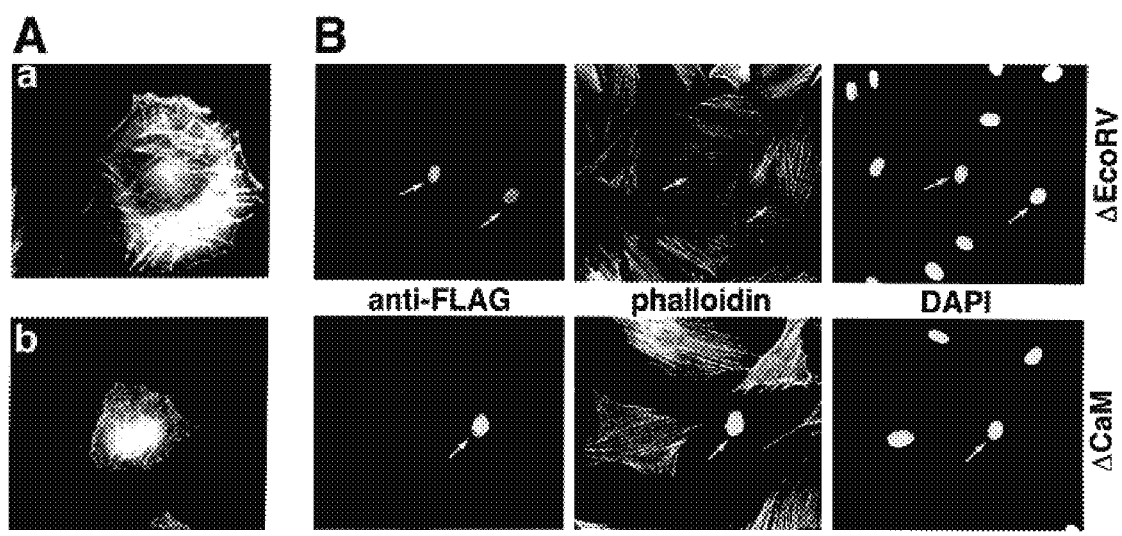

FIGS. 47A & 47B show changes in actin cytoskeletal organization in the IFN-γ-induced cell death and upon ectopic expression of constitutive DAP-kinase.

FIG. 47A shows HeLa cells, grown on glass coverslips, were treated with IFN-γ (1000 U/ml) (b) or were left untreated (a). After 4 days the cells were stained with fluorescein-conjugated phalloidin (magnification×1000).

FIG. 47B shows REF-52 cells were transiently transfected with DAP-kinase mutants as indicated. After 48 hours the cells were triple stained with anti-FLAG antibodies, fluorescein-conjugated phalloidin and DAPI as described below (magnification×100). The arrows point to the transfected cells.

DETAILED DESCRIPTION OF THE INVENTION

I. Isolation of Antisense cDNA's that Protect Cells from the Cytotoxic Effects of IFN-γ

(A) Experimental Procedure (A₁) Obtaining cDNA Clones

A cDNA library (100 μg DNA) was generated from a mixture of mRNA's harvested before and at 1, 2, 4, 12, 24 and 48 hours after treatment of HeLa cells with IFN-γ (200 U/ml). It was cloned in antisense orientation into the EBV-based pTKO1 expression vector, as previously described in detail (Deiss and Kimchi, supra). The resulting expression library of about $10^5$ independent clones was introduced into $8 \times 10^6$ HeLa cells ($10^6$ cells per 9 cm plate) by the calcium phosphate transfection technique. In order to determine the efficacy of transfection, a fraction of the transfectants was selected with hygromycin B (200 βg/ml, Calbiochem). The resulted efficacy was around 5%. In parallel, the majority of the transfected cells were plated at a cell density of 1500 cells per cm² and were selected with both hygromycin B (200 μg/ml) and IFN-γ (750 U/ml). Selective media was changed every 3–4 days. After 28 days the cells that survived and/or grew in the presence of IFN-γ were expanded for 2 weeks and pooled. The extrachromosal DNA was obtained according to the method of Hirt (Hirt, B. (1967) *J. Mol. Biol.*, 26:365), cleaved with the restriction enzyme DpnI and introduced into *Escherichia coli* HB101 host cells. The cleavage with DpnI ensured that only episomal DNA that have replicated in HeLa cells was transfected into bacteria.

A few bacterial clones were obtained by the above procedure which included DNA antisense sequences, some of which were able to protect the cells from the death-promoting effects of IFN-γ.

(A₂) Classification of the Antisense cDNA Clones

Plasmid DNAs were prepared from 10 individual bacterial clones. PCR amplified cDNA inserts were generated from each plasmid using specific primers that correspond to the immediate flanking sequence of the cDNA insertion sites in the pTKO1 vector. The size of the cDNA inserts ranged between 300 to 800 bp. The PCR fragments were used as labeled probes to search on Southern blots for possible cross hybridization between some of the rescued antisense cDNA clones.

(B) Results (B₁) Classification of Clones

The above 10 cDNA clones were classified into six distinct non-overlapping groups, some constituting several members (clones) and some constituting of a single member. Those clones relevant for the present invention are shown in the following Table 1:

TABLE 1

Initial characterization of antisense cDNA clones rescued from IFN-γ-treated HeLa cells

| No. | antisense cDNA clones | cDNA length (bp) | mRNA size (Kb) | DNA product |
|---|---|---|---|---|
| 1. | 230, 254, 255, 264, 258 | 320 | 2.4 | DAP-1 |
| 2. | 256 | 367 | 6.3 | DAP-2 (kinase) |
| 3. | 259 | 252 | 1.7 | DAP-3 |
| 4. | 253 | 200 | 4.5 | DAP-4 |
| 5. | 260 | 763 | 3.8 | DAP-5 |
| 6. | 229 | 370 | 2.5 | Cathepsin D |

Inserts 230, 254, 255, 264 and 258 of group 1 seemed to be completely identical to one another. The PCR fragments were sequenced and the results were compared with sequences present in the EMBA nucleic acid database. All inserts of groups 1 through 5 were found to be novel.

(B₂) Detection of mRNA

The DNA fragments thus obtained were used to detect and determine the expression level in HeLa cells of mRNA which hybridized to these fragments. 20 μg of total RNA from the parental HeLa cells were fractionated on gels, blotted and reacted with the different probes. Each probe recognized a single mRNA transcript of a different size (Table 1). Expression levels of mRNA's reactive with group 2 were low while those reactive with group 1 were relatively high.

II. Second Transfection by Isolated Antisense cDNA Levels of Expression of Antisense RNA in Secondary Transfectants (A) Experimental Procedure To ensure that the above isolated antisense cDNA's are sufficient in order to protect cells from the death promoting effects of IFN-γ, subconfluent monolayers of HeLa cells were transfected with 40 μg DNA of the individual rescued pTKO1 plasmids (in duplicates) and subjected to the single selection of hygromycin B. Pools of approximately 10⁴ hygromycin resistant clones were generated from each transfection and were kept as 6 duplicates of stable polyclonal populations. The sensitivities of the above clones to an application of IFN-γ was then determined.

The vector pTKO1-DHFR (Deiss and Kimchi, supra) which carried a non-relevant construct served as control. The control vector was introduced in parallel into HeLa cells and produced two independent polyclonal population of stable transfectants designated DHFR-t1 and t2.

The double stranded cDNA fragments from construct 230 and 256 (from groups 1 and 2, respectively) were used as probes in Northern blot analysis in order to detect mRNA transcripts both in non-transfected and transfected HeLa cells. These two specific cDNA inserts were labelled by commonly used commercial labelling kits. They were subcloned into Bluescript™ vectors (Stratagene, USA) to facilitate both the preparation of the cDNA inserts and the production of single stranded RNA probes therefrom.

(B) Results

Constructs 230 (group 1)

Figure 1A:
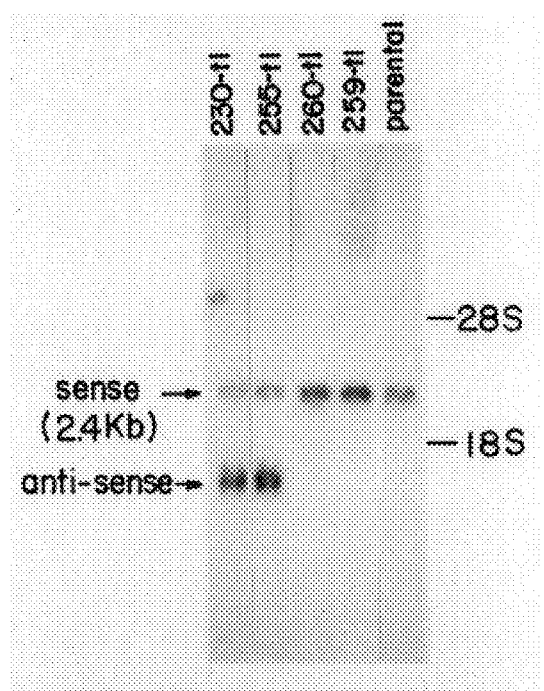

As can be seen in FIG. 1A the cDNA insert in this construct hybridized to a single endogenous 2.4 Kb mRNA transcript, both in non-transfected and transfected HeLA cells. In stable transfectants containing the antisense constructs of clones 230 and 255, an additional composite antisense transcript was detected by this 230 probe. It consisted of 320 bases of the original cDNA insert and 800 additional bases of sequences derived from the expression cassette (SV40 early promoter together with sequences till the polyadenylation signal). One of the RNA labeled strands produced by the Bluescript™ vector hybridized exclusively to the endogenous 2.4 Kb mRNA while the complementary strand hybridized only to the 1.1 Kb RNA confirming that the latter is indeed an antisense mRNA (data not shown).

Figure 1B:
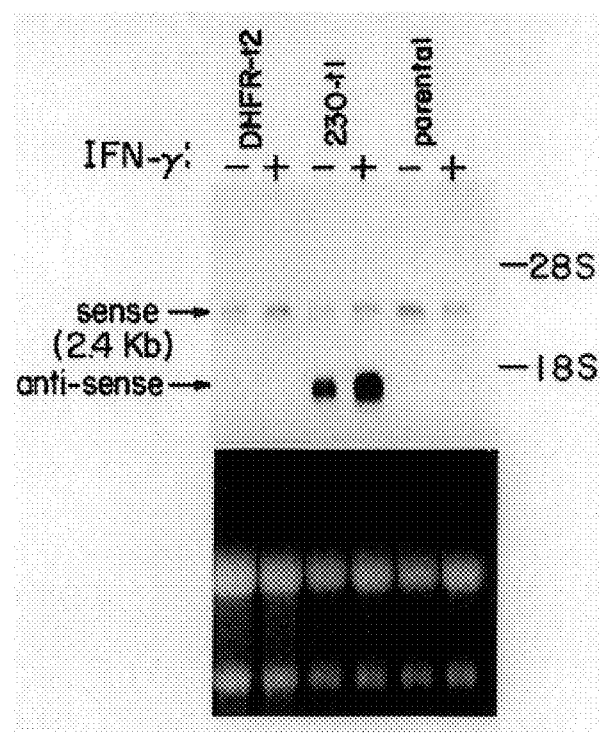

The amount of the antisense RNA in clones 230 and 255 exceeded the sense mRNA levels by 3 to 6 fold (FIGS. 1A, 1B). After IFN-γ treatment the level of antisense expression was further elevated due to the presence of IFN-γ-stimulated response element (ISRE) in the pTKO1 vector (Deiss and Kimchi, supra), thus leading to 15 fold excess of antisense over sense transcripts (FIG. 1B). The endogenous 2.4 Kb mRNA level was neither modulated by IFN-γ, nor influenced by the high antisense expression.

Construct 256 (group 2)

Figure 2A:
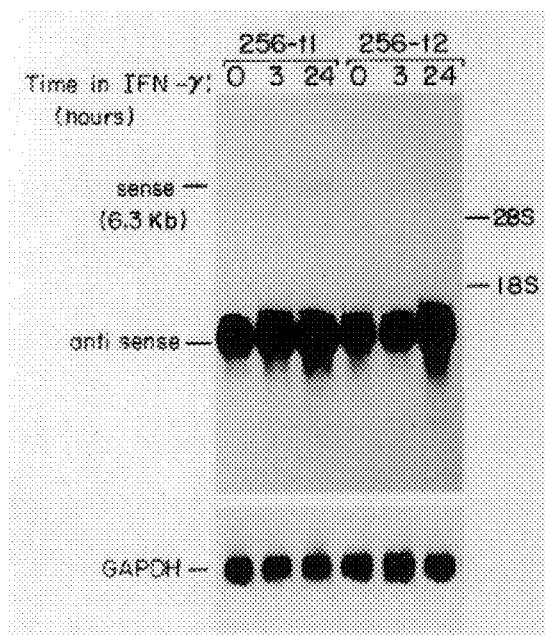
Figure 2B:
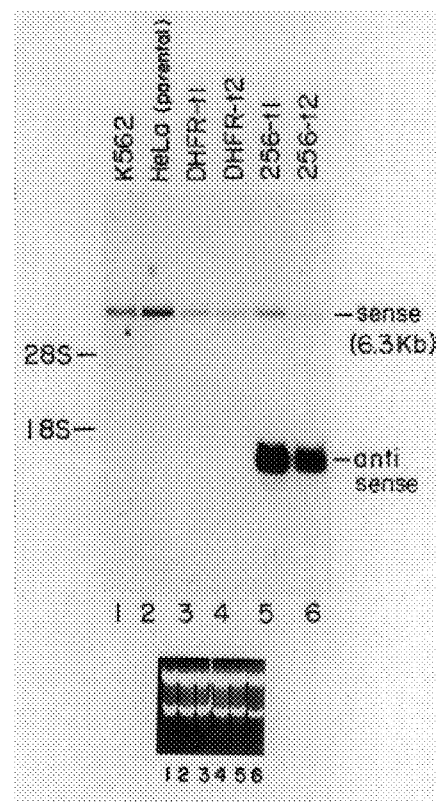

As can be seen in FIGS. 2A and 2B, the construct of the 256 clone (367 bp in size) hybridized on Northern blots to a single endogenous 6.3 Kb mRNA transcript which was expressed in all tested cells at relatively low levels. In the 256-t1 and t2 transfected cells it also hybridized to a composite 1.2 Kb RNA that consisted of 367 bases of the cDNA insert and 800 bases of sequences derived from the expression cassette in the vector (FIG. 2). The antisense orientation of fragment #256 in the pTKO1 vector was confirmed upon sequencing of the sense cDNA clone (FIG. 7). The amount of the antisense RNA expressed from pTKO-1 plasmid #256 in non-treated HeLa cells exceeded the sense mRNA levels by more than 100 fold. Moreover, due to the presence of IFN-stimulated response element (ISRE) in the pTKO1 vector, the levels of antisense mRNA expression were further elevated after IFN-γ treatment (FIG. 3).

III. Response of Cells Transfected with Antisense cDNAs to IFN-γ

(A) Experimental Procedure

The HeLa polyclonal population transfected with the individual antisense cDNAs were cultured in the presence of both hygromycin B and IFN-γ (750 U/ml). Growth and viability parameters were examined: (1) under the light microscope, (2) by electron microscopy, and (3) by DAPI staining (0.5 μg/ml; Sigma). For more detailed quantitation, a neutral red uptake assay was performed: the different polyclonal HeLa cell populations were cultivated in 96-well microtiter plates at subconfluent cell densities and then treated with IFN-γ (750 U/ml) or left untreated. All the cells were continuously maintained in a hygromycin B-containing medium to select for transfected cells. The two DHFR-transfected HeLa cell populations (t1, t2), prepared as described above, served as control cultures that display the typical growth sensitivity curves to IFN-γ. The examined antisense cDNA transfected cells were the 230-t1, 255-t1 (group 1) and 256-t1, 256-t2 (group 2). Viable cells were stained with neutral-red and the dye uptake was quantified by measuring O.D. at 540 nm in quadruplicates during the 14 days of the experiment.

(B) Results

The microscopic examination of parental and control DHFR-transfected HeLa cells revealed that IFN-γ triggered a biphasic pattern of responses. The cells stopped proliferating during the first four days of IFN-γ treatment but still remained viable (in trypan-blue exclusion tests) and displayed a flattened morphology characteristic of the cytostatic responses to IFN-γ (FIG. 3A, b). The reduction in the proliferation rate during this period was also measured by a sharp decline (by more than 90%) in the thymidine uptake into DNA (not shown). This type of IFN-γ-induced proliferation arrest was then followed by massive cell death that occurred in a non-synchronous fashion over a period of an additional 10 days. The cells gradually reduced their size, rounded up and detached from the plates (FIGS. 3A, d). Staining of DNA with DAPI after detachment of cells from the substratum revealed gross changes in the nuclear morphology characteristic of programmed cell death. This included nuclear pyknosis, chromatin condensation, sometimes detected preferentially at the nuclear periphery, and chromatin segmentation (FIG. 3B, b). Transmission electron micrographs of the IFN-γ-treated cells prior to their detachment revealed other morphological changes including the disappearance of surface microvilli, surface blebbing, budding off cytoplasmic projections and cytoplasmic disintegration, in addition to the nuclear pyknosis and chromatin condensation (details shown in FIG. 3C, d). The antisense RNA expression from pTKO-1 plasmid of group 1 reduced the susceptibility of the cells to the killing effects of IFN-γ: more cells survived on the plates and the above-mentioned death associated morphological changes appeared at much lower frequency (compare the scanning electron micrographs of the IFN-γ-treated DHFR-transfected cells in FIG. 3C, b to the IFN-γ-treated 230-t1 cells in FIG. 3C, f). Similar microscopic observations, showing protection from the IFN-γ-induced cell death, were also made with respect to three other clones from the aforementioned groups of antisense cDNAs, i.e. 2–6 (see below).

Figure 4A:
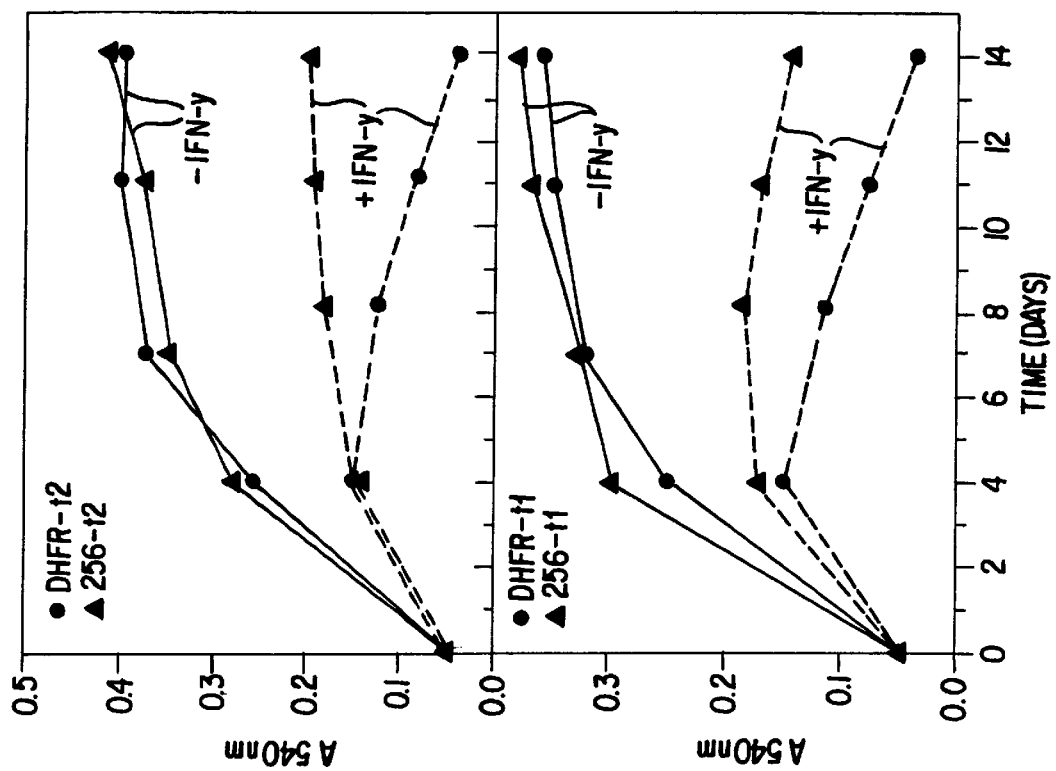
FIGS. 4A–C show that the antisense RNA expression from plasmids of groups 1 and 2 reduces the susceptibility of HeLa cells to the killing effects of IFN-γ but has no effect on early IFN-γ signalling.
Figure 4B:
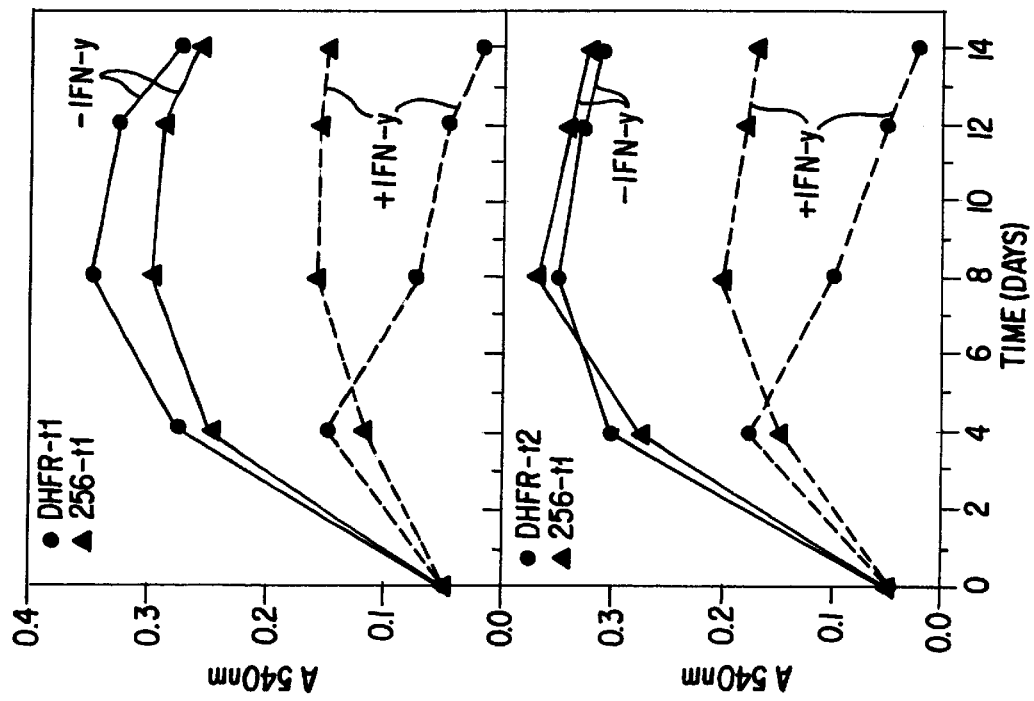
Figure 4C:
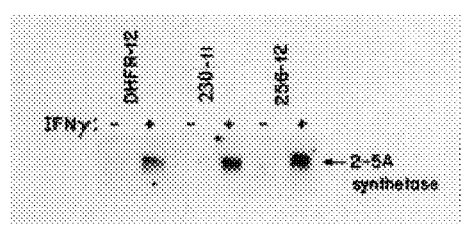

A neutral-red uptake assay was then performed to determine more accurately, on a quantitative basis, both the typical biphasic responses of control cultures to IFN-γ and the reduced susceptibility of the antisense expressing cultures to the IFN-γ-induced cell death. The two DHFR-transfected HeLa cell populations (t1, t2) served as the control cultures in this assay and the antisense cDNA transfected cells examined were the 230-t1, 255-t1 (group 1) (FIG. 4A) and 256-t1, 256-t2 (group 2) (FIG. 4B). In the absence of IFN-γ, all the transfected HeLa cells behaved the same and displayed practically identical growth curves suggesting that the antisense RNA expression had no effects on the normal growth of cells. Another feature that was not changed by the antisense RNA expression was the extent of the cytostatic responses to IFN-γ. As shown in FIGS. 4A and 4B, IFN-γ has similarly reduced the proliferation rate of all the transfected cultures and they all displayed the same extent of reduction in the neutral-red dye uptake during the first 4 days (before cell death starts to be microscopically evident). After 4 days of treatment the picture changed drastically. While almost all control cells died during the subsequent days of IFN-γ treatment leading to minimal values of the neutral-red dye uptake on day 14, a significant fraction of cells that expressed antisense RNA survived in the presence of IFN-γ, as reflected by the sustained values of the dye uptake. The resistance to the IFN-γ-induced cell killing was very similar in all the four tested cultures that expressed the two different antisense RNAs (FIGS. 4A, 4B). These data indicate that expression of antisense RNA from groups 1 and 2 protects the HeLa cells exclusively from the IFN-γ-induced cell death and not from its cytostatic action. It is noteworthy that the antisense RNA expression did not affect the early biochemical steps in the signaling of IFN-γ as deduced from the normal mRNA induction by IFN-γ of the 2-5A synthetase gene in these transfected cells (FIG. 4C). Altogether, it is concluded that among all criteria tested only the death inducing effects of IFN-γ were interrupted by the antisense RNA expression.

IV. Responses of Cells Transfected with Antisense Constructs to Necrotic Cell Death It became interesting at this stage to check whether the antisense RNA expression can also protect the HeLa cells from a necrotic type of cell death. For this, the effect of TNF-α added in combination with cycloheximide (CHX) was examined in the various HeLa cell populations. Unlike the effect of IFN-γ, the cell death that was induced by TNF-α+CHX in HeLa cells was very rapid (50% killing after 3 hours) and displayed typical features of necrosis such as swelling of the cells before their lysis. As shown in Table 2, while the antisense RNA expression from groups 1 and 2 protected the cells from the IFN-γ-induced cell killing, there was no protection from the TNF-α-induced necrotic cell death. All the examined HeLa cell transfectants were killed by the TNF+CHX combination with similar time kinetics and at the same efficiency. Northern blot analysis demonstrated that the levels of the antisense mRNA transcripts in 256-t1 cells were not reduced by the TNF+CHX treatment at 5 hours (not shown) thus excluding the possibility that loss of the antisense RNA expression, caused by the treatment, may be the reason for lack of protective effects from the necrotic cell death. This further suggests a certain specificity of the protective mechanisms regarding the type of cell killing.

TABLE 2

Expression of antisense RNA (from groups 1 and 2) protects from the IFN-γ-induced programmed cell death but not from the TNF-induced necrotic cell death. (A = 540 nm)

|  |  | DHFR-t1 | DHFR-t2 | 230-t1 | 255-t1 | 256-t1 |
|---|---|---|---|---|---|---|
| 14 days | No treatment | 0.396 | 0.345 | 0.385 | 0.324 | 0.336 |
|  | IFN-γ | 0.026 | 0.017 | 0.136 | 0.158 | 0.159 |
| 5 hours | No treatment | N.D. | 0.148 | 0.130 | N.D. | 0.140 |
|  | TNF-α + CHX | N.D. | 0.053 | 0.026 | N.D. | 0.022 |
| 20 hours | No treatment | 0.211 | 0.248 | 0.223 | 0.173 | 0.190 |
|  | TNF-α + CHX | 0.002 | 0.001 | 0.003 | 0.0015 | 0.002 |

Each treatment was done in quadruplicates and the average values of dye uptake, measured by the OD at 1=540 nm, is presented at the indicated time intervals. The SD was between 2–4%. N.D, not done.

V. Cloning of DAP-1 cDNA and Determination of Amino Acid Sequence

Figure 5:
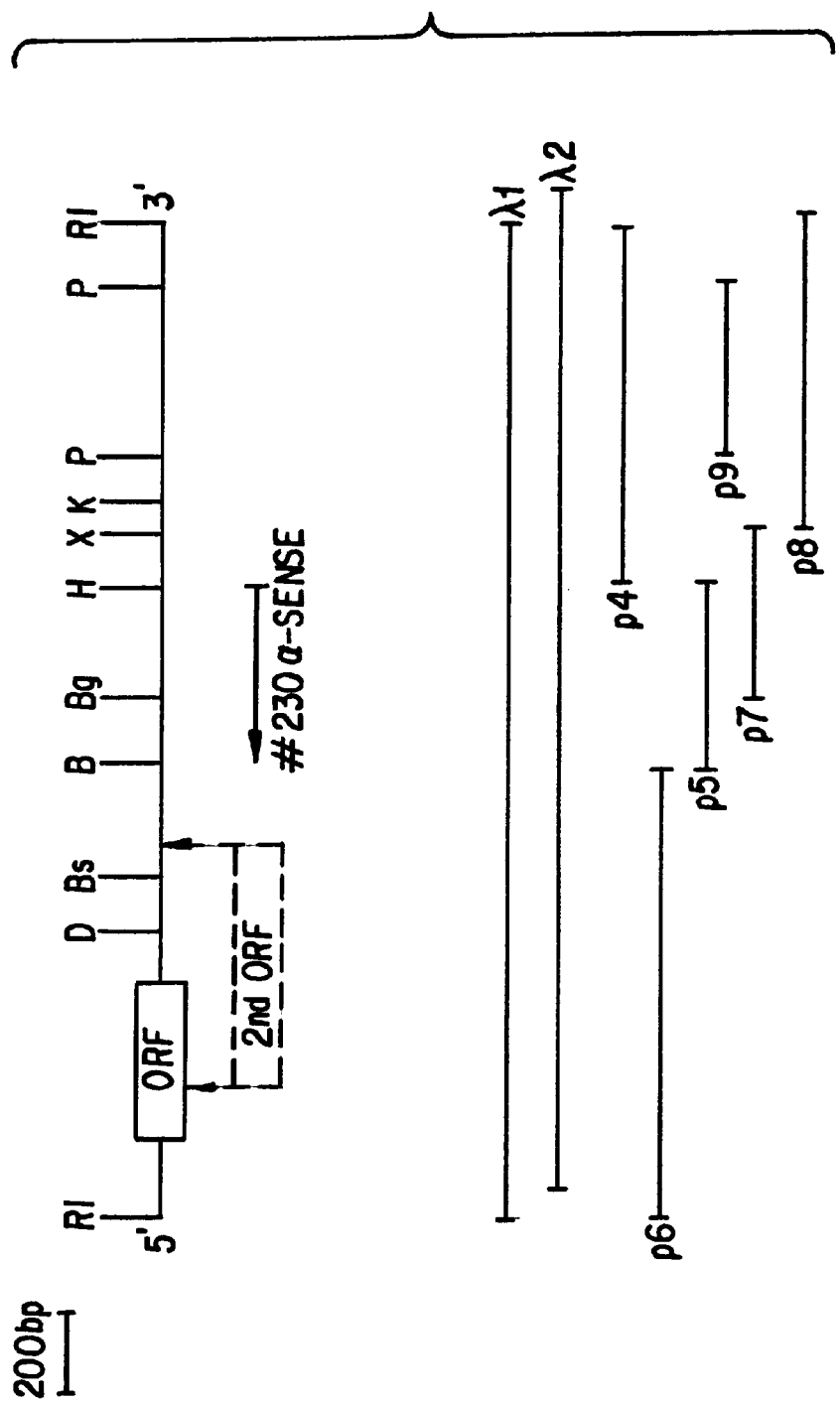
FIG. 5 shows the restriction map of the γ1 cDNA clone that carries the DAP-1 cDNA.

An HL-60 cDNA library constructed in λgt10 vector was screened with the cDNA insert of pTKO1-230. Two independent clones, λ1 and λ2, almost completely overlapping and carrying cDNA inserts of about 2.3 Kb were analysed. λ1 cDNA clone encompasses the 5'-untranslated region, short coding region(s) and a relatively long 3'-untranslated region that constitutes more than 60% of the cDNA clone (FIG. 5).

Figure 6A:
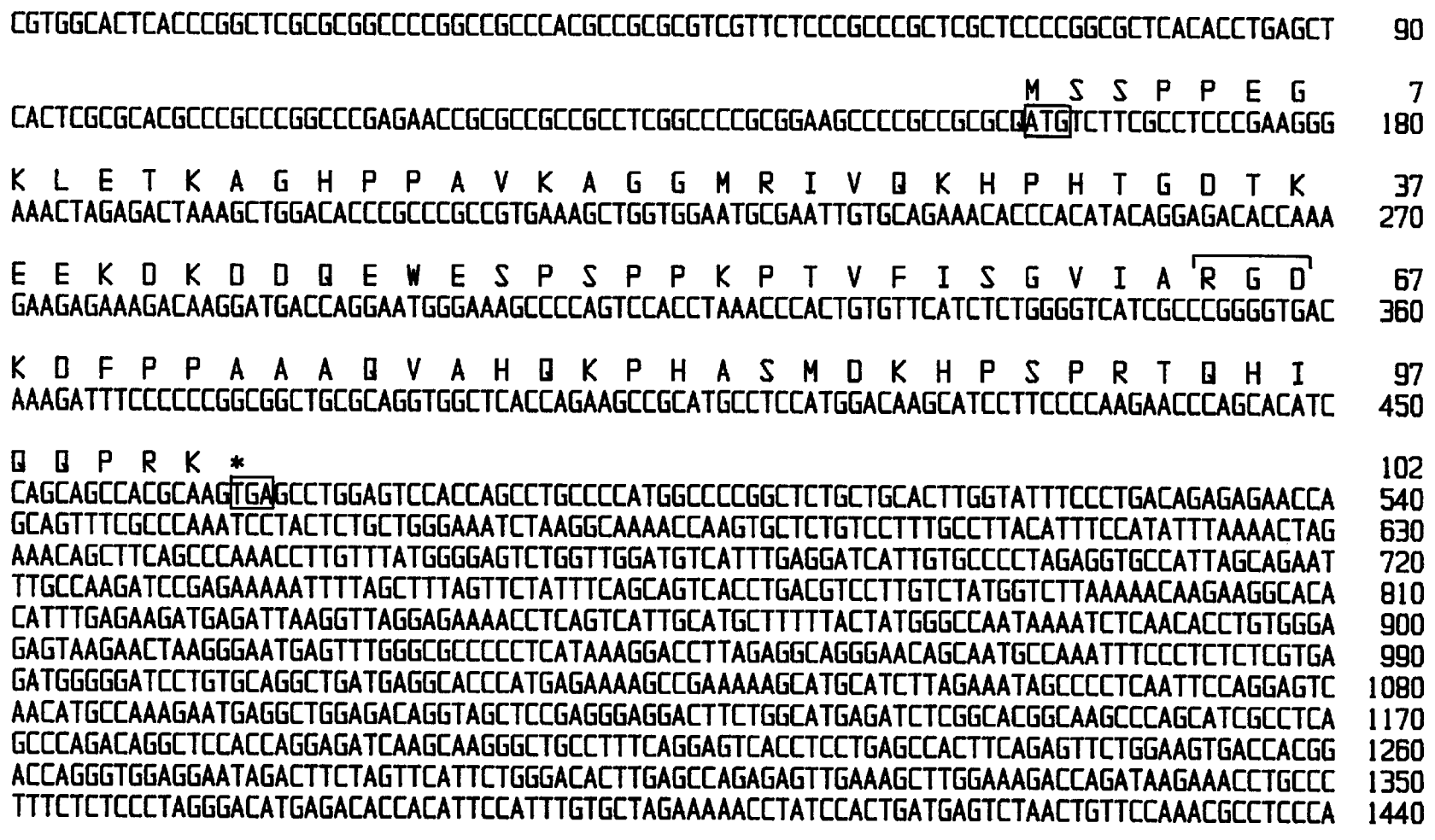

The nucleotide sequence of the cDNA carried by λ1 and its predicted amino acid pattern are presented in FIG. 6 (SEQ ID NO: 8). This cDNA is 2232 bp long and contains a potential polyadenylation signal ATTAAA at its 3' end. The open reading frame (ORF) is very short, starting from the initiation codon at nucleotide positions 160–162 and ending at termination codon TGA at positions 466–468. This ORF is preceded by an extremely GC-rich 5'-untranslated region and potentially codes for a protein consisting of 102 amino acids with calculated MW of 11.2 kDa. The amino acid composition predicts a basic protein (isoelectric point=10), rich in prolines (15%) which displays two blocks of charged residues, one in the middle and the other at the 3' end of the protein. The high proline content may cause some nomalies in the protein's migration on gels. Search for motifs ("Motifs" program; GCG Software Package) indicated that the protein contains two potential sites for cascin kinase II phosphorylation at positions 3 and 36, a single potential protein kinase C phosphorylation site at the C-terminus (position 91) and a consensus phosphorylation site of the cdks at position 51. In addition, the protein contains the consensus sequence RGD at position 65–67, a tripeptide that in some proteins plays a role in cell adhesion, and a potential SH3 binding motif, SPSPP (SEQ ID NO: 12), at position 49–53 (Cowburn (1994) Struc. Biol. 1, 489–491). No indications for the presence of signal peptide or transmembranal domain have been found (SAPS prediction; Brendel et al., (1992) PNAS USA, 89:2002–2006). The amino acid sequence showed no significant homology to known proteins.

Fragment #230 was used as a probe on Southern blots containing human genomic DNA, digested with various restriction enzymes that do not cut it. A single band was visualized upon hybridization with DNA cleaved with EcoRI, BamHI, PstI and XbaI, suggesting the existence of a single copy gene (not shown). This new gene was termed DAP-1 (Death Associated Protein-1).

Figure 1C:
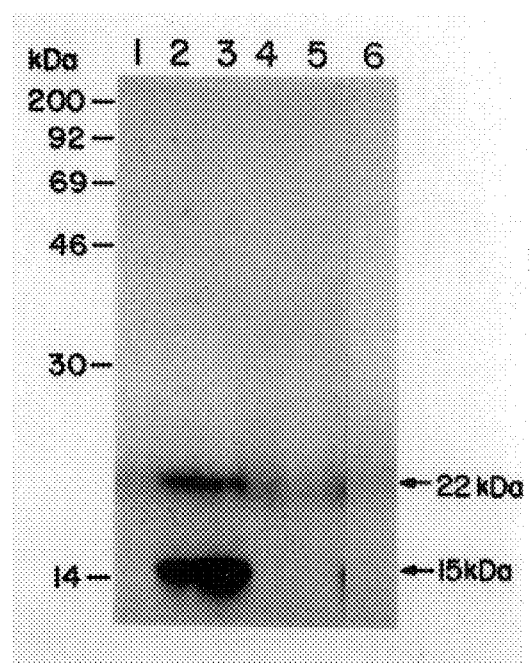

In vitro translation assays in reticulocyte lysates confirmed that the predicted ORF codes for the major 15 kDa protein translated from the cloned 2.4 Kb transcript. The full length cDNA insert as well as four subclones that span different regions of the molecule (i.e., p6, p5, p8, and p4; see FIG. 5) were transcribed and translated in vitro. Among all the tested subclones, only the 5'1 Kb portion of the DAP-1 cDNA (p6) directed the in vitro synthesis of proteins (FIG. 1C). The major translated product migrated on gels as a 15 kDa protein. Mutation at the ATG codon at position 160–162 (ATG to GGC) completely eliminated the synthesis of the 15 kDa protein, thus confirming the position of the start point of this protein (data not shown). In addition to the 15 kDa protein product, a second protein of 22 kDa was also translated at lower efficiency from λ1 and the p6 cDNAs (FIG. 1C). Its translation was not influenced by the elimination of the ATG codon at position 160 but the protein was shortened to a size of 16 and 18 kDa upon cleavage of the p6 subclone with DraI and BstYI restriction endonucleases, respectively (not shown; for restriction map see FIG. 5). These criteria fit another potential open reading frame, which is detected in the nucleotide sequence in a different phase with respect to the first ORF (FIG. 6). It starts at the ATG codon (positions 287–289) and ends at termination codon TGA (positions 816–818). It has the potential to code for a protein consisting of 176 amino acids with a calculated molecular weight of 19.9 kDa, and has no significant homology to any known proteins.

Figure 1D:
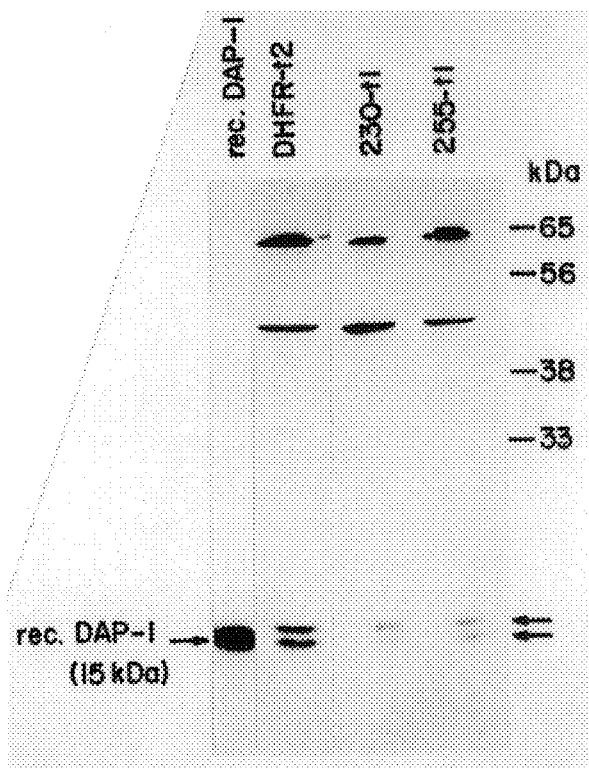

To analyze the expression of the major DAP-1 protein in cells, rabbit polyclonal antibodies were prepared against the bacterially produced 15 kDa protein. The affinity purified antibodies recognized on immunoblots two closely migrating proteins in extracts of HeLa cells; the lower band co-migrated on gels with the bacterially produced 15 kDa DAP-1 protein. The slower migrating form may represent a post-translationally modified version of the protein. In the HeLa cell transfectants, 230-t1 and 255-t1, expressing the elevated levels of antisense RNA that develop in the presence of IFN-γ (15 to 1 ratio), the DAP-1 protein levels were reduced by 75% and 78%, respectively, as compared to the DHFR-tranfected cultures (FIG. 1D). The two upper non specific bands (that are not competed with excess of the bacterially produced DAP-1) were not affected by the antisense expression, thus supporting the selectivity of the effect.

VI. Cloning of DAP-2 and Determination of Amino Acid Sequence

As mentioned above, expression studies indicated that the double-stranded cDNA fragment #256 (367 bp in size) hybridized on Northern blots to an endogenous 6.3 Kb mRNA transcript. The same single 6.3 Kb mRNA transcript was detected in HeLa (parental and transfectants) and in K562 cells when the full length cDNA (see below) was used as a probe on Northern blots (FIG. 2B). The cDNA insert from pTKO1-256 was therefore used to screen a K562 cDNA library.

Approximately $4 \times 10^6$ pfu were screened with the #256 cDNA insert and 40 positive clones were isolated after two rounds of sequential walking screening. The sequencing was performed on an Applied Bio-systems DNA sequencer 373 A. Sequence uniqueness and relatedness were determined using FASTA (GCG software package) at the nucleotide level and FASTA, BLASTP, and BLOCKS programs at the amino acid level (S. Henikoff and J. G. Henikoff, Nucleic Acids Res. 19, 6565 (1991).

Figure 2C:
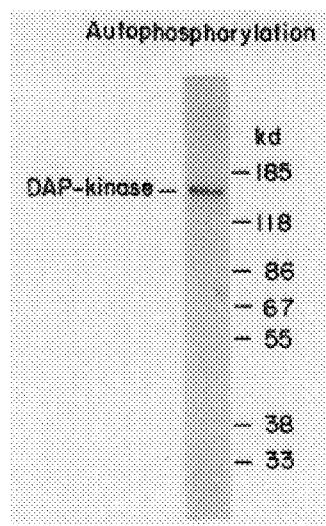
Figure 2D:
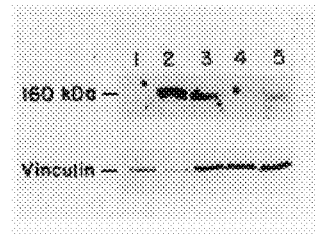
Figure 8C:
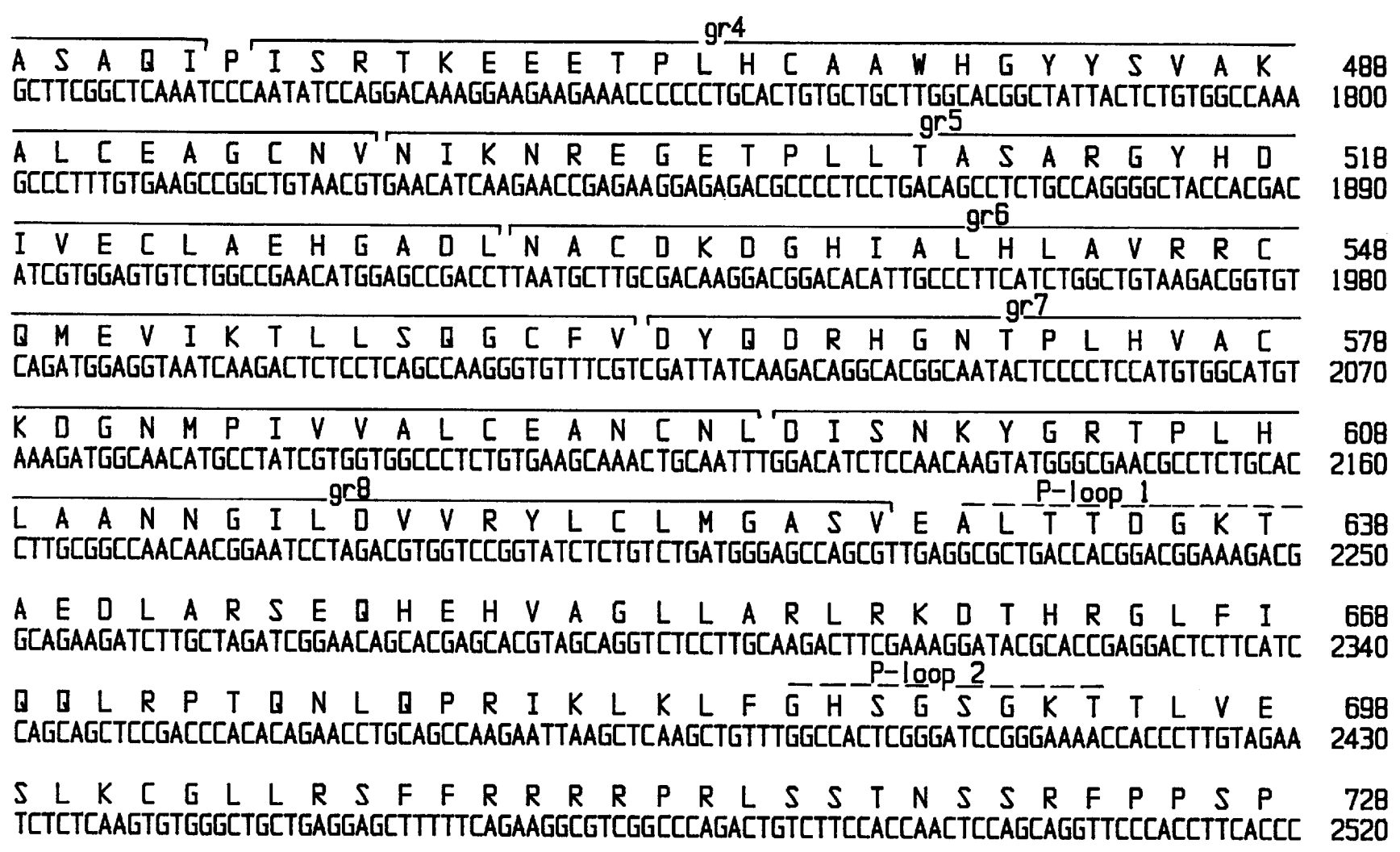
Figure 8F:
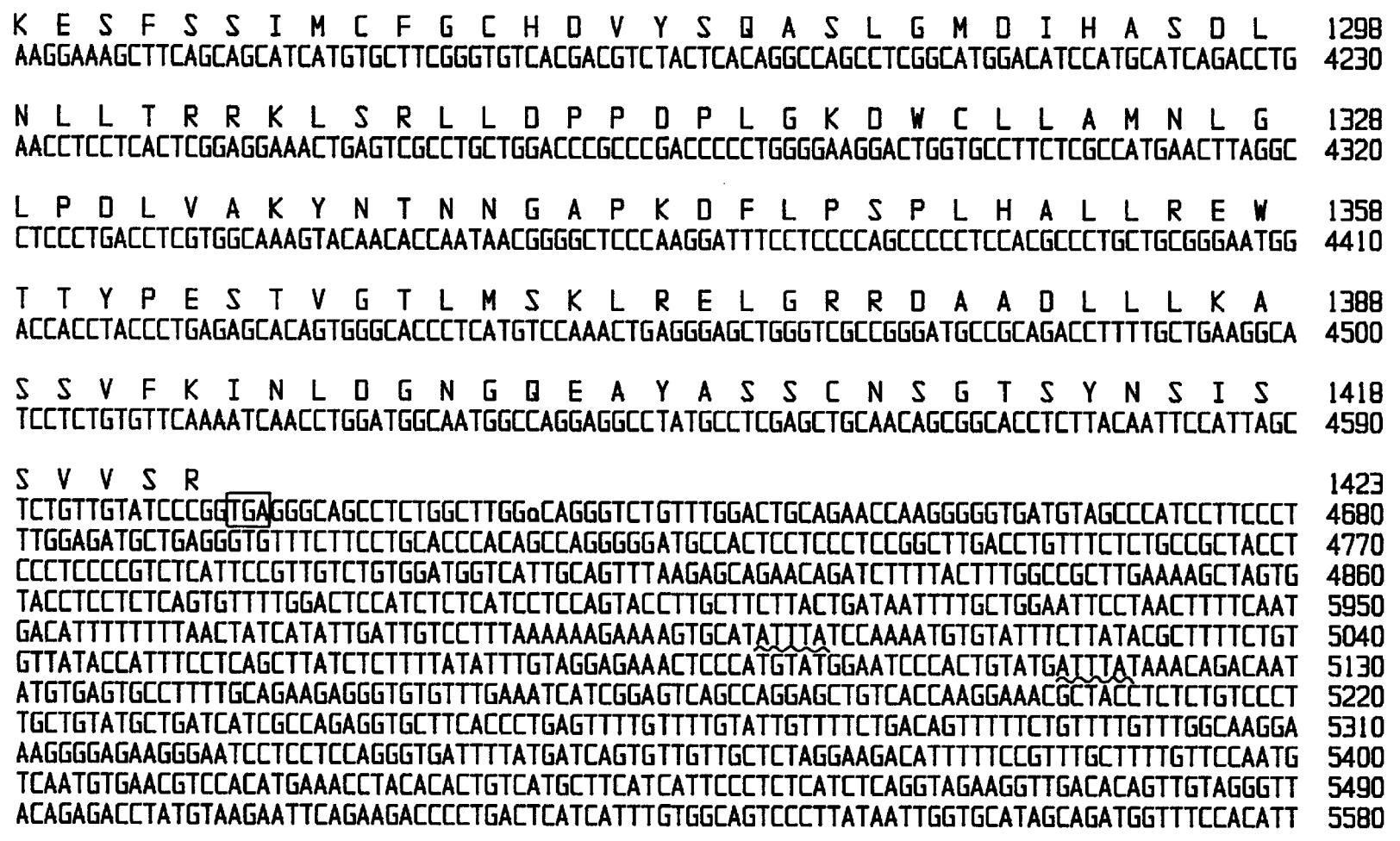
Figures 8G, 9C, 9D:
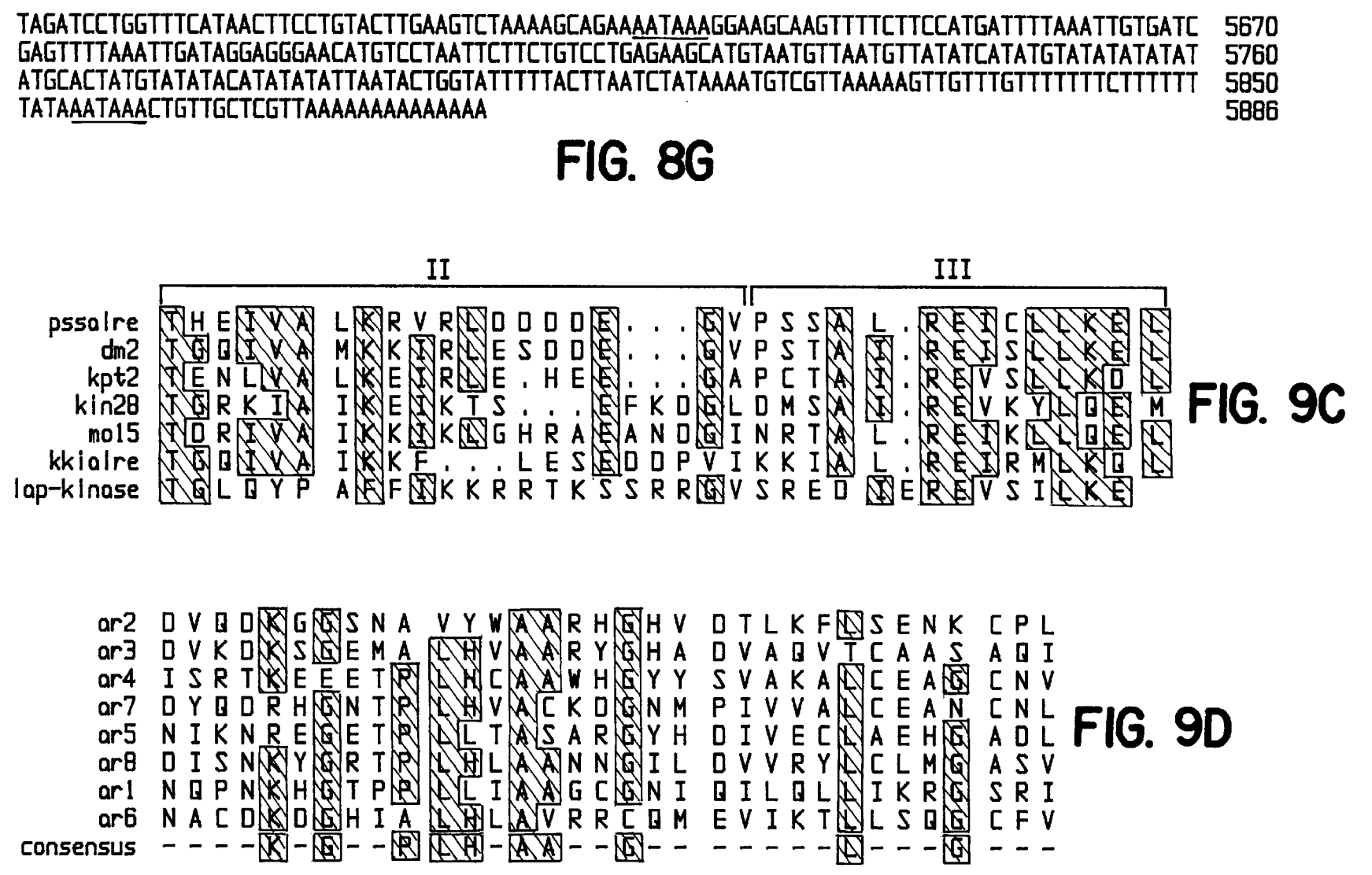

Two clones, λ29 and λ32, were chosen for sequencing (FIG. 7). The resulting composite sequence of both cDNAs consists of 5886 nucleotides and contains a poly A tail that starts at position 5872 and is preceded by two polyadenylation signals AATAAA (FIG. 8). The 3'-untranslated region also contains two ATTTA instability motifs found in the 3'-noncoding portions of short-lived mRNAs (G. Shaw and R. Kamen, Cell 46, 659 (1986)). The mRNA contains a single long open reading frame that starts at position 337, ends at position 4605 and potentially codes for a protein of 1423 amino acids (FIG. 8, SEQ ID NO: 9). The calculated molecular weight of the protein product is about 160 kDa. Affinity purified polyclonal antibodies were raised against the N-terminal 20 amino acid peptide of the protein. These antibodies recognized on immunoblots a 160 kDa recombinant protein that was produced in COS-1 cells after transfection with a vector that expressed the entire coding region of the cDNA (FIG. 2D). These antibodies reacted in HeLa cells with an endogenous protein of the same size. In the antisense RNA expressing cells, 256-t1 and 256-t2, the steady state levels of the 160 kDa protein were 10 and 5 fold lower than in the DHFR control cells while a non relevant protein, vinculin, displayed similar expression levels in all HeLa cell transfectants (FIG. 2D). Thus, expression of anti-sense RNA from pTKO-1 plasmid #256 in HeLa cells resulted in a significant reduction in the amount of the corresponding protein.

We were able to define several known domains and motifs that are present in this protein. Its extreme N-terminus is composed of a protein kinase domain that spans 255 amino acids from position 13–267. On the basis of its structure, it is likely to be a serine/threonine type of protein kinase having a classical composition of XI subdomains with all conserved motifs present (FIG. 8 SEQ ID NO: 10) (S. K. Hanks and A. M. Quinn, Methods Enzymol. 200, 38 (1991)). This novel kinase was termed DAP-2 or DAP-kinase (Death Associated Protein-kinase).

Figure 9A:
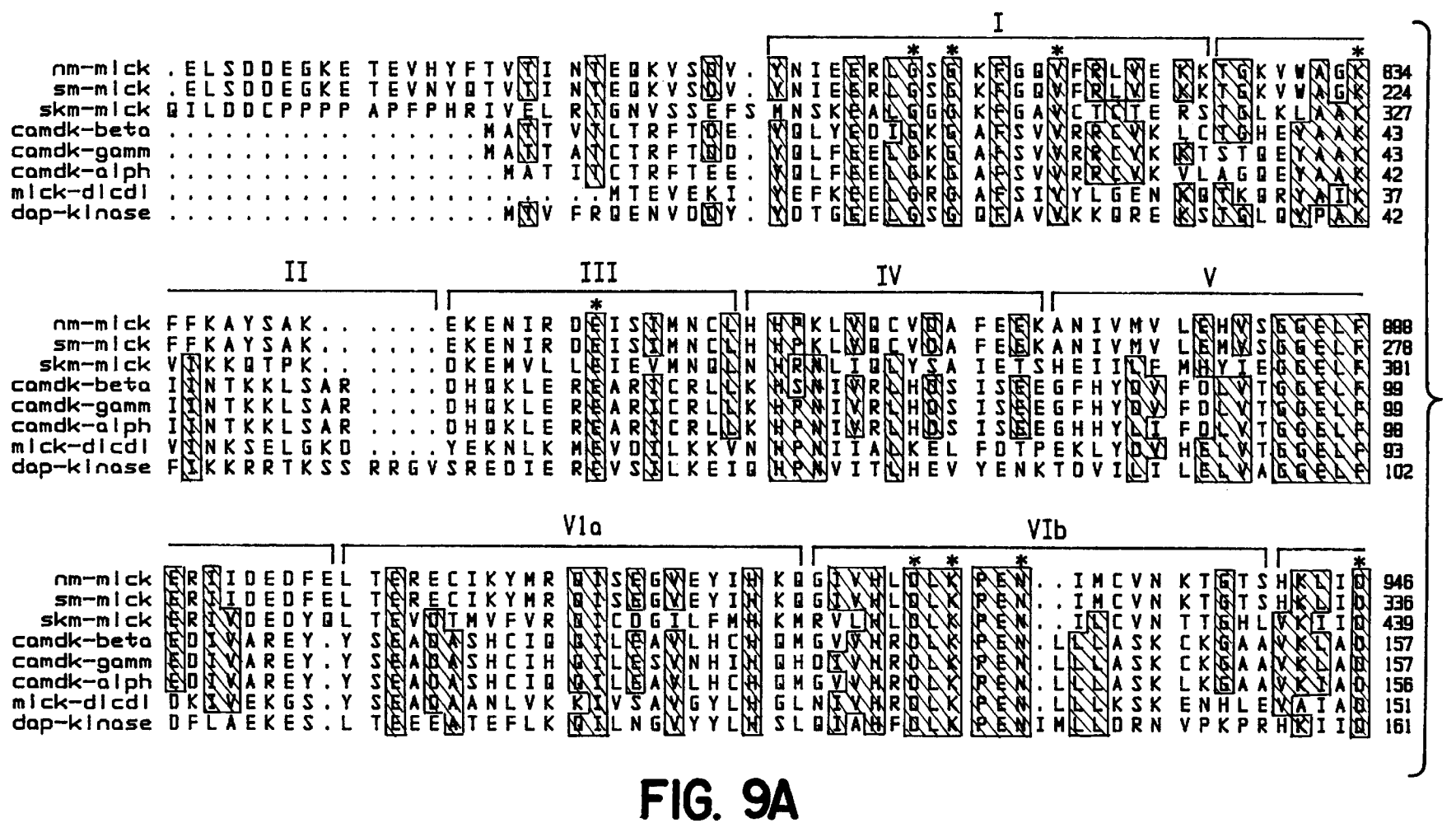
Figure 9B:
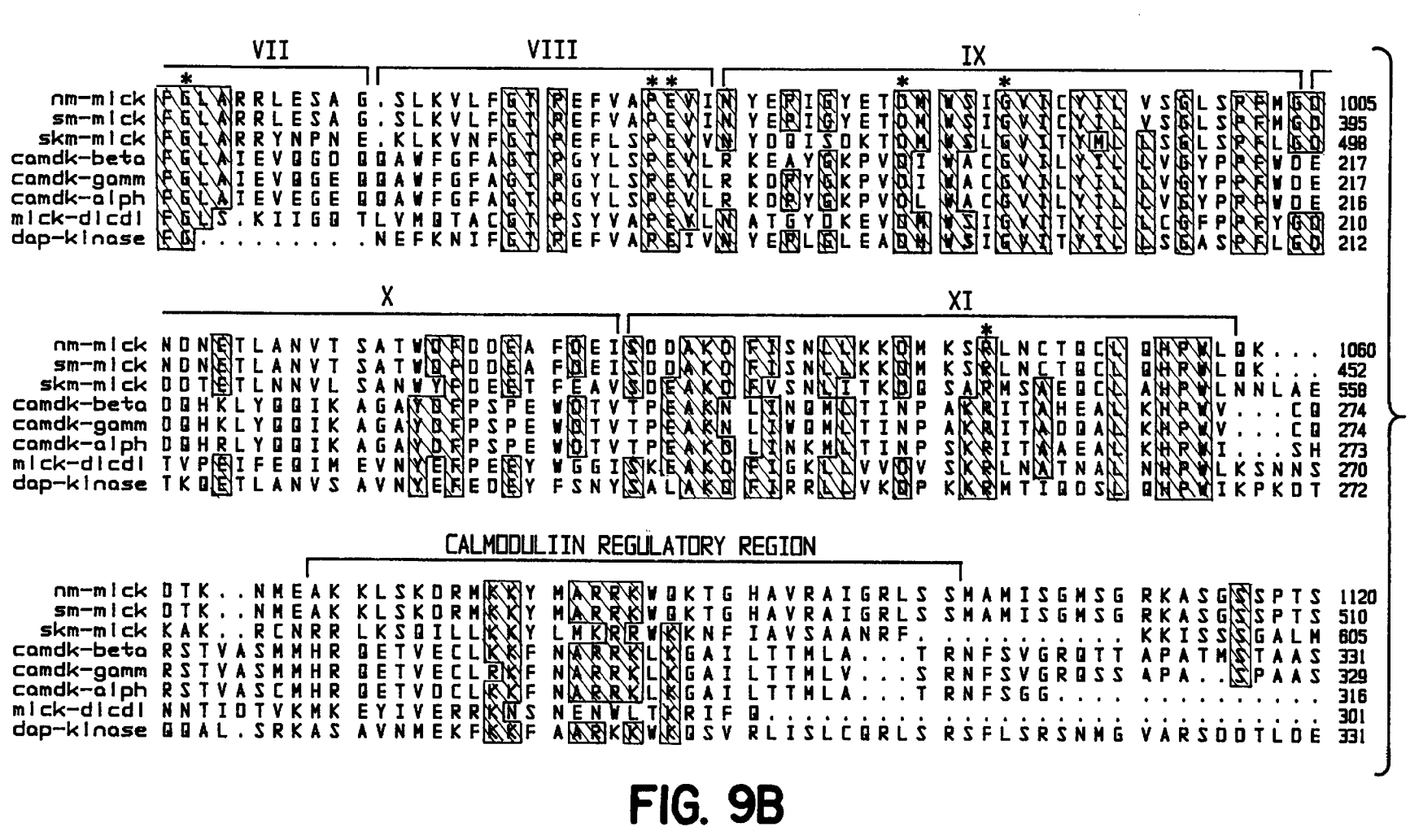

The kinase domain falls into a family of that of calmodulin-dependent kinases. The homology to known kinase domains that constitute this group, including the myosin light chain kinases, ranges between 34%–49% (FIG. 9A). Three main differences distinguish the kinase domain of DAP-kinase from other members of calmodulin-dependent kinase family: 1) Subdomain II is relatively long and has a stretch of basic amino acids (KKRRTKSSRR) SEQ ID NO: 13; 2) Subdomain III mostly resembles that of the cell cycle dependent kinases (FIG. 9B). Interestingly, the typical sequences of the cell cycle dependent kinases (PSTAIRE, PSSALRE, PCTAIRE, KKIALRE) SEQ ID NOS: 14–17, respectively are located in subdomain III; and 3) Subdomain VII is extremely short and consists of only 7 amino acids.

Right downstream to the kinase domain there is an additional stretch of homology that is present in almost all members of the family of calmodulin-dependent kinases, and was implicated in calmodulin-recognition and binding; B. P. Herring, J. T. Stull, P. J. Gallagher, J. Biol. Chem. 265, 1724 (1990); M. O. Shoemaker et al., J. Cell. Biol. 111, 1107 (1990); F. H. Cruzalegui et al., Proc. Nath. Acad. Sci. USA 89, 12127 (1992)). Down-stream of the calmodulin-recognition domain, an ankyrin repeats domain was identified spanning 265 amino acids from position 365 to 629. It is composed of 8 repeats of 33 amino acids each, not separated by spacers except for a single proline residue that separates three N-terminal repeats from five C-terminal ones (FIGS. 8 SEQ ID NO: 10 and 9C). Ankyrin repeats are involved in protein-protein interactions in a variety of proteins (P. Michaely and V. Bennett, Trends in Cell Biology 2, 127 (1992)), but were not described before in the context of serine/threonine kinases. One tyrosine kinase carrying ankyrin repeats has been recently identified in Hydra vulgaris (T. A. Chan et al., Oncogene 9, 1253 (1994)). In the DAP-kinase, the 8 ankyrin repeats may mediate the interaction with a putative effector or a regulatory molecule, or influence the substrate selectivity and/or stability of the kinase-substrate interactions.

Immediately downstream to ankyrin repeats there are two subsequent potential P-loop motifs, ALTTDGKT (SEQ ID NO: 18 and GHSGSGKT (SEQ ID NO: 19, identified through the consensus sequence, G[A]XXXXGKT[S] (SEQ ID NO: 20. Comparison of DAP-kinase potential P-loop motifs to the corresponding consensus sequences within seven ATP or GTP-binding protein families demonstrates that only the 3' P-loop has some similarity to P-loop consensus of elongation factors, ATP synthase b-subunits and thymidine kinase. Actually, a stretch of 33 amino acids following the eighth ankyrin repeat that encompasses the putative 5' P-loop, may represent a ninth ankyrin repeat that is less conserved than others. DAP-kinase also carries multiple potential sites for post-translational modifications, and has neither transmembranal domain nor signal peptide. The Prosite bank search, using the program Motifs (GCG Software Package) revealed that the DAP-kinase protein contains a consensus sequence for the C-terminal amidation site at position 1376 (this suggests that 47 C-terminal amino acids can be cleaved from the protein body ). It also contains consensus sequences for six N-glycosylation sites, and potential phosphorylation sites for cAMP-dependent kinase (six), casein kinase II (twenty eight) and protein kinase C (twenty).

Altogether, the deduced amino acid sequence of the DAP-kinase suggests that a very unique type of calmodulin-regulated serine/threonine kinase has been rescued. The combination of serine/threonine kinase domain, ankyrin repeats and additional possible ATP/GTP binding sites outside the kinase domain in one protein (FIG. 10) has not been previously described. A size of 160 kDa is rare among serine/threonine kinases and DAP-kinase is actually the largest calmodulin-dependent kinase known to date. The ability of DAP-kinase to bind calmodulin, recently confirmed in yeast two hybrid system (not shown), is consistent with the notion that in many cases programmed cell death is $Ca^{2+}$ dependent (S. Sen, Biol. Rev. Camb. Philos. Soc. 67, 287 (1992); S. Lee, S. Christakos, M. B. Small, Curr. Opin. Cell. Biol. 5, 286 (1993)). Moreover, it has been recently reported that calmodulin antagonists inhibited the glucocorticoid-induced apoptosis (D. R. Dowd, D. P. Mac, B. S. Komm, M. R. Haussler, R. Miesfeld, J. Biol. Chem. 266, 18423 (1991)), and that inhibitors of myosin light chain kinases blocked the TNF-induced apoptotic cell death (S. C. Wright, H. Zheng, J. Zhong, F. M. Torti, J. W. Larrick, J. Cell. Biochem. 53, 222 (1993)).

In order to verify that DAP-2 is truely a kinase, COS cells were transiently transfected with an expression vector (PECE-FLAG) that carries fragment of the λ29 cDNA that encompasses the entire coding region (from the abovementioned start ATG to the first EcoRI site at the 3' end). Cell lysates were immunoprecipitated by anti-FLAG monoclonal antibodies and washed immunoprecipitates were assayed for in-vitro autophosphorylation in the presence of calmodulin and $Ca^{2+}$. As shown in FIG. 2C, a single phosphorylated band of 160 kDa appeared upon fractionation of the in-vitro reaction products on polyacrylamide gels. This experiment provides the first direct proof that the recombinant protein has intrinsic kinase activity, as suggested by the predicted amino acid structure.

VII. Assessment of In Vitro DAP-kinase Activity (A) Experimental Procedures

1. Cell Culture

The HeLa human epithelial carcinoma cells, COS-7 monkey kidney cells, SV-80 cells (human fibroblasts transformed with SVO-40 large T-antigen), and REF-52 rat embryo fibroblasts, were grown in DMEM (BioLab) supplemented with 10% FCS (Gibco), 4 mM glutamine, 100 U/ml penicillin and 0.1 mg/ml streptomycin. HeLa-tTA were grown in the presence of 200 µg/ml G-418 (Gossen and Bujard, 1992). Transfections were performed by the standard calcium phosphate technique. Recombinant human interferon-γ ($3 \times 10^7$ U/ml) was purchased from PeproTech. Nocodazol was purchased from Sigma, Latronculin A was a gift from A. D. Bershadsky of the Weizman Institute, Rehovot, Israel.

2. Plasmid Construction

DAP-kinase expression constructs for transient transfections into SV-80, REF-52 or COS cells and for stable transfections into the HeLa cells were prepared in either the pECE (Deng & Karin, 1993) or pCDNA3 (In Vitrogen) vectors. In all the constructs the DAP-kinase sequences were tagged with the FLAG epitope at their N-terminus. In C-terminal deletion constructs the DAP-kinase sequences were fused to the FLAG epitope via the Nde I restriction site that was introduced at the initiation ATG codon by oligonucleotide directed mutagenesis. In other constructs DAP-kinase sequences were fused to the FLAG epitope via the corresponding restriction sites. C-terminal deletion constructs: 1–1271, 1–835, 1–641 and 1–305, —were prepared by digestion of the DAP-kinase cDNA with Hind III (nt 4146), Xba I (nt 2838), Bgl II (nt 2256), and EcoR V (nt 1247), respectively. The full-length DAP-kinase cDNA construct reaches the EcoR I site at position 4932 of the 3' UTR. DAP-kinase expression constructs 305–641, 641–835, and 641–1423 contain cDNA fragments obtained by double digestion with EcoRV and Bgl II (nt 1247–2256), Bgl II and Xba I (nt 2256–2838), or by digestion with Bgl II (nt 2256–4827), respectively. Three DAP-kinase mutants: K42A, ΔCaM and ΔCyto, were prepared using oligonucleotide directed mutagenesis with the 5'-GTATC CCGCCGCATTCATCAAGA-3' (SEQ ID NO: 21), 5'-CAGCATCCCTGGATCAAGTCCAGAAGTAACATG AGT-3' (SEQ ID NO: 22, and 5'-AAGACGGCAGAAGA TCTAGAAGAGCCCTAT-3' (SEQ ID NO: 23) oligonucleotides, respectively. All the nucleotide numbers are given according to X76104.

DAP-kinase was expressed transiently in HeLa cells from the tetracycline repressible promoter as a bicistronic message with the LacZ sequences. DAP-kinase sequence was tagged with the HA epitope at the N-terminus via the Nde I site introduced at the initiation ATG codon. The vector for expression of DAP-kinase-LacZ bicistronic message was prepared by insertion of BH-LacZ fusion gene from pUT535 vector (Cayla) into the Not I site of pSBC vector (Korchhoff et al., 1995). The resulting vector was named pSBC-b1.

(B) Results

The deduced amino acid structure of DAP-kinase protein predicts a few functional motifs and domains as depicted in FIG. 31. The amino terminus is composed of a protein kinase domain of the serine/threonine type (Deiss et al. 1995), that spans 255 amino acids from position 13 to 267. In order to measure the kinase activity an in vitro immune complex kinase assay was developed for DAP-kinase. FLAG-tagged wild type DAP-kinase, or DAP-kinase mutants, were transiently expressed in COS cells. DAP-kinase proteins were immunoprecipitated by the anti-FLAG antibodies and were subjected to in vitro kinase assay, in the presence of 0.5 mM $Ca^{2+}$ and 1 mM recombinant calmodulin (CaM). Two mutant versions of DAP-kinase were used in this experiment: a C-terminus truncated DAP-kinase that lacks the last 152 amino acids—a region that contains the death domain, and the serine/threonine rich stretch of amino acids (Feinstein et al., 1995) (named DAP-kinase 1–1271-ΔDD; FIG. 31), and a mutant in which a conserved lysine in the kinase subdomain II (at position 42) was substituted with alanine (DAP-kinase-K42A). The latter mutation, was shown in other kinases to interfere with the phosphotransfer reaction, giving rise to a catalytically inactive protein (Hanks & Quinn, 1991).

As can be seen in FIG. 32, the recombinant DAP-kinase protein that was present in the immune complex was phosphorylated in vitro resulting in a prominent $^{32}P$—labeled band at the expected protein size. In contrast, the mutant DAP-kinase-K42A failed to be phosphorylated, suggesting that the mutation indeed inactivated the enzyme, and that the label of DAP-kinase resulted from autophosphorylation. The homology of the kinase domain of DAP-kinase to the myosin light chain kinase (MLCK) (Deiss et al., 1995), prompted the testing of the myosin light chain (MLC) as a potential exogenous substrate for the in vitro DAP-kinase assays. As can be seen in FIG. 32, DAP-kinase, but not its catalytically inactive mutant DAP-kinase-K42A), phosphorylated the MLC under the in vitro kinase assay conditions. The truncated ΔDD mutant, DAP-kinase 1–1271, was capable of undergoing autophosphorylation as well as phosphorylating the MLC. This indicates, first, that the region of the C-terminus, especially the most terminal stretch of amino acids that is rich in serines and threonines (Feinstein et al., 1995), is either not subjected to autophosphorylation or most probably is not the sole target for that activity; and second, that the 152 C-terminal amino acids do not participate in recognition of the MLC as a substrate. The amount of the recombinant DAP-kinase protein present in each immune complex was determined by reacting the blots, after the visualization of the $^{32}P$ signals, with anti-FLAG antibodies (FIG. 32).

VIII. DAP-kinase is a Calmodulin-regulated Serine/threonine Kinase.

(A) Experimental Procedure

1. Calmodulin Overlay

Transfection into COS cells, preparation of cell lysates, SDS-PAGE, and transfer of proteins to nitrocellulose, were performed as previously described (Deiss et al., 1995). Protein extracts (300 µg per lane) from COS cells, nontransfected or transfected with FLAG-DAP-kinase or DAP-kinase mutants were run on 7.5% SDS-PAGE and blotted onto nitrocellulose membrane. The membrane was preincubated for 30 minutes in calmodulin binding buffer (50 mM Tris-HCl pH 7.5, 150 mM NaCl, 1 mM $CaCl_2$) containing 1% non-fat dry milk powder. Recombinant $^{35}S$-labeled calmodulin (Baum et al., 1993) was supplemented, and the membrane was subjected to gentle shaking at room temperature for 16 h, washed three times (5 minutes each) in calmodulin binding buffer, dried and exposed to X-ray film. Detection of FLAG-DAP-kinase was done using anti-FLAG antibodies (1:500; IBI, Kodak) and the ECL western blotting detection system as described (Deiss et al., 1995).

2. In vitro kinase assay

Cell lysates of COS transfected cells were prepared as described previously (Deiss et al, 1995). Immunoprecipitation of recombinant DAP-kinase protein from 150 μg total extract was done with 20 μl anti-FLAG M2 gel (IBI, Kodak) in 200 μl of PLB supplemented with protease and phosphatase inhibitors for 2 h at 40° C. Following three washes with PLB, the immunoprecipitates were washed once with reaction buffer (50 mM Hepes pH 7.5, 8 mM MgCl$_2$, 2 mM MnCl$_2$ and 0.1 mg/ml BSA). The proteins bound to the beads were incubated for 15 min. at 25° C. in 50 μl of reaction buffer containing 15 μCi [γ-$^{32}$P] ATP (3 pmole), 50 mM ATP, 5 μg MLC (Sigma) and where indicated also 1 mM bovine calmodulin (Sigma), 0.5 mM CaCl$_2$, or 3 mM EGTA in the absence of CaCl$_2$. Protein sample buffer was added to terminate the reaction, and after boiling the proteins were analyzed on 1% SDS-PAGE. The gel was blotted onto a nitrocellulose membrane and $^{32}$P labeled proteins were visualized by autoradiography.

(B) Results

A region, located downstream to the kinase domain (amino acids 280–312; FIG. 32), was predicted to bind CaM, based on sequence homology with the CaM-regulatory domains of several members of the CaM-dependent kinase family (Deiss et al., 1995). A few different assays performed and described below confirmed both the binding of CaM to the DAP-kinase protein and the regulation of the kinase activity by CaM.

The ability of DAP-kinase to bind CaM was first tested by using labeled CaM in an overlay binding assay. In this assay various FLAG-tagged recombinant DAP-kinase constructs were expressed in COS cells and the protein extracts were electrophoresed on SDS-PAGE, blotted to nitrocellulose membranes, and reacted with $^{35}$S-Met labeled recombinant CaM (Baum et al., 1993). The wild type DAP-kinase was tested, as well as a deleted version of DAP-kinase that lacks the calmodulin regulatory and binding region (i.e., amino acids 266–312; named DAP-kinase-ΔCaM), and the previously mentioned ΔDD mutant. The same blots were also reacted with anti-FLAG antibodies to confirm the presence of the recombinant protein appearing at the predicted size in each slot. Both, the wild type DAP-kinase and the truncated ΔDD, were capable of binding the labeled CaM, whereas the DAP-kinase-ΔCaM failed to do so (FIG. 33A).

The ability of DAP-kinase to bind CaM was further confirmed by using the yeast two-hybrid selection system (Fields & Sterglanz, TIG 10:286–292, 1994). In this assay the region comprising the end of the kinase domain, the CaM regulatory region, the ankyrin repeats domain, and the first P-loop (see FIG. 31 for details), was used as a bait to fish interacting proteins from the HeLa expression cDNA library (Clontech). About 90 positive clones were obtained, all of them being identical to the human CaM full length cDNA. The rescued CaM clones also reacted in the yeast system with a truncated construct of DAP-kinase which was exclusively comprised of the end of the kinase domain and the CaM regulatory domain (amino acids 251–364). Altogether, the CaM overlay assays and the interactions between DAP-kinase fragments and calmodulin in the yeast two hybrid system, confirmed the prediction that DAP-kinase binds CaM through the conserved domain that lies downstream to the kinase domain.

The Ca$^{2+}$/CaM regulation of the kinase activity was further investigated in the in vitro kinase assays. In the absence of Ca$^{2+}$/CaM, both the autophosphorylation and the MLC phosphorylation by DAP-kinase were 8–10 fold lower than the phosphorylation in the presence of Ca$^{2+}$/CaM (FIG. 33B). Interestingly, the CaM regulatory domain deletion mutant (DAP-kinase-ΔCaM) displayed a high level of enzymatic activity in the absence of Ca$^{2+}$/CaM, suggesting a negative regulatory function of this region that could be relieved by the interactions with calmodulin (FIG. 33C). These results were consistent with the stimulatory effects which were imposed by the deletion of this region in other CaM-dependent kinases (Shoemaker et al, 1990). We therefore concluded from the in vitro kinase assays that the kinase activity of DAP-kinase is regulated by Ca$^{2+}$/CaM, and that the removal of the CaM regulatory domain generates a deregulated kinase that is constitutively active.

This type of mutation is an example of a 'gain of function' mutation, i.e. a mutation which results in the DAP gene product having additional function(s). Such a mutation would be useful, e.g. in the death promoting aspect of the invention.

IX. Ectopic Expression of DAP-kinase Induces the Death of HeLa Cells

(A) Experimental Procedure

1. Detergent Extraction Assay

Sub-confluent cultures of COS transfected or HeLa cells, grown on 9 cm plate, were washed once with PBS and then with MES buffer (50 mM MES pH 6.8, 2.5 mM EGTA, 2.5 mM MgCl$_2$) where indicated, HeLa cells were pretreated with 1 mg/ml nocodazol for 0.5 hour, or with 5 mM latrunculin A for 1 hour, before extraction. The cells were extracted for 3 min. with 0.5 ml of 0.5% Triton X-100 in MES buffer supplemented with protease inhibitors. The supernatant (the soluble fraction—Sol) was collected, centrifuged for 2 min. at 16,000×g at 4° C., and the clear supernatant was then transferred to new tubes. Two volumes of cold ethanol were added and the tubes were incubated at −20° C. for overnight, centrifuged 10 min. at 16,000×g at 4° C. and resuspended in 200 μl of 2×protein sample buffer without dye. The detergent insoluble matrix (InSol) remaining on the plate was extracted in 200 μl of 2×protein sample buffer, scraped from the plate with rubber policeman and collected into tube. The samples were loaded on 10% SDS-PAGE, 100 μg protein extracts were loaded on each lane from the Sol fraction, equivalent volumes of InSol were loaded. Analysis of the proteins was done using anti FLAG antibodies (Kodak), the monoclonal antibodies against DAP-kinase (1:1000 dilution; Sigma), anti-tubulin antibodies (1:2000 dilution; Sigma) or polyclonal anti actin antibodies (1:100 dilution; Sigma) as described above.

2. Immunostaining of Cells

Transfected cells (SV-80, REF-52 or COS cells) were plated on glass cover-slips (13 mm diam.), 20,000 cells/well in 1 ml medium within a 24-wells plate. After 48 hours, the cells were washed twice with PBS, fixed and permeabilized simultaneously. This was carried out by incubating the coverslips for 5 minutes in a mixture of 3% paraformaldehyde and 0.3% Triton X-100 in PBS, and then incubating with 3% paraformaldehyde alone for additional 20 minutes. The cells were washed three times in PBS and then incubated in blocking solution (5% normal goat serum and 1% BSA in PBS) for 60 minutes. The cells were incubated with 30 ml of the first antibody (anti FLAG 1:300) for 60 minutes at room temperature, then washed three times in PBS and incubated for 30 minutes with 30 ml of rhodamine-conjugated goat anti mouse antibodies (dilution 1:200; Jakson Immuno Research Lab.) DAPI (0.5 μg/ml; Sigma) and fluoresceine-conjugated phalloidin (1:100; Molecular Probes Inc.) were added at this step. The coverslips were washed three times in PBS, drained and mounted in Mowiol. Microscopy was done under conditions of fluorescent light. Photography was done using Kodak TMX400 film.

3. X-Gal Staining

To detect LacZ expression, cells were fixed with 3% paraform-aldehyde for 5 min., rinsed twice with PBS and stained for 3 h in X-Gal buffer containing 77 mM $Na_2HPO_4$, 23 mM $NaH_2PO_4$, 1.3 mM $MgCl_2$ 1 mg/ml X-Gal, 3 mM $K_3Fe(CN)_6$ 3 mM $K_4Fe(CN)_6$. Reaction was stopped by 70% ethanol. Photography was done under phase microscopy using Kodak Ektachrome 160T.

(B) Results

The first indication that attributed a function to DAP-kinase, as a positive mediator of cell death, was based on the finding that its reduced expression by the anti-sense RNA protected HeLa cells from apoptotic cell death initiated by the IFN-γ receptors. It was therefore interesting to test whether elevated levels of DAP-kinase protein, generated by the ectopic expression of the full length sense cDNA, may cause cell death on its own without any external stimulus.

In order to express DAP-kinase in mammalian cells, the full length cDNA was cloned into pcDNA3 vector (InVitrogen), under the control of the CMV promoter. Similar constructs were prepared containing the catalytically inactive DAP-kinase-K42A mutant, and the CaM regulatory domain deletion mutant (DAP-kinase ΔCaM). DAP-kinase constructs, as well as the empty vector were transfected into HeLa cells by the calcium phosphate co-precipitation technique. After 2–3 weeks of growth in selection medium (G-418), the drug resistant cells were stained with crystal-violet. It was found that transfection with the wild type DAP-kinase significantly reduced the number of surviving colonies compared to the transfections with the empty vector (FIG. 34A). The inhibitory effect was even more pronounced upon transfections with the constitutively active DAP-kinase-ΔCaM mutant, suggesting that this mutant had the most prominent growth restrictive effects. In contrast, the catalytically inactive DAP-kinase mutant did not reduce at all the number of colonies. Instead, the number of colonies generated by transfection with the K42A mutant was slightly increased, compared to the transfections with the empty vector, and the size of individual colonies was often larger (FIG. 34A). Transfection with the catalytically inactive DAP-kinase mutant therefore seemed to confer some growth advantage to cells during the process of colony formation. These results were repeated in six independent experiments, with different preparations of plasmid DNA. They were also repeated with other types of expression vectors (not shown). These data provided the first indication that the ectopic expression of DAP-kinase was not compatible with continuous cell growth, and that this feature depended on the intrinsic kinase activity. They also provided the first hint that the catalytically inactive mutant of DAP-kinase may have a dominant-negative function, an issue that was examined later under the restrictive effects of IFN-γ (see below).

In order to determine more precisely the fate of the cells and to understand the basis for the suppression of colony formation, the cells were examined two days after the transfection with the DAP-kinase gene. In these experiments, the LacZ marker gene was used to facilitate the recognition of the transfected cells that ectopically express the DAP-kinase. A vector was constructed for this purpose containing the internal ribosomal entry site (IRES) of polio-virus and thus directing the expression of both LacZ and the wild-type DAP-kinase genes within a single bicistronic message. The bicistronic mRNA was expressed from the tetracycline-repressible promoter (Gossen & Bujard, PNAS 89:5547–5551, 199Z). The morphology of LacZ containing blue cells was determined 48 hours post transfection, in cultures which were maintained in the absence of tetracycline to allow the continuous expression of both genes. It was found that 34% of the lacZ containing cells which expressed the wild-type DAP-kinase displayed the morphology of apoptotic cells, i.e., cell shrinkage and rounding up followed by detachment from the plates. In contrast, in the control vector a background of less than 5% apoptotic cells was detected (FIG. 34B). Altogether, the morphological assessments and the colony formation assays suggest that overexpression of DAP-kinase promotes cell death, thus reinforcing the role of DAP-kinase as a positive mediator of cell death.

X. The Catalytically Inactive DAP-kinase Protects Cells from the IFN-γ-induced Cell Death The hypothesis that DAP-kinase-K42A mutant may function in a trans-dominant negative manner was tested. This was done by checking whether the catalytically inactive mutant kinase may protect HeLa cells from the IFN-γ induced cell death, similar to the protection conveyed by the anti-sense RNA expression. In this experiment the empty pcDNA3 vector and the one containing the DAP-kinase-K42A mutant, were transfected into HeLa cells. Forty eight hours after transfection, the cells were split and subjected to double selection with 700 μg/ml G-418 and 200 U/ml of IFN-γ. Under these stringent conditions, the transfectants that expressed the control vector were efficiently killed, and the background of G-418 resistant cells was extremely low. In contrast, transfection with the K42A mutant had significantly increased the number of surviving cells (FIG. 35A). On average, the relative number of colonies that survived in the presence of IFN-γ was 5-fold higher in the K42A transfectants than in the corresponding pcDNA3 transfectants (FIG. 35B). Also the average cell number per colony was higher in the K42A transfectants. These results indicate that the K42A mutant can protect HeLa cells from the IFN-γ induced cell death, presumably by acting in a dominant negative manner, thus interfering with the normal function of the endogenous DAP-kinase.

This is an example of a mutation which can result in the neutralization of the endogenous DAP gene product. Such a mutation would be useful, e.g. in the death preventing aspect of the invention.

XI. Cytoskeleton Localization of DAP-kinase

One of the key questions in understanding the DAP-kinase mode of action concerns its intracellular localization. In order to define, by immunofluorescent staining, the intracellular localization of DAP-kinase, we have transiently transfected SV-80 human fibroblasts with the aforementioned FLAG-DAP-kinase-K42A construct, and immunostained the cells with anti-FLAG antibodies. The K42A mutant was chosen to avoid death-related morphological changes upon overexpression (transfection of SV80 cells with wild-type DAP-kinase induced cell death similar to that observed in HeLa cells, as detailed below).

The FLAG-DAP-kinase-K42A was stained as a network of delicate fibers reaching the cell periphery; nuclei were not stained (FIG. 45A). The same pattern was also revealed by staining with anti-DAP-kinase mono-clonal antibodies (not shown). This was the first indication which suggested a cytoskeletal localization of DAP-kinase protein. Double staining of the transfectants with anti-FLAG antibodies and with fluoresceine-conjugated phalloidin which binds to actin fibers, revealed a considerable overlap (FIG. 45A). In contrast, there was no overlap with the microtubule staining (not shown).

The cytoskeletal localization of DAP-kinase was subsequently confirmed by the biochemical fractionations of both the endogenously and exogenously expressed protein. We used the well elaborated protocol of gentle cell extraction with nonionic detergent (0.5% Triton X-100) that removes lipids and soluble proteins, leaving intact the detergent insoluble matrix composed of the nucleus, the cytoskeleton framework, and cytoskeleton-associated proteins. In non-transfected HeLa cells, the endogenous DAP-kinase (recognized by monoclonal antibodies raised against the C-terminus of the protein) appeared exclusively in the detergent insoluble fraction (FIG. 45B). In contrast, β-tubulin and actin that both have a constant soluble pool, were found both in the detergent soluble and insoluble fractions. We used nocodazol, a microtubule disrupting drug, to change the solubility of β-tubulin. As can be seen in FIG. 45B, after treatment of HeLa cells with nocodazol, all of the β-tubulin protein was found in the soluble fraction, whereas the solubility of both DAP-kinase and actin did not change. On the other hand, after treatment of the cells with latrunculin A, a microfilament disrupting agent, a substantial portion of DAP-kinase was found in the soluble fraction. Here, actin was found almost exclusively in the soluble fraction, whereas the solubility of β-tubulin did not change. These results in combination with the double immunostaining suggest that DAP-kinase might be localized to the microfilament system of the cytoskeleton.

The detergent extraction assay was further used to map the region within the DAP-kinase that associates with the cytoskeleton. For this purpose, we used COS cells transfected with FLAG-DAP-kinase, in which the pattern of staining with anti-FLAG antibodies was similar to that observed in the aforestudied SV-80 and HeLa cells (FIG. 46A). A series of constructed DAP-kinase deletion mutants in the pECE-FLAG or pcDNA3—FLAG expression vectors were transfected into COS cells. These transfected COS cells were subjected to detergent extraction as described above, and the immunoblots were reacted with the anti-FLAG antibodies to monitor in each case the elution profile of each DAP-kinase mutant product. The results are summarizes in FIG. 46B. From the detailed analysis it was concluded that the region comprising amino acids 641–835 contributes to the detergent insolubility of DAP-kinase and therefore it is a critical region responsible for the association with the cytoskeleton. Its deletion interfered with the cytoskeletal association, and conversely, this region by itself was detergent insoluble. Interestingly, fragments containing the ankyrin repeats without the cytoskeletal binding domain were completely detergent soluble.

The intracellular localization of DAP-kinase may be relevant to the cytoskeletal alterations that occur during the IFN-γ-induced death of HeLa cells. Staining of actin with the phalloidin showed that after the treatment with the cytokine a complete distruption of microfilament organization took place, and stress fibers disappeared (FIG. 47A). The loss of stress fibers occurred before the typical nuclear alterations, which consist of chromatin condensation and segmentation (Deiss et al., 1995), had taken place. In order to follow the possible effects of DAP-kinase overexpression on the cytoskeleton network, REF-52 fibroblasts possessing a well organized actin cytoskeleton were used.

The constitutively active FLAG-DAP-kinase-ΔCaM mutant was transiently transfected into these cells. After 48 hours, the cells which were positively stained with the anti FLAG antibodies, were examined for nuclear and cytoskeletal alterations, in comparison to the adjacent non-transfected cells. This was achieved by triple staining with DAPI (for nuclei) and phalloidin (for the microfilament system) (FIG. 47B). It was found that the FLAG positive cells displayed a disrupted pattern of microfilament staining that was reminiscent of the cytoskeletal alterations occurring in the IFN-γ-treated cells. No signs of chromatin condensation or fragmentation could be detected at this time point in the DAP-kinase—transfected cells (FIG. 47B). In contrast, transfections with the truncated catalytically active DAP-kinase (DAP-kinase-DEcoRV; amino acids 1–305 in FIG. 46B) which was mislocalized in the cells, and showed a nuclear rather than cytoskeletal staining, did not lead to any cytoskeletal alterations. In these transfections, the FLAG positive cells displayed a normal pattern of microfilament staining which could not be distinguished from the adjacent non-transfected cells (FIG. 47B). These results were repeated in SV80 cells, in which more than 80% of transfectants expressing the FLAG-DAP-kinase-DCaM mutant showed abnormal pattern of microfilament staining, whereas no change was caused by the DAP-kinase—DEcoRV transfections (not shown). These results suggest a link between the correctly localized active DAP-kinase and the cell death-related cytoskeletal and morphological changes that develop in response to IFN-γ. Thus, the cytoskeleton localization of DAP-kinase, and perhaps other DAP proteins, can be important with respect to the death-promoting and death-preventing aspects of the invention, e.g. with respect to drugs which can prevent protein localization in the cytoskeleton.

XII. Expression of DAP-1 and DAP-2 Proteins in Various Cells and Tissues

Figure 10:
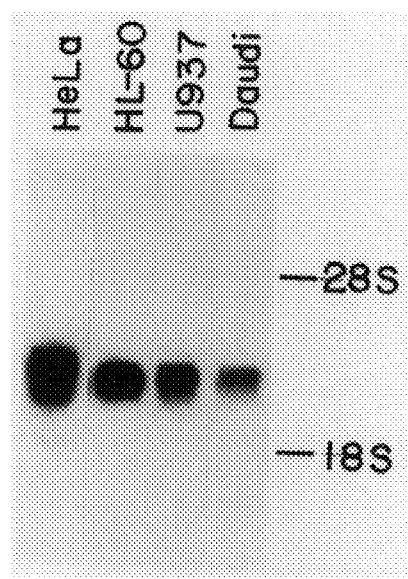
FIG. 10 shows Northern blot analysis of mRNA obtained from several hematopoietic cells probed with labeled DAP-1 cDNA.
Figure 11:
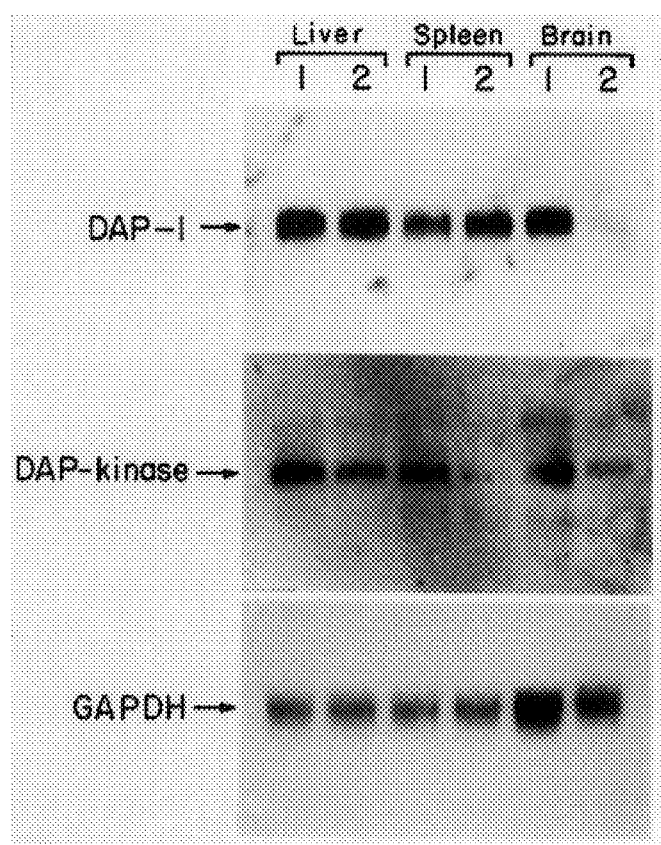
FIG. 11 shows Northern blot analysis of mRNA obtained from liver, spleen or brain of normal embryos (2) and embryos with Down Syndrome (1) both probed with the labeled cDNA or DAP-1 or DAP-2. In order to evaluate levels of total mRNA, GAPDH was used (bottom).

Examination of a variety of cell lines and tissues revealed that these two genes are likely to be ubiquitously expressed. FIG. 10 shows the Northern blot analysis of RNA from different hematopoietic cells probed with the DAP-1 cDNA. The 2.4 Kb mRNA transcript of this gene was detected in granulocytes (HL-60) B lymphoid (Daudi) and macrophage (U937) cells. The expression levels in the hematopoietic cells was lower than in HeLa cells. FIG. 11 shows results of examination of the mRNA expression in human embryonic tissues: brain, spleen (predominantly B cells) and liver (predominantly erythrocytes). Again the single 2.4 Kb mRNA transcript was detected in these tissues by the DAP-1 cDNA probe.

The DAP-2 cDNA probe 2 recognized the 6.3 Kb mRNA encoded by this gene in these different tissues (FIG. 11). The embryonal liver and spleen tissues from Down syndrome seemed in this blot to express higher levels of the DAP-2 gene (compared to the GAPDH levels) while the brain tissue from Down syndrome contained higher levels of DAP-1 mRNA than the corresponding normal brain.

XIII. Screening Cell Lines for DAP-kinase Activity (A) Experimental Procedure 1. Maintenance of cell lines and treatment with 5-Azadeoxy-cytidine—All haematopoictic cell lines (see ATCC for description of various lines) were grown in RPMI 1640 supplemented with 10% complement-inactivated FCS (Gibco-BRL), 100 IU/ml penicillin and streptomycin, and 2 mM L-glutamine, at 37° C. and 5% $CO_2$. For the bladder carcinoma derived cell lines (see ATCC for description of various lines), DMEM was used. The bladder carcinoma cell lines were plated at $1E^5$ cells/100 mm dish, and treated 24 hours later with 5-Aza-2'-deoxycytidine (Sigma Chemical Co., St. Louis, Mo.) at final concentration of 1 µM. The medium was changed 24 hours after addition of the drug and every 3 days thereafter. Proteins were extracted 9 and 16 days after treatment for the early passage and late passage, respectively.

2. Northern blot analysis—Total RNA was extracted from the various cell lines using Trireagent (MRC). Samples of 3 μg poly A+ RNA, prepared with oligo-dT Dynabeads (Dynal) as described by manufacturer, were separated on 1% agarose gels, and hybridized to Hybond-N nylon membranes (Amersham), as described (Sambrook, 1989). DNA probes were prepared using [α-$^{32}$P]dCTP with commercially available random priming kits (Boehringer Mannheim). Prehybridization, hybridization and washing of filters were performed as described (Sambrook,1989).

3. Immunoblot analysis—Cells were harvested and protein extracts were prepared as previously described (Deiss et al., 1995). The protein extracts (200 μg/lane) were fractionated on 7.5% SDS-PAGE. The proteins were transferred to a nitrocellulose filters (Schleicher and Schuell) with a semi-dry semi-phor blotter (Hoefer Scientific Instruments). The mouse anti-human DAP-kinase monoclonal antibodies were from BioMaker (Rehovot, Israel). Anti-human vinculin antibodies were from Sigma. Anti-human DAP3 were prepared as previously described (Kissil et al., 1995). Immunodetection was carried out using the ECL detection system (Amersham).

(B) Results

Figure 36:
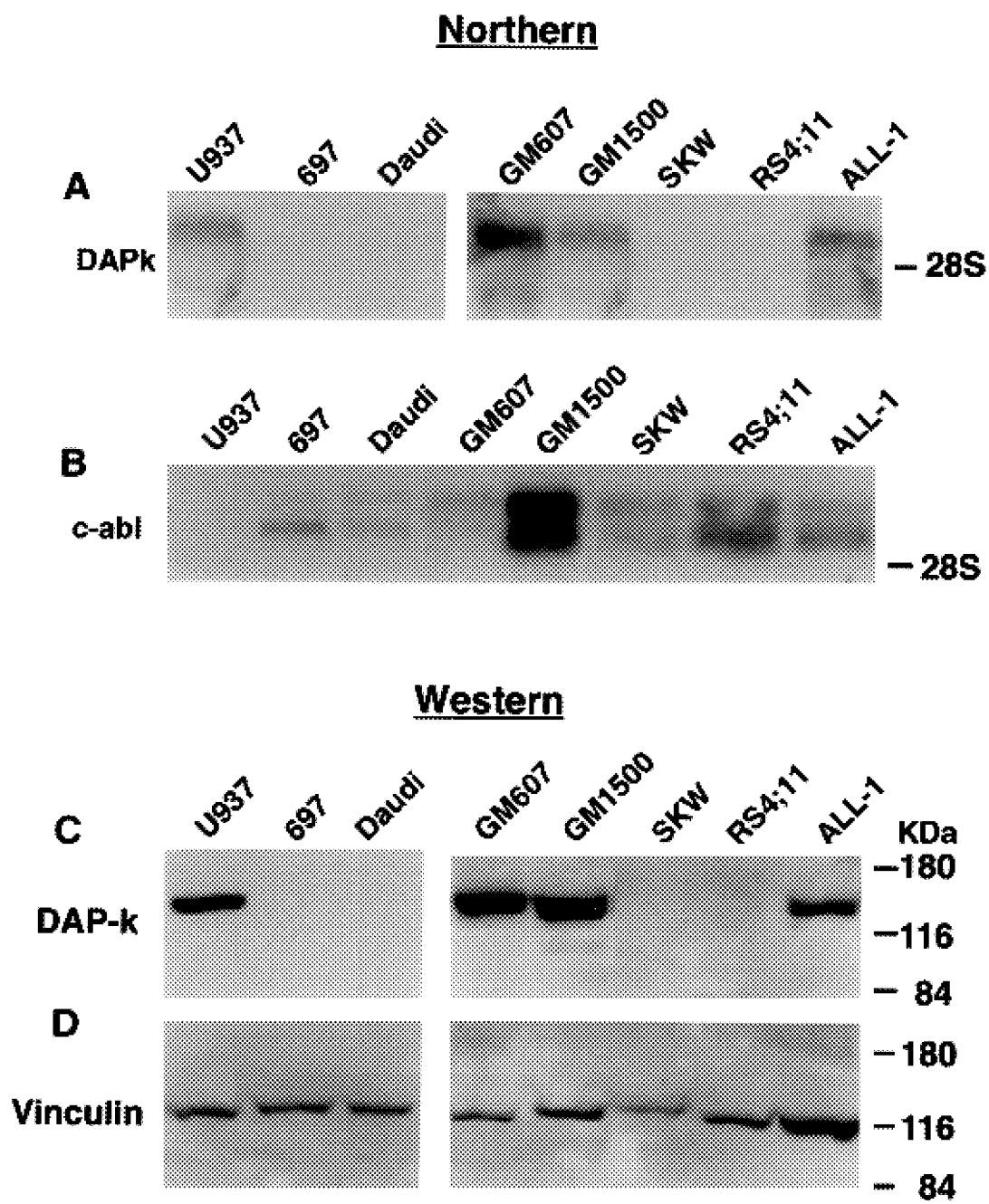

When analyzing the expression of the DAP-kinase mRNA transcript in various cell lines, it was found that it was not expressed in a substantial proportion of cell lines derived from human B-cell neoplasms. Nine different cell lines, representing different stages of B cell maturation, were examined. Seven of them—SKW, 697, Daudi, RS4:11, MV4:11, SK-DHL and B380 failed to express detectable levels of the DAPk mRNA. Two cell lines: ALL-1 representing a premature B cell stage (Erikson et at. PNAS 83:1807–11, 1986) and the B-1 representing an early progenitor (Erikson et al., 1986; Cohen et al., 1991) expressed DAP-kinase (FIG. 36 and Table 3). In EBV-immortalized B-cell lines established from normal peripheral B cells, GM1500 and GM607, the DAP-kinase mRNA was present (FIG. *[1]37A). The signals in the DAP-kinase negative cell lines remained below detection limits also when higher amounts of poly A+ RNA (15 μg) were analyzed (not shown).

TABLE 1

Summary of cell types that were examined for expression of DAP-kinase at the protein level. The data was grouped according to the origin of the cell line, and the expression pattern of DAP-kinase.

| Cell line origin | DAP-K expression Positive | DAP-K expression Negative | DAP-K expression <1% (a) |
| --- | --- | --- | --- |
| Normal B-cells (2) | (2) GM607, GM1500 | (—) | (—) |
| B-cell Neoplasms (9) | (2) ALL-1, B-1 | (7) Daudi, 697, RS4:11, B380, MV4:11, SKW, SK-DHL | (—) |
| Bladder Carcinomas (14) | (8) RT4, RT112, JO'N, 5637, HT1-197, 253J, J82, SW1710 | (4) SCa-BER, T24, 609CR, HT1376 | (2) UM-UC-3, VM-CUB-2 |

(a) Determined by comparison of signal intensity on western blot to signal levels of the DAP-kinase positive bladder carcinoma cell lines.

Interestingly, the c-Abl mRNA transcripts were expressed in all the examined cell lines. The c-Abl gene is the closest known marker to DAP-kinase (Feinstein et al., 1995) The expression of c-Abl appeared to be normal and the two expected mRNA transcripts were observed in all the cell lines irrespective of whether they expressed DAP-kinase mRNA (FIG. 36B). The undisturbed pattern of c-Abl expression minimized the possibility that lack of DAPk expression is a consequence of gross rearrangements or deletions at 9q34.

The protein analysis confirmed the RNA data. Protein extracts prepared from the various cell lines were examined for the presence of the DAP-kinase protein by immunoblot analysis. It was found that in all the cell lines that did express DAP-kinase mRNA transcript, the protein product with the expected size of 160 kDa, was also detected. In contrast, in cell lines in which DAP-kinase transcript was not detected there was no trace of the DAP-kinase protein (FIG. 36C). The same immunoblots were also reacted with anti-vinculin antibodies as an internal control (FIG. 36D). Together, the RNA and protein data indicate that the absence of DAP-kinase expression is most probably a genuine phenomenon and not an artifact of the assays.

The expression of DAP-kinase protein was then examined in various cell lines of bladder carcinoma origin. This was done by Western blot analysis of protein extracts prepared from 14 different cell lines. Out of the 14 lines examined eight lines expressed DAP-kinase, four showed no detectable DAP-kinase protein expression, and two other lines expressed it at levels lower than 1% in comparison to the DAP-kinase positive lines (Table 3). These results indicated that loss, or very low levels of DAP-kinase expression also occurs at a statistically significant frequency in bladder carcinoma cell lines. Two DAP-kinase negative bladder carcinoma cell lines were chosen (T24 and HT1376) and treated with 5-azadeoxycytidine in order to test whether the absence of DAP-kinase expression was due to DNA hypermethylation. Treatment of cells with 5-azadeoxycytidine causes the removal of methyl groups from CpG dinucleotides and thus may reverse promoter shut-off/silencing due to hypermethylation and may restore expression of the relevant gene (Jones, 1985). Cells were treated with the drug for 24 hours, washed, and protein extracts were prepared at early and late passages thereafter. The expression of DAP-kinase was analyzed by reacting the immunoblots with anti-DAP-kinase antibodies. It was found that while the DAP-kinase was undetectable before treatment (FIG. 37, lane 1 and 4), the addition of 5-azadeoxycytidine to the growth medium restored DAP-kinase expression and strong signals at the expected protein size were detected early after the drug treatment (FIG. 37, lane 2 and 5). The restored levels of DAP-kinase expression are similar to the average expression levels of DAP-kinase in several DAP-kinase positive bladder carcinoma cell lines that were tested (data not shown). The effect was specific since the expression of two other proteins, which unlike DAP-kinase were initially present in this cell line: vinculin, and DAP-3, was not influenced at all by the 5-azadeoxycytidine treatment (FIG. 37, lanes 1 through 5). Late after drug treatment of the T24 cells (after six passages), the expression of DAP-kinase was again completely abolished, probably due to de novo methylation of the gene (FIG. 37, lane 3).

XIV. Cloning and Sequencing of DAP-3, DAP-4 and DAP-5

Clone 259 (DAP-3) was sequenced and used to screen a K562 λgt10 cDNA library as described above for DAP-1 and DAP-2. The sequence of the full length cDNA of DAP-3 and the deduced amino acid sequence is shown in FIG. 12 SEQ ID NOS: 14–17, respectively.

Clone 253 (DAP-4) was partially sequenced as described above for DAP-1 and DAP-2 and the results arc shown in FIG. 13 (SEQ ID NO: 5).

Clone 260 was among the rescued vectors described in Table 1 which protected the HeLa cells from IFN-γ-induced programmed cell death. It was isolated as described in the detailed description of the invention (section I(A)). It carried a cDNA fragment of 763 bp and the sequence analysis indicated that it corresponded to a novel gene (named DAP-5). Northern blot analysis indicated that DAP-5 is transcribed into a 3.8 Kb mRNA. DAP-5 mRNA was found to be widely expressed in a variety of normal tissues.

The 763 cDNA fragment was used for screening a cDNA library originating from K562 cells. The phage clone that carried the longest cDNA insert (3.8 Kb) was sequenced. This cDNA clone comprises of an open reading frame (ORF) that corresponds to 940 amino acids (SEQ ID NO: 7), as shown in FIG. 15. The deduced amino acid sequence predicts that the protein is highly homologous, yet not identical, to the translation initiation factor 4γ(eIF4γ,p220). Thus, DAP-5 may be regarded as a novel member of what appears to be a family of the eIF4γ type of translation initiation factors. Most interestingly, and very much unexpectedly, the 763 bp fragment that was presented in the original clone #260 was inserted in the vector in the sense orientation. In this region (marked by a solid line in FIG. 14 (SEQ ID NO: 10); nucleotides 1764–2528) there is an ATG codon that could drive the synthesis of a mini protein that is 230 amino acids long. Indeed, in vitro transcription and translation of this fragment yielded a protein of that predicted size, and mutation of this ATG eliminated the miniprotein synthesis. Transfections of HeLa cells with vectors that express the 763 cDNA fragment from the tetracycline regulated promoter protected the cells from cytokine-induced cell death. One possibility is that the mini-protein functions as a dominant negative mutant that competes with the death-inducing properties of the full length protein. Other possibilities also exist.

XV. Expression of the DAP-5 cDNA Fragment (#260) Exerts a Dual Effect on HeLa Cells (A) Experimental Procedure 1. Transfections and Selection Procedures Two secondary polyclonal HeLa cell populations, expressing the DAP-5 763 bp cDNA fragment from the pTKO1 vector were generated. This was performed by the transfection of subconfluent monolayers of $1.5 \times 10^6$ HeLa cells with 40 μg of the corresponding plasmid (named pTKO1–260). In parallel, HeLa cells were transfected with a control vector, pTKO1-DHFR (Deiss & Kimchi, 1991). Pools of $10^4$ independent stable clones were generated from each transfection. The stable transfectants were maintained in the presence of 200 μg/ml hygromycin B (Calbiochem). Subconfluent monolayers of $1.5 \times 10^6$ HeLa-tTA cells were transfected with 15 μg of pSBc-bl plasmid or pSBc-bl plasmid carrying either the #260 fragment (pSBc-bl-260) or its mutant derivatives (single & triple ATG mutants) and selected in the presence of either 10 or 50 μg/ml bleomycin. Pools of $10^2$–$10^3$ independent stable clones were generated from each transfection.

2. In Vitro Translation of DAP-5 Protein in Reticulocyte Lysate

The full length cDNA insert, or the #260 variants, cloned into the Bluescript vector (Stratagene), were used as templates for in vitro transcription from the T7-promoter. These RNAs were then translated in reticulocyte lysates (Promega) using the conventional procedures with [$^{35}$S]-methionine (Amersham) as a labeled precursor. The reaction products were resolved by fractionation on 12.5% SDS polyacrylamide gel, followed by salicylic acid amplification of the radioactive signal performed as described in Kissil, J. L., et al, J. Biol. Chem. 270:27932–936 (1995). ATG codons at position 1785–1787, 2010–2012 or 2040–2042 were mutated by oligonucleotide directed mutagenesis (ATG was converted into AAG or TTC or ATC respectively).

3. Preparation of Antibodies and Immunoblot Analysis

The DAP-5 sequence corresponding to amino acids 522–776 of the coding region encompassed in the #260 fragment, was fused in-frame to pGEX1 (GST260). Expression of the glutathione S-transferase (GST) fused chimera was induced in E. Coli strain XL1-Blue by IPTG. The GST fused product purified on glutathione beads was used to immunize two rabbits. The antiserum was depleted of the anti-GST antibodies by passing it through CNBr-activated sepharose beads (Pharmacia Biotech Inc.) coupled to GST. Affinity purification was then carried out on CNBr-activated sepharose beads coupled to GST260. In several experiments the signal of the mini-protein in the HeLa cell transfectants was below detection limits.

4. Western Analysis

HeLa-tTA cells were harvested and lysed by boiling in Sample buffer. The protein samples were fractionated by 10% SDS-PAGE and then transferred to nitrocellulose filter (Schleicher & Schuell). The blots were reacted with the affinity purified polyclonal antibodies (1:20 dilution) and immunodetection was done using the ECL detection system (Amersham Corp.)

(B) Results

The pTKO1 construct containing DAP-5 cDNA fragment #260, was transfected (in duplicates) into HeLa cells to generate two stable polyclonal cell populations (named 260-t1 and 260-t2). A control polyclonal HeLa cell population (designated DHFR-t1) was obtained by transfection of the pTKO1 vector carrying the DHFR gene. These three transfected cell cultures were subjected to the long-term treatment with IFN-γ. As shown in FIG. 38B, there was a 100 to 200-fold increase in the number of growing colonies in the 260-t1 and 260-t2 cell cultures, as compared to the DHFR-t1 cell population. This means that the total number of colonies which were rescued from the inhibitory effects of IFN-γ by this cDNA fragment, corresponded only to 0.1–1% of the initial cell population. This pattern, in which only a small fraction of cells were protected from programmed cell death was very similar to the effect that was conferred by the anti-thioredoxin RNA (FIG. 4 in Deiss & Kimchi, 1991) and by fragment #253 (not shown), all classified in subgroup II.

The size of exogenous DAP-5 RNA in the 260-t1 and 260-t2 transfectants was 1.7 Kb (consisting of 763 bases of the cDNA insert, 800 bases of sequences derived from the expression cassette (Deiss & Kimchi, 1991) and of the poly (A) tail). The expression levels of the exogenous RNA were much lower than those of the endogenous 3.8 kb transcript (FIG. 38A). This stood in sharp contrast to the eight plasmids of subgroup I, whose RNA products accumulated in HeLa cells in large excess over the endogenous mRNA transcripts (i.e., antisense corresponding to DAP-1, DAP-kinase, DAP-3 and cathepsin D). A more detailed comparison between the two subgroups was performed by hybridization of Northern blots, containing RNA from the different HeLa transfectants, with a common DNA probe derived from the pTKO1 vector. As shown in FIG. 38C, under conditions where the RNA expressed from pTKO1–230 vector (containing the antisense fragment of DAP-1) gave a strong signal, the RNA transcribed from fragment #260 was still below detection limits. Similar low levels of RNA were expressed from other two subgroup II cDNA fragments carried by the same vector, thioredoxin (Deiss & Kimchi, 1991) and DAP-4 (#253) (FIG. 38C). Thus, the low levels of the ectopically expressed RNA in the established polyclonal populations provided a second characteristic feature of subgroup II cDNA fragments. This could reflect either RNA instability, or alternatively the selection of transfectants with low copy number of episomes. The latter seemed to be true since a transcript common to all the transfectants—the mRNA expressed from the hygromycin B resistance gene placed within the pTKO1 under the control of the thymidine kinase promoter—paralleled the expression levels of the inserted cDNA fragments (FIG. 38D). Thus, it was postulated that during the establishment of the polyclonal cell populations, done in the presence of hygromycin B only, cells containing a low copy number of the pTKO1-260 episomes gained significant growth advantage.

To further pursue this possibility, the question of whether indeed high expression levels of the DAP-5 partial cDNA were incompatible with continuous cell growth was tested. For this purpose, a polycistronic vector was constructed (pSBc-bl-260) which directed the expression of a bicistronic message containing both the #260 cDNA fragment and the SH-LacZ, which directs the synthesis of a fused protein conferring resistance to bleomycin and producing b-galactosidase (Cayla). The LacZ was used as a marker to evaluate the bicistronic mRNA levels in individual cells. The #260 cDNA fragment was translated in a cap-dependent manner, whereas the SH-LacZ fused gene was placed downstream to the poliovirus internal ribosomal entry site (IRES). Since IRES-directed translation is less efficient than the cap-dependent one, high levels of bicistronic message, had to be expressed in order to allow the survival of cells under bleomycin selection. This enforced the system to produce high levels of #260-derived expression products in the cells.

It was found that transfections of HeLa-tTA cells with the pSBc-bl-260 vector, did not yield stable clones in the presence of 50 μg/ml bleomycin, while transfection with the control vector lacking the insert (pSBc-bl) readily generated clones. At lower drug concentrations (10 μg/ml bleomycin), small clones did arise after transfections with the pSBc-bl-260 vector; yet, they slowly died thereafter. This indicated that high levels of expression from #260 cDNA fragment was lethal to cells, and that the #260-dependent cell death displayed slow pattern of killing. The expression levels of the bicistronic mRNA and hence of fragment #260, that were permissive for cell growth, were not sufficient for conferring bleomycin resistance and therefore the drug had to be removed in order to enable further analysis of these transfectants.

The β-galactosidase activity, served to quantify the expression on a single-cell basis in surviving cells. In the pSBc-bl-260-transfected cultures, the extent of blue staining was very weak in all the cells on the plate. In contrast, the polyclonal cell populations obtained from transfection with the control vector, and selected under identical conditions, showed a strong pattern of β-galactosidase staining, exceeding by many fold the one in pSBc-bl-260 transfectants (FIG. 39A). Together, the reduced cloning efficiency and the weak β-galactosidase activity in the survived cells, proved that there was a negative selection against high expression of the #260 cDNA fragment. We concluded that expression from the rescued DAP-5 cDNA fragment had a dual effect: at low levels it conferred IFN-γ resistance (a property that led to its functional cloning); at higher levels, it was toxic and not permissive to continuous cell growth.

XVI. Fragment #260 Directs the Expression of a Functional Mini Protein

Three AUG codons, that could serve as potential initiators of translation, were found in the ORF of fragment #260. One was located at the beginning of the fragment and could potentially initiate the synthesis of a 28 kDa protein; the two others were located 85 and 75 aa downstream and could give rise to 20 and 18.8 kDa proteins, respectively. In vitro translation of the RNA transcribed from the 763 bp DAP-5 cDNA fragment, generated a doublet of proteins that had an approximate size of 28 kDa (FIG. 40A, lane 3). A missense mutation in the first ATG codon completely eliminated the synthesis of these two closely migrating proteins, without affecting the two downstream ones. Missense mutation of the next two ATG codons without affecting the first one, did not interfere with the translation of the doublet; a triple mutation in all potential initiation codons completely prevented the protein translation as did the single mutation in the first ATG codon (FIG. 40A lanes 4–6, respectively). Thus it was concluded that the rescued cDNA fragment could drive the expression of a mini-protein starting at Met 529. This mini-protein was also detected in the aforementioned population of HeLa cells that had been transfected with the pSBc-bl vector harboring the #260 fragment. As shown in FIG. 40B, affinity purified polyclonal antibodies, raised against the recombinant mini-protein, identified two closely migrating proteins with approximate size of 28 kDa exclusively in the cells transfected with the pSBc-bl-260 and not in cells transfected with the empty vector.

The question was raised whether the biological effects conferred on the transfected cells by fragment #260 resulted from expression of the mini-protein. For that purpose we have subcloned each of the two mutant cDNA fragments, which failed to be translated in vitro, into the pSBc-bl vector. In contrast to the transfections with the protein expressing DAP-5 fragment, polyclonal cell populations obtained with the mutant ones were established in the presence of bleomycin, with an efficiency similar to that of the control vector. In addition, the β-galactosidase activity in these transfectants was as high as in the cells transfected with the control vector (FIG. 39B). Thus, high levels of expression of mutant DAP-5 cDNA fragment proved to be compatible with continuous cell growth. The translated mini-protein is therefore responsible for the cellular effects that the rescued DAP-5 fragment exerts on cells.

XVII. Characterization of Cathepsin D as a DAP Molecule

The initial microscopic observations, performed on the different HeLa cells that had been transfected with the individual rescued pTKO1 clones (described in Table 1), indicated that plasmid pKTO1–229 (group 6) conveyed similar effects to those conferred by the plasmids from group 1. It reduced the susceptibility of the cells to the IFN-γ-induced cell death but not to its cytostatic effects.

The cDNA carried by plasmid pTKO1–229 was identified upon sequencing as a BamHI-HindIII fragment of human cathepsin D cDNA, which was present in the expression vector in the antisense orientation. The DNA probe, corresponding to fragment #229, hybridized as expected to a single endogenous 2.5 Kb mRNA, both in control and in the transfected HeLa cells. The steady state levels of cathepsin D sense mRNA were increased 3–4 fold by the IFN-γ treatment. In the pTKO1–229 transfected cells the DNA probe also hybridized to the composite antisense RNA. The levels of antisense cathepsin D RNA were stimulated 5-fold in response to IFN-γ due to the presence of an ISRE enhancer element in the pTKO1 expression vector (not shown).

Cathepsin D is an aspartic protease that is found normally in lysosomes where it functions in protein catabolism. Yet, in some pathological situations it has been suggested that this protease can function in the cytosol, and its activity was associated with degenerative brain changes, muscular dystrophy and connective tissue disease pathology (Matus and Green (1987); Biochemistry, 26, 8083–8036). The present invention shows for the first time that the expression of this protease is indispensable for the execution of programmed cell death that is induced by IFN-γ and other cytokines (see below). Thus, cathepsin D joins the growing list of proteases that play a key role in different scenarios of programmed cell death.

The DNA sequence and amino acid sequence of cathepsin D are shown in FIG. 14 (SEQ ID NO: 11) (Faust, P. L. et al. (1985) PNAS USA 82, 4910–4914).

XVIII. Anti-sense Cathepsin D RNA and Pepstatin A Protect HeLa Cells from IFN-γ-induced Cell Death (A) Experimental Procedure 1. Neutral-Red Dye Uptake Assay The HeLa cells were cultivated in 96-well microtiter plates at an initial number of 15,000 or 20,000 cells/well and were treated with either IFN-γ or anti-APO-1 antibodies, respectively, or were left untreated. Where indicated, pepstatin A (pepA) (Sigma) or DMSO were added to the culture medium. The culture medium and drugs were replaced every 3–4 days. Viable cells were stained with neutral-red (Sigma) as detailed before (Wallach D., J. Immunol. 132:2464–2469, 1984). The dye uptake was measured in quadruplicates at λ=540 nm using an automated Micro-Elisa auto-reader.

2. RNA Analysis

Total cellular RNA was extracted using Tri-Reagent™ (Molecular Research Center, Inc.). Samples of 20 μg total RNA were processed on Northern blots as previously described in detail (Yarden and Kimchi, Science 234: 1419–21, 1986). DNA fragments, used as probes, were purified from agarose gels with the Geneclean kit (BIO 101 Inc.). The fragments were labeled with 5 μCi of [α-$^{32}$P]-dCTP (Amersham>3000 Ci/mmole), using a Random Priming kit (Boehringer).

3. Protein Analysis

Cells were extracted in RIPA (10 mM Tris-HCl pH 7.2, 150 mM NaCl, 1% Triton X-100, 0.1% SDS, 1% deoxycholate and 5 mM EDTA) containing a mixture of protease and phosphatase inhibitors (1 mM PMSF, 4 μg/ml aprotenin, 100 μg/ml leupeptin, 1.5 μg/ml pepstatin A, 2 μg/ml antipain, 2 μg/ml chymostatin, 0.1 mM NaVO3 and 0.1 mM NaF). Protein concentration was determined using a Protein assay reagent (Bio-Rad). Aliquots of 300 μg of the cell lysates were fractionated by SDS polyacrylamide gel electrophoresis (12%). The proteins were then electroblotted onto a nitrocellulose membrane and blots were incubated in blocking solution (10% skimmed milk and 0.05% Tween-20 (Sigma) in PBS) for 2 hours at room temperature, and then reacted with an antibody-containing solution for 18 hours at 4° C.

The washed membranes were incubated with peroxidase-conjugated second antibodies, either goat anti mouse IgG (IgG(H+L) chains, Jackson immuno Research Lab.) at a 1:10,000 dilution, or Protein A-conjugated to horse-radish peroxidase (Amersham) at a 1:10,000 dilution. Detection of the bound antibodies was carried out using ECL detection reagents (Amersham). The anti cathepsin-D monoclonal antibodies (EURO/DPC—U.K.) were used at 1:5 dilution; these antibodies recognize an epitope in the 30 Kd heavy chain. Polyclonal antibodies against the copper zinc superoxide dismutase (SOD) were used at a 1:250 dilution. These antibodies were kindly provided by Y. Groner (Weizman Institute, Rehovot, Israel).

4. Transient Transfections

Cathepsin D cDNA insert (2176 bp; SalI-EcoRI fragment containing the full length coding sequences and flanking non-coding regions (see Faust et al., 1985) was subcloned into the tetracycline-controlled expression vector (pSBC-TtA) (Dirks et al., Gene 128:247–249, 1993). The vector (40 μg) was transiently transfected into a HeLa cell clone (HtTA-1) that expresses the tetracycline transactivator gene, by the standard calcium phosphate technique ($2 \times 10^5$ cells were seeded in 9cm plates 18–20 hours prior to transfection). An empty tetracycline-promoter containing vector was used as a control in the assays. In order to exclusively follow the transfected cells, these constructs were co-transfected with either the (CMV-β-galactosidase gene (Clontech), or with the SEAP gene expressed from the SV40 promoter (the pSBC-2 vector) (Dirks et al., 1993). The molar ratio was 6:1 in favor of the tetracycline vectors. Each transfection was divided into two plates, one of which was immediately supplemented with tetracycline (1.5 mg/ml). All the enzymatic activities were assessed 48 h after transfections.

5. β-galactosidase Staining and Determination of SEAP Activity

To detect LacZ expression, cells were fixed with 3% paraformaldehyde for 5 min., rinsed twice with PBS and stained for 3 hrs in X-Gal buffer containing 77 mM Na$_2$HPO$_{4, 23}$ mM NaH$_2$PO$_{4, 1.3}$ mM MgCl$_{2, 1}$ mg/ml X-Gal, 3 mM K$_3$Fe(CN)$_6$, and 3 mM K$_4$Fe(CN)$_6$. The reaction was topped by 70% ethanol. Photography was done under phase microscopy sing Kodak Ektachrome 160T.

For the SEAP activity assay, the medium of transfected cells was changed 5 hrs before the assay. Aliqouts of 100 μl medium were removed from the transfected plates and heated at 65° C. for 5 min. The medium was then clarified by centrifugation at 14000×g for 2 min. The medium aliqouts were adjusted to 1×SEAP assay buffer containing 2M diethanolamine pH 9.8, 1M MgCl$_2$ and 20 mM L-homoarginine. 20 ml of 120 mM p-nitrophenylphosphate dissolved in water was then added to each mixture. The reaction mixtures were then incubated for 30 min. at 37° C. The hydrolysis of p-nitrophenylphosphate was measured at 405 nm.

(B) Results

Figure 41:
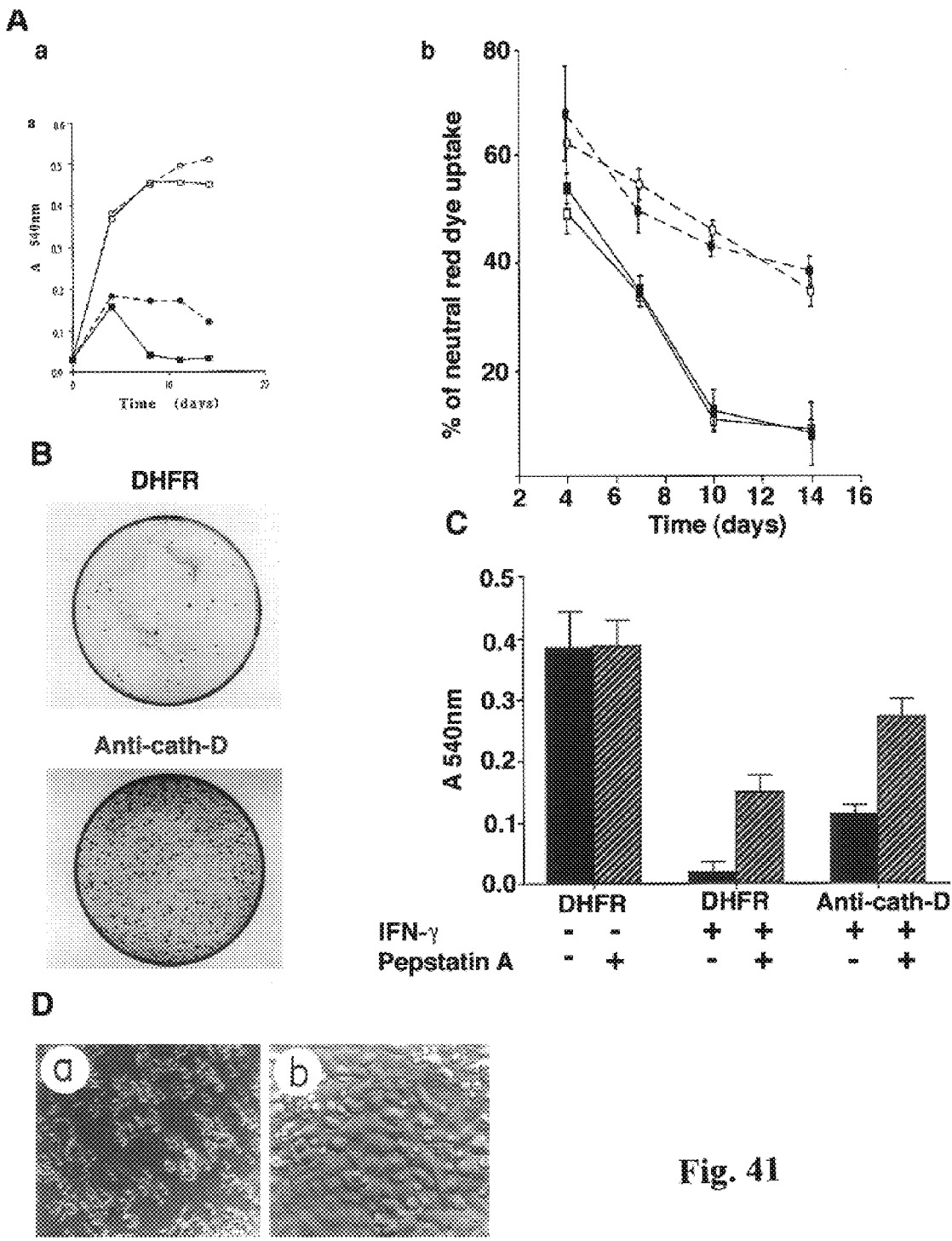

First, the stable HeLa cells transfectants were tested for their growth sensitivity to IFN-γ. It was previously shown that parental HeLa cells displayed a biphasic pattern of response to IFN-γ, in which cells first ceased to proliferate but remained viable, followed by massive cell death with cytological characteristics of PCD (Deiss et al., Genes Dev. 9:15, 1995). One of the assays that was used to measure the anti-sense RNA mediated effects was based on neutral-red dye uptake into viable cells. In the absence of IFN-γ, both cell lines (DHFR and anti-cathepsin D-transfected cells) behaved the same and displayed identical growth curves. This suggested that the anti-sense RNA expression had no effects on the normal growth of cells (FIG. 41Aa). Also the extent of reduction in the neutral-red dye uptake during the first four days, corresponding to the cytostatic effects of IFN-γ (Deiss et al., 1995), was similar in both cell lines. This indicated that cathepsin D anti-sense RNA expression also did not interfere with the cell cycle inhibitory effects of the cytokine. The difference between the two cell populations became prominent later on during the IFN-γ-induced cell death phase. In the IFN-γ-treated DHFR-transfected cells, the dye uptake dropped from day 4 on (FIGS. 41Aa, 41Ab).

The microscopic observations confirmed that this was due to massive cell death that eliminated almost all the viable-adherent cells from the plates (FIG. 41Da). Death was significantly (but not completely) inhibited by the anti-sense cathepsin-D RNA expression, as shown by the sustained values of the dye uptake (FIG. 41Aa). Each of the two anti-sense cathepsin D RNA expressing polyclonal populations displayed a significant increase in the fraction of cells that were stained by the viable dye during the IFN-γ-induced cell death phase (FIG. 41Ab).

Another way to measure protection from cell killing consisted of counting the number of colonies that were formed after releasing the cultures from long term treatment with the cytokine. The reduced susceptibility of the anti-sense transfected cells to cell killing by IFN-γ was manifested by a 1–2 logs increase in the number of cells that could form colonies, following the removal of IFN-g from treated cell cultures (FIG. 41B).

To further explore the participation of cathepsin D in the IFN-γ-induced PCD, the HeLa cells were incubated with pepstatin A, a specific inhibitor of aspartic proteases (Shields et al., Biochem. Biophys. Res. Comm. 177:1006, 1991). Due to the fact that cathepsin D is the major intracellular aspartic protease in cells, the outcome of the intracellular effects of this penta-peptide are commonly attributed to the specific inhibition of cathepsin D activity. Pepstatin A was added to the culture medium at a final concentration of $10^{-4}$M in 0.2% DMSO, in accordance with previous reports whereby similar incubation protocols led to effective intracellular concentrations of the drug (Shields et al., 1991). Pepstatin A had no effect on growing HeLa cells that were not treated with IFN-γ. Addition of pepstatin A to the IFN-γ-treated DHFR-transfected cells inhibited, to some extent, the killing process, as reflected by the elevated values of neutral-red dye uptake (FIG. 41C). The highest values of dye uptake that could be measured in the presence of IFN-γ were obtained by applying the pepstatin A to the anti-sense cathepsin D RNA expressing cells (FIG. 41C).

Microscopic examination of the IFN-γ-induced cell cultures that were protected by the double treatment (anti-sense RNA+pepstatin A) revealed that the majority of cells displayed the normal adherent phenotype, whereas only about 20% of the cells had a round-apoptotic morphology (FIG. 41Db). This further indicated that the combined reduction of both expression and activity of this endoprotease was most effective in protecting cells from IFN-γ-induced cell death. In summary, the anti-sense RNA and pepstatin A data suggest an active role for cathepsin D in the IFN-γ-mediated PCD.

XIX. Regulation of Cathepsin D Protein Expression and Processing During the IFN-γ-induced PCD.

The effects of IFN-γ on the expression and processing of cathepsin D protein were then analyzed on immunoblots. A typical change in the relative abundance of the different cathepsin D forms was detected in the treated cells (FIGS. 42A and 42B). The 48 Kd form of cathepsin D, usually detected in trace amounts in untreated HeLa cells, gradually accumulated to high levels between days 4–7 of IFN-γ-treatment. In contrast, the steady state levels of the 30 Kd form were not increased (FIG. 42B) and in some experiments were even reduced at the late time points (FIG. 42A).

Figure 42:
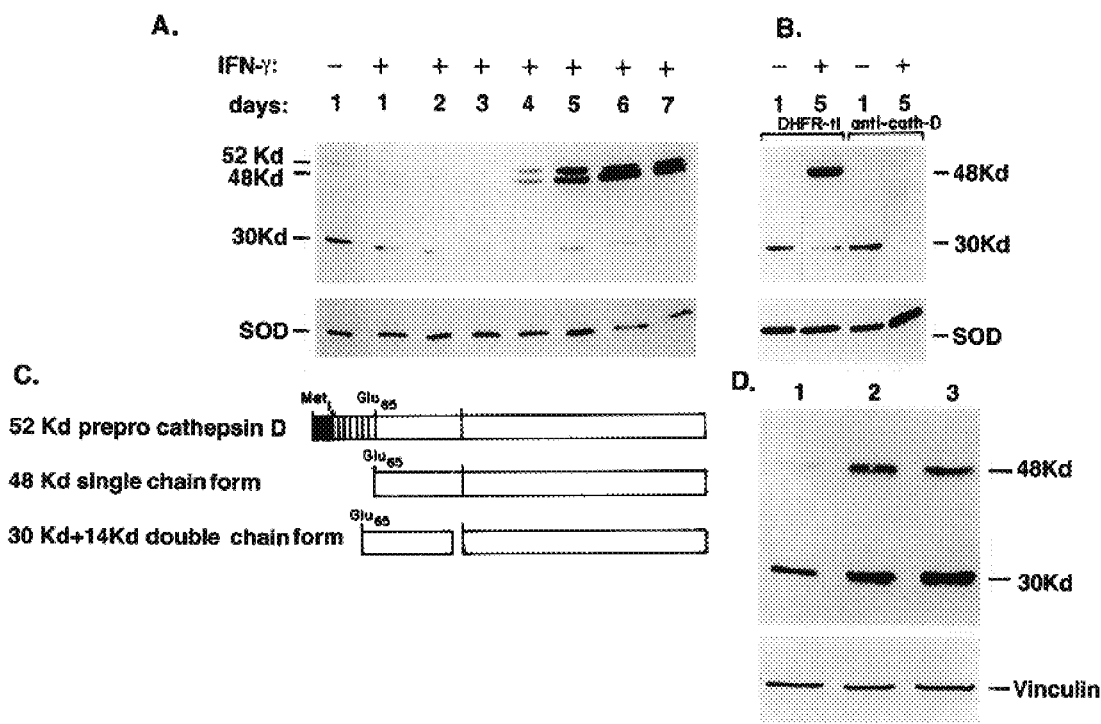

The 48 Kd cathepsin D is a proteolytic active, single chain form often found in pre-lysosomal vesicles. It is normally targeted to lysosomes whereby it is further processed into the double-chain form (30 and 14 Kd) of the enzyme (see the scheme in FIG. 42C—note that the monoclonal antibodies used in FIG. 42 are directed against an epitope in the heavy 30 Kd chain). The unusual accumulation of the 48 Kd form, therefore, suggested that the normal processing of the protease was interrupted during the IFN-γ-mediated cell death. In addition, on days 5–7 of IFN-γ treatment, the levels of the 48 Kd precursor were 8–10 fold higher than the levels of the 30 Kd form before treatment (FIG. 42A). The increased steady state levels of cathepsin D proteins could result, at least partially, from the RNA elevations.

It is noteworthy that in some, but not all experiments, the intracellular levels of the 52 Kd prepro-cathepsin D form increased as well after IFN-γ treatment of the parental cells (FIG. 42A). Traces of the 52 Kd form were also found in the culture medium, but no effects of IFN-γ on the levels of this secreted form were detected (not shown).

The prominent IFN-γ-mediated elevation of cathepsin D protein and the accumulation of the intermediate forms were both prevented in the HeLa polyclonal cell population expressing the anti-sense RNA (FIG. 42B; the calculated values were 8.2 and 1.1 fold increase by IFN-γ in the cathepsin D protein forms for DHFR and anti-cathepsin D transfectants, respectively). A few independently generated anti-sense expressing polyclonal populations were examined and none of them displayed elevated levels of cathepsin D in response to IFN-γ. These findings, therefore, confirmed that the large excess of anti-sense over sense RNA during the IFN-γ selection effectively reduced the total levels of cathepsin D protein, as was expected. The question as to why the residual levels that continued to be expressed in these IFN-γ-treated cells, did not accumulate as intermediate forms of cathepsin D, is still open.

XX. Cathepsin D Aspartic Protease Mediates the APO-1/Fas and the TNF-α-induced PCD.

The question of whether cathepsin D protease is also involved in other apoptotic systems, triggered by the activation of cell surface receptors that differ from the IFN-γ receptors was also studied. The different HeLa cell transfectants were treated with the agonistic anti-APO-1 monoclonal antibody, in order to determine whether cathepsin D mediates the Fas/APO-1-induced apoptosis. The parental and DHFR-transfected cells were efficiently killed by anti-Fas/APO-1 antibodies. Cell death exhibited features characteristic of apoptosis, similar to the IFN-γ effects. By 40 hours, about 70% of the cells rounded up and detached from the plates (not shown) and the uptake of neutral red dye was reduced accordingly (FIG. 43A). The killing required a short pretreatment of the cells with a low dosage of IFN-γ (50 U/ml), which had no effect by itself on cell viability. The low dosage of IFN-γ sensitized the cells to killing by the agonistic antibody, due to elevation of the Fas/APO-1 expression. Expression of anti-sense cathepsin D RNA, or alternatively the addition of pepstatin A to the culture meduim of the DHFR-transfected cells, substantially suppressed the Fas/APO-1-mediated cell death resulting in an increased fraction of viable cells (FIG. 43A). The latter indicated that cathepsin D is essential for the Fas/APO-1-induced PCD.

It was also found that pepstatin A interfered with the apoptotic process that is triggered in U937 histiocytic lymphoma cells by tumor necrosis factor-α (TNF-α). The killing in this system was very rapid, and characterized by typical nuclear changes such as chromatin condensation followed by its fragmentation. DAPI staining of U937 nuclei indicated that 6 hours after TNF-α administration approximately a third of the cell population already contained nuclei with typical fragmented chromatin (FIG. 43B). Addition of pepstatin A to the culture showed a significant reduction in the number of fragmented nuclei (FIG. 43B). Interestingly, the earlier step of chromatin condensation seemed less susceptible to the effect of pepstatin A. These data indicated that cathepsin D endoprotease also mediates some critical steps along the apoptotic pathway, which leads to U937 cell death.

Examination of the pattern of cathepsin D expression in the TNF-α-treated U937 cells revealed that it shared a few common features with the HeLa cell system. The total levels of cathepsin D proteins were significanly increased. Moreover, the proteolytic active 48 Kd intermediate form accumulated in these TNF-α-treated U937 cells, indicating that again the processing into the double chain form was interrupted (FIG. 42D). Yet, in contrast to the HeLa cell system, this conversion was not completely blocked and a mild increase in the 30 Kd form was detected as well. These data suggest a common pattern of changes in the expression/processing of cathepsin D protein in a few apoptotic systems.

XXI. Ectopic Expression of Cathepsin D is not Compatible with Cell Viability.

Figure 44:
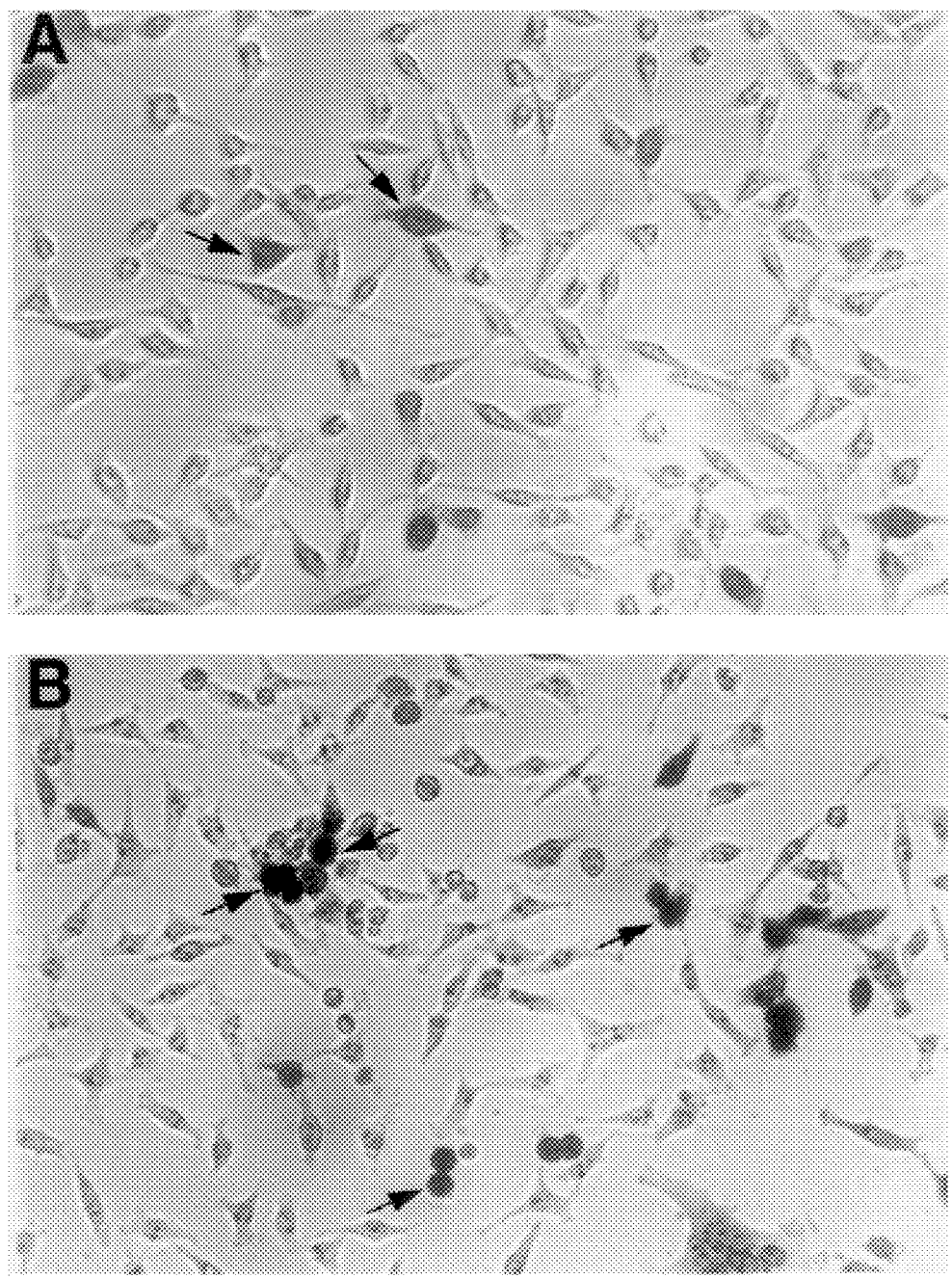

The outcome of overexpression of cathepsin D was directly measured in HeLa cells by co-transfections with the lacZ gene used as a marker of gene expression. Cathepsin D was driven by the tetracycline-repressible promoter (Gossen and Bujard, PNAS 89:5547–5551, 1992) and the β-galactosidase gene was driven by the CMV constitutive promoter. The morphology of lacZ containing blue cells was determined 48 hours post transfection, in cultures which were maintained in the absence of tetracycline to allow cathepsin D transcription/translation. It was found that 70% of the lacZ containing cells displayed a round apoptotic phenotype upon co-transfections with cathepsin D, whereas co-transfections with the control tetracycline vector displayed a background of less than 20% apoptotic cells (FIGS. 44A, 44B, 44C).

In order to further quantitate the effects of ectopic expression of cathepsin D on cells, in a second independent approach, co-transfections were performed with vectors expressing the secreted alkaline phosphatase (SEAP) instead of lacZ. In these experiments the outcome of tetracycline withdrawal on SEAP activity, released by transfectants carrying the cathepsin D gene was measured. It was found that the activation of cathepsin D by tetracycline withdrawal significantly reduced the SEAP activity secreted into the culture medium around 48 hours post-transfection, as compared to the values obtained from the same population maintained in the presence of tetracycline (FIG. 44D). In contrast, tetracycline withdrawal had no effect on SEAP activity released by control cultures which were co-transfected with the empty vector.

XII. DAP Kinase Expression in Metastatic Cell Lines (A) Experimental Procedure (A$_1$) Transfections Transfections were performed by the standard calcium phosphate technique.

(A$_2$) In Vitro Immune Complex Assay for DAP-kinase

Immunoprecipitation of recombinant DAP-kinase protein from 1 mg total extract of transfected cells was done with 20 μl anti-FLAG M2 gel (IBI, Kodak) in 200 μl of PLB supplemented with protease and phosphatase inhibitors for 2 h at 4° C. Following three washes with PLB, the immunoprecipitates were washed once with reaction buffer (50 mM Hepes pH 7.5, 8 mM MgCl$_2$, 2 mM MnCl$_2$ and 0.1 mg/ml BSA). The proteins bound to the beads were incubated for 15 min. at 25° C. in 50 μl of reaction buffer containing 15 μCi[γ-$^{32}$P] ATP (3 pmole), 50 mM ATP, 5 μg MLC (Sigma) and 1 μM bovine calmodulin (Sigma), and 0.5 mM CaCl$_2$. Protein sample buffer was added to terminate the reaction, and after boiling the proteins were analyzed on 11% SDS-PAGE. The gel was blotted onto a nitrocellulose membrane and $^{32}$P labeled proteins were visualized by autoradiography.

(A$_3$) DAPI staining of nuclei before and after treatment with TNF-α.

Exponentially growing cells were treated with a combination of murine TNF-α (100 ng/ml; R&D Systems, Minneapolis) and cycloheximide (5 μg/ml; Sigma) (right panels marked by +), or with cycloheximide along (left panels marked by -). DAPI staining was performed after 6 hours. The cells were plated on glass cover-slips (13 mm diam.), 20,000 cells/well in 1 ml medium within a 24-wells plate. Cells were washed twice with PBS, fixed and permeabilized simultaneously. This was carried out by incubating the cover-slips for 5 min. in a mixture of 3% paraformaldehyde and 0.3% Triton X-100 in PBS, and then incubating with 3% paraformaldehyde alone for additional 20 min. The cells were washed three times in PBS and then incubated in blocking solution (5% normal goat serum and 1% BSA in PBS) for 60 min. DAPI (0.5 μg/ml; Sigma) was added at this stage.

(B) Results

DAP-kinase protein expression was examined in two sets of high- and low-metastatic cell lines selected from the mouse Lewis and CMT64 lung carcinoma cells. Intriguingly, the two different high-metastatic cell lines did not express DAP-kinase mRNA (not shown) or protein, whereas their low-metastatic cell counterparts were DAP-kinase positive (see FIG. 17 for A9-F and D122 sublines of the murine Lewis lung carcinona, displaying low and high metastatic capabilities, respectively). The goal was then to introduce into the high-metastatic D122 cells a functional DAP-kinase and to test the influence of this genetic manipulation on the tumorigenic and metastatic potential of these aggressive tumor cells.

Figure 17:
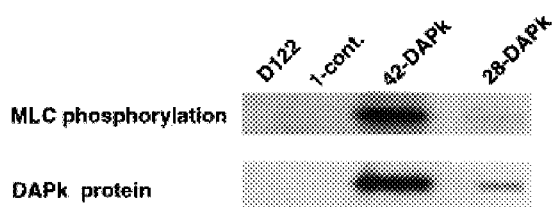
FIG. 17 shows the in vitro kinase activity of the ectopically expressed DAP-kinase gene. Samples of 1000 µg of total cell extracts were immunoprecipitated by anti-FLAG antibodies and subjected to kinase assay (upper panel) using myosin light chain (MLC) protein (5 µg; Sigma) as exogenous substrate. The lower panel shows the DAP-kinase protein levels upon incubation of the same blot with anti-DAP-kinase antibodies.

FLAG-tagged wild type DAP-kinase, cloned in pCDNA3 was transfected into the D122 cells by the calcium phosphate co-precipitation technique. An empty pCDNA3 vector was used for the control transfections. Several stable DAP-kinase positive clones were isolated which were classified into low (6-DAP-kinase), low-mid (48-DAP-kinase), mid (28-DAP-kinase) and high (42-DAP-kinase) expressing cells (FIG. 17; the A9-F low-metastatic cells were used as a reference). Three clones transfected with the control vector, did not express DAP-kinase, as expected (FIG. 17). Next, an in vitro immune complex assay for DAP-kinase was performed following immunoprecipitation by the anti-FLAG antibodies, in order to test whether the exogenously expressed kinase is active. It was found, by using the myosin light chain (MLC) protein as a substrate, that the DAP-kinase protein expressed from the transfected vector was catalytically active (FIG. 18).

The growth rate in culture of the DAP-kinase positive transfectants, in medium containing 10% or 1% fetal calf serum (FCS), was similar to that of the control and the parental clones (FIG. 19). A single exception was the 42-DAP-kinase clone which at the high serum concentration grew slightly slower (two fold increase in the doubling time) due to some disruptions of cytokinesis. DAPI staining of the nuclei of the 42-DAP-kinase cells, growing in 10% FCS-containing medium, showed that the frequency of the fragmented nuclei was below 0.1% (FIG. 27), thus indicating that DAP-kinase by itself, even in the high-expressing stable clone, did not trigger apoptosis. Altogether, it was concluded that the restoration of DAP-kinase expression had either null or subtle effects on the continuous growth of the cells in culture.

XXIII. In Vivo Activity of DAP-kinase Transfected Cells (A) Experimental Procedures (A$_1$) Experimental Metastasis The different D122-transfected clones were injected into tail veins of 10–12 week old C57BL/6 female mice (5×10$^5$ cells per mouse). Mice were sacrificed 30–32 days later, and their lungs were removed, weighed and fixed in Bouin's solution. The number of metastatic nodules were determined by counting surface nodules under a binocular.

(A$_2$) Local Tumor Growth Assay

The different D122-transfected clones were injected into the footpads of C57BL/6 mice (10–12 week old females); (2×10$^5$ cells per mouse). Diameters of tumor bearing feet were measured using calipers every 1–3 days. When tumor diameter reached 8–9 mm, tumor bearing feet were amputated below the knee and the day of death resulting from spontaneous lung metastasis was scored for each individual mouse. In a few cases, the tumor cells were recovered in culture from dissected lung nodules and grown, like all the D122 transfectants, in medium containing 10% fetal calf serum supplemented with G418 (800 µg/ml).

(B) Results

The tumorigenic and metastatic potential of DAP-kinase transfected cells were assayed in mice, where they may be exposed to a variety of death-inducing signals. For example, in the blood stream, the invading tumor cells must resist programmed cell death that is induced by interactions with cytotoxic T lymphocytes, natural killer cells, and macrophages, and with the cytokines which these hematopoietic cells secrete (e.g., IFN's, TNF, IL-1β). They must also resist the apoptotic cell death induced by nitric oxide anions produced by the endothelial cells, and withstand mechanical shearing forces caused by the hemodynamic turbulence. Moreover, during the intravasation or extravasation processes, and during the growth in a foreign hostile micro environment, locally produced inhibitory cytokines (e.g., TGF-β) or loss of cell-matrix interactions (e.g., detachment from the basement membranes) also trigger apoptotic cell death.

The injections into the C57BL/6 syngeneic mice consisted of two different experimental systems and were repeated in three independent experiments. One group received intrafootpad injections (2×10$^5$ cells per injection) in order to follow the local tumor growth. The second group received intravenous injections (5×10$^5$ cells per injection) in order to follow experimental metastases in the lungs.

It was found that the growth of the local tumor in the footpads was significantly delayed as compared to the parental and the G-418 resistant control clones, and that the length of the delay was directly propotional to the levels of the ectopically expressed DAP-kinase (FIG. 20; a lag of 10 days was characteristic of the mid-expressing clone (28-DAP-kinase) and a delay of more than 50 days characterized the high-expressing clone (42-DAP-kinase)).

To examine the effect of DAP-kinase on the experimental metastasis, the lungs were examined 30–32 days after the intravenous injections. Metastasis was strongly suppressed, as measured by the average lung weight and by the mean number of metastatic lesions (FIGS. 21, 22). The experimental metastasis assay was much more sensitive to DAP-kinase expression than the local tumor growth assay. In the lung assay even the low and low-mid expressing clones (6-DAP-kinase; 48-DAP-kinase, respectively) displayed almost maximal reduction of lung weight and of the number of metastatic lesions, while the effects on the local tumor growth were very mild or even undetectable in the low-mid and low expressing clones, respectively.

XXIV. Loss and Restoration of Metastatic Suppression (A) Results

Spontaneous metastasis eventually appeared in the lungs of all the experiments that used the 28-DAP-kinase clone, and in some but not all of the 42-DAP-kinase clone injections, after the tumor bearing legs were amputated. It was interesting to test whether the mid- and high-DAP-kinase expressing clones, which eventually grew in the mice footpads (after the lag period), and which were capable of generating spontaneous metastases in the lungs after the amputation of the tumor bearing legs, were selected in vivo for loss or inactivation of the transfected gene. It was found that the cells which were released in cultures from the lungs of mice that received intrafootpad injections of the 28-DAP-kinase and 42-DAP-kinase clones, expressed traces or even undetectable levels of exogenous DAP-kinase (FIG. 23, lanes 1,2; FIG. 24, lanes 1,2; FIG. 25, lane 1). A strong selection for attenuation of DAP-kinase ectopic expression, therefore occurred in vivo, probably during the lag period before the tumor took in the footpads.

It was possible to restore the full expression capacity of the transfected gene, in clone 28-DAP-kinase that underwent the in vivo selection, by treating the cells in culture with the demethylating agent, 5-aza-2'-deoxycytidine (FIG. 25, lanes 1,2). The restoration was transient and the DAP-kinase levels returned to their suppressed levels a few passages after the removal of the drug (FIG. 25, lanes 3,4). No effects were detected in the parental D122 cells that continued to lack DAP-kinase expression after similar treatments with 5-aza-2'-deoxycytidine (not shown). The in vivo selection for attenuated expression of the transfected DAP-kinase gene, therefore occurred by DNA methylation, an epigenetic mechanism that is frequently used by human tumors to turn off various tumor suppressor genes including the endogenous DAP-kinase gene in bladder carcinoma cells. This attenuation did not occur in the 28-DAP-kinase transfectants that were released from experimental metastasis, i.e., from the very few small metastases that were present in the lungs after the intravein injections. As shown in FIG. 23 (lanes 3,4), the DAP-kinase levels were identical to those detected in the original injected clone. This is consistent with the strong suppression of the metastatic phenotype described above.

XXV. Response of DAP-kinase Transfected Cells to Apoptotic Stimuli (A) Experimental Procedure (A$_1$) In Situ TUNEL Staining-apoptic Index.

Fragments of mice footpads were fixed for 12 hours in 4% buffer formaldehyde (Frutarom), embedded in paraffin, and sectioned (4 µm thick). TUNEL assays on these sections (peroxidase staining of fragmented DNA and counterstaining of the sections by methyl green dye) was performed according to manufacturer's instructions (ApopTag® Plus Peroxidase Kit; Oncor, Gaithersburg). Six different sections were scored; in each case 500–1000 tumor cells were counted and the mean apoptic index was calculated. The mean values were 6.3%±1.13 and 1.9%±0.35 for 42-DAP-kinase and 4-cont., respectively. The difference was significant at $P<<0.001$.

(A₂) Soft Agar-anchorage Independent Growth.

The different clones were cultured in 0.33% soft agar (Bactoagar; Difco) at an initial cell number of $5 \times 10^3$ cells per 6 cm plate, on top of a layer containing 0.5% agar. (A) The diameters of the clones that appeared on day 7 were measured under a light microscope. Values are the mean colony diameter of 100 clones from each group±SD. The difference between the controls (e.g., 18-cont.) and the DAP-kinase-transfectants (e.g., 1-DAP-kinase) was significant at P<<0.001. (B) Microscopy of the clones cultured in soft agar for seven days as in (A), comparing the parental D122 cells (left: a,c) to DAP-kinasc-42 cells (right: b,d). The bars correspond to 350 mm in the upper panels (a,b) and to 80 mm in the lower panes (c,d).

(B) Results

In order to find out whether the anti-tumorigenic and anti-metastatic effects of DAP-kinase resulted from the increased sensitivity of the cells to apoptotic signals, in situ TUNEL staining was performed on histological sections of the mice footpads, five days post-injection. The staining illustrated that the apoptotic index in the slow growing local tumors formed by the DAP-kinase-transfected cells, was significantly higher than the value measured in the tumor mass formed by the control clone (FIG 26). The calculated values were 6% and 2%, respectively, which should reflect a tremendous difference in total cell death, in view of the rapid elimination of apoptotic cells by macrophages and by neighbor cells. The in situ staining provided the first hint implicating the DAP-kinase gene in augmenting the threshold sensitivity of the tumor cells to different apoptotic signals.

To further address this issue directly, some more defined types of apoptotic stimuli were applied in culture, one of which was the death-inducing cytokine-TNF-α. It was found that clone 42-DAP-kinase displayed higher sensitivity to the TNF-α-induced cell death, as measured by DAPI staining of the nuclei a few hours after administration of the cytokine (FIG. 27; 28). Interestingly, this increased sensitivity to the apoptotic effects of TNF-α was lost following the in vivo selection of clone 42-DAP-kinase for attenuated DAP-kinase expression, thus linking more directly, within the same genetic background, DAP-kinase expression and apoptosis (FIG. 28).

Other types of apoptotic stresses were imposed on the cells by transferring them into soft agar, where their anchorage-independent growth could be tested. In contrary to the large colonies formed in soft agar by the parental D122 cells and the control clones, the DAP-kinase transfectants formed abortive small colonies in which most of the cells died (FIGS. 29,30). A reversion to large colonies was obtained when the aforementioned in vivo selected 42-DAP-kinase clone, which displays the attenuated DAP-kinase expression, was tested (data not shown). It is therefore concluded that cell death which is induced by detachment from the extracellular matrix, or by other yet unidentified mechanisms that may operate during the loss of anchorage-dependent growth, depends on the presence of functional DAP-kinase. This is an example of non-cytokine induced programmed cell death.

While the present invention has been described in terms of several preferred embodiments, it is expected that various modifications and improvements will occur to those skilled in the art upon consideration of this disclosure.

The scope of the invention is not to be construed as limited by the illustrative embodiments set forth herein, but is to be determined in accordance with the appended claims.

What is claimed is:

1. An isolated DNA molecule comprising a nucleic acid sequence selected from the group consisting of:
   (i) SEQ ID NO: 1;
   (ii) SEQ ID NO: 2;
   (iii) SEQ ID NO: 3;
   (iv) SEQ ID NO: 5;
   (v) a DNA sequence comprising a coding sequence beginning at the nucleic acid triplet at position 201–203 and ending at the triplet 3018–3020 of the sequence depicted in FIG. 15 (SEQ ID NO: 6).

2. A vector comprising a DNA molecule as defined in claim 1 and sequences required for propagating and replicating the DNA molecule in a host cell.

3. The vector according to claim 2, being an expression vector comprising also sequences required for translation of said DNA into an mRNA.

4. A nucleic acid molecule which comprises an antisense sequence which is complementary to a sequence selected from the group consisting of:
   (i) nucleotides 1000 to 1320 of FIG. 6 (SEQ ID NO:8);
   (ii) nucleotides 3781 to 4148 of FIG. 8 (SEQ ID NO:9);
   (iii) nucleotides 108 to 360 of FIG. 12 (SEQ ID NO:3) and
   (iv) nucleotides 1203 to 1573 of FIG. 15 (SEQ ID NO:6).

5. A vector comprising a nucleic acid molecule as defined in claim 4 and sequences required for propagating and replicating the nucleic acid molecule in a host cell.

6. The vector according to claim 5, being an expression vector and further comprising sequences required for translation of said nucleic acid molecule into mRNA.

7. A DNA molecule having a modified sequence of SEQ ID NO: 9 in which one or more nucleotide triplets has been added, deleted or replaced, the protein or polypetide encoded by the modified sequence having dominant negative effect and which inhibits the function of the protein or polypeptide encoded by a DNA molecule having the sequence of SEQ ID NO: 9.

8. The modified DNA molecule according to claim 7 wherein the nucleotide triplet coding for lysine at amino acid position 42 in FIG. 8 (SEQ ID NO: 9) is replaced by a nucleotide triplet coding, for alanine.

9. A DNA sequence comprising a nucleic acid sequence beginning at position 1764 and ending at position 2528 of the sequence depicted in FIG. 15 (SEQ ID NO:6).

10. An isolated DNA molecule comprising a nucleic acid sequence expressed in cells, the expression product of which is involved in programmed cell death, said isolated DNA being selected from the group consisting of:

(i) SEQ ID NO: 1;

(ii) SEQ ID NO: 3; and (iii) SEQ ID NO: 6.

* * * * *

UNITED STATES PATENT AND TRADEMARK OFFICE
CERTIFICATE OF CORRECTION

PATENT NO. : 6,160,106
DATED : December 12, 2000
INVENTOR(S) : Adi Kimchi

Page 1 of 1

It is certified that error appears in the above-identified patent and that said Letters Patent is hereby corrected as shown below:

Title page,
Item [30], Foreign Application Priority Data,
Please change "107256" to -- 107250 --

Item [63], Related U.S. Application Data,
Please add in turn is a National Phase of PCT/US94/11598 filed 12 October 1994.

Signed and Sealed this

Fourth Day of December, 2001

Attest:

Nicholas P. Godici

NICHOLAS P. GODICI
Attesting Officer    Acting Director of the United States Patent and Trademark Office